(12) United States Patent
Burgard et al.

(10) Patent No.: US 8,865,439 B2
(45) Date of Patent: *Oct. 21, 2014

(54) MICROORGANISMS FOR THE PRODUCTION OF METHACRYLIC ACID

(75) Inventors: Anthony P. Burgard, Bellefonte, PA (US); Mark J. Burk, San Diego, CA (US); Robin E. Osterhout, San Diego, CA (US); Priti Pharkya, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/545,880

(22) Filed: Jul. 10, 2012

(65) Prior Publication Data

US 2012/0276605 A1    Nov. 1, 2012

Related U.S. Application Data

(63) Continuation of application No. 12/433,829, filed on Apr. 30, 2009, now Pat. No. 8,241,877.

(60) Provisional application No. 61/049,730, filed on May 1, 2008.

(51) Int. Cl.
| | | |
|---|---|---|
| C12P 7/40 | (2006.01) | |
| C12P 7/52 | (2006.01) | |
| C12P 7/42 | (2006.01) | |
| C12N 9/00 | (2006.01) | |
| C12N 1/20 | (2006.01) | |
| C07H 21/04 | (2006.01) | |

(52) U.S. Cl.
CPC .... *C12P 7/40* (2013.01); *C12P 7/42* (2013.01)
USPC ........... 435/146; 435/136; 435/141; 435/183; 435/252.3; 435/320.1; 536/23.2

(58) Field of Classification Search
None
See application file for complete search history.

(56) References Cited

U.S. PATENT DOCUMENTS

| | | | |
|---|---|---|---|
| 5,079,143 A | 1/1992 | Klein et al. | |
| 5,143,833 A | 9/1992 | Datta | |
| 5,143,834 A | 9/1992 | Glassner et al. | |
| 5,168,055 A | 12/1992 | Datta et al. | |
| 5,173,429 A | 12/1992 | Gaddy et al. | |
| 5,182,199 A | 1/1993 | Hartley | |
| 5,192,673 A | 3/1993 | Jain et al. | |
| 5,413,922 A | 5/1995 | Matsuyama et al. | |
| 5,416,020 A | 5/1995 | Severson et al. | |
| 5,457,040 A | 10/1995 | Jarry et al. | |
| 5,504,004 A | 4/1996 | Guettler et al. | |
| 5,521,075 A | 5/1996 | Guettler et al. | |
| 5,573,931 A | 11/1996 | Guettler et al. | |
| 5,686,276 A | 11/1997 | Lafend et al. | |
| 5,770,435 A | 6/1998 | Donnelly et al. | |
| 5,807,722 A | 9/1998 | Gaddy et al. | |
| 5,869,301 A | 2/1999 | Nghiem et al. | |
| 5,908,924 A | 6/1999 | Burdette et al. | |
| 5,958,745 A | 9/1999 | Gruys et al. | |
| 6,117,658 A | 9/2000 | Dennis et al. | |
| 6,133,014 A | 10/2000 | Mukouyama et al. | |
| 6,136,577 A | 10/2000 | Gaddy et al. | |
| 6,159,738 A | 12/2000 | Donnelly et al. | |
| 6,187,569 B1 | 2/2001 | Bramucci et al. | |
| 6,274,790 B1 | 8/2001 | Kunst et al. | |
| 6,280,986 B1 | 8/2001 | Hespell et al. | |
| RE37,393 E | 9/2001 | Donnelly et al. | |
| 6,432,686 B1 | 8/2002 | Bulthuis et al. | |
| 6,448,061 B1 | 9/2002 | Pan et al. | |
| 6,455,284 B1 | 9/2002 | Gokarn et al. | |
| 6,485,947 B1 | 11/2002 | Rajgarhia et al. | |
| 6,743,610 B2 | 6/2004 | Donnelly et al. | |
| 6,852,517 B1 | 2/2005 | Suthers et al. | |
| 7,127,379 B2 | 10/2006 | Palsson et al. | |
| 7,186,541 B2 | 3/2007 | Gokarn et al. | |
| 7,223,567 B2 | 5/2007 | Ka-Yiu et al. | |
| 7,241,594 B2 | 7/2007 | Lee et al. | |
| 7,244,610 B2 | 7/2007 | San et al. | |

(Continued)

FOREIGN PATENT DOCUMENTS

| | | |
|---|---|---|
| EP | 1 473 368 | 11/2004 |
| EP | 2 017 344 | 1/2009 |
| WO | WO 82/03854 | 11/1982 |
| WO | WO 99/06532 | 2/1999 |
| WO | WO 99/58686 | 11/1999 |
| WO | WO 01/16346 | 3/2001 |

(Continued)

OTHER PUBLICATIONS

Abadjieva et al., "The Yeast ARG7 Gene Product is Autoproteolyzed to Two Subunit Peptides, Yielding Active Ornithine Acetyltransferase," *J. Biol. Chem.* 275(15):11361-11367 (2000).

(Continued)

*Primary Examiner* — Christian Fronda
(74) *Attorney, Agent, or Firm* — Kagan Binder, PLLC

(57) ABSTRACT

The invention provides a non-naturally occurring microbial organism having a 2-hydroxyisobutyric acid, 3-hydroxyisobutyric acid or methacrylic acid pathway. The microbial organism contains at least one exogenous nucleic acid encoding an enzyme in a 2-hydroxyisobutyric acid, 3-hydroxyisobutyric acid or methacrylic acid pathway. The invention additionally provides a method for producing 2-hydroxyisobutyric acid, 3-hydroxyisobutyric acid or methacrylic acid. The method can include culturing a 2-hydroxyisobutyric acid, 3-hydroxyisobutyric acid or methacrylic acid producing microbial organism expressing at least one exogenous nucleic acid encoding a 2-hydroxyisobutyric acid, 3-hydroxyisobutyric acid or methacrylic acid pathway enzyme in a sufficient amount and culturing under conditions and for a sufficient period of time to produce 2-hydroxyisobutyric acid, 3-hydroxyisobutyric acid or methacrylic acid.

105 Claims, 18 Drawing Sheets

(56) References Cited

U.S. PATENT DOCUMENTS

| | | | |
|---|---|---|---|
| 7,256,016 B2 | 8/2007 | San et al. | |
| 7,262,046 B2 | 8/2007 | Ka-Yiu et al. | |
| 7,285,402 B2 | 10/2007 | Gaddy et al. | |
| 7,309,597 B2 | 12/2007 | Liao et al. | |
| 7,371,558 B2 | 5/2008 | Cervin et al. | |
| 7,393,676 B2 | 7/2008 | Gokarn et al. | |
| 7,569,380 B2 | 8/2009 | San et al. | |
| 7,901,915 B2 | 3/2011 | Symes et al. | |
| 7,923,225 B2 | 4/2011 | Mueller et al. | |
| 7,947,483 B2 | 5/2011 | Burgard et al. | |
| 8,067,214 B2 | 11/2011 | Burk et al. | |
| 8,241,877 B2 * | 8/2012 | Burgard et al. | 435/136 |
| 8,349,596 B2 | 1/2013 | Mueller et al. | |
| 2002/0012939 A1 | 1/2002 | Palsson | |
| 2002/0168654 A1 | 11/2002 | Maranas et al. | |
| 2003/0032153 A1 | 2/2003 | Yamamoto et al. | |
| 2003/0059792 A1 | 3/2003 | Palsson et al. | |
| 2003/0170836 A1 | 9/2003 | Bramucci et al. | |
| 2003/0224363 A1 | 12/2003 | Park et al. | |
| 2003/0233218 A1 | 12/2003 | Schilling | |
| 2004/0009466 A1 | 1/2004 | Maranas et al. | |
| 2004/0029149 A1 | 2/2004 | Palsson et al. | |
| 2004/0072723 A1 | 4/2004 | Palsson et al. | |
| 2007/0111294 A1 | 5/2007 | Burgard et al. | |
| 2008/0261230 A1 | 10/2008 | Liao et al. | |
| 2008/0274526 A1 | 11/2008 | Bramucci et al. | |
| 2009/0047719 A1 | 2/2009 | Burgard et al. | |
| 2009/0075351 A1 | 3/2009 | Burk et al. | |
| 2009/0191593 A1 | 7/2009 | Burk et al. | |
| 2009/0246842 A1 | 10/2009 | Hawkins et al. | |
| 2010/0068773 A1 | 3/2010 | Marx | |
| 2010/0190224 A1 | 7/2010 | Poetter | |
| 2010/0291644 A1 | 11/2010 | Marx et al. | |
| 2011/0151530 A1 | 6/2011 | Soucaille et al. | |

FOREIGN PATENT DOCUMENTS

| | | |
|---|---|---|
| WO | WO 02/42418 | 5/2002 |
| WO | WO 02/055995 | 7/2002 |
| WO | WO 02/090312 | 11/2002 |
| WO | WO 03/106998 | 12/2003 |
| WO | WO 2005/026338 | 3/2005 |
| WO | WO 2005/047498 | 5/2005 |
| WO | WO 2006/031424 | 3/2006 |
| WO | WO 2006/034156 | 3/2006 |
| WO | WO 2007/001982 | 1/2007 |
| WO | WO 2007/030830 | 3/2007 |
| WO | WO 2007/039415 | 4/2007 |
| WO | WO 2007/110394 | 10/2007 |
| WO | WO 2007/141208 | 12/2007 |
| WO | WO 2008/018930 | 2/2008 |
| WO | WO 2008/024023 | 2/2008 |
| WO | WO 2008/027742 | 3/2008 |
| WO | WO 2008/115840 | 3/2008 |
| WO | WO 2008/080124 | 7/2008 |
| WO | WO 2008/119738 | 10/2008 |
| WO | WO 2008/131286 | 10/2008 |
| WO | WO 2008/137403 | 11/2008 |
| WO | WO 2008/145737 | 12/2008 |
| WO | WO 2008/152016 | 12/2008 |
| WO | WO 2009/014437 | 1/2009 |
| WO | WO 2009/023493 | 2/2009 |
| WO | WO 2009/049274 A2 | 4/2009 |
| WO | WO 2009/094485 A1 | 7/2009 |
| WO | WO 2009/103026 | 8/2009 |
| WO | WO 2009/131040 | 10/2009 |
| WO | WO 2010/022763 | 3/2010 |
| WO | WO 2010/023206 | 3/2010 |

OTHER PUBLICATIONS

Abe et al., "Discovery of amide (peptide) bond synthetic activity in Acyl-CoA synthetase," *J. Biol. Chem.* 283(17):11312-11321 (2008).
Aberhart and Hsu, "Stereospecific hydrogen loss in the conversion of [2H7] isobutyrate to β-hydroxyisobutyrate in *Pseudomonas putida*. The stereochemistry of β-hydroxyisobutyrate dehydrogenase," *J. Chem. Soc. [Perkin1]* 6:1404-1406 (1979).
Abiko et al., "Localization of NAD-isocitrate dehydrogenase and glutamate dehydrogenase in rice roots: candidates for providing carbon skeletons to NADH-glutamate synthase," *Plant Cell Physiol.* 46:1724-1734 (2005).
Abo-Dalo et al., "A novel member of the GCN5-related N-acetyltransferase superfamily from *Caenorhabditis elegans* preferentially catalyses the N-acetylation of thialysine [S-(2-aminoethyl)-L-cysteine]," *Biochem. J.* 384:129-137 (2004).
Accession CAB40912. (Apr. 5, 2005).
Accession P28817. (Dec. 1, 1992).
Accession Q6M2R3. (Jul. 5, 2004).
Acrylic Acid, National Library of Medicine HSDB Database, url_toxnet_NlmNIH_govCGI_17Feb2010_AA.
Adams and Kletzin, "Oxidoreductase-type enzymes and redox proteins involved in fermentative metabolisms of hyperthermophilic Archaea," *Adv. Protein Chem.* 48:101-180 (1996).
Aevarsson et al., "Crystal structure of 2-oxoisovalerate and dehydrogenase and the architecture of 2-oxo acid dehydrogenase multienzyme complexes," *Nat. Struct. Biol.* 6:785-792 (1999).
Agnihotri and Liu, "Enoyl-CoA Hydratase: Reaction, Mechanism, and Inhibition," *Bioorg. Med. Chem.* 11(1):9-20 (2003).
Akashi et al., "Molecular and biochemical Characterization of 2-Hydroxyisoflavanone Dehydratase. Involvement of Carboxylesterase-Like Proteins in Leguminous Isoflavone Biosynthesis," Plant. Physiol. 137:882-891 (2005).
Akhtar and Jones, "Construction of a synthetic YdbK-dependent pyruvate:H2 pathway in *Escherichia coli* BL21(DE3)," *Metab. Eng.* 11(3):139-147 (2009).
Alber et al., "3-Hydroxypropionyl-Coenzyme A synthetase from *Metallosphaera sedula*, an enzyme involved in autotrophic CO2 fixation," J. Bacteriol. 190:1383-1389 (2008).
Alber et al., "Malonyl-Coenzyme A reductase in the modified 3-hydroxypropionate cycle for autotrophic carbon fixation in archaeal *Metallosphaera* and *Sulfolobus* spp.," J. Bacteriol. 188(24):8551-8559 (2006).
Alber et al., "Propionyl-Coenzyme A synthase from *Chloroflexus aurantiacus*, a key enzyme of the 3-hydroxypropionate cycle for autotrophic CO$_2$ fixation," *J. Biol. Chem.* 277:12137-12143 (2002).
Alber et al., "Study of an alternate glyoxylate cycle for acetate assimilation by *Rhodobacter sphaeroides*," *Mol. Microbiol.* 61(2):297-309 (2006).
Aldor and Keasling, "Metabolic engineering of poly(3-hydroxybutyrate-co-3- hydroxyvalerate) composition in recombinant *Salmonella enterica* serovar typhimurium," *Biotechnol. Bioeng.* 76(2):108-114 (2001).
Aldor et al., "Metabolic Engineering of a Novel Propionate-Independent Pathway for the Production of Poly(3-Hydroxybutyrate-co-3-Hydroxyvalerate) in Recombinant *Salmonella enterica* Serovar Typhimurium," *Appl. Environ. Microbiol.* 68(8):3848-3854 (2002).
Alexeeva et al., "Requirement of ArcA for redox regulation in *escherichia coli* under microaerobic but not anaerobic or aerobic conditions," *J. Bacteriol.* 185(1):204-209 (2003).
Alexson et al., "NADH-sensitive propionyl-CoA hydrolase in brown-adipose-tissue mitochondria of the rat," Biochim. Biophys. Acta 1005(1):13-19 (1989).
Alhapel et al., "Molecular and functional analysis of nicotinate catabolism in *Eubacterium barkeri*," *Proc. Natl. Acad. Sci. U.S.A.* 103(33):12341-12346 (2006).
Alper et al., "Engineering yeast transcription machinery for improved ethanol tolerance and production," Science 314(5805):1565-1568 (2006).
Altamirano et al., "Decoupling cell growth and product formation in Chinese hamster ovary cells throguh metabolic control," *Biotechnol. Bioeng.* 76(4):351-360 (2001).
Altmiller and Wanger, "Purification and properties of dihydroxy acid dehydratase from soluble and mitochondrial fractions of *Neurospora crassa*," Arch. Biochem. Biophys. 138:160-170 (1970).
Andersen et al., "A gene duplication led to specialized γ-aminobutyrate and β-alanine aminotransferase in yeast," *FEBS J.* 274:1804-1817 (2007).

(56) References Cited

OTHER PUBLICATIONS

Anderson and Dawes, "Occurrence, metabolism, metabolic role, and industrial uses of bacterial polyhydroxyalkanoates," *Microbiol. Rev.* 54(4):450-472 (1990).

Andersson et al., "Effect of different carbon sources on the production of succinic acid using metabolically engineered *Escherichia coli*," Biotechnol. Prog. 23(2):381-388 (2007).

Aneja and Charles, "Poly-3-hydroxybutyrate degradation in *Rhizobium* (*Sinorhizobium*) *meliloti*: isolation and characterization of a gene encoding 3-hydroxybutryate dehydrogenase," J. Bacteriol. 181(3):849-857 (1999).

Aoshima, "Novel enzyme reactions related to the tricarboxylic acid cycle: phylogenetic/functional implications and biotechnological applications," *Appl. Microbiol. Biotechnol.* 75(2):249-255 (2007).

Aragon and Lowenstein, "A survey of Enzymes Which Generate or Use Acetoacetyl Thioesters in Rat Liver," *J. Biol. Chem.* 258(8):4725-4733 (1983).

Arendsen et al., "Nitrate-Dependent Regulation of Acetate Biosynthesis and Nitrate Respiration by *clostridium* thermoaceticum," *J. Bacteriol.* 181:1489-1495 (1999).

Argyrou and Blanchard, "Kinetic and chemical mechanism of *Mycobacterium tuberculosis* 1-deoxy-D-xylulose-5-phosphate isomeroreductase," *Biochemistry* 43:4375-4384 (2004).

Aristidou et al., "Metabolic Engineering of *Escherichia coli* to Enhance Recombinant Protein Production through Acetate Reduction," *Biotechnol. Prog.* 11(4):475-478 (1995).

Aristidou et al., "Metabolic flux analysis of *Escherichia coli* expressing the *Bacillus subtilis* Acetolactate Synthase in Batch and Continuous Cultures," *Biotechnol. Bioeng.* 63(6):737-749 (1999).

Armstrong et al., "Steroselectivity and sterospecificity of the α,β-dihydroxyacid dehydratase from *Salmonella typhimurium*," *Biochim. Biophys. Acta* 498:282-293 (1977).

Arps et al., "Genetics of serine pathway enzymes in *Methylobacterium extorquens* AM1: phosphoenolpyruvate carboxylase and malyl Coenzyme A lyase," *J. Bacteriol.* 175:3776-3783 (1993).

Asano and Kato, "Crystalline 3-methylaspartase from a facultative anaerobe, *Escherichia coli* strain YG1002," *FEMS Microbiol. Lett.* 118(3):255-258 (1994).

Asano et al., "Alteration of substrate specificity of aspartase by directed evolution," *Biomol. Eng.*, 22(1-3):95-101 (2005).

Asanuma et al., "Characterization and transcription of the genes encoding enzymes involved in butyrate production in *Butyrivibrio fibrisolvens*," Curr. Microbiol. 45:203-207 (2003).

Asuncion et al., "Overexpression, purification, crystallization and data collection of 3-methylaspartase from *Clostridium tetanomorphum*," *Acta. Crystallogr. D. Biol. Crystallogr.* 57(Pt 5):731-733 (2001).

Asuncion et al., "The structure of 3-methylaspartase from *Clostridium tetanomorphum* functions via the common enolase chemical step," *J. Biol. Chem.* 277(10):8306-8311 (2002).

Atsumi et al., "Metabolic engineering of *Escherichia coli* for 1-butanol production," *Metab. Eng.* 10(6):305-311 (2007).

Atsumi et al., "Non-fermentative pathways for synthesis of branched-chain higher alcohols as biofuels," *Nature* 451(7174):86-89 (2008).

Atteia et al., "Pyruvate formate-lyase and a novel route of eukaryotic ATP synthesis in *Chlamydomonas* mitochondria," *J. Biol. Chem.* 281:9909-9918 (2006).

Auerbach et al., "Lactate dehydrogenase from the hyperthermophilic bacterium *thermotoga maritima*: the crystal structure at 2.1 Å resolution reveals strategies for intrinsic protein stabilization," *Structure* 6:769-781 (1998).

Baba et al., "Construction of *Escherichia coli* K-12 in-frame, single-gene knockout mutants: the Keio collection," *Mol. Syst. Biol.* 2:2006.0008 (2006).

Baird et al., "Enzymes involved in acetoacetate formation in various bovine tissues," Biochem. J. 117(4):703-709 (1970).

Barber et al., "Structure and regulation of acetyl-CoA carboxylase genes of metazoa," Biochimica. Biophysica. Acta 1733:1-28 (2005).

Barker et al., "Butyryl-CoA:Acetoacetate CoA-transferase from Lysine-fermenting *clostridium*," *J. Biol. Chem.* 253(4):1219-1225 (1978).

Barker et al., "Pathway of Lysine Degradation in *Fusobacterium nucleatum*," *J. Bacteriol.* 152(1):201-207 (1982).

Barrowman et al., "Immunological comparison of microbial TPP-dependent non-oxidative α-keto acid decarboxylase," *FEMS Microbiol. Lett.* 34:57-60 (1986).

Barthelmebs et al., "Expression of *Escherichia coli* of Native and chimeric Phenolic Acid Decarboxylases with Modified Enzymatic Activities and Method for Screening Recombinant *E. coli* Strains Expressing These Enzymes," *Appl. Environ. Microbiol.* 67:1063-1069 (2001).

Bartsch et al., "Molecular analysis of two genes of the *Escherichia coli* gab cluster: nucleotide sequence of the glutamate:succinic semialdehyde transaminase gene (gabT) and characterization of the succinic semialdehyde dehydrogenase gene (gabD)," J. Bacteriol. 172(12):7035-7042 (1990).

Battaile et al., "Structures of isobutyryl-CoA dehydrogenase and enzyme-product complex: Comparison with isovaleryl- and short-chain acyl-CoA dehydrogenases," *J. Biol. Chem.* 279:16526-16534 (2004).

Baudin et al., "A simple and efficient method for direct gene deletion in *Saccharomyces cerevisiae*," *Nucleic Acids Res.* 21(14):3329-3330 (1993).

Benner et al., "Stereospecificity and sterochemical infidelity of acetoacetate decarboxylase (AAD)," *J. Am. Chem. So.* 103:993-994 (1981).

Benning et al., "New reactions in the crotonase superfamily: Structure of methylmalonyl CoA decarboxylase from *Escherichia coli*," Biochemistry 39:4630-4639 (2000).

Berg et al., "A 3-Hydroxypropionate/4-Hydroxybutyrate Autotrophic Carbon Dioxide Assimilation Pathway in Archaea," *Science* 318(5857) 1782-1786 (2007).

Berkovitch et al., "A locking mechanism preventing radical damage in the absence of substrate, as revealed by the x-ray structure of lysine 5,6-aminomutase," *Proc. Natl. Acad. Sci. U.S.A.* 101:15870-15875 (2004).

Berman and Magasanik, "The pathway of myo-inositol degradation in *Aerobacter aerogenes*," *J. Biol. Chem.* 241(4):800-806 (1966).

Bermejo et al., "Expression of *Clostridium acetobutylicum* ATCC 824 Genes in *Escherichia coli* for Acetone Production and Acetate Detoxification," *Appl. Environ. Microbiol.* 64(3):1079-1085 (1998).

Berthold et al., "Structure of the branched-chain keto acid decarboxylase (KdcA) from *Lactococcus* lacti prvides insights into structural basis for the chemoselective enantioselective carboligation reaction," *Acta. Crystallogr. D. Biol. Crystallogr.* 63(Pt. 12):1217-1224 (2007).

Biellmann et al., "Aspartate-β-semialdehyde dehydrogenase from *Escherichia coli*. Purification and general properties," *Eur. J. Biochem.* 104(1):53-58 (1980).

Binieda et al., "Purification, characterization, DNA sequence and cloning of a pimeloyl-CoA synthetase from *Pseudomonas mendocina* 35," Biochem. J. 340:793-801 (1999).

Binstock and Schulz, "Fatty acid oxidation complex from *Escherichia coli*," Methods Enzymol. 71(Pt C):403-411 (1981).

Birch et al., "Cloning, sequencing, and expression of the gene encoding methylmalonyl-Coenzyme A mutase from *Streptomyces cinnamonensis*," J. Bacteriol. 175(11):3511-3519 (1993).

Bisswanger, "Substrate specificity of the Pyruvate Dehydrogenase Complex from *Escherichia coli*," *J. Biol. Chem.* 256(2):815-822 (1981).

Blanco et al., "Critical catalytic functional groups in the mechanism of aspartate-β-semialdehyde dehydrogenase," *Acta. Crystallogr. D. Biol. Crystallogr.* 60(Pt 10):1808-1815 (2004).

Blanco et al., "The role of substrate-binding groups in the mechanism of aspartate-β-semialdehyde dehydrogenase," *Acta. Crystallogr. D. Biol. Crystallogr.* 60(Pt 8):1388-1395 (2004).

Blaschkowski et al., "Routes of flavodoxin and ferredoxin reduction in *Escherichia coli*. CoA-acylating pyruvate: flavodoxin and NADPH: flavodoxin oxidoreductases participating in the activation of pyruvate formate-lyase," *Eur. J. Biochem.* 123(3):563-569 (1982).

(56) References Cited

OTHER PUBLICATIONS

Blazquez et al., "Identification and analysis of a glutaryl-CoA dehydrogenase-encoding gene and its cognate transcriptional regulator from *Azoarcus* sp. CIB," Environ. Microbiol. 10(2):474-482 (2008).
Blombach et al., "*Corynebacterium glutamicum* tailored for high-yield L-valine production," *Appl. Microbiol. Biotechnol.* 79(3):471-479 (2008).
Blomqvist et al., "Characterization of the genes of the 2,3-butanediol operons from *Klebsiella terrigena* and *Enterobacter aerogenes*," J. Bacteriol. 175:1392-1404 (1993).
Bobik and Rasche, "HPLC assay for methylmalonyl-CoA epimerase," *Anal. Bioanal. Chem.* 375(3):344-349 (2003).
Bobik and Rasche, "Identification of the human methylmalonyl-CoA racemase gene based on the analysis of prokaryotic gene arrangements. Implications for decoding the human genome," *J. Biol. Chem.* 276(40):37194-37198 (2001).
Bobik et al., "Propanediol Utilization Genes (pdu) of *Salmonella typhimurium*: Three Genes for the Propanediol Dehydratase," J. Bacteriol. 179(21):6633-6639 (1997).
Bonnarme et al., "Itaconate biosynthesis in *Aspergillus terreus*," J. Bacteriol. 177(12):3573-3578 (1995).
Bonner and Bloch, "Purification and properties of fatty acyl thioesterase I from *Escherichia coli*," J. Biol. Chem. 247(10):3123-3133 (1972).
Bott et al., "Methylmalonyl-CoA decarboxylase from *Propionigenium modestum*. Cloning and sequencing of the structural genes and purification of the enzyme complex," Eur. J. Biochem. 250:590-599 (1997).
Botting et al., "Substrate Specificity of the 3-Methylaspartate Ammonia-Lyase Reactin: Observation of Differential relative Reaction Rates for Substrate-Product Pairs," Biochemistry 27:2953-2955 (1988).
Boylan and Dekker, "L-Threonine Dehydrogenase of *Escherichia Coli* K-12," Biochem. Biophys. Res. Commun. 85(1):190-197 (1978).
Boynton et al., "Cloning, sequencing, and expression of clustered genes encoding β-hydroxybutyryl-Coenzyme A (CoA) dehydrogenase, crotonase, and butyryl-CoA dehydrogenase from *Clostridium acetobutylicum* ATCC 824," J. Bacteriol. 178(11):3015-3024 (1996).
Brachmann et al., "Designer deletion strains derived from *Saccharomyces cerevisiae* S288C: a useful set of strains and plasmids for PCR-mediated gene disruption and other applications," Yeast 14(2):115-132 (1998).
Branlant, "Nucleotide sequence of *Escherichia coli* gap gene. Different evolutionary behavior of the NAD+-binding domain and of the catalytic domain of D-glyceraldehyde-3-phosphate dehydrogenase," Eur. J. Biochem. 150:61-66 (1985).
Bräsen and Schönheit, "Unusual ADP-forming acetyl-Coenzyme A synthetases from the mesophilic halophilic euryarchaeon *Haloarcula marismortui* and from the hyperthermophilic crenarchaeon *Pyrobaculum aerophilum*," Arch. Microbiol. 182(4):277-287 (2004).
Breitkruez et al., "A novel γ-hydroxybutyrate dehydrogenase: Identification and expression of an *Arabidopsis* cDNA and potential role under oxygen deficiency," *J. Biol. Chem.* 278:41552-41556 (2003).
Bremer, "Pyruvate Dehydrogenase, Substrate Specificity and Product Inhibition," Eur. J. Biochem. 8:535-540 (1969).
Brey et al., "Cloning of multiple genes involved with cobalamin (Vitamin $B_{12}$) biosynthesis in *Bacillus megaterium*," J. Bacteriol. 167:623-630 (1986).
Brooke et al., "GAMS: a User's Guide. GAMS Development Corporation" (1998).
Broun et al., "Catalytic plasticity of fatty acid modification enzymes underlying chemical diversity of plant lipids," Science 282:1315-1317 (1998).
Brown et al., "Comparative structural analysis and kinetic properties of lactate dehydrogenases from the four species of human malarial parasites," Biochemistry 43:6219-6229 (2004).

Browner et al., "Sequence analysis, biogenesis, and mitochondrial import of the α-subunit of rat liver propionyl-CoA carboxylase," *J. Biol. Chem.* 264:12680-12685 (1989).
Bu and Tobin, "The exon-intron organization of the genes (GAD1 and GAD2) encoding two human glutamate decarboxylases ($GAD_{67}$ and $GAD_{65}$) suggests that they derive from a common ancestral GAD," *Genomics* 21:222-228 (1994).
Bu et al., "Two human glutamate decarboxylases, 65-kDa GAD and 67-kDa GAD, are each encoded by a single gene," *Proc. Natl. Acad. Sci. U.S.A.* 89:2115-2119 (1992).
Buck et al., "Primary structure of the succinyl-CoA synthetase of *Escherichia coli*," Biochem. 24(22):6245-6252 (1985).
Buckel and Barker, "Two pathways of glutamate fermentation by anaerobic bacteria," *J. Bacteriol.* 117(3):1248-1260 (1974).
Buckel and Golding, "Radical enzymes in anaerobes," *Annu. Rev. Microbiol.* 60:27-49 (2006).
Buckel et al., "ATP-Driven electron transfer in enzymatic radical reactions," *Curr. Opin. Chem. Biol.* 8:462-467 (2004).
Buckel et al., "Glutaconate CoA-Transferase from *Acidaminococcus fermentans*," Eur. J. Biochem. 118:315-321 (1981).
Buckel et al., "Radical-mediated dehydration reactions in anaerobic bacteria," *Biol. Chem.* 386:951-959 (2005).
Buckel, "Sodium ion-translocating decarboxylases," *Biochimica. Biophysica. Acta* 1505:15-27 (2001).
Bueding and Yale, "Production of α-methylbutyric acid by bacteria-free *Ascaris lumbricoides*," *J. Biol. Chem.* 193:411-423 (1951).
Bunch et al., "The IdhA gene encoding the fermentative lactate dehydrogenase of *Escherichia coli*," Microbiol. 143:187-195 (1997).
Burgard and Maranas, "Probing the performance limits of the *Escherichia coli* metabolic network subject to gene additions or deletions," *Biotechnol. Bioeng.* 74:364-375 (2001).
Burgard et al., "Minimal Reaction Sets for *Escherichia coli* Metabolism under Different Growth Requirements and Uptake Environments," *Biotechnol. Prog.* 17:791-797 (2001).
Burgard et al., "Optknock: a bilevel programming framework for identifying gene knockout strategies for microbial strain optimization," *Biotechnol. Bioeng.* 84(6):647-657 (2003).
Burks et al., "Stereochemical and Isotopic Labeling Studies of 2-Oxo-hept-4-ene-1,7-dioate Hydratase: Evidence for an Enzyme-Catalyzed Ketonization Step in the Hydration Reaction," *J. Am. Chem. Soc.* 120(31):7665-7675 (1998).
Buu et al., "Functional characterization and localization of acetyl-CoA hydrolase, Ach1p, in *Saccharomyces cerevisiae*," *J. Biol. Chem.* 278:17203-17209 (2003).
Buzenet et al., "Purification and properties of 4-Aminobutyrate 2-Ketoglutarate Aminotransferase From Pig Liver," *Biochimica. Biophysica. Acta* 522:400-411 (1978).
Campbell et al., "A new *Escherichia coli* metabolic competency: growth on fatty acids by a novel anaerobic β-oxidation pathway," *Mol. Microbiol.* 47(3):793-805 (2003).
Cao et al., "Simultaneous Production and recovery of Fumaric Acid from Immobilized *Rhizopus oryzae* with a Rotary biofilm Contactor and an Adsorption Column," Appl. Environ. Microbiol. 62(8):2926-2931 (1996).
Carta et al., "Production of fumaric acid by fermentation of enzymatic hydrolysates derived from Cassava bagasse," Biores. Tech. 68:23-28 (1999).
Cary et al., "Cloning and Expression of *Clostridium acetobutylicum* ATCC 824 Acetoacetyl-Coenzyme A:Acetate/Butyrate:Coenzyme A-Transferase in *Escherichia coli*," *App. Environ. Microbiol.* 56(6):1576-1583 (1990).
Cary et al., "Cloning and expression of *Clostridium acetobutylicum* phosphotransbutyrylase and butyrate kinase genes in *Escherichia coli*," *J. Bacteriol.* 170(10):4613-4618 (1988).
Casero and Pegg, "Spermidine/spermine $N^1$-acetyltransferase—the turning point in polyamine metabolism," *FASEB J.* 7:653-661 (1993).
Cavin et al., "Gene cloning, transcriptional analysis, purification, and characterization of phenolic acid decarboxylase from *bacillus subtilis*," Appl. Environ. Microbiol. 64(4):1466-1471 (1998).
Cha and Parks, Jr., "Succinic Thiokinase. I. Purification of the Enzyme from Pig Heart," *J. Biol. Chem.* 239:1961-1967 (1964).

(56) References Cited

OTHER PUBLICATIONS

Chandra et al. "Pyruvate decarboxylase: a key enzyme for the oxidative metabolism of lactic acid by *Acetobacter* pasteurianus," *Arch. Microbiol.* 176:443-451 (2001).
Chang et al., "Effects of deletions at the carboxyl terminus of *Zymomonas* mobills pyruvate decarboxylase on the kinetic properties and substrate specificity," Biochemistry 39(31):9430-9437 (2000).
Charrier et al., "A novel class of CoA-transferase involved in short-chain fatty acid metabolism in butyrate-producing human colonic bacteria," Microbiology 152:179-185 (2006).
Chatterjee et al., "Mutation of the ptsG Gene Results in Increased Production of Succinate in Fermentation of Glucose by *Escherichia coli*," Appl. Env. Microbiol. 67:148-154 (2001).
Chen and Hiu, "Acetone-Butanol-Isopropanol Production by *Clostridium beijerinckii* (Synonym, *Clostridium* Butylicum)," *Biotechnology Letters* 8(5):371-376 (1986).
Chen et al., "A novel lysine 2,3-aminomutase encoded by the yodO gene of *Bacillus subtilis*: characterization and the observation of organic radical intermediates," *Biochem. J.* 348:539-549 (2000).
Chen et al., "Cloning, Sequencing, Heterologous Expression, Purification, and Characterization of Adenosylcobalamin-dependent D-Ornithine Aminomutase from *Clostridium sticklandii*," *J. Biol. Chem.* 276:44744-44750 (2001).
Cheng et al., "Mammalian Wax Biosynthesis. I. Identification of two fatty acyl-Coenzyme A reductases with different substrate specificities and tissue distributions," *J. Biol. Chem.* 279(36):37789-37797 (2004).
Cheng et al., "Mammalian Wax Biosynthesis. II. Expression cloning of wax synthase cDNAs encoding a member of the acyltransferase enzyme family," *J. Biol. Chem.* 279(36):37798-37807 (2004).
Chicco et al., "Regulation of Gene Expression of Branched-chain Keto Acid Dehydrogenase Complex in Primary Cultured Hepatocytes by Dexamethasone and a cAMP Analog," *J. Biol. Chem.* 269(30):19427-19434 (1994).
Chirpich et al., "Lysine 2,3-Aminomutase. Purification and Properties of Pyridoxal Phosphate and S-Adenosylmethionine-Activated Enzyme," *J. Biol. Chem.* 245(7):1778-1789 (1970).
Choi-Rhee and Cronan, "The biotin carboxylase-biotin carboxyl carrier protein complex of *Escherichia coli* acetyl-CoA carboxylase," *J. Biol. Chem.* 278:30806-30812 (2003).
Chopra et al., "Expression, purification, and biochemical characterization of *Mycobacterium tuberculosis* aspartate decarboxylase, PanD," *Protein Expr. Purif.* 25:533-540 (2002).
Chowdhury et al., "3-Hydroxyisobutyrate dehydrogenase from *Pseudomonas putida* E23: purification and characterization," *Biosci. Biotechnol. Biochem.* 60(12):2043-2047 (1996).
Chowdhury et al., "Cloning and overexpression of the 3-hydroxyisobutyrate dehydrogenase gene from *pseudomonas putida* E23," *Biosci. Biotechnol. Biochem.* 67(2):438-441 (2003).
Christenson et al., "Kinetic analysis of the 4-methylideneimidazole-5-one-containing tyrosine aminomutase in enediyne antitumor antibiotic C-1027 biosynthesis," *Biochemistry* 42:12708-12718 (2003).
Chuakrut et al., "Characterization of a bifunctional archael acyl Coenzyme A carboxylase," *J. Bacteriol.* 185:938-947 (2003).
Clarke et al., "Rational construction of a 2-Hydroxyacid Dehydrogenase With New Substrate Specificity," *Biochem. Biophys. Res. Commun.* 148:15-23 (1987).
Clausen et al., "PAD1 encodes phenylarcrylic acid decarboxylase which confers resistance to cinnamic acid in *Saccharomyces cerevisiae*," Gene 142:107-112 (1994).
Colby and Chen, "Purification and properties of 3-hydroxybutyryl-Coenzyme A dehydrogenase from *Clostridium beijerinckii* ("*Clostridium* butylicum") NRRL B593," *Appl. Environ. Microbiol.* 58:3297-3302 (1992).
Coleman, "Expression of a glutamate decarboxylase homologue is required for normal oxidative stress tolerance in *Saccharomyces cerevisiae*," *J. Biol. Chem.* 276:244-250 (2001).
Conrad et al., "D- and L-Isoleucine Metabolism and Regulation of Their Pathways in *Pseudomonas Putida*," *J. Bacteriol.* 118(1):103-111 (1974).
Cooper, "Glutamate-$\gamma$-aminobutyrate transaminase," Methods Enzymol. 113:80-82 (1985).
Corthesy-Theulaz et al., "Cloning and Characterization of *Helicobacter pylori* Succinyl CoA:Acetoacetate CoA-transferase, a Novel Prokaryotic Member of the CoA-transferase Family," *J. Biol. Chem.* 272(41):25659-25667 (1997).
Cox et al., "Development of a metabolic network design and optimization framework incorporating implementation constraints: a succinate production case study," Metab. Eng. 8(1):46-57 (2006).
Cukalovic et al., "Feasibility of production method for succinic acid derivatives: a marriage of renewable resources and chemical technology," *Biofuels Bioprod. Bioref.* 2:505-529 (2008).
Cunningham et al., "Transcriptional regulation of the aconitase genes (acnA and acnB) of *Escherichia coli*," Microbiology 143(Pt 12):3795-3805 (1997).
Dakoji et al., "Studies on the inactivation of bovine liver enoyl-CoA hydratase by (methylenecyclopropyl)formyl-CoA: elucidation of the inactivation mechanism and identification of cysteine-114 as the entrapped nucleophile," J. Am. Chem. Soc. 123(4):9749-9759 (2001).
Datsenko et al., "One-step inactivation of chromosomal genes in *Escherichia coli* K-12 using PCR products," *Proc. Natl. Acad. Sci. U.S.A.* 97:6640-6645 (2000).
Datta et al., "Covalent structure of biodegradative threonine dehydratase of *Escherichi coli*: homology with other dehydratases," Proc. Natl. Acad. Sci. U.S.A. 84(2):393-397 (1987).
Davids et al, "Characterization of the N-acetyltransferases respectively responsible for arylalkylamine and diamine acetylation in *Ascaris suum*," Mol. Biochem. Parasitol. 64(2):341-344 (1994).
Davie et al., "Expression and assembly of a functional E1 component ($\alpha_2\beta_2$) of mammalian branched-chain $\alpha$-ketoacid dehydrogenase complex in *Escherichia coli*," *J. Biol. Chem.* 267:16601-16606 (1992).
De Biase et al., "Isolation, overexpression, and biochemical characterization of the two isoforms of glutamic acid decarboxylase from *Escherichia coli*," *Protein Expr. Purif.* 8:430-438 (1996).
De Bok et al., "Two W-containing formate dehydrogenases ($CO_2$-reductases) involving syntrophic propionate oxidation by *Syntrophobacter fumaroxidans*," *Eur. J. Biochem.* 270:2476-2485 (2003).
De La Torre et al., "Identification and functional analysis of a prokaryotic-type aspartate aminotransferase: implications for plant amino acid metabolism," *Plant. J.* 46(3):414-425 (2006).
De Smidt et al., "The alcohol dehydrogenases of *Saccharomyces cerevisiae*: a comprehensive review," *FEMS Yeast Rev.* 7:967-978 (2008).
Deana, "Substrate specificity of a dicarboxyl-CoA: dicarboxylic acid Coenzyme A transferase from rat liver mitochondria," *Biochem. Int.* 26(4):767-773 (1992).
Dellomonaco et al., "Engineered reversal of the $\beta$-oxidation cycle for the synthesis of fuels and chemicals," Nature, 476(7360):355-359 (2011).
Di Gennaro, "Styrene lower catabolic pathway in *Pseudomonas fluorescens* ST: identification and characterization of genes for phenylacetic acid degradation," Arch. Microbiol. 188(2):117-125 (2007).
Diao et al., "Crystal structure of butyrate kinase 2 from *Thermotoga maritima*, a member of the ASKHA superfamily of phosphotransferases," *J. Bacteriol.* 191:2521-2529 (2009).
Diao et al., "Crystallization of the butyrate kinase 2 from *Thermotoga maritima* mediated by vapor diffusion of acetic acid," *Acta. Crystallogr. D. Biol. Crystallogr.* 59(Pt 6):1100-1102 (2003).
Diaz et al., "Gene cloning, heterologous overexpression and optimized refolding of the NAD-glutamate dehydrogenase from *Haloferax mediterranei*," Extremophiles 10:105-115 (2006).
Diderichsen et al., "Cloning of aldB, Which Encodes $\alpha$-Acetolactate Decarboxylase, an Exoenzyme from *bacillus brevis*," *J. Bacteriol.* 172(8):4315-4321 (1990).

(56) References Cited

OTHER PUBLICATIONS

Do et al., "Engineering *Escherichia coli* for fermentative dihydrogen production: potential role of NADH-ferredoxin oxidoreductase from the hydrogenosome of anaerobic protozoa," *Appl. Biochem. Biotechnol.* 153(1-3):21-33 (2009).
Dombek and Ingram, "Ethanol production during batch fermentation with *Saccharomyces cerevisiae*: Changes in glycolytic enzymes and internal pH," *Appl. Environ. Microbiol.* 53:1286-1291 (1987).
Donnelly and Cooper, "Succinic semialdehyde dehydrogenases of *Escherichia coli*: Their role in the degradation of p-hydroxyphenylacetate and γ-aminobutyrate," *Eur. J. Biochem.* 113:555-561 (1981).
Donnelly and Cooper, "Two succinic semialdehyde dehydrogenases are induced when *Escherichia coli* K-12 is grown on γ-aminobutyrate," *J. Bacteriol.* 145:1425-1427 (1981).
Donnelly et al., "A novel fermentation pathway in an *Escherichia coli* mutant producing succinic acid, acetic acid, and ethanol," *App. Biochem. Biotech.* 70-72:187-198 (1998).
Doyle et al., "Structural Basis for a Change in substrate Specificity: Crystal Structure of S113E Isocitrate Dehydrogenase in a Complex with Isopropylmalate, Mg2+ and NAPD," *Biochemistry* 40:4234-4241 (2001).
Drake, "Acetogenesis, acetogenic bacteria, and the acetyl-CoA "Wood/Ljungdahl" pathway: past and current perspectives," in Acetogenesis, H. L. Drake, (ed.), Chapman & Hall, New York, p. 3-60 (1994).
Drevland et al., "Enzymology and Evolution of the Pyruvate Pathway to 2-Oxobutyrate in *Methanocaldococcus jannachii*," J. Bacteriol. 189(12):4391-4400 (2007).
Drewke et al., "Ethanol formation in adh) mutants reveals the existence of a novel acetaldehyde-reducing activity in *Saccharomyces cerevisiae*," J. Bacteriol. 172:3909-3917 (1990).
Drummond and Stern, "Enzymes of ketone body metabolism. II. Properties of an acetoacetate-synthesizing enzyme prepared from ox liver," *J. Biol. Chem.* 235:318-325 (1960).
Du et al., "Succinic acid production from wheat using a biorefining strategy," *Appl. Microbiol. Biotechnol.* 76:1263-1270 (2007).
Duckworth et al., "The Binding of Reduced Nicotinamide Adenine Dinucleotide to Citrate Synthase of *Escherichia coli* K12," Biochemistry 15(1):108-114 (1976).
Duncan et al., "Acetate utilization and butyryl Coenzyme A (CoA):acetate-CoA transferase in butyrate-producing bacteria from the human large intestine," *Appl. Environ. Microbiol.* 68(10):5186-5190 (2002).
Duncombe and Frerman, "Molecular and catalytic properties of the acetoacetyl-Coenzyme A thiolase of *Escherichia coli*," *Arch. Biochem. Biophys.* 176(1):159-170 (1976).
Duran et al., "Characterization of cDNA clones for the 2-methyl branched-chain enoyl-CoA reductase. An enzyme involved in branched-chain fatty acid synthesis in anerobic mitochondria of the parasitic nematode *Ascaris suum*," J. Biol. Chem. 268(30):22391-22396 (1993).
Durner et al., "Accumulation of Poly[(R)-3-Hydroxyalkanoates] *Pseudomonas oleovorans* during Growth with Octanoate in continuous culture at Different Dilution Rates," *Appl. Environ. Microbiol.* 66(8):3408-3414 (2000).
Durre and Bahl, "Microbial Production of Acetone/Butanol/Isopropanol," in Biotechnology vol. 6: "Products of Primary Metabolism", Second edition pp. 229-268, M. Roehr, ed. Published jointly by: VCH Verlagsgesellschaft mbH, Weinheim, Federal Republic of Germany and VCH Publishers Inc., New York, NY (1996).
Dürre et al., "Solventogenic enzymes of *Clostridium acetobutylicum*: catalytic properties, genetic organization, and transcriptional regulation," *FEMS Microbiol. Rev.* 17:251-262 (1995).
Dürre, "Biobutanol: an attractive biofuel," *Biotechnol. J.* 2(12):1525-1534 (2007).
Dürre, "New insights and novel developments in clostridial acetone/butanol/isopropanol fermentation," *Appl. Microbiol. Biotechnol.* 49:639-648 (1998).

Dusch et al., "Expression of the *Corynebacterium glutamicum* panD gene encoding L-aspartate-α-decarboxylase leads to pantothenate overproduction in *Escherichia coli*," *Appl. Environ. Microbiol.* 65(4)1530-1539 (1999).
Dutscho et al., "Cloning and sequencing of the genes of 2-hydoxyglutaryl-CoA dehydratase from *Acidaminococcus fermentans*," *Eur. J. Biochem.* 181(3):741-746 (1989).
Dwiarti et al., "Purification and characterization of cis-aconitic acid decarboxylase from *Aspergillus terreus* TN484-M1," *J. Biosci Bioeng.* 94(1):29-33 (2002).
Dwyer et al., "Proton Abstraction reaction, Steady-State kinetics, and Oxidation-Reduction Potential of Human Glutaryl-CoA Dehydrogenase," *Biochemistry* 39:11488-11499 (2000).
Eberhard and Gerlt, "Evolution of Function in the Crotonase Superfamily: The Stereochemical course of the Reaction catalyzed by 2-Ketocyclohexanecarboxyl-CoA Hydrolase," *J. Am. Chem. Soc.* 126:7188-7189 (2004).
Edegger et al., "Biocatalytic deuterium- and hydrogen-transfer using over-expressed ADH-'A': enhanced steroselectivity and $^2$H-labeled chiral alcohols," *Chem. Commun.* 22:2402-2404 (2006).
Eden et al., "Involvement of branched-chain amino acid aminotransferases in the production of fusel alcohols during fermentation in yeast," *Appl. Microbiol. Biotechnol.* 55:296-300 (2001).
Edwards and Palsson, "Metabolic flux balance analysis and the in silico analysis of *Escherichia coli* K-12 gene deletions," *BMC Bioinform.* 1:1 (2000).
Edwards and Palsson, "Systems properties of the *Haemophilus influenzae* Rd metabolic genotype," *J. Biol. Chem.* 274(25):17410-17416 (1999).
Edwards and Palsson, "The *Escherichia coli* MG1655 in silico Metabolic Genotype: Its Definition, Characteristics, and Capabilities," *Proc. Natl. Acad. Sci. U.S.A.* 97(10):5528-5533 (2000).
Edwards et al., "Metabolic modelling of microbes: the flux-balance approach," *Environ. Microbiol.* 4(3):133-140 (2002).
Edwards et al., "In Silico Predictions of *Escherichia coli* metabolic capabilities are Consistent with Experimental Data," *Nat. Biotechnol.* 19(2):125-130 (2001).
Efe et al., "Options for biochemical production of 4-hydroxybutyrate and its lactone as a substitute for petrochemical production," *Biotechnol. Bioeng.* 99:1392-1406 (2008).
Egland et al., "A cluster of bacterial genes for anaerobic benzene ring biodegradation,"*Proc. Natl. Acad. Sci. U.S.A.* 94:6484-6489 (1997).
Eikmanns et al., "The phosphoenolpyruvate carboxylase gene of *Corynebacterium glutamicum*: Molecular cloning, nucleotide sequence, and expression." *Mol. Gen. Genet.* 218:330-339 (1989).
Engel, "Butyryl-CoA Dehydrogenase from *Megasphaera elsdenii*," *Methods Enzymol.* 71:359-366 (1981).
Enomoto et al., "Cloning and sequencing of the gene encoding the soluble fumarate reductase from *Saccharomyces cerevisiae*," *DNA Res.* 3:263-267 (1996).
Estévez et al., "X-ray crystallographic and kinetic correlation of a clinically observed human fumarase mutation," *Protein Sci.* 11(6):1552-1557 (2002).
Evans et al., "[13C]propionate oxidatin in wild-type and citrate synthase mutant *Escherichia coli*: evidence for multiple pathways of propionate utilization," *Biochem. J.* 291(Pt 3):927-932 (1993).
Ezeji et al., "Butanol fermentation research: upstream and downstream manipulations," *Chem. Rec.* 4(5):305-314 (2004).
Faehnle et al., "A New Branch in the Family: Structure of Aspartate-β-semialdehyde Dehydrogenase from *Methanococcus jannaschii*," *J. Mol. Biol.* 353:1055-1068 (2005).
Fell and Small, "Fat Synthesis in Adipose Tissue. An Examination of Stoichiometric Constraints," *Biochem. J.* 238(3):781-786 (1986).
Fernandez-Canon and Penalva, "Characterization of a fungal maleylacetoacetate isomerase gene and indentification of its human homologue," *J. Biol. Chem.* 273:329-337 (1998).
Fernandez-Valverde et al., "Purification of *Pseudomonas putida* Acyl Coenzyme A Ligase Active with a Range of aliphatic and Aromatic substrates," *Appl. Environ. Microbiol.* 59(4):1149-1154 (1993).
Fitzgerald and Flanagan, "Characterization and sequence analysis of the human ornithine decarboxylase gene," DNA 8:(9):623-634 (1989).

(56) References Cited

OTHER PUBLICATIONS

Flint et al., "The role and properties of the iron-sulfur cluster in *Escherichia coli* dihydroxy-acid dehydratase," J. Biol. Chem. 268:14732-14742 (1993).
Fochi, "Selective catalytic dehydrogenation of 1,4-cyclohexadiene to benzene. 1. Radical anions derived from stransition-metal arene complexes as promoters," Organometallics 7:2255-2256 (1988).
Fong and Palsson, "Metabolic gene-deletion strains of *Escherichia coli* evolve to computationally predicted growth phenotypes," Nat. Genet. 36(10):1056-1058 (2004).
Fong et al., "Description and Interpretation of Adaptive Evolution of *Escherichia coli* K-12 MG1655 by Using a Genome-Scale in Silico Metabolic Model," J. Bacteriol. 185(21):6400-6408 (2003).
Fong et al., "In Silico design and adaptive evolution of *escherichia coli* for production of lactic acid," Biotechnol. Bioeng. 91(5):643-648 (2005).
Fontaine et al., "Molecular charcterization and transcriptional analysis of adhE2, the gene encoding the NADH-dependent aldehyde/ alcohol dehydrogenase responsible for butanol production in alcohologenic cultures of *Clostridium acetobutylicum* ATCC 824," J. Bacteriol. 184:821-830 (2002).
Forouhar et al., "Structural and Functional Evidence for *Bacillus subtilis* PaiA as a Novel N1-Spermidine/spermine Acetyltransferase," J. Biol. Chem. 280(48):40328-40336 (2005).
Freiberg et al., "Identification and characterization of the first class of potent bacterial acetyl-CoA carboxylase inhibitors with antibacterial activity," J. Biol. Chem. 279:26066-26073 (2004).
Freidrich et al., "The complete stereochemistry of the enzymatic dehydration of 4-hydroxybutyryl Coenzyme A to crontonyl Coenzyme A," Angew. Chem. Int. Ed. 47:3254-3257 (2008).
Frerman and Duncombe, "Studies on the subunits of *Escherichia coli* Coenzyme A transferase. Reconstitution of an active enzyme," Biochim. Biophys. Acta 580(2):289-297 (1979).
Fries et al., "Reaction Mechanism of the heterotetrameric ( 2 2) E1 Component of 2-Oxo Acid Dehydrogenase Multienzyme Complexes," Biochemistry 42:6996-7002 (2003).
Fu et al., "Crystal structures of human glutaryl-CoA dehydrogenase with and without an alternate substrate: structural bases of dehydrogenation and decarboxylation reactions," Biochemistry 43(30):9674-9684 (2004).
Fujii et al., "Characterization of L-lysine 6-aminotransferase and its structural gene from *Flavobacterium* lutescens IFO3084," J. Biochem. 128:391-397 (2000).
Fujii, T. et al. "Molecular Cloning, Sequence Analysis, and Expression of the Yeast Alcohol Acetyltransferase Gene," Appl. Environ. Microbiol. 60:2786-2792 (1994).
Fujishiro et al., "Crystallization and Some Properties of Acetylpolyamine Amidohydrolase From *Mycoplana* Bullata," Biochem. Biophys. Res. Commun. 157(3):1169-1174 (1988).
Fujita et al., "Novel Substrate Specificity of Designer 3-Isopropylmalate Dehydrogenase Derived from *Thermus thermophilus* HB8," Biosci. Biotechnol. Biochem. 65(12):2695-2700 (2001).
Fukao et al., "Succinyl-CoA:3-ketoacid CoA transferase (SCOT): cloning of the human SCOT gene, tertiary structural modeling of the human SCOT monomer, and characterization of three pathogenic mutations," Genomics 68:144-151 (2000).
Fukuda and Wakagi, "Substrate recognition by 2-oxoacid:ferredoxin oxidoreductase from *Sulfolobus* sp. Strain 7," Biochim. Biophys. Acta 1597:74-80 (2002).
Fukuda et al., "Role of a highly conserved YPITP motif in 2-oxoacid:ferredoxin oxidoreductase Heterologous expression of the gene from *Sulfolobus* sp. Strain 7, and characterization of the recombinant and variant enzymes," Eur. J. Biochem. 268:5639-5646 (2001).
Fukui et al., "Engineering of *Ralstonia eutropha* for production of poly(3-hydroxybutyrate-co-3-hydroxyhexanoate) from fructose and solid-state properties of the copolymer," Biomacromolecules 3(3):618-624 (2002).

Fuller and Leadlay, "Proton transfer in methylmalonyl-CoA epimerase from *Propionibacterium* shermanii. The reaction of (2R)-methylmalonyl-CoA in tritiated water," Biochem. J. 213(3):643-650 (1983).
Furdui and Ragsdale, "The role of pyruvate ferredoxin oxidoreductase in pyruvate synthesis during autotrophic growth by the Wood-Ljungdahl pathway," J. Biol. Chem. 275(37):28494-28499 (2000).
Furukawa et al., "Increased alcohol acetyltransferase activity by inositol limitation in *Saccharomyces cerevisiae* in sake mash," J. Biosci. Bioeng. 96(4):380-386 (2003).
Gangloff et al., "Molecular cloning of the Yeast Mitochondrial Aconitase Gene (ACO1) and Evidence of a Synergistic Regulation of Expression by Glucose plus Glutamate," Mol. Cell. Biol. 10(7):3551-3561 (1990).
Garras et al., "Subcellular localisation and induction of NADH-sensitive acetyl-CoA hydrolase and propionyl-CoA hydrolase activities in rat liver under lipogenic conditions after treatment with sulfur-substituted fatty acids," Biochim. Biophys Acta 1255(2):154-160 (1995).
Garvie, "Bacterial lactate dehydrogenases," Microbiol. Rev. 44:106-139 (1980).
Genda et al., "Purification and characterization of fumarase from *Corynebacterium glutamicum*," Biosci. Biotechnol. Biochem. 70:1102-1109 (2006).
Gerhardt et al. "Fermentation of 4-aminobutyrate by *Clostridium aminobutyricum*: cloning of two genes involved in the formation dehydration of 4-hydroxybutyrl-CoA," Arch. Microbiol. 174:189-199 (2000).
Gescher et al., "Genes coding for a new pathway of aerobic benzoate metabolism in *Azoarcus evansii*," J Bacteriol. 184(22):6301-6315 (2002).
Gibson and McAlister-Henn, "Physical and genetic interactions of cytosolic malate dehydrogenase with other gluconeogenic enzymes," J. Biol. Chem. 278:25628-25636 (2003).
Giesel and Simon, "On the occurrence of enoate reductase and 2-oxo-carboxylate reductase in clostridia and some observations on the amino acid fermentation by *Peptostreptococcus anaerobius*," Arch. Microbiol. 135(1):51-57 (1983).
Gillyon et al., "Putrescine Breakdown in the Yeast *Candida boidinii*: Subcellular Location of Some of the Enzymes Involved and Properties of Two Acetamidoaldehyde Dehydrogenases," J. of Gen. Microbiol. 133:2477-2485 (1987).
Glasemacher et al., "Purification and properties of acetyl-CoA synthetase (ADP-forming), an archael enzyme of acetate formation and ATP synthesis, from the hyperthermophile *Pyrococcus furiosus*," Eur. J. Biochem. 244:561-567 (1997).
Göbel et al., "Degradation of Aromatics and Chloroaromatics by *Pseudomonas* sp. Strain B13: Cloning, Characterization, and analysis of Sequences Encoding 3-Oxoadipate:Succinyl-Coenzyme A (CoA) Transferase and 3-oxoaipyl-CoA Thiolase," J. Bacteriol. 184(1):216-223 (2002).
Goda et al., "Cloning, sequencing, and expression in *Escherichia coli* of the *Clostridium* tetanomorphum gene encoding β-methylaspartase and characterization of the recombinant protein," Biochemistry 31(44):10747-10756 (1992).
Gokarn et al., "Expression of pyruvate carboxylase enhances succinate production in *Escherichia coli* without affecting glucose uptake," Biotechnol. Lett. 20:795-798 (1998).
Gokarn et al., "Metabolic Analysis of *Escherichia coli* in the Presence and Absence of the Carboxylating Enzymes Phosphoenolpyruvate Carboxylase and Pyruvate Carboxylase," Appl. Environ. Microbiol. 66:1844-1850 (2000).
Gokarn, et al., "The physiological effects and metabolic alterations caused by the expression of *Rhizobium* etli pyruvate carboxylase in *Escherichia coli*," Appl. Microbiol. Biotechnol. 56(1-2):188-195 (2001).
Gokulan et al., "Crystal structure of *Mycobacterium tuberculosis* diaminipimelate decarboxylase, an essential enzyme in bacterial lysine biosynthesis," J. Biol. Chem. 278(20):18588-18596 (2003).
Goldberg et al., "Improved Conversion of Fumarate to Succinate by *Escherichia coli* Strains Amplified for Fumarate Reductase," Appl. Environ. Microbiol. 45:1838-1847 (1983).

(56) References Cited

OTHER PUBLICATIONS

Gong et al., "Specificity Determinants for the Pyruvate Dehydrogenase Component Reaction Mapped with Mutated and Prosthetic Group Modified Lipoyl Domains," *J. Biol. Chem.* 275(18):13645-13653 (2000).

Gonzalez et al., "Characterization of a (2R,3R)-2,3-Butanediol Dehydrogenase as the *Saccharomyces cerevisiae* YAL060W Gene Product," *J. Biol. Chem.* 275(46):35876-35885 (2000).

Gonzalez-Pajuelo et al., "Metabolic engineering of *Clostridium acetobutylicum* for the industrial production of 1,3-propanediol from glycerol," *Met. Eng.* 7:329-336 (2005).

Gordon and Doelle, "Purification, properties and immunological relationship of L(+)-lactate dehydrogenase from *Lactobacillus casei*," *Eur. J. Biochem.* 67:543-555 (1976).

Goupil et al., "Imbalance of Leucine Flux in *Lactococcus lactis* and Its Use for the Isolation of Diacetyl-Overproducing Strains," *Appl. Environ. Microbiol.* 62(7):2636-2640 (1996).

Goupil-Feuillerat et al., "Transcriptional and Translational Regulation of α-Acetolactate Decarboxylase of *Lactococcus lactis* subsp. *Lactis*," *J. Bacteriol.* 182(19):5399-5408 (2000).

Grant and Patel. "The non-oxidative decarboxylation of p-hydroxybenzoic acid, gentisic acid, protocatechuic acid and gallic acid by *Klebsiella* aerogenes (*Aerobacter aerogenes*)," Antonie Van Leeuwenhoek 35:325-343 (1969).

Green et al., "Catabolism of -ketoglutarate by a sucA mutant of *Bradyrhizobium japonicum*: evidence for an alternative tricarboxylic acid cycle," J. Bacteriol. 182:2838-2844 (2000).

Guest et al., "The fumarase genes of *Escherichia coli*: location of the fumB gene and discovery of a new gene (fumC)," *J. Gen. Microbiol.* 131(11):2971-2984 (1985).

Guettler et al., "*Actinobacillus succinogenes* sp. nov., a novel succinic-acid-producing strain from the bovine rumen," *Int. J. Syst. Bacteriol.* 49:207-216 (1999).

Guirard and Snell, "Purification and properties of ornithine decarboxylase from *Lactobacillus* sp. 30a," *J. Biol. Chem.* 255:5960-5964 (1980).

Guterman et al., "Generation of phenylpropanoid pathway-derived volatiles in transgenic plants: rose alcohol acetyltransferase produces phenylethyl acetate and benzyl acetate in petunia flowers," *Plant Mol. Biol.* 60(4):555-563 (2006).

Gutierrez et al., "A mutant D-amino acid aminotransferase with broad substrate specificity: construction by replacement of the interdoman loop Pro119-Arg120-Pro121 by Gly-Gly-Gly," *Protein Eng.* 11:53-58 (1998).

Hadfield et al., "Active Site Analysis of the Potential Antimicrobial Target Aspartate Semialdehyde Dehydrogenase," *Biochemistry* 40:14475-14483 (2001).

Hadfield et al., "Structure of Aspartate-β-semialdehyde Dehydrogenase from *Escherichia coli*, a Key Enzyme in the Aspartate Family of Amino Acid Biosynthesis," *J. Mol. Biol.* 289:991-1002 (1999).

Hagemeier et al., "Insight into the mechanism of biological methanol activation based on the crystal structure of the methanol-cobalamin methyltransferase complex," *Proc. Natl. Acad. Sci. U.S.A.* 103(50):18917-18922 (2006).

Hahm et al., "Characterization and evaluation of a pta (phosphotransacetylase) negative mutant of *Escherichia coli* HB101 as a production host of foreign lipase," *Appl. Microbiol. Biotechnol.* 42:100-107 (1994).

Haller et al., "Discovering new enzymes and metabolic pathways: conversion of succinate to propionate by *Escherichia coli*," *Biochem.* 39(16):4622-4629 (2000).

Hamilton-Kemp et al., "Production of the long-chain alcohols octanol, decanol, and dodecanol by *Escherichia coli*," *Curr. Microbiol.* 51:82-86 (2005).

Hammer and Bode, "Purification and characterization of an inducible L-lysine:2-oxoglutarate 6-aminotransferase from *Candida utilis*," *J. Basic Microbiol.* 32:21-27 (1992).

Hanai et al., "Engineered synthetic pathway for isopropanol production in *Escherichia coli*," *Appl. Environ. Microbiol.* 73(24):7814-7818 (2007).

Harder, "Anaerobic degradation of cyclohexane-1,2-diol by a new *Azoarcus* species," Arch. Microbiol. 168:199-204 (1997).

Harms and Thauer, "Methylcobalamin: Coenzyme M methyltransferase isoenzymes MtaA and MtbA from *Methanosarcina barkeri*. Cloning, sequencing and differential transcription of the encoding genes, and functional overexpression of the mtaA gene in *Escherichia coli*," *Eur. J. Biochem.* 235(3):653-659 (1996).

Harrison and Harwood, "The pimFABCDE operon from *Rhodopseudomonas palustris* mediates dicarboxylic acid degradation and participates in anaerobic benzoate degradation," *Microbiology* 151:727-736 (2005).

Hartel et al., "Purification of glutaryl-CoA dehydrogenase from *Pseudomonas* sp., an enzyme involved in the anaerobic degradation of benzoate," *Arch. Mirobiol.* 159:174-181 (1993).

Harwood et al., "Anaerobic metabolism of aromatic compounds via the benzoyl-CoA pathway," FEMS Microbiol. Rev. 22:439-458 (1999).

Hasegawa et al., "Transcriptional regulation of ketone body-utilizing enzyme, acetoacetyl-CoA synthetase, by C/EBPα during adipocyte differentiation," *Biochim. Biophys. Acta.* 1779(6-7):414-419 (2008).

Haselbeck and McAlister-Henn, "Isolation, nucleotide sequence, and disruption of the *Saccharomyces cerevisiae* gene encoding mitochondrial NADP(H)-specific isocitrate dehydrogenase," *J. Biol. Chem.* 266(4):2339-2345 (1991).

Hashidoko et al., "Cloning of a DNA fragment carrying the 4-hydroxycinnamate decarboxylase (pofK) gene from *Klebsielss oxytoca* and its constitutive expression in *Escherichia coli* JM109 cells," *Biosci. Biotech. Biochem.* 58(1):217-218 (1994).

Hashimoto et al., "Activation of L-Lysine ε-Dehydrogenase from *Agrobacterium tumefaciens* by Several Amino Acids and Monocarboxylates," *J. Biochem.* 106:76-80 (1989).

Hasson et al., "The crystal structure of benzoylformate decarboxylase at 1.6 Å resolution: diversity of catalytic residues in thiamin diphosphate-dependent enzymes," *Biochemistry* 37:9918-9930 (1998).

Hatakeyama et al., "Analysis of oxidation sensitivity of maleate cis-trans isomerase from *Serratia marcescens*," *Biosci. Biotechnol. Biochem.* 64:1477-1485 (2000).

Hatakeyama et al., "Gene Cloning and Characterization of Maleate cis-trans Isomerase from *Alcaligenes faecalis*," *Biochem. Biophys. Res. Comm.* 239:74-79 (1997).

Hawes et al., "Primary structure and tissue-specific expression of human β-hydroxyisobutyryl-Coenzyme A hydrolase," *J. Biol. Chem.* 271:26430-26434 (1996).

Hawes et al., "Mammalian 3-hydroxyisobutyrate dehydrogenase," *Methods Enzymol.* 324:218-228 (2000).

Hayashi et al., "Properties of 2-hydroxyglutarate dehydrogenase from *Fusobacterium*," *J. Nihon. Univ. Sch. Dent.* 28(1):12-21 (1986).

Hayden et al., "Glutamate dehydrogenase of *Halobacterium salinarum*: evidence that the gene sequence currently assigned to the NADP+-dependent enzyme is in fact that of the NAD+-dependent glutamate dehydrogenase," FEMS Microbiol. Lett. 211:37-41 (2002).

Haywood et al., "Characterization of two 3-ketothiolases possessing differing substrate specificities in the polyhydroxyalkanoate synthesizing organism *Alcaligenes eutrophus*," *FEMS Microbiol. Lett.* 52:91-96 (1988).

He and Wiegel. "Purification and characterization of an oxygen-sensitive reversible 4-hydroxybenzoate decarboxylase from *Clostridium hydroxybenzoicum*," *Eur. J Biochem.* 229:77-82 (1995).

Heidlas and Tressl, "Purification and Properties of two oxidoreductases catalyzing the enantioselective reduction of diacetyl and other diketones from baker's yeast," *Eur. J. Biochem.* 188:165-174 (1990).

Heipieper and Isken, "Ethanol tolerance and membrane fatty acid adaptation in adh multiple and null mutants of *Kluyveromyces lactis*," *Res. Microbiol.* 151:(9):777-784 (2000).

(56) References Cited

OTHER PUBLICATIONS

Heller et al., "Cloning and expression of the gene for the vitamin $B_{12}$ receptor protein in the outer membrane of *Escherichia coli*," *J. Bacteriol.* 161:896-903 (1985).
Hemschemeier et al., "Biochemical and physiological characterization of the pyruvate formate-lyase Pfl1 of *Chlamydomonas reinhardtii*, a typically bacterial enzyme in eukaryotic alga," *Eukaryot. Cell* 7:518-526 (2008).
Henne et al., "Construction of environmental DNA libraries in *Escherichia coli* and screening for the presence of genes conferring utilization of 4-hydroxybutyrate," *Appl. Environ. Microbiol.* 65(9):3901-3907 (1999).
Hennessy et al., "The reactivity of gamma-hydroxybutyric acid (GHB) and gamma-butyrolactone (GBL) in alcoholic solutions," *J. Forensic. Sci.* 49(6):1220-1229 (2004). (provided electronically by publisher as pp. 1-10).
Henning et al., "Identification of novel benzoylformate decarboxylases by growth selection," *Appl. Environ. Microbiol.* 72:7510-7517 (2006).
Herrmann et al., "Two β-alanyl-CoA:ammonia lyases in *Clostridium propionicum*," *FEBS J.* 272:813-821 (2005).
Hespell et al., "Stabilization of pet Operon Plasmids and Ethanol Production in *Escherichia coli* Strains Lacking Lactate Dehydrogenase and Pyruvate Formate-Lyase Activities," *Appl. Environ. Microbiol.* 62:4594-4597 (Dec. 1996).
Hesslinger et al., "Novel keto acid formate-lyase and propionate kinase enzymes are components of an anaerobic pathway in *Escherichia coli* that degrades L-threonine to propionate," *Mol. Microbiol.* 27(2):477-492 (1998).
Hester et al., "Purification of active $E1\alpha_2\beta_2$ of *Pseudomonas putida* branched-chain-oxoacid dehydrogenase," *Eur. J. Biochem.* 233:828-836 (1995).
Hetzel et al., "Acryloyl-CoA reductase from *clostridium propionicum*. An enzyme complex of pripionyl-CoA dehydrogenase and electron-transferring flavoprotein," *Eur. J. Biochem.* 270:902-910 (2003).
Heydari et al., "Highly Stable L-Lysine 6-Dehydrogenase from the thermophile *Geobacillus stearothermophilus* Isolated from a Japanese Hot Spring: characterization, Gene Cloning and sequencing, and Expression," Appl. Environ. Microbiol. 70(2):937-942 (2004).
Highbarger et al., "Mechanism of the reaction catalyzed by acetoacetate decarboxylase. Importance of lysine 116 in determining the pKa of active-site lysine 115," Biochemistry 35(1):41-46 (1996).
Hillmer and Gottschalk, "Particulate Nature of Enzymes Involved in the Fermentation of Ethanol and Acetate by *Clostridium Kluyveri*," *FEBS Lett.* 21(3):351-354 (1972).
Hillmer and Gottschalk, "Solubilization and partial characterization of particulate dehydrogenases from *Clostridium kluyveri*," *Biochim. Biophys. Acta.* 334:12-23 (1974).
Hirano et al., "Purification and characerization of the Alcohol Dehydrogenase with a Broad Substrate Specificy Originated from 2-Phenylethanol-Assimilating *Brevibacterium* sp. KU 1309," J. Biosci. Bioeng. 100(3): 318-322 (2005).
Hiser et al., "ERG10 from *Saccharomyces cerevisiae* encodes acetoacetyl-CoA thiolase," *J. Biol. Chem.* 269:31383-31389 (1994).
Ho et al., "Regulation of serine biosynthesis in *Arabidopsis*. Crucial role of plastidic 3-phosphoglycerate dehydrogenase in non-photosynthetic tissues," *J. Biol. Chem.* 274:397-402 (1999).
Hoffmann and Dimroth, "Sterochemistry of the methylmalonyl-CoA decarboxylation reaction," FEBS Lett. 220:121-125 (1987).
Hoffmeister et al., "Mitochondrial trans-2-enoyl-CoA reductase of wax ester fermentation from *Euglena gracilis* defines a new family of enzymes involved in lipid synthesis," *J. Biol. Chem.* 280(6):4329-4338 (2005).
Hofmeister and Buckel, "(R)-lactyl-CoA dehydratase from *Clostridium propionicum*. Stereochemistry of the dehydration of (R)-2-hydroxybutyryl-CoA to crotonly-CoA," *Eur. J. Biochem.* 206(2):547-552 (1992).
Hofmeister et al., "Cloning and expression of the two genes coding for L-serine dehydratase from *Peptostreptococcus asaccharolyticus*: relationship of the iron-sulfur protein to both L-serine dehydratases from *Escherichia coli*," *J. Bacteriol.* 179(15):4937-4941 (1997).
Hogan et al., "Improved Specificity toward Substrates with Positively Charged Side chains by Site-Directed Mutagenesis of the L-Lactate Dehydrogenase of *Bacillus stearothermophilus*," *Biochemistry* 34:4225-4230 (1995).
Holloway and Marsh, "Adenosylcobalamin-dependent glutamate mutase from *Clostridium* tetanomorphum. Overexpression in *Escherichia coli*, purification, and characterization of the recombinant enzyme," *J. Biol. Chem.* 269(32):20425-20430 (1994).
Holms, "The central metabolic pathways in *Escherichia coli*: relationship between flux and control at a branch point, efficiency of conversion to biomass, and excretion of acetate," *Curr. Top Cell. Regul.* 28:69-105 (1986).
Hong and Lee, "Metabolic flux analysis for succinic acid production by recombinant *Escherichia coli* with amplified malic enzyme activity," *Biotechnol. Bioeng.* 74(2):89-95 (2001).
Hong and Lee, "Enhanced Production of Succinic Acid by Metabolically Engineered *Escherichia coli* with Amplified Activities of Malic Enzyme and Fumarase," Biotechnol. Bioprocess. Eng. 9:4:252-255 (2004).
Hong et al., "Importance of redox balance on the production of succinic acid by metabolically engineered *Escherichia coli*," *Appl. Microbiol. Biotechnol.* 58:286-290 (2002).
Horswill and Escalante-Semerena, "In vitro conversion of propionate to pyruvate by *Salmonella enterica* enzymes: 2-methylcitrate dehydratase (PrpD) and aconitas Enzymes catalyze the conversion of 2-methylcitrate to 2-methylisocitrate," *Biochemistry* 40(15):4703-4713 (2001).
Horton et al., "Heterologous expression of the *Saccharomyces cerevisiae* alcohol acetyltransferase genes in *Clostridium acetobutylicum* and *Escherichia coli* for the production of isoamyl acetate," *J. Ind. Microbiol. Biotechnol.* 30(7):427-432 (2003).
Hsu et al., "Expression of an aromatic-dependent decarboxylase which provides growth-essential $CO_2$ equivalents for the acetogenic (Wood) pathway of *Clostridium* thermoaceticum," *J. Bacteriol.* 172:5901-5907 (1990).
Hu et al., "The catalytic intermediate stabilized by a "down" active site loop for diaminopimelate decarboxylase from *Helicobacter pylori*. Enzymatic characterization with crystal structure analysis," *J. Biol. Chem.* 283(30):21284-21293 (2008).
Huang et al., "Genetic characterization of the resorcinol catabolic pathway in *Corynebacterium glutamicum*," *Appl. Environ. Microbiol.* 72:7238-7245 (2006).
Huang et al., "Purification and characterization of a ferulic acid decarboxylase from *Pseudomonas fluorescens*," *J. Bacteriol.* 176:5912-5918 (1994).
Huang et al., "Identification and characterization of a second butyrate kinase from *Clostridium acetobutylicum* ATCC 824," *J. Mol. Microbiol. Biotechnol.* 2(1):33-38 (2000).
Hübner et al., "The mechanism of substrate activation of pyruvate decarboxylase: A first approach," *Eur. J. Biochem.* 92:175-181 (1978).
Huder and Dimroth, "Sequence of the sodium ion pump methylmalonyl-CoA decarboxylase from *Veillonella parvula*," *J. Biol. Chem.* 268:24564-24571 (1993).
Hughes et al.,"Evidence for isofunctional enzymes in the degradation of phenol, m- and p-toluate, and p-cresol via catechol meta-cleavage pathways in *Alcaligenes eutrophus*," *J. Bacteriol.* 158(1):79-83 (1984).
Hugler et al., "Malonyl-Coenzyme A Reductase from *Chloroflexus aurantiacus*, a Key Enzyme of the 3-Hydroxypropionate Cycle for Autotrophic CO2 Fixation," *J. Bacteriol.* 184(9):2404-2410 (2002).
Husain and Steenkamp, "Partial purification and characterization of glutaryl-Coenzyme A dehydrogenase, electron transfer flavoprotein, and electron transfer flavoprotein-Q oxidoreductase from *Paracoccus denitrificans*," *J. Bacteriol.* 163:709-715 (1985).
Hustede et al., "Cloning of poly(3-hydroxybutyric acid) synthase genes of *Rhodobacter* sphaeroides and *Rhodospirillum* rubum and heterologous expression in *Alcaligenes* eutrophys," *FEMS Microbiol. Lett.* 93:285-290 (1992).

(56) References Cited

OTHER PUBLICATIONS

Ibarra et al., "*Escherichia coli* K-12 undergoes adaptive evolution to achieve in silico predicted optimal growth," *Nature* 420(6912):186-189 (2002).

Ikai and Yamamoto, "Identification and analysis of a gene encoding L-2,4-diaminobutyrate:2-ketoglutarate 4-aminotransferase involved in the 1,3-diaminopropane production pathway in *Acinetobacter baummanni*," *J. Bacteriol.* 179:5118-5125 (1997).

Ingoldsby et al., "The discovery of four distinct glutamate dehydrogenase genes in a strain of *Halobacterium salinarum*," *Gene* 349:237-244 (2005).

Inui et al., "Occurrence of Oxygen-Sensitive, $NADP^+$-Dependent Pyruvate-Dehydrogenase in Mitochondria of *Euglena-Gracilis*," *J. Biochem.* 96:931-934 (1984).

Inui et al., "Pyruvate-$NADP^+$ Oxidoreductase from *Euglena-Gracilis*—the Kinetic-Properties of the Enzyme," *Arch. Biochem Bipophys.* 274:434-442 (1989).

Inui et al., "Wax Ester Fermentation in *euglena-Gracilis*," *FEBS Lett.* 150:89-93 (1982).

Inui et al., "Fatty acid synthesis in mitochondria of *Euglena gracilis*," *Euro. J. Biochem.* 142(1):121-126 (1984).

Inui et al., "Production and Composition of Wax Esters by Fermentation of *Euglena gracilis*," *Agr. Biol. Chem.* 47(11):2669-2671 (1983).

Inui et al., "Purification and characterization of pyruvate:$NADP^+$ oxidoreductase in *Euglena gracilis*," *J. Biol. Chem.* 262(19):9130-9135 (1987).

Inui et al., "Pyruvate:$NADP^+$ oxidoreductase from *Euglena gracilis*: mechanism of $O_2$-inactivation of the enzyme and its stability in the aerobe," *Arch. Biochem. Biophys.* 280:292-298 (1990).

Inui et al., "The physiological role of oxygen-sensitive pyruvate dehydrogenase in mitochondrial fatty acid synthesis in *Euglena gracilis*," *Arch. Biochem. Biophys.* 237(2):423-429 (1985).

Ishida et al., "Efficient production of L-Lactic acid by metabolically engineered *Saccharomyces cerevisiae* with a genome-integrated L-lactate dehydrogenase gene," *Appl. Envirom. Microbiol.* 71:1964-1970 (2005).

Ishige et al, "Long-chain aldehyde dehydrogenase that participates in n-alkane utilization and wax ester synthesis in *Acinetobacter* sp. strain M-1," *Appl. Environ. Microbiol.* 66:3481-3486 (2000).

Ishige et al., "Wax ester production from n-alkanes by *Acinetobacter* sp. strain M-1: ultrastructure of cellular inclusions and role of acyl Coenzyme A reductase," *Appl. Environ. Microbiol.* 68(3):1192-1195 (2002).

Ismaiel et al., "Purification and Characterization of a Primary-Secondary Alcohol Dehydrogenase from Two Strains of *Clostridium beijerinckii*," *J. Bacteriol.* 175(16):5097-5105 (1993).

Ismail et al., "Functional genomics by NMR spectroscopy. Phenylacetate catabolism in *Escherichia coli*," *Eur. J. Biochem.* 270(14):3047-3054 (2003).

Ismail et al., "Functional genomics by NMR spectroscopy. Phenylacetate catabolism in *Escherichia coli*," *Eur. J. Biochem.* 270(14):3047-3054 (2005).

Ito et al., "D-3-hydroxybutyrate dehydrogenase from *Pseudomonas fragi*: molecular cloning of the enzyme gene and crystal structure of the enzyme," *J. Mol. Biol.* 355(4):722-733 (2006).

Iverson et al., "Structure of the *Escherichia coli* fumarate reductase respiratory complex," *Science* 284(5422):1961-1966 (1999).

Izumi et al., "Structure and Mechanism of HpcG, a Hydratase in the Homoprotocatechuate Degradation Pathway of *Escherichia coli*," *J. Mol. Biol.* 370:899-911 (2007).

Jacques et al., "Characterization of yeast homoserine dehydrogenase, an antifungal target: the invariant histidine 309 is important for enzyme integrity," *Biochem. Biophys. Acta* 1544:28-41 (2001).

Jäger and Färber, "Die Alanatreduktion von β-Carbonyl-oxalylsäure-estern," *Chem. Ber.* 92:2492-2499 (1959).

James and Cronan, "Expression of two *Escherichia coli* acetyl-CoA carboxylase subunits is autoregulated," *J. Biol. Chem.* 279:2520-2527 (2004).

James and Viola, "Production and characterization of bifunctional enzymes. Domain swapping to produce new bifunctional enzymes in the aspartate pathway," *Biochemistry* 41(11) 3720-3725 (2002).

Jansen and Wanders, "L-2-hydroxyglutarate dehydrogenase: identification of a novel enzyme activity in rat and human liver. Implications for L-2-hydroxyglutaric academia," *Biochim. Biophys. Acta* 1225(1):53-56 (1993).

Janssen, "Propanol as an end product of theonine fermentation," *Arch. Microbiol.* 182:482-486 (2004).

Jantama et al., "Combining metabolic engineering and metabolic evolution to develop nonrecombinant strains of *Escherichia coli* C that produce succinate and malate," *Biotechnol. Bioeng.* 99(5):1140-1153 (2008).

Jantama et al., "Eliminating Side Products and Increasing succinate Yields in Engineered Strains of *Escherichia coli* C," *Biotechnol. Bioeng.* 101(5) 881-893 (2008).

Jeng et al., "Ornithine degradation in *Clostridium sticklandii*; pyridoxial phosphate and Coenzyme A dependent thiolytic cleavage of 2-amino-4-ketopentanoate to alanine and acetyl Coenzyme A," *Biochemistry* 13(14):2898-2903 (1974).

Jenkins and Nunn, "Genetic and molecular characterization of the genes involved in short-chain fatty acid degradation in *Escherichia coli*: the ato system," *J. Bacteriol.* 169(1):42-52 (1987).

Jeon et al., "Heterologous expression of the alcohol dehydrogenase (adhI) gene from *Geobacillius thermoglucosidasius* strain M10EXG," *J. Biotechnol.* 135:127-133 (2008).

Jewell et al., "Bioconversion of propionic, valeric and 4-hydroxybutyric acids into the corresponding alcohols by *Clostridium acetobutylicum* NRRL 527," *Curr. Microbiol.* 13(4):215-219 (1986).

Jin and Sonenshein, "Characterization of the major citrate synthase of *Bacillus subtilis*," *J. Bacteriol.* 178(12):3658-3660 (1996).

Johanson et al., "Strain engineering for steroselective bioreduction of dicarbonyl compounds by yeast reductases," *FEMS Yeast Res.* 5:513-525 (2005).

Johnson et al., "Alteration of a single amino acid changes the substrate specificity of dihydroflavonol 4-reductase," *Plant J.* 25(3):325-333 (2001).

Jojima et al., "Production of isopropanol by metabolically engineered *Escherichia coli*," *Appl. Microbiol. Biotechnol.* 77:1219-1224 (2008).

Jones and Woods, "Acetone-butanol fermentation revisited," *Microbiol. Rev.* 50(4):484-524 (1986).

Junker and Ramos, "Involvement of the cis/trans isomerase Cti in solvent resistance of *Pseudomonas putida* DOT-T1E," *J. Bacteriol.* 181:5693-5700 (1999).

Kaclikova et al., "Fumaric acid overproduction in yeast mutants deficient in fumarase," *FEMS Microbiol. Lett.* 91(2):101-106 (1992).

Kai et al., "Phosphoenolpyruvate carboxylase: three-dimensional structure and molecular mechanisms," *Arch. Biochem. Biophys.* 414:170-179 (2003).

Kakimoto et al., "β-aminoisobutyrate-α-ketoglutarate transaminase in relation to α-aminoisobutyric aciduria," *Biochim. Biophys. Acta* 156(2):374-380 (1968).

Kalousek et al., "Isolation and characterization of propionyl-CoA carboxylase from normal human liver. Evidence for a protomeric tetramer of nonidentical subunits," *J. Biol. Chem.* 255:60-65 (1980).

Kalpos, "On the mammalian acetone metabolism: from chemistry to clinical implications," *Biochim. Biophys. Acta* 1621(2):122-139 (2003).

Kalscheuer and Steinbuchel, "A novel bifunctional wax ester synthase/acyl-CoA:diacylglycerol acyltransferase mediates wax ester and triacylglycerol biosynthesis in *Acinetobacter calcoaceticus* ADP1," *J. Biol. Chem.* 278(10):8075-8082 (2003).

Kalscheuer et al., "Analysis of storage lipid accumulation in *Alcanivorax borkumensis*: Evidence for alternative triacylglycerol biosynthesis routes in bacteria," *J. Bacteriol.* 189(3):918-928 (2007).

Kanamasa et al., "Cloning and functional characterization of the cis-aconitic acid decarboxylase (CAD) gene from *Aspergillus terreus*," *Appl. Microbiol. Biotechnol.* 80(2):223-229 (2008).

(56) References Cited

OTHER PUBLICATIONS

Kanao et al., "Characterization of isocitrate dehydrogenase from the green sulfur bacterium Chlorbium *limicola*. A carbon dioxide-fixing enzyme in the reductive tricarboxylic acid cycle," *Eur. J. Biochem.* 269(7):1926-1931 (2002).

Kasberg et al., "Cloning, characterization, and sequence analysis of the cIcE gene encoding the maleylacetate reductase of Pseufomonas sp. Strain B13," *J. Bacteriol.* 179:3801-3803 (1997).

Kaschabek and Reineke, "Degradation of chloroaromatics: purification and characterization of maleylacetate reductase from *Pseudomonas* sp. Strain B13," *J. Bacteriol.* 175:6075-6081 (1993).

Kaschabek and Reineke, "Maleylacetate reductase of Pseufomonas sp. Strain B13: specificity of substrate conversion and halide elimination," *J. Bacteriol.* 177:320-325 (1995).

Kaschabek et al., "Degradation of aromatics and chloroaromatics by *Pseudomonas* sp. strain B13: purification and characterization of 3-oxoadipate:succinyl-Coenzyme A (CoA) transferase and 3-oxoadipyl-CoA thiolase," *J. Bacteriol.* 184(1):207-215 (2002).

Kato and Asano, "3-Methylaspartate ammonia-lyase as a marker enzyme of the mesaconate pathway for (S)-glutamate fermentation in Enterobacteriaceae," *Arch. Microbiol.* 168(6):457-463 (1997).

Kazahaya et al, "Aerobic Dissimilation of Glucose by Heterolactic Bacteria III. Aldehyde dehydrogenase and alcohol dehydrogenase of luconostoc mesenteroids" *J. Gen. Appl. Microbiol.* 18(1):43-55 (1972).

Kenealy et al., "Biochemical Aspects of Fumaric Acid Accumulation by *Rhizopus arrhizus*," Appl. Environ. Microbiol. 52:128-133 (1986).

Kern et al., "Isoamyl alcohol-induced morphological change in *Saccharomyces cerevisiae* involves increases in mitochondria and cell wall chitin content," FEMS Yeast Res. 5:43-49 (2004).

Kessler et al., "Pyruvate-formate-lyase-deactivase and acetyl-CoA reductase activities of *Escherichia coli* reside on a polymeric protein particle encoded by adhE," *FEBS Lett.* 281(1-2):59-63 (1991).

Khan et al., "Molecular Properties and Enhancement of Thermostability by Random Mutagenesis of Glutamate Dehydrogenase from *Bacillus subtilis*," *Biosci. Biotechnol. Biochem.* 69(10):1861-1870 (2005).

Killenberg-Jabs et al., "Active oligomeric states of pyruvate decarboxylase and their functional characterization," *Eur. J. Biochem.* 268:1698-1704 (2001).

Kim et al, "Effect of Overexpression of *Actinobacillus succinogenes* Phosphoenolpyruvate Carboxykinase on Succinate Production in *Escherichia coli*," *Appl. Env. Microbiol.* 70(2) 1238-1241 (2004).

Kim et al., "2-Hydroxyisocaproyl-CoA dehydratase and its activator from *Clostridium difficile*," *FEBS J.* 272:550-561 (2005).

Kim et al., "Dehydration of (R)-2-hydroxyacyl-CoA to enoyl-CoA in the fermentation of a-amino acids by anaerobic bacteria," *FEMS Microbiol. Rev.* 28:455-468 (2004).

Kim et al., "Dihydrolipoamide dehydrogenase mutation alters the NADH sensitivity of pyruvate dehydrogenase complex of *Escherichia coli* K-12," J. Bacteriol. 190:3851-3858 (2008).

Kim, "Purification and Properties of a diamine α-Ketoglutarate Transminase from *Escherichia coli*," *J. Biol. Chem.* 239(3):783-786 (1964).

Kino et al. Synthesis of DL-tryptophan by modified broad specificity amino acid racemase from *Pseudomonas putida* IFO 12996, *Appl. Microbiol. Biotechnol.* 73:1299-1305 (2007).

Kinoshita, "Purification of two alcohol dehydrogenases from *Zymomonas mobilis* and their properties," Appl. Microbiol. Biotechnol. 22:249-254 (1985).

Klatt et al., "Comparative genomics provides evidence for the 3-hydroxypropionate autotrophic pathway in filamentous anoxygenic phototrophic bacteria and in hot spring microbial mats," Environ. Microbiol. 9:2067-2078 (2007).

Klyosov, "Kinetics and specificity of human liver aldehyde dehydrogenases toward aliphatic, aromatic, and fused polycyclic aldehydes," *Biochemistry* 35(14):4457-4467 (1996).

Knapp et al., "Crystal Structure of the Truncated Cubic Core component of the *Escherichia coli* 2-Oxoglutarate Dehydrogenase Multienzyme Complex," *J. Mol. Biol.* 280:655-668 (1998).

Knappe and Sawers, "A radical-chemical route to acetyl-CoA: the anaerobically induced pyruvate formate-lyase system of *Escherichia coli*," *FEMS. Microbiol. Rev.* 75:383-398 (1990).

Knappe et al., "Post-translational activation introduces a free radical into pyruvate formate-lyase," *Proc. Natl. Acad. Sci. U.S.A.* 81:1332-1335 (1984).

Knothe, "'Designer' Biodiesel: Optimizing Fatty Ester Composition to Improve Fuel Properties," *Energy Fuels* 22:1358-1364 (2008).

Kobayashi et al., "Physicochemical, catalytic, and immunochemical properties of fumarases crystallized separately from mitochondrial and cytosolic fractions of rat liver," *J. Biochem.* 89(6):1923-1931 (1981).

Koch and Fuchs, "Enzymatic reduction of benzoyl-CoA to alicyclic compounds, a key reaction in anaerobic aromatic metabolism," *Eur. J. Biochem.* 205:195-202 (1992).

Koch et al., "Products of enzymatic reduction of benzoyl-CoA, a key reaction in anaerobic aromatic metabolism," *Eur. J. Biochem.* 211:649-661 (1993).

Koland and Gennis, "Proximity of Reactive Cysteine Residue and Flavin in *Escherichia coli* Pyruvate Oxidase As Estimated by Flourescence Energy Transfer," *Biochemistry* 21:4438-4442 (1982).

Kollmann-Koch et al.,"Nicotinic acid metabolism. Dimethylmaleate hydratase," *Hoppe Seylers Z Physiol Chem.* 365:s.847-857 (1984).

Koo et al., "Cloning and characterization of the bifunctional alcohol/acetaldehyde dehydrogenase gene (adhE) in *Leuconostoc mesenteroides* isolated from kimchi," *Biotechnol. Lett.* 27(7):505-510 (2005).

Korbert et al., "Crystallization of the NADP$^+$-dependent Glutamate Dehydrogenase from *Escherichia coli*," *J. Mol. Biol.* 234:1270-1273 (1993).

Kornberg, "The role and control of the glyoxylate cycle in *Escherichia coli*," *Biochem. J.* 99:1-11 (1966).

Korolev et al., "Autotracing of *Escherichia coli* acetate CoA-transferase a-subunit structure using 3.4 Å MAD and 1.9 Å native data," *Acta. Crystallogr. D. Biol. Crystallogr.* 58(Pt 12):2116-2121 (2002).

Korotkova and Lidstrom, "Connection between poly-β-hydroxybutyrate biosynthesis and growth on C1 and C2 compounds in the methylotroph *Methylobacterium extorquens* AM1," J. Bacteriol. 183(3):1038-1046 (2001).

Korotkova and Lidstrom, "MeaB is a component of the methylmalonyl-CoA mutase complex required for protection of the enzyme from inactivation," *J. Biol. Chem.* 279(14):13652-13658 (2004).

Kort et al., "Glutamate dehydrogenase from the hyperthermophilic bacterium *Thermotoga maritima*: molecular characterization and phylogenetic implications," *Extremophiles* 1:52-60 (1997).

Kosaka et al., "Characterization of the sol operon in butanol-hyperproducing *Clostridium saccharoperbutylacetonicum* strain N1-4 and its degeneration mechanism," *Biosci. Biotechnol. Biochem.* 71:58-68 (2007).

Kosjek et al., "Purification and characterization of a chemotolerant alcohol dehydrogenase applicable to coupled redox reactions," *Biotechnol. Bioeng.* 86(1):55-62 (2004).

Kouzarides, "Acetylation: a regulatory modification to rival phosphorylation?" *EMBO J.* 19(6):1176-1179 (2000).

Kovachy et al., "Recognition, Isolation, and Characterization of Rat Liver D-Methylmalonyl Coenzyme A Hydrolase," *J. Biol. Chem.* 258(18):11415-11421 (1983).

Kraus et al., "Biosynthesis and mitochondrial processing of the β subunit of propionyl Coenzyme A carboxylase from rat liver," *J. Biol. Chem.* 258:7245-7248 (1983).

Krieger et al., "Pyruvate decarboxylase from *Kluyveromyces lactis* an enzyme with an extraordinary substrate activation behaviour," Eur. J. Biochem. 269:3256-3263 (2002).

Krug et al., "Identification of AcnR, a TetR-type repressor of the aconitase gene acn in *Corynebacterium glutamicum*," *J. Biol. Chem.* 280(1):585-595 (2005). (Epub Oct. 19, 2004).

(56) References Cited

OTHER PUBLICATIONS

Kuchta and Abeles, "Lactate Reduction in *Clostridium* propionicum Purification and properties of lactyl-CoA dehydratase" *J. Biol Chem.* 260(24):13181-13189 (1985).

Kühnl et al., "Functional analysis of the methylmalonyl-CoA epimerase from *Caenorhabditis elegans*," *FEBS J.* 272(6):1465-1477 (2005).

Kumari et al., "Cloning, Characterization, and Functional Expression of acs, the Gene Which Encodes Acetyl Coenzyme A Synthetase in *Escherichia coli*," *J. Bacteriol.* 177(10):2878-2886 (1995).

Kuntze et al., "6-Oxocyclohex-1-ene-1-carbonyl-Coenzyme A hydrolases from obligately anaerobic bacteria: characterization and indentification of its gene as a functional marker for aromatic compounds degrading anaerobes," *Environ. Microbiol.* 10(6):1547-1556 (2008).

Kwok and Hanson, "GFP-labelled Rubisco and aspartate aminotransferase are present in plastid stromules and traffic between plastids," *J. Exp. Bot.* 55(397):595-604 (2004).

Kwon et al., "Influence of gluconegoenic phosphoenolpyruvate carbosykinase (PCK) expression on succinic acid fermentation in *Escherichi coli* under high bicarbonate condition," *J. Microbiol. Biotechnol.* 16(9):1448-1452 (2006).

Laempe et al., "6-Hydroxycyclohex-1-ene-1-carbonyl-CoA dehydrogenase and 6-oxocyclohex-1-ene-1-carbonyl-CoA hydrolase, enzymes of the benzoyl-CoA pathway of anaerobic aromatic metabolism in the denitrifying bacterium *Thauera aromatica*," *Eur. J. Biochem.* 263(2):420-429 (1999).

Laivenieks et al., "Cloning sequencing, and overexpression of the *Anaerobiospirillum succinicproducens* phosphoenolpyruvate carboxykinase (pckA) gene," *Appl. Environ. Microbiol.* 63:2273-2280 (1997).

Lamed and Zeikus, "Novel NADP-linked alcohol-aldehyde/ketone oxidoreductase in thermophilic ethanologenic bacteria," *Biochem. J.* 195:183-190 (1981).

Lardizabal et al., "Purification of a jojoba embryo wax synthase, cloning of its cDNA, and production of high levels of wax in seeds of transgenic *arabidopsis*," *Plant Physiol.* 122(3):645-655 (2000).

Lawrence and Roth, "Evolution of Coenzyme B12 synthesis among enteric bacteria: evidence for loss and reacquisition of a multigene complex," *Genetics* 142(1):11-24 (1996).

Lawrence and Roth, "The cobalamin (Coenzyme B12) biosynthetic genes of *Escherichia coli*," *J. Bacteriol.* 177(22):6371-6380 (1995).

Lebbink et al., "Engineering activity and stability of *Thermotoga maritima* glutamate dehydrogenase I. Introduction of a six-residue ion-pair network in the hinge region," *J. Mol. Biol.* 280:287-296 (1998).

Lebbink et al., "Engineering Activity and Stability of *Thermotoga maritima* glutamate Dehydrogenase. II: construction of a 16-Residue Ion-pair Network at the Subunit Interface," *J. Mol. Biol.* 289:357-369 (1999).

Leduc et al., "The hotdog thioesterase EntH (YbdB) plays a role in vivo in optimal enterobactin biosynthesis by interacting with the ArCP domain of EntB," *J. Bacteriol.* 189(19):7112-7126 (2007).

Lee and Cho, "Identification of essential active-site residues in ornithine decarboxylase of *Nicotiana* glutinosa decarboxylating both L-ornithine and L-lysine," *Biochem. J.* 360:657-665 (2001).

Lee et al., "Biosynthesis of enantiopure (S)-3-hydroxybutyric acid in metabolically engineered *Escherichia coli*," App. Microbiol. Biotechnol. 79:633-641 (2008).

Lee et al., "Cloning and Characterization of *Mannheimia* succiniciproducens MBEL55E Phosphoenolpyruvate Carboxykinase (pckA) Gene," *Biotechnol. Bioprocess Eng.* 7:95-99 (2002).

Lee et al., "Fermentative production of chemicals that can be used for polymer synthesis," *Macromol. Biosci.* 4:157-164 (2004).

Lee et al., "Genome-based metabolic engineering of *Mannheimia succiniciproducens* for succinic acid productiion," *Appl. Environ. Microbiol.* 72(3):1939-1948 (2006).

Lee et al., "Isolation and characterization of a new succinic acid-producing bacterium, *Mannheimia* succiniciproducens MBEL55E, from bovine rumen," *Appl. Microbiol. Biotechnol.* 58(5):663-668 (2002).

Lee et al., "Phylogenetic diversity and the structural basis of substrate specificity in the β/α-barrel fold basic amino acid decarboxylases," *J. Biol. Chem.* 282:27115-27125 (2007).

Lee et al., "High production of D-β-hydroxyisobutyric acid from methacrylic acid by *Candida* rugosa and its mutant," *Bioprocess Eng.* 16(5):247-252 (1997).

Lee et al., "Metabolic engineering of *Escherichia coli* for enhanced production of succinic acid, based on genome comparison and in silico gene knockout simulation," *Appl Environ. Microbiol.* 71(12):7880-7887 (2005).

Lehtio and Goldman, "The pyruvate format lyase family: sequences, structures and activation," *Protein Eng. Des.Sel.* 17:545-552 (2004).

Lei et al., "A shared binding site for NAD+ and Coenzyme A in an acetaldehyde dehydrogenase involved in bacterial degradation of aromatic compounds," Biochemistry 47:6870-6882 (2008).

Lemonnier and Lane, "Expression of the second lysine decarboxylase gene of *Escherichia coli*," Microbiology 144(Pt 3):751-760 (1998).

Leonardo et al., "Anaerobic Regulation of the adhE gene, Encoding the Fermentative Alcohol Dehydrogenase of *Escherichia coli*," *J. Bacteriol.* 175(3):870-878 (1993).

Lepore et al., "The x-ray crystal structure of lysine-2,3-aminomutase from *Clostridium* subterminale," *Proc. Natl. Acad. Sci U.S.A.* 102:13819-13824 (2005).

Leppänen et al., "Pyruvate formate lyase is structurally homologous to type I ribonucleotide reductase," *Structure* 7:733-744 (1999).

Leutwein and Heider, "Succinyl-CoA(R)-benzylsuccinate CoA-Transferase: an enzyme of the anaerobic toluene catabolic pathway in denitrifying bacteria," *J. Bacteriol.* 183(14):4288-4295 (2001).

Lian et al., "Stereochemical and Isotopic Labeling Studies of 4-Oxalocrotonate Decarboxylase and Vinylpyruvate hydratase: Analysis and Mechanistic Implications," *J. Am. Chem Soc.* 116:10403-10411 (1994).

Lin et al., "Chemostat culture characterization of *Escherichia coli* mutant strains metabolically engineered for aerobic succinate production: A study of the modified metabolic network based on metabolite profile, enzyme activity, and gene expression profile," *Metab. Eng.* 7(5-6):337-352 (2005).

Lin et al., "Effect of carbon sources differing in oxidation state and transport route on succinate production in metabolically engineered *Escherichia coli*," J. Ind. Microbiol. Biotechnol. 32:87-93 (2005).

Lin et al., "Fed-batch culture of a metabolically engineered *Escherichia coli* strain designed for high-level succinate production and yield under aerobic conditions," *Biotechnol. Bioeng.* 90:775-779 (2005).

Lin et al., "Genetic Reconstruction of the Aerobic Central Metabolism in *Escherichia coli* for the Absolute Aerobic Production of Succinate," *Biotechnol. Bioeng.* 89(2):148-156 (2005).

Lin et al., "Increasing the Acetyl-CoA pool in the Presence of Overexpressed Phosphoenolpyruvate Carboxylase or Pyruvate Carboxylase Enhances Succinate Production in *Escherichia coli*," *Biotechnol. Prog.* 20(5):1599-1604 (2004).

Lin et al., "Metabolic engineering of aerobic succinate production systems in *Escherichia coli* to improve process productivity and achieve the maximum theoretical succinate yield," *Metab. Eng.* 7(2):116-127 (2005).

Lin, H et al., "Effect of *Sorghum vulgare* phosphoenolpyruvate carboxylase and *Lactococcus lactis* pyruvate carboxylase coexpression on succinate production in mutant strains of *Escherichia coli*," *Appl. Microbiol. Biotechnol.* 67(4): 515-523 (2005).

Lingen et al., "Alteration of the substrate specificity of benzoylformate decarboxylase from *Pseudomonas putida* by directed evolution," *Chembiochem.* 4:721-726 (2003).

Lingen et al., "Improving the carboligase activity of benzoylformate decarboxylase from *Pseudomonas putida* by a combination of directed evolution and site-directed mutagenesis," *Protein Eng.* 15:585-593 (2002).

(56) References Cited

OTHER PUBLICATIONS

Liu et al., "Kinetic and crystallographic analysis of active site mutants of *Escherichia coli* γ-aminobutyrate aminotransferase," *Biochemistry* 44:(8):2982-2992 (2005).

Liu et al., "Microbial production of R-3-hydroxybutyric acid by recombinant *E. coli* harboring genes of phbA, phbB, and tesB," *Appl. Microbiol. Biotechnol.* 76:811-818 (2007).

Liu et al., "Purification and characterization of ornithine acetyltransferase from *Saccharomyces cerevisiae*," *Eur. J. Biochem.* 228:291-296 (1995).

Liu et al., "A Novel Genetically Engineered Pathway for Synthesis of Poly(Hydroxyalkonoic Acids) in *Escherichia coli*," *Appl. Environ. Microbiol.* 66(2):739-743 (2000).

Liu et al., "Crystal structures of unbound and aminooxyacetate-bound *Escherichia coli* γ-aminobutyrate aminotransferase," *Biochemistry* 43(34):10896-10905 (2004).

Liu et al., "Economical succinic acid production from cane molasses by *Actinobacillus succinogenes*," *Bioresour Technol* 99(6):1736-1742 (2008).

Locher et al., "Crystal structure of the *Acidaminococcus fermentans* 2-hydroxyglutaryl-CoA dehydratase component A," *J. Mol. Biol.* 307(1):297-308 (2001).

Loh et al., "A previously undescribed pathway for pyrimidine catabolism," *Proc. Natl. Acad. Sci. U. S. A.* 103(13):5114-5119 (2006). (Epub Mar. 15, 2006).

Lokanath et al., "Crystal structure of novel NADP-dependent 3-hydroxyisobutyrate dehydrogenase from *Thermus thermophilus* HB8," *J. Mol. Biol.* 352(4):905-917 (2005).

Loke et al., "Active acetyl-CoA synthase from *Clostridium thermoaceticum* obtained by cloning and heterologous expression of acsAB in *Escherichia coli*," Proc. Natl. Acad. Sci. U.S.A. 97:12503-12535 (2000).

Louis et al., "Restricted distribution of the butyrate kinase pathway among butyrate-producing bacteria from the human colon," *J. Bacteriol.* 186:2099-2106 (2004).

Luersen, "*Leishmania major* thialsine $N^{\epsilon}$-acetyltransferase: Identification of amino acid residues crucial for substrate binding," *Febs Lett.* 579:5347-5352 (2005).

Luli and Strohl, "Comparison of Growth, Acetate Production, and Acetate Inhibition of *Escherichia coli* Strains in Batch and Fed-Batch Fermentations," *Appl. Environ. Microbiol.* 56:1004-1011 (1990).

Lupa et al., "Distribution of genes encoding the microbial non-oxidative reversible hydroxyarylic acid decarboxylases/phenol carboxylases," *Genomics* 86:342-351 (2005).

Lupa et al., "Properties of the reversible nonoxidative vanillate/4-hydroxybenzoate decarboxylase from *Bacillus subtilis*," *Can. J. Microbiol* 54:75-81 (2008).

Lütke-Eversloh and Steinbüchel, "Biochemical and molecular characterization of a succinate semialdehyde dehydrogenase involved in the catabolism of 4-hydroxybutyric acid in *Ralstonia eutropha*," *FEMS Microbiol. Lett.* 181(1):63-71 (1999).

Ma et al., "Induced rebuilding of aspartase conformation," *Ann. NY Acad. Sci.* 672:60-65 (1992).

Macis et al., "Properties and sequence of the Coenzyme $B_{12}$-dependent glycerol dehydratase of *Clostridium pasteruianum*," *FEMS Microbiol. Lett.* 164:21-28 (1998).

Mack and Buckel, "Conversion of glutaconate CoA-transferase from *Acidaminococcus fermentans* into an acyl-CoA hydrolase by site-directed mutagenesis," *FEBS Lett.* 405(2):209-212 (1997).

Mack et al., "Location of the two genes encoding glutaconate Coenzyme A-transferase at the beginning of the hydroxyglutarate operon in *Acidaminococcus fermentans*," *Eur. J. Biochem.* 226:41-51 (1994).

Maes et al., "Crystallization of ornithine acetyltransferase from yeast by counter-diffusion and preliminary x-ray study," *Acta. Crystallogr. Sect. F. Struct. Biol. Cryst. Commun.* 62(Pt. 12):1294-1297 (2006).

Mahadevan and Schilling, "The effects of alternate optimal solutions in constraint-based genome-scale metabolic models," *Metab. Eng.* 5(4):264-276 (2003).

Mai and Adams, "Purification and characterization of two reversible and ADP-dependent acetyl Coenzyme A synthetases from the hyperthermophilic archaeon *Pyrococcus furiosus*," J. Bacteriol. 178:5897-5903 (1996.).

Majewski and Domach, "Simple Constrained-Optimization View of Acete Overflow in *E. Coli*," *Biotechnol. Bioeng.* 35(7):732-738 (1990).

Maklashina et al., "Anaerobic expression of *Escherichia coli* succinate dehydrogenase: functional replacement of fumarate reductase in the respiratory chain during anaerobic growth," *J. Bacteriol.* 180(22):5989-5996 (1998).

Manjasetty et al., "Crystallization and preliminary X-ray analysis of dmpFG-encoded 4-hydroxy-2-ketovalerate aldolase-aldehyde dehydrogenase (acylating) from *Pseudomonas* sp strain CF600," *Acta. Crystallogr. D. Biol. Crystallogr.* 57(Pt 4):582-585 (2001).

Manning and Pollitt, "Tracer studies of the interconversion of R- and S-methylmalonic semialdehydes in man," *Biochem. J.* 231(2):481-484 (1985).

Marks et al., "Molecular cloning and characterization of (R)-3-hydroxybutyrate dehydrogenase from human heart," J. Biol. Chem. 267(22):15459-15463 (1992).

Martinez-Carrion and Jenkins, "D-Alanine-D-glutamate transminase. I. Purification and characterization," J. Biol. Chem. 240(9):3538-3546 (1965).

Martins et al., "Crystal structure of 4-hydroxybutyryl-CoA dehydratase: radical catalysis involving a [4Fe-4S] cluster and flavin," *Proc. Natl. Acad. Sci. U.S.A.* 101(44):15645-15649 (2004).

Mason and Dufour, "Alcohol acetyltransferases and the significance of ester synthesis in yeast," *Yeast* 16(14):1287-1298 (2000).

Mat-Jan et al., "Mutants of *Escherichia coli* Deficient in the Fermentative Lactate Dehydrogenase," J. Bacteriol. 171(1):342-348 (1989).

Matsushima et al., "An enone reductase from *Nicotiana tabacum*: cDNA cloning, expression in *Escherichia coli*, and reduction of enones with the recombinant proteins," Bioorg. Chem. 36:23-28 (2008).

Mattevi et al., "Atomic structure of the cubic core of the pyruvate dehydrogenase multienzyme complex," *Science* 255(5051):1544-1550 (1992).

Matthies and Schink, "Reciprocal Isomerization of Butyrate and Isobutyrate by the Strictly Anaerobic Bacterium Strain WoG13 and Methanogenic Isobutyrate Degradation by a Defined Triculture," *Appl. Environ. Microbiol.* 58(5):1435-1439 (1992).

Maurus et al., "Insights into the Evolution of Allosteric Properties. The NADH Binding Site of Hexameric Type II Citrate Synthases," Biochemistry 42:5555-5565 (2003).

Maynard et al., "Autocatalytic activation of acetyl-CoA synthase," J. Biol. Inorg. Chem. 9:316-322 (2004).

McAlister-Henn and Thompson, "Isolation and expression of the gene encoding yeast mitochondrial malate dehydrogenase," J. Bacteriol. 169:5157-5166 (1987).

McCarthy et al., "Crystal structure of methylmalonyl-Coenzyme A epimerase from P. shermanii: a novel enzymatic function on an ancient metal binding scaffold," *Structure* 9(7):637-646 (2001).

McCullough et al., "Enzymatic decarboxylation of the aminobenzoates," J. Am. Chem. Soc. 79:628-630 (1957).

McKinlay et al., "Prospects for a bio-based succinate industry," *Appl. Microbiol. Biotechnol.* 76(4):727-740 (2007).

McPherson et al., "Multiple interactions of lysine-128 of *Escherichia coli* glutamate dehydrogenase revealed by site-directed mutagenesis studies," *Protein Eng.* 2(2):147-152 (1988).

Meagher, "Purification and partial amino acid sequence of the cyanogen bromide fragments of muconolactone isomerase from *Pseudomonas putida*," *Biochim. Biophys. Acta* 494:33-47 (1977).

Megraw et al., "Formation of lactyl-Coenzyme A and pyruvyl-Coenzyme A from lactic acid by *Escherichia coli*," J. Bacteriol. 90(4):984-988 (1965).

Melchiorsen et al., "The level of pyruvate-formate lyase controls the shift from homolactic to mixed-acid product formation in *Lactococcus lactis*," *Appl. Microbiol. Biotechnol.* 58:338-344 (2002).

Meng and Chuang, "Site-directed Mutagenesis and Functional Analysis of the Active-Site Residues of the E2 Component of Bovine Branched-Chain α-Keto Acid Dehydrogenase Complex," *Biochemistry* 33:12879-12885 (1994).

(56) References Cited

OTHER PUBLICATIONS

Meng and Li, "Cloning, expression and characterization of a thiolase gene from *Clostridium pasteurianum*," *Biotechnol. Lett.* 28(16):1227-1232 (2006).

Menon and Ragsdale, "Mechanism of the *Clostridium thermoaceticum* pyruvate:ferredoxin oxidoreductase: evidence for the common catalytic intermediacy of the hydroxyethylthiamine pyropyrosphate radical," *Biochemistry* 36(28):8484-8494 (1997).

Menzel et al., "Enzymatic evidence for an involvement of pyruvate dehydrogenase in the anaerobic glycerol metabolism of *Klebsiella pneumoniae*," *J. Biotech.* 56:135-142 (1997).

Menzel et al., "Kinetic, dynamic, and pathway studies of glycerol metabolism by *Klebsiella pneumoniae* in anaerobic continuous culsutre: IV. Enzymes and fluxes of pyruvate metabolism," *Botechnol. Bioeng.* 60(5):617-626 (1998).

Metz et al., "Purification of a jojoba embryo fatty acyl-Coenzyme A reductase and expression of its cDNA in high erucic acid rapeseed," *Plant Phys.* 122:635-644 (2000).

Meynial-Salles, I., et al., "A new process for the continuous production of succinic acid from glucose at high yield, titer and productivity," *Biotechnol. Bioeng.* 99(1):129-135 (2008).

Millard et al., "Enhanced production of succinic acid by overexpression of phosphoenolpyruvate carboxylase in *Escherichia coli*," *Appl. Environ. Microbiol.* 62(5):1808-1810 (1996).

Miller and Jenesel, "Enzymology of butyrate Formation by Butyrivibrio-Fibrisolvens," *J. Bacteriol.* 138:99-104 (1979).

Minard and McAlister-Henn, "Isolation, nucleotide sequence analysis, and disruption of the MDH2 gene from *Saccharomyces cerevisiae*: evidence for three isozymes of yeast malate dehydrogenase," *Mol. Cell. Biol.* 11:370-380 (1991).

Misono and Nagasaki, "Occurrence of L-Lysine ϵ-Dehydrogenase in *Agrobacterium tumefaciens*," *J. Bacteriol.* 150(1):398-401 (1982).

Misono et al., "Properties of L-lysine epsilon-dehydrogenase from *Agrobacterium tumefaciens*," *J. Biochem.* 105(6):1002-1008 (1989).

Miura et al., "Molecular Cloning of the nemA Gene Encoding N-Ethylmaleimide Reductase from *Escherichia Coli*," *Biol. Pharm. Bull.* 20(1):110-112 (1997).

Miyazaki et al., "α-Aminoadipate aminotransferase from an extremely thermophilic bacterium, *Thermus thermophilus*," *Microbiology* 150:2327-2334 (2004).

Mizobata et al., "Purification and characterization of a thermostable class II fumarase from *Thermus thermophilus*," Arch. Biochem. Biophys. 355(1):49-55 (1998).

Mizugaki et al. "Studies on the metabolism of unsaturated fatty acids. IX. Stereochemical studies of the reaction catalyzed by trans-2-enoyl-Coenzyme A reductase of *Escherichia coli*," *J. Biochem.* 92(5):1649-1654 (1982).

Mizugaki et al., "Studies on the Metabolism of Unsaturated Fatty Acids. V. Isomerization of Thiol Esters of cis-2-Alkenoic Acids during Their Preparation and Alkaline Hydrolysis," *Chem. Pharm. Bull.* 30(1):206-213 (1982).

Momany et al., "Crystallization of diaminopimelate decarboxylase from *escherichia coli*, a stereo specific D-amino-acid decarboxylase," *Acta. Crystallogr. D. Biol. Crystallogr.* 58(Pt. 3):549-552 (2002).

Momany et al., "Crystallographic Structure of PLP-Dependent Ornithine Decarboxylase from *Lactobacillus* 30a to 3.0 å Resolution," *J. Mol. Biol.* 252:643-655 (1995).

Monnet et al., "Regulation of branched-chain amino acid biosynthesis by α-acetolactate decarboxylase in *Streptococcus thermophilus*," *Lett. Appl. Microbiol.* 36(6):399-405 (2003).

Moon et al., "Metabolic engineering of *Escherichia coli* for the production of malic acid," *Biochem. Eng. J.* 40(2):312-320 (2008).

Moore et al., "Expression and Purification of Aspartate β-Semialdehyde Dehydrogenase from Infectious Microorganisms," *Protein Expr. Purif.* 25:189-194 (2002).

Moresi et al., "Fumaric acid production from hydrolysates of starch-based substrates," *J. Chem. Technol. Biotechnol.* 54(3):283-290 (1992).

Mori et al., "Characterization, Sequencing, and Expression of the Genes Encoding a Reactivating Factor for Glycerol-inactivated Adenosylcobalamin-dependent Diol Dehydratase," *J. Biol. Chem.* 272(51):32034-32041 (1997).

Morton et al., "Cloning, sequencing, and expressions of genes encoding enzymes of the autotrophic acetyl-CoA pathway in the acetogen *Clostridium thermoaceticum*," in M. Sebald (ed.), Genetics and molecular biology of anaerobic bacteria, Springer Verlag, New York, 389-406 (1992).

Moskowitz et al., "Metabolism of poly-β-hydroxybutyrate. II. Enzymatic synthesis of D-(-)-β-hydroxybutyryl Coenzyme A by an enoyl hydrase from *rhodospirillum rubrum*," Biochemistry 8:2748-2755 (1969).

Mouttaki et al., "Cyclohexane Carboxylate and Benzoate Formation from Crotonate in *Syntrophus aciditrophicus*," *Appl. Environl. Microbiol.* 73(3):930-938 (2007).

Müh et al., "4-Hydroxybutyryl-CoA dehydratase from *Clostridium aminobutyricum*: characterization of FAD and iron-sulfur clusters involved in an overall non-redox reaction," *Biochemistry* 35:11710-11718 (1996).

Müh et al., "Mössbauer study of 4-hydroxybutyryl-CoA dehydratase probing the role of an iron-sulfur cluster in an overall non-redox reaction," *Eur. J. Biochem.* 248:380-384 (1997).

Mukhopadhyay and Purwantini, "Pyruvate carboxylase from *Mycobacterium smegmatis*: stabilization, rapid purification, moleculare and biochemical characterization and regulation of the cellular level," *Biochim. Biophys. Acta* 1475(3):191-206 (2000).

Muller and Buckel, "Activation of (R)-2-hydroxyglutaryl-CoA dehydratase from *Acidaminococcus fermentans*" *Eur. J. Biochem.* 230(2):698-704 (1995).

Muller et al., "Carbon Conversion Efficiency and Limits of Productive Bacterial Degradation of Methyl tert-Butyl Ether and Related Compounds," *Appl. Environ. Microbiol.* 73(6):1783-1791 (2007).

Muratsubaki and Enomoto, "One of the fumarate reductase isoenzymes from *Saccharomyces cerevisiae* is encoded by the OSM1 gene," *Arch. Biochem. Biophys.* 352:175-181 (1998).

Musfeldt and Schönheit, "Novel type of ADP-forming acetyl Coenzyme A synthetase in hyperthermophilic archaea: heterologous expression and characterization of isoenzymes from the sulfate reducer *Archaeoglobus fulgidus* and the methanogen *Methanococcus jannaschii*," *J. Bacteriol.* 184(3):636-644 (2002).

Nagasawa et al., "Cloning and Nucleotide Sequence of the Alcohol Acetyltransferase II gene (ATF2) from *Saccharomyces cerevisiae* Kyokai No. 7," *Biosci. Biotechnol. Biochem.* 62:1852-1857 (1998).

Nagasawa et al., "Production of acrylic acid and methacrylic acid using *Rhodococcus rhodochrous* J1 nitrilase," *Appl. Microbiol. Biotechnol.* 34:322-324 (1990).

Nagata et al., "Gene cloning, purification, and characterization of thermostable and halophilic leucine dehydrogenase from a halophilic thermophile, *Bacillus licheniformis* TSN9," *Appl. Microbiol. Biotechnol.* 44:432-438 (1995).

Naggert et al., "Cloning, sequencing, and characterization of *Escherichia coli* thioesterase II," *J. Biol. Chem.* 266(17):11044-11050 (1991).

Najafpour and Younesi, "Ethanol and acetate synthesis from waste gas using batch culture of *Clostridium ljungdahlii*," *Enzyme Microb. Technol.* 38:223-228 (2006).

Najmudin et al., "Purification, crystallization and preliminary X-ray crystallographic studies on acetolactate decarboxylase," *Acta. Crystallogr. D. Biol. Crystallogr.* 59(Pt 6):1073-1075 (2003).

Nakahigashi and Inokuchi, "Nucleotide sequence of the fadA and fadB genes from *Escherichia coli*," *Nucleic Acids Res.* 18(16):4937 (1990).

Namba et al., "Coenzyme A- and Nicotinamide Adenine Dinucleotide-dependent Branched Chain -Keto Acid Dehydrogenase," J. Biol. Chem. 244(16):4437-4447 (1969).

Niegemann et al., "Molecular organization of the *Escherichia coli* gab cluster: nucleotide sequence of the structural genes gabD and gabP and expression of the GABA permease gene," *Arch.Microbiol* 160:454-460 (1993).

Nimmo, "Kinetic mechanism of *Escherichia coli* isocitrate dehydrogenase and its inhibition by glyoxylate and oxaloacetate," *Biochem. J.* 234(2):317-323 (1986).

(56) References Cited

OTHER PUBLICATIONS

Nishimaki et al., "Studies on the Metabolism of Unsaturated Fatty Acids. XIV. Purification and Properties of NADPH-Dependent trans-2-Enoyl-CoA Reductase of *Escherichia coli* K-12," *J. Biochem.* 95(5):1315-1321 (1984).
Nishizawa et al., "Gene expression and characterization of two 2-oxoacid:ferredoxin oxidoreductases from *Aeropyrum pernix* K1," *FEBS Lett.* 579:2319-2322 (2005).
Nissen et al., "Expression of a cytoplasmic transhydrogenase in *Saccharomyces cerevisiae* results in formation of 2-oxoglutarate due to depletion of the NADPH pool," *Yeast* 18:19-32 (2001).
Nogales et al., "Characterization of the last step of the aerobic phenylacetic acid degradation pathway," *Microbiology* 153(Pt 2):357-365 (2007).
Noichinda et al., "Subcellular Localization of Alcohol Acetyltransferase in Strawberry Fruit," *Food Sci. Technol. Res.* 5(3):239-242 (1999).
Nowicki et al., "Recombinant tyrosine aminotransferase from *Trypanosoma cruzi*: structural characterization and site directed mutagenesis of a broad substrate specificity enzyme," Biochim. Biophysica Acta 1546:268-281 (2001).
O'Brien et al., "Insight into the Mechanism of the $B_{12}$-Independent Glycerol Dehydratase from *Clostridium butyricum*: Preliminary Biochemical and Structural Characterization," *Biochemistry* 43:4635-4645 (2004).
Ofman et al., "2-Methyl-3-hydroxybutyryl-CoA dehydrogenase deficiency is caused by mutations in the HADH2 gene," *Am. J. Hum. Genet.* 72:1300-1307 (2003).
Ohgami et al., "Expression of acetoacetyl-CoA synthetase, a novel cytosolic ketone body-utilizing enzyme, in human brain," *Biochem. Pharmacol.* 65:989-994 (2003).
Ohsugi et al., "Metabolism of L-β-Lysine by Pseudomonas. Purification and Properties of a Deacetylase-Thiolestrerase Utilizing 4-Acetamidobutyryl CoA and Related Compounds," *J. Biol. Chem.* 256(14):7642-7651 (1981).
Okino et al., "An effeicient succinic acid production process in a metabolically engineered *Corynebacterium glutamicum* strain," *Appl. Microbiol. Biotechnol.* 81(3):459-464 (2008).
Oku and Kaneda, "Biosynthesis of branched-chain fatty acids in *bacillus subtilis*. A decarboxylase is essental for branched-chain fatty acid synthetase," *J. Biol. Chem.* 263:18386-18396 (1988).
Okuno et al., "2-Aminoadipate-2-oxoglutarate aminotransferase isoenzymes in human liver: a plausible physiological role in lysine and tryptophan metabolism," *Enzyme Protein* 47:136-148 (1993).
Olivera et al., "Molecular characterization of the phenylacetic acid catabolic pathway in *Pseudomonas putida* U: the phenylacetyl-CoA catabolon," *Proc. Natl. Acad. Sci. U.S.A.* 95(11):6419-6424 (1998).
Onuffer and Kirsch, "Redesign of the substrate specificity of *Escherichia coli* aspartate aminotransferase to that of *Escherichia coli* tyrosine aminotransferase by homology modeling and site-directed mutagenesis," Protein Sci. 4:1750-1757 (1995).
Orencio-Trejo et al., "Metabolic reglulation analysis of an ethanologenic *Escherichia coli* strain based on RT-PCR and enzymatic activities," Biotechnol. Biofuels 1:8 (2008). (provided electronically by publisher as pp. 1-13).
O'Sullivan et al., "Purification and characterisation of acetolactate decarboxylase from *Leuconostoc lactis* NCW1," FEMS Microbiol. Lett 194(2):245-249 (2001).
Overkamp et al., "In vivo analysis of the mechanism for oxidation of cytosolic NADH by *Saccharomyces cerevisiae* mitochondria," J. Bacteriol. 182:2823-2830 (2000).
Padovani and Banerjee, "Assembly and protection of the radical enzyme, methylmalonyl-CoA mutase, by its chaperone," *Biochem.* 45(30):9300-9306 (2006).
Palosaari and Rogers, "Purification and Properties of the Inducible Coenzyme A-Linked Butyraldehyde Dehydrogenase from *Clostridium acetobutylicum*," *J. Bacteriol.* 170(7):2971-2976 (1988).

Parales and Harwood, "Characterization of the Genes Encoding β-Ketoadipate: Succinyl-Coenzyme A Transferase in *Pseudomonas putida*," J. Bacteriol. 174(14):4657-4666 (1992).
Park and Lee, "Biosynthesis of poly(3-hydroxybutyrate-co-3-hydroxyalkanoates) by metabolically engineered *Escherichia coli* strains," *Appl. Biochem. Biotechnol.* 113-116:335-346 (2004).
Park and Lee, "Identification and characterization of a new enoyl Coenzyme A hydratase involved in biosynthesis of medium-chain-length polyhydroxyalkanoates in recombinant *Escherichia coli*," *J. Bacteriol.* 185(18):5391-5397 (2003).
Park and Lee, "New FadB homologous enzymes and their use in enhanced biosynthesis of medium-chain-length polyhydroxyalkanoates in FadB mutant *Escherichia coli*," *Biotechnol. Bioeng.* 86(6):681-686 (2004).
Park et al., "Metabolic engineering of *Escherichia coli* for the production of L-valine based on transcriptome analysis and in silico gene knockout simulation," Proc. Natl. Acad. Sci. U.S.A. 104(19):7797-7802 (2007).
Park et al., "Regulation of succinate dehydrogenase (sdhCDAB) operon expression in *Escherichia coli* in response to carbon supply and anaerobiosis: role of ArcA and Fnr," *Mol. Microbiol.* 15(3):473-482 (1995).
Park et al., "Utilization of Electrically Reduced Neutral Red by *Actinobacillus succinogenes*: Physiological Function of Neutral Red in Membrane-Driven Fumarate Reduction and Energy Conservation," *J. Bacteriol* 181(8):2403-2410 (1999).
Parsot et al., "Nucleotide sequence of *Escherichia coli* argB and argC genes: comparison of N-acetylglutamate kinase and N-acetylglutamate-γ-semialdehyde dehydrogenase with homologous and analogous enzymes," *Gene* 68:275-283 (1988).
Patel and Clark, "Acetoacetate metabolism in rat brain. Development of acetoacetyl-Coenzyme A deacylase and 3-hydroxy-3-methylglutaryl-Coenzyme A synthase," *Biochem. J.* 176(3):951-958 (1978).
Patel et al., "β-ketoadipate enol-lactone hydrolases I and II from *Acinetobacter calcoaceticus*," *J. Biol. Chem.* 250:6567-6577 (1975).
Pauli and Overath, "ato Operon: a Highly Inducible System for Acetoacetate and Butyrate Degradation in *Escherichia coli*," *Eur. J. Biochem.* 29:553-562 (1972).
Pauwels et al., "The N-acetylglutamate synthase/N-acetylgltamate kinase metabolon of *Saccharomyces cerevisiae* allows co-ordinated feedback regulation of the first two steps in arginine biosynthesis," *Eur. J. Biochem.* 270:1014-1024 (2003).
Paxton et al., "Role of branched-chain 2-oxo acid dehydrogenase and pyruvate dehydrogenase in 2-oxobutyrate metabolism," *Biochem. J.* 234:295-303 (1986).
Peisach et al., "Crystallographic study of steps along the reaction pathway of D-amino acid aminotransferase," *Biochemistry* 37(14)4958-4967 (1998).
Pelletier and Harwood, "2-Ketocyclohexanecarboxyl Coenzyme A Hydrolase, the Ring cleavage Enzyme Required for Anaerobic Benzoate Degradation of *Rhodopseudomonas palustris*," J. Bacteriol. 180(9):2330-2336 (1998).
Peoples and Sinskey, "Fine structural analysis of the *Zoogloea ramigera* phbA-phbB locus encoding β-ketothiolase and acetoacetyl-CoA reductase: nucleotide sequence of phbB," *Mol. Microbiol.* 3:349-357 (1989).
Pereira et al., "Active site mutants of *Escherichia coli* citrate synthase. Effects of mutations on catalytic and allosteric properties," *J. Biol. Chem.* 269:412-417 (1994).
Peretz and Burstein, "Amino acid sequence of alcohol dehydrogenase from the thermophilic bacterium *Thermoanaerobium brockii*," *Biochemistry* 28(16):6549-6555 (1989).
Peretz et al., "Molecular cloning, nucleotide sequencing, and expression of genes encoding alcohol dehydrogenases from the thermophile *Thermoanaerobacter brockii* and the mesophile *Clostridium beijerinckii*," Anaerobe. 3:259-270 (1997).
Perez et al., "*Escherichia coli* YqhD exhibits aldehyde reductase activity and protects from the harmful effect of lipid peroxidation-derived aldehydes," *J. Biol. Chem.* 283(12):7346-7353 (2008).

(56) References Cited

OTHER PUBLICATIONS

Petersen and Bennett, "Purification of acetoacetate decarboxylase from *clostridium acetobutylicum* ATCC 824 and cloning of the acetoacetate decarboxylase gene in *Escherichia coli*," *Appl. Environ. Microbiol.* 56:3491-3498 (1990).
Petitdemange et al., "Regulation of the NADH and NADPH-ferredoxin oxidoreductases in clostridia of the butyric group," *Biochim. Biophys. Acta* 421(2):334-347 (1976).
Pfluger et al., "Lysine-2,3-Aminomutase and β-Lysine Acetyltransferase Genes of Methanogenic Archaea Are Salt Induced and Are Essential for the Biosynthesis of $N^\varepsilon$-Acetyl-β-Lysine and Growth at High Salinity," *Appl. Environ. Microbiol.* 69(10):6047-6055 (2003).
Phalip et al., "Purification and properties of the α-acetolactate decarboxylase from *lactococcus lactis* subsp. Lactis NCDO 2118," *FEBS Lett.* 351(1):95-99 (1994).
Pharkya et al., "OptiStrain: a computational Framework for redesign of microbial production systems," *Genome Res.* 14(11):2367-2376 (2004).
Pharkya et al., "Exploring the overproduction of amino acids using the bilevel optimization framework OptKnock," *Biotechnol. Bioeng.* 84(7):887-899 (2003).
Pieulle et al., "Isolation and analysis of the gene encoding the pyruvate-ferredoxin oxidoreductase of *Desulfovibrio africanus*, production of the recombinant enzyme in *Escherichia coli*, and effect of carboxy-terminal deletions on its stability," *J. Bacteriol.* 179(18):5684-5692 (1997).
Ploux et al., "The NADPH-linked acetoacetyl-CoA reductase from *Zoogloea ramigera*, Characterization and mechanistic studies of the cloned enzyme over-produced in *Escherichia coli*," *Eur. J. Biochem.* 174:177-182 (1988).
Pohl et al., "Remarkably broad Sutstrate Tolerance of Malonyl-CoA Synthetase, an Enzyme Capable of Intracellular Synthesis of Polyketide Precursors," *J. Am. Chem. Soc.* 123:5822-5823 (2001).
Pollard et al., "Purification, characterisation and reaction mechanisms of monofunctional 2-hydroxypentadienoic acid hydratase from *Escherichia coli*," *Eur. J. Biochem. FEBS* 251:98-106 (1998).
Pollard et al., "Substrate Selectivity and biochemical Properties of 4-Hydroxy-2-Keto-Pentanoic Acid Aldolase from *Escherichia coli*," *Appl. Environ. Microbiol.* 64(10):4093-4094 (1998).
Polovnikova et al., "Structural and kinetic analysis of catalysis by a thiamine diphosphate-deptendent enzyme, benzoylformate decarboxylase," *Biochemistry* 42:1820-1830 (2003).
Ponce, E., et al., "Cloning of the two pyruvate kinase isoenzyme structural genes from *Escherichia coli*: the relative roles of these enzymes in pyruvate biosynthesis," *J. Bacteriol.* 177(19):5719-5722 (1995).
Postma et al., "Phosphoenolpyruvate Carbohydrate Phosphotransferase Systems of Bacteria," *Microbiol Rev.* 57(3):543-594 (1993).
Poston, "Assay of leucine 2,3-aminomutase," *Methods Enzymol.* 166:130-135 (1988).
Powlowski et al., "Purification and properties of the physically associated meta-cleavage pathway enzymes 4-hydroxy-2-ketovalerate aldolase and aldehyde dehydrogenase (acylating) from *Pseudomonas* sp. strain CF600," *J. Bacteriol.* 175(2):377-385 (1993).
Price et al., "Genome-scale models of microbial cells: evaluating the consequences of constraints," *Nat. Rev. Microbiol.* 2(11):886-897 (2004).
Prieto et al., "Molecular Characterization of the 4-Hydroxyphenylacetate Catabolic Pathway of *Escherichia coli* W: Engineering a Mobile Aromatic Degradative Cluster," *J. Bacteriol.* 178(1):111-120 (1996).
Pronk et al., "Pyruvate metabolism in *Saccharomyces cerevisiae*," *Yeast* 12:1607-1633 (1996).
Pucci et al., "*Staphylococcus haemolyticus* contains two D-glutamic acid biosynthetic activities, a glutamate racemase and a D-amino acid transminase," *J. Bacteriol.* 177(2):336-342 (1995).
Purnell et al., "Modulation of higher-plant NAD(H)-dependent glutamate dehydrogenase activity in transgenic tobacco via alteration of β subunit levels," *Planta* 222:167-180 (2005).
Qiu et al., "Metabolic engineering of *Aeromonas hydrophila* for the enhanced production of poly(3-hydroxybutyrate-co-3-hydroxyhexanoate)," *Appl. Microbiol. Biotechnol.* 69(5):537-542 (2006).
Qu et al., "Inhibition of human ornthine decarboxylase activity by enantiomers of difluoromethylornithine," *Biochem. J.* 375:465-470 (2003).
Quail and Guest, "Purification, characterization and mode of action of pdhR, the transcriptional repressor of the PdhR-aceEF-lpd operon of *Escherichia coli*," *Mol. Microbiol.* 15(3):519-529 (1995).
Rado and Hoch, "Phosphotransacetylase from *Bacillus subtilis*: purification and physiological studies," Biochim. Biophys. Acta 321:114-125 (1973).
Ragsdale, "Pyruvate ferredoxin oxidoreductase and its radical intermediate," *Chem. Rev.* 103(6):2333-2346 (2003).
Ramjee et al., "*Escherichia coli* L-aspartate- -decarboxylase: preprotein processing and observation of reaction intermediates by electrospray mass spectrometry," *Biochem. J.* 323(Pt 3):661-669 (1997).
Ramos et al., "Mutations affecting the enzymes involved in the utilization of 4-aminobutyric acid as nitrogen source by the yeast *Saccharomyces cerevisiae*," Eur.J Biochem. 149:401-404 (1985).
Rasmussen, L.J., et al. "Carbon Metabolism Regulates Expression of the pfl (Pyruvate-Formate-Lyase) Gene in *Escherichia coli*," J. Bacteriol. 173(20):6390-6397 (1991).
Rathinasabapathi, "Propionate, a source of β-alanine, is an inhibitor of β-alanine methylation in *Limonium* latifoilium Plunbaginaces," J. Plant Physiol. 159:671-674 (2002).
Ratnatilleke et al., "Cloning and sequencing of the Coenzyme B12-binding domain of isobutyryl-CoA mutase from *Streptomyces* cinnamonensis, reconstitution of mutase activity, and characterization of the recombinant enzyme produced in *Escherichia coli*," *J. Biol. Chem.* 274(44):31679-31685 (1999).
Raux et al., "The role of *Saccharomyces cerevisiae* Met1p and Met8p in sirohaem and cobalamin biosynthesis," Biochem. J. 338 (pt. 3):701-708 (1999).
Raux et al., "*Salmonella* typhimurium cobalamin (vitamin B12) biosynthetic genes: functional studies in S. typhimurium and *Escherichia coli*," *J. Bacteriol.* 178(3):753-767 (1996).
Raybuck et al., "Kinetic characterization of the carbon monoxide-acetyl-CoA (carbonyl group) exchange activity of the acetyl-CoA synthesizing CO dehydrogenase from *Clostridium* thermoaceticum," *Biochemistry* 27(20):7698-7702 (1988).
Raynaud et al., "Molecular characterization of the 1,3-propanediol (1,3-PD) operon of *clostridium butyricum*," Proc. Natl. Acad. Sci. U.S.A. 100:5010-5015 (2003).
Rea et al., "Structure and Mechanism of HpcH: a Metal Ion Dependent Class II Aldolase from the Homoprotocatechuate Degradation Pathway of *Escherichia coli*," *J. Mol. Biol.* 373:866-876 (2007).
Recasens et al., "Cystein Sulfinate Aminotransferase and Aspartate Aminotransferase Isoenzymes of Rat Brain. Purification, Characterization, and Further Evidence of Identity," *Biochemistry* 19:4583-4589 (1980).
Reed et al., "An expanded genome-scale model of *Escherichia coli* K-12 (iJR904 GSM/GPR)," *Genome. Biol.* 4(9):R54 (2003).
Regev-Rudzki et al., "Yeast Aconitase in Two Locations and Two Metabolic Pathways: Seeing Small Amounts Is Believing," Mol. Biol. Cell 16:4163-4171 (2005).
Reiser and Somerville, "Isolation of mutants of *Acinetobacter calcoaceticus* deficient in wax ester synthesis and complementation of one mutation with a gene encoding a fatty acyl Coenzyme A reductase," J. Bacteriol. 179(9):2969-2975 (1997).
Reitzer et al., "Crystallization and preliminary X-ray analysis of recombinant glutamate mutase and of the isolated component S from *Clostridium* cochlearium," *Acta. Crystallogr. D. Biol. Crystallogr.* 54(Pt 5):1039-1042 (1998).
Repetto and Tzagoloff, "Structure and Regulation of KGD1, the Structural Gene for Yeast α-Ketoglutarate Dehydrogenase," Mol. Cell. Biol. 9(6):2695-2705 (1989).

(56) References Cited

OTHER PUBLICATIONS

Resnekov et al., "Organization and regulation of the *Bacillus subtilis* odhAB operon, which encodes two of the subenzymes of the 2-oxoglutarate dehydrogenase complex," *Mol. Gen. Genet.* 234:285-296 (1992).
Rhodes et al., "Production of fumaric acid by *Rhizopus* arrhuzus," *Appl. Microbiol.* 7:74-80 (1959).
Rhodes et al., "Production of Fumaric Acid in 20-Liter Fermentors," *Appl. Microbiol.* 10(1)9-15 (1962).
Rigden et al., "A cofactor-dependent phosphoglycerate mutase homolog from *Bacillus stearothermophilus* is actually a broad specificity phosphatase," *Protein Sci.* 10:1835-1846 (2001).
Ringer et al., "Monoterpene double-bond reductases of the (−)-menthol biosynthetic pathway: isolation and characterization of cDNAs encoding (−)-isopiperitenone reductase and (+)-pulegone reductase of peppermint," Arch. Biochem. Biophys. 418(1):80-92 (2003).
Rioux et al., "Two Outer Membrane Transport Systems for Vitamin B12 in *Salmonella* Typhimurium," *J. Bacteriol.* 171:2986-2993 (1989).
Rioux et al., "Vitamin $B_{12}$ transport in *Escherichia coli* K12 does not require the btuE gene of the btuCED operon," *Mol. Gen. Genet.* 217:301-308 (1989).
Riviere et al., "Acetyl:succinate CoA-transferase in procyclic *Trypanosoma brucei*. Gene identification and role in carbohydrate metabolism." *J. Biol. Chem.* 279:45337-45346 (2004).
Roa Engel et al., "Fumaric acid production by fermentation," *Appl. Microbiol. Biotechnol.* 78(3):379-389 (2008).
Roberts et al, "The Role of Enoyl-CoA Hydratase in the Metabolism of Isoleucine by *Pseudomonas putida*," *Arch. Microbiol.* 117:99-108 (1978).
Roberts et al., "Acetyl-Coenzyme A synthesis from methyltetrahydrofolate, CO, and Coenzyme A by enzymes purified from *Clostridium* thermoaceticum: attainment of in vivo rates and identification of rate-limiting steps," *J. Bacteriol.* 174(14):4667-4676 (1992).
Roberts et al., "Cloning and expression of the gene cluster encoding key proteins involved in acetyl-CoA synthesis in *Clostridium* thermoaceticum: CO dehydrogenase, the corrinoid/Fe-S protein, and methyltransferase," *Proc. Natl. Acad. Sci. U.S.A.* 86(1):32-36 (1989).
Robinson et al., "Studies on Rat Brain Acyl-Coenzyme A Hydrolase (Short Chain)," *Biochem. Biophys. Res. Commun.* 71(4):959-965 (1976).
Roca et al., "Metabolic engineering of ammonium assimilation in xylose-fermenting *Saccharomyces cerevisiae* improves ethanol production," *Appl. Environ. Microbiol.* 69:4732-4736 (2003).
Rodriguez et al., "Characterization of the p-Coumaric Acid Decarboxylase from *Lactobacillus* plantarium CECT 748T," J. Agric. Food Chem. 56:3068-3072 (2008).
Rohdich et al., "Enoate reductases of Clostridia. Cloning, sequencing, and expression," *J. Biol. Chem.* 276(8):5779-5787 (2001).
Rohwerder et al., "The alkyl tert-butyl ether intermediate 2-hydroxyisobutyrate is degraded via a novel cobalamin-dependent mutase pathway," *Appl. Environ. Microbiol.* 72(6):4128-4135 (2006).
Romero et al., "Partial purification and characterization and nitrogen regulation of the lysine-aminotransferase of *Streptomyces* clavuligers," J. Ind. Microbiol. Biotechnol. 18:241-246 (1997).
Rose and Weaver, "The role of the allosteric B site in the fumarase reaction," Proc. Natl. Acad. Sci. U.S.A. 101(10):3393-3397 (2004).
Rose et al., "Enzymatic phosphorylation of acetate," J. Biol. Chem. 211(2):737-756 (1954).
Roth et al., "Characterization of the cobalamin (vitamin B12) biosynthetic genes of *Salmonella* typhimurium," J. Bacteriol. 175:3303-3316 (1993).
Roux and Walsh, "p-aminobenzoate synthesis in *Escherichia coli*: kinetic and mechanistic characterization of the amidotransferase PabA," *Biochemistry* 31:6904-6910 (1992).
Roux and Walsh, "p-Aminobenzoate synthesis in *Escherichia coli*: mutational analysis of three conserved amino acid residues of the amidotransferase PabA," *Biochemistry* 32:3763-3768 (1993).

Roy and Dawes, "Cloning and Characterization of the gene Encoding Lipoamide Dehydrogenase in *Saccharomyces cerevisiae*," *J. Gen. Microbiol.* 133:925-933 (1987).
Roymoulik et al., "Rearrangement of L-2-hydroxyglutarate to L-threo-3-methylmalate catalyzed by adenosylcobalamin-dependent glutamate mutase," Biochem. 39(33):10340-10346 (2000).
Rozell and Benner, "Stereochemical Imperative in Enzymic Decarboxylations. Stereochemical Course of Decarboxylation Catalyzed by Acetoacetate Decarboxylase," J. Am. Chem. Soc. 106:4937-4941 (1984).
Rudman and Meister, "Transamination in *Escherichia coli*," *J. Biol. Chem.* 200(2):591-604 (1953).
Ruldeekulthamrong et al., "Molecular characterization of lysine 6-dehydrogenase from *Achromobacter denitrificans*," *BMB Reports* 790-795 (2008).
Sabo et al., "Purification and physical properties of inducible *Escherichia coli* lysine decarboxylase," *Biochemistry* 13:622-670 (1974).
Saito and Doi, "Microbial synthesis and properties of poly(3-hydroxybutyrate-co-4-hydroxybutyrate) in *Comamonas acidovorans*," *Int. J Biol Macromol.* 16:99-104 (1994).
Sakai et al, "Acetate and Ethanol Production from $H_2$ and $CO_2$ by *Morrella* sp. Using a Repeated Batch Culture," *J. Biosci. Bioeng.* 99:252-258 (2005).
Sakanyan et al., "A re-examination of the pathway for ornithine biosynthesis in a thermophilic and two mesophilic *Bacillus* species," *J. Gen. Microbiol.* 138:125-130 (1992).
Sakurada et al., "Acetylpolyamine Amidohydrolase from *Mycoplana ramosa*: Gene Cloning and Characterization of the Metal-Substituted Enzyme," J. Bacteriol. 178(19):5781-5786 (1996).
Samanta and Harwood, "Use of *Rhodopseudomonas palustris* genome sequence to identify a single amino acid that contributes to the activity of Coenzyme A ligase with chlorinated substrates," Mol. Microbiol. 55(4):1151-1159 (2005).
Samuelov et al., "Whey fermentation by *anaerobiospirillum* succiniciproducens for production of a succinate-based animal feed additive," *Appl. Environ. Microbiol.* 65(5):2260-2263 (1999).
San et al., "Metabolic Engineering through Cofactor Manipulation and its Effects on Metabolic Flux Redistribution in *Escherichia coli*," *Metab Eng.* 4(2):182-192 (2002).
Sanchez et al., "Efficient succinic acid production from glucose through overexpression of pyruvate carboxylase in an *Escherichia coli* alcohol dehydrogenase and lactate dehydrogenase mutant," *Biotechnol. Prog.* 21(2):358-365 (2005).
Sanchez et al., "Novel pathway engineering design of the anaerobic central metabolic pathway in *Escherichia coli* to increase succinate yield and productivity," Metab. Eng. 7(3): 229-239 (2005).
Sanchez et al., "Batch culture characterization and metabolic flux analysis of succinate-producing *Escherichia coli* strains," *Metab Eng.* 8(3):209-226 (2006).
Sanchez et al., "Effect of different levels of NADH availability on metabolic fluxes of *Escherichia coli* chemostat cultures in defined medium," *J. Biotechnol.* 117(4):395-405 (2005).
Sankaranarayanan et al., "Preliminary x-ray crystallographic analysis of ornithine acetyltransferase (Rv1653) from *Mycobacterium tuberculosis*," *Acta. Crystallogr. Sect. F. Struct. Biol. Cryst. Commun.* 65(Pt 2):173-176 (2009).
Sanyal et al., "Biosyntehsis of pimeloyl-CoA, a biotin precursor in *Escherichia coli*, follows a modified fatty acid synthesis pathway: 13C-labeling studies," J. Am. Chem. Soc. 116:2637-2638 (1994).
Sass et al., "Folding of fumarase during mitochondrial import determines its dual targeting in yeast," J. Biol. Chem. 278(46):45109-45116 (2003).
Sato et al., "Poly[(R)-3-hydroxybutyrate] formation in *Escherichia coli* from glucose through an enoyl-CoA hydratase-mediated pathway," J. Biosci. Bioeng. 103(1):38-44 (2007).
Sauer and Thauer, "Methanol:Coenzyme M methyltransferase from *Methanosarcina barkeri*. Identification of the active-site histidine in the corrinoid-harboring subunit MtaC by site-directed mutagenesis," *Eur. J. Biochem.* 253(3):698-705 (1998).

(56) References Cited

OTHER PUBLICATIONS

Sauer et al., "Methanol:Coenzyme M methyltransferase from *Methanosarcina barkeri*. Purification, properties and encoding genes of the corrinoid protein MT1," *Eur. J. Biochem.* 243(3):670-677 (1997).

Sauvageot et al., "Characterisation of the diol dehydratase pdu operon of *Lactobacillus collinoides*," FEMS Microbiol. Lett. 209:69-74 (2002).

Saz and Weil, "The mechanism of the formation of -methylbutyrate from carbohydrate by *Ascaris lumbricoides* muscle," J. Biol. Chem. 235:914-918 (1960).

Scher and Jakoby, "Maleate isomerase," *J. Biol. Chem.* 244:1878-1882 (1969).

Scherf and Buckel, "Purification and properties of 4-hydroxybutyrate Coenzyme A transferase from *Clostridium* aminobutyricum," *Appl. Environ. Microbiol.* 57(9):2699-2702 (1991).

Scherf and Buckel, "Purification and properties of an iron-sulfur and FAD-containing 4-hydroxybutyryl-CoA dehadratase/vinylacetyl-CoA $\Delta^3$-$\Delta^2$-isomerase from *Clostridium* aminobutricum," *Eur. J. Biochem.* 215:421-429 (1993).

Scherf et al, "Succinate-ethanol fermentation in *clostridium kluyveri*: purification and characterisation of 4-hydroxybutyryl-CoA dehydratase/vinylacetyl-CoA $\Delta^3$-$\Delta^2$-isomerase," *Arch. Microbiol.* 161(3):239-245 (1994).

Schilling et al., "Combining Pathway Analysis with Flux Balance Analysis for the Comprehensive Study of Metabolic Systems," *Biotechnol. Bioeng.* 71(4):286-306 (2000-2001).

Schilling et al., "Theory for the Systematic Definition of Metabolic Pathways and Their Use in Interpreting Metabolic Function from a Pathway-Oriented Perspective," *J. Theor. Biol.* 203(3):229-248 (2000).

Schilling et al., "Toward Metabolic Phenomics: Analysis of Genomic Data Using Flux Balances," *Biotechnol. Prog.* 15(3):288-295 (1999).

Schmitzberger et al., "Structural constraints on protein self-processing in L-aspartate-α-decarboxylase," *EMBO J.* 22:6193-6204 (2003).

Schneider and Betz, "Waxmonoester Fermentation in *Euglena-Gracilis* T Factors Favoring the Synthesis of Odd-Numbered Fatty-Acids and Alcohols," *Planta.* 166:67-73 (1985).

Schneider et al., "The *Escherichia coli* gabDTPC operon: specific γ-aminobutyrate catabolism and nonspecific induction," *J. Bacteriol.* 184:6976-6986 (2002).

Schousboe et al., "Purification and Characterization of the 4-Aminobutyrate-2-Ketoglurate Transminase from Mouse Brain," Biochem. 2(15):2868-2873 (1973).

Schulz et al., "Stereospecific production of the herbicide phosphinothricin (glufosinate) by transamination: isolation and characterization of a phosphinothricin-specific transaminase from *Escherichia coli*," Appl. Environ. Microbiol. 56(1):1-6 (1990).

Schurmann and Sprenger, "Fructose-6-phosphate aldolase is a novel class I aldolase from *Escherichia coli* and is related to a novel group of bacterial transaldolases," J. Biol. Chem. 276(14): p. 11055-11061 (2001).

Schweiger and Buckel, "On the dehydration of (R)-lactate in the fermentation of alanine to propionat by *Clostridium propionicum*," FEBS Lett. 171:79-84 (1984).

Schweiger et al., "Purification of 2-hydroxyglutaryl-CoA dehydratase from *Acidaminococcus fermentans*. An iron-sulfur protein," Eur. J. Biochem. 169(2):441-448 (1987).

Scott and Jakoby, "Soluble γ-Aminobutyric-Glutamic Transaminase from *Pseudomonas fluorescens*," *J. Biol. Chem.* 234:932-936 (1959).

Scott, A.I., "Discovering nature's diverse pathways to vitamin $B_{12}$: a 35-year odyssey," *J. Org. Chem.* 68:2529-2539 (2003).

Seedorf et al., "The genome of *Clostridium kluyveri*, a strict anaerobe with unique metabolic features," Proc. Natl. Acad. Sci. U.S.A. 105(6):2128-2133 (2008).

Seibert et al., "Characterization of a gene cluster encoding the maleylacetate reductase from *Ralstonia eutropha* 335T, and enzyme recruited for growth with 4-fluorobenzoate," *Microbiology* 150:463-472 (2004).

Seibert et al., "Characterization of the maleylacteate reductase MacA of *Rhodococcus opacus* 1CP and evidence for the presence of an isofunctional enzyme," *J. Bacteriol.* 180:3503-3508 (1998).

Seibert et al., "Purification and characterization of maleylacetate reductase from *Alcaligenes eutrophys* JMP134(pJP4)," *J. Bacteriol.* 175:6745-6754 (1993).

Selmer et al., "Propionate CoA-transferase from *Clostridium propionicum*. Cloning of gene identification of glutamate 324 at the active site," *Eur. J. Biochem.* 269:372-380 (2002).

Seltzer, "Purification and properties of maleylacetone cis-trans isomerase from *Vibrio* 01," *J. Biol. Chem.* 248:215-222 (1973).

Sennett et al., "Transmembrane transport of cobalamin in prokaryotic and eukaryotic cells," *Ann. Rev. Biochem.* 50:1053-1086 (1981).

Seravalli et al., "Evidence that NiNi acetyl-CoA synthase is active and that the CuNi enzyme is not," *Biochemistry* 43(13):3944-3955 (2004).

Seyfried et al., "Cloning, Sequencing, and Overexpression of the Genes Encoding Coenzyme $B_{12}$-Dependent Glycerol Dehydratase of *Citrobacter freundii*," *J. Bacteriol.* 178(19):5793-5796 (1996).

Shafiani et al., "Cloning and characterization of aspartate-β-semialdehyde dehydrogenase from *Mycobacterium tuberculosis* H37 Rv," *J. Appl. Microbiol.* 98:832-838 (2005).

Shalel-Levanon et al., "Effect of ArcA and FNR on the expression of genes related to the oxygen regulation and the glycolysis pathway in *Eschericiha coli* under microaerobic growth conditions," *Biotechnol. Bioeng.* 92(2):147-159 (2005).

Shames et al., "Interaction of Aspartate and Aspartate-derived Antimetabolites with the Enzymes of the Threonine Biosynthetic Pathway of *escherichia coli*," J. Biol. Chem. 258(24):15331-15339 (1984).

Shi et al., "The Structure of I-Aspartate Ammonia-Lyase from *Escherichia coli*," *Biochemistry* 36:9136-9144 (1997).

Shiba et al., "Engineering of the pyruate dehydrogenase bypass in *Saccharomyces cerevisiae* for high-level production of isoprenoids," *Metab. Eng.* 9:160-168 (2007).

Shibata et al., "Purification, characterization, and immunological properties of fumarase from *Euglena gracilis* var. bacillaris," *J. Bacteriol.* 164(2):762-768 (1985).

Shigeoka and Nakano, "Characterization and molecular properties of 2-oxoglutarate decarboxylase from *Euglena gracilis*," *Arch. Biochem. Biophys.* 288:22-28 (1991).

Shigeoka and Nakano, "The effect of thiamin on the activation of thiamin pyrophosphate-dependent 2-oxoglutarate decarboxylase in *Euglena gracilis*," *Biochem. J.* 292 (Pt 2):463-467 (1993).

Shigeoka et al., "Effect of L-glutamate on 2-oxoglutarate decarboxylase in *Euglena gracilis*," *Biochem. J.* 282 (Pt 2):319-323 (1992).

Shimomura et al., "3-hydroxyisobutyryl-CoA hydrolase," *Methods Enzymol.* 324:229-240 (2000).

Shimomura et al., "Purification and partial characterization of 3-hydroxyisobutyryl-Coenzyme A hydrolase of rat liver," *J. Biol. Chem.* 269(19):14248-14253 (1994).

Shimoyama et al., "MmcBC in *Pelotomaculum thermopropionicum* represents a novel group of prokaryotic fumarases," *FEMS Microbiol Lett.* 270(2):207-213 (2007).

Shingler et al., "Nucleotide sequence and functional analysis of the complete phenol/3,4-dimethylphenol catabolic pathway of *Pseudomonas* sp. strain CF600," *J. Bacteriol.* 174(3):711-724 (1992).

Shukla et al., "Production of D(−)-lactate from sucrose and molasses," Biotechnol. Lett. 26(9):689-693 (2004).

Sibilli et al., "Two regions of the bifunctional protein aspartokinase l-homoserine dehydrogenase I are connected by a short hinge," J. Biol. Chem. 256 (20):10228-10230 (1981).

Siegert et al., "Exchanging the substrate specificities of pyruvate decarboxylase from *Zymomonas mobilis* and benzoylformate decarboxylase from *Pseudomonas putida*," Protein. Eng. Des. Sel. 18:345-357 (2005).

Siew et al., "Localization and characteristics of rat liver mitochondrial aldehyde dehydrogenases," *Arch. Biochem. Biophys.* 176(2):638-649 (1976).

(56) References Cited

OTHER PUBLICATIONS

Simanshu et al., "Structure and function of enzymes involved in the anaerobic degradation of L-threonine to propionate," *J. Biosci.* 32(6):1195-1206 (2007).
Siminov et al., "Application of Gas Chromatography and Gas Chromatography-Mass Spectrometry to the Detection of γ-Hydroxybutyric Acid and Its Precursors in Various Materials," *J. Anal. Chem.* 59:965-971 (2004).
Sinclair et al., "Purification and characterization of the branched chain α-ketoacid dehydrogenase complex from *Saccharomyces cerevisiae*," Biochem. Mol. Biol. Int. 31(5):911-922 (1993).
Sjöström et al., "Purification and characterisation of a plasminogen-binding protein from *Haemophilus influenzae*. Sequence determination reveals identity with aspartase," *Biochim. Biophys. Acta* 1324(2):182-190 (1997).
Skarstedt and Silverstein, "*Escherichia coli* acetate kinase mechanism studied by net initial rate, equilibrium, and independent isotopic exchange kinetics," *J. Biol. Chem.* 251:6775-6783 (1976).
Slater et al., "Multiple β-ketothiolases mediate poly(β-hydroxyalkanoate) copolymer synthesis in *Ralstonia eutropha*," *J. Bacteriol.* 180(8):1979-1987 (1998).
Slock et al., "An apparent *Bacillus subtilis* folic acid biosynthetic operon containing pab, an amphibolic trpG gene, a third gene required for synthesis of para-aminobenzoic acid, and the dihydropteroate synthase gene," *J. Bacteriol.* 172:7211-7226 (1990).
Smit et al., "Identification, cloning and characterization of *Lactococcus lactis* branched-chain α-keto acid decarboxylase involved in flavor formation," *Appl. Environ. Microbiol.* 71:303-311 (2005).
Smith and Kaplan, "Purification, properties and kinetic mechanism of Coenzyme A-linked aldehyde dehydrogenase from *Clostridium kluyveri*," Arch. Biochem. Biophys. 203:663-675 (1980).
Smith et al., "Fumarate metabolism and the microaerophily of *Campylobacter* species," *Int. J. Biochem. Cell Biol.* 31(9):961-975 (1999).
Smith et al., "Structural and functional organization of the animal fatty acid synthase," Prog. Lipid. Res. 42(4):289-317 (2003).
Soda and Misono, "L-Lysine:α-ketoglutarate aminotransferase. II. Purification, crystallization, and properties," *J. Bacteriol.* 7:4110-4119 (1968).
Söhling and Gottschalk, "Molecular analysis of the anaerobic succinate degradation pathway in *Clostridium kluyveri*," *J. Bacteriol.* 178:871-880 (1996).
Söhling and Gottschalk, "Purification and characterization of a Coenzyme-A-dependent succinate-semialdehyde dehydrogenase from *Clostridium kluyveri*," *Eur. J. Biochem.* 212:121-127 (1993).
Sokatch et al., "Purification of a Branched-Chain Keto Acid Dehydrogenase from *Pseudomonas putida*," J. Bacteriol. 148(2):647-652 (1981).
Sone et al., "Nucleotide sequence and expression of the *Enterobacter aerogenes* α-acetolactate decarboxylase gene in brewer's yeast, " *Appl. Environ. Microbiol.* 54:38-42 (1988).
Song et al, "Effects of dissolved $CO_2$ levels on the growth of *Mannheimia succiniproducens* and succinic acid production," *Biotechnol. Bioeng.* 98(6):1296-1304 (2007).
Song et al., "Construction of recombinant *Escherichia coli* strains producing poly (4-hydroxybutyric acid) homopolyester from glucose," *Wei Sheng Wu Xue.Bao.* 45:382-386 (2005).
Song et al., "Recovery of succinic acid produced by fermentation of a metabolically engineered *Mannheimia succiniciproducens* strain," *J. Biotechnol.* 132:445-452 (2007).
Song et al., "Structure, function, and mechanism of the phenylacetate pathway hot dog-fold thioesterase PaaI," *J. Biol. Chem.* 281(16):11028-11038 (2006).
Soucaille et al., "Butanol tolerance and autobacteriocin production by *Clostridium acetobutylicum*," *Curr. Microbiol.* 14:295-299 (1987).
Sovik, "Mitochondrial 2-methylacetoacetyl-CoA thiolase deficiency: an inborn error of isoleucine and ketone body metabolism," *J. Inherit. Metab. Dis.* 16:46-54 (1993).

Sramek and Frerman, "Purification and properties of *Escherichia coli* Coenzyme A-transferase," *Arch. Biochem. Biophys.* 171(1):14-26 (1975).
St. Maurice et al., "Flavodoxin:quinone reductase (FqrB): a redox partner of pyruvate:ferredoxin oxidoreductase that reversibly couples pyruvate oxidation to NADPH production in *Helicobacter pylori* and *Campylobacter jejuni*," *J. Bacteriol.* 189:4764-4773 (2007).
Stadtman, "The enzyme synthesis of β-alanyl Coenzyme A," *J. Plant Chem. Soc.* 77:5765-5766 (1955).
Stanley et al., "Expression and stereochemical and isotope effect studies of active 4-oxalocrotonate decarboxylase," *Biochemistry* 39:718-726 (2000).
Starai et al., "Acetate excretion during growth of *salmonella* enerica on ethanolamine requires phosphotransacetylase (EutD) activity, and acetate recapture requires acetyl-CoA synthetase (Acs) and phosphotransacetylase (Pta) activities," *Microbiology* 151:3793-3801 (2005).
Starai et al., "Residue Leu-641 of Acetyl-CoA synthetase is critical for the acetylation of residue Lys-609 by the Protein acetyltransferase enzyme of *Salmonella enterica*," *J. Biol. Chem.* 280(28):26200-26205 (2005).
Starnes et al., "Threonine-sensitive aspartokinase-homoserine dehydrogenase complex, amino acid composition, molecular weight, and subunit composition of the complex," *Biochemistry* 11:677-687 (1973).
Steen et al., "Metabolic engineering of *Saccharomyces cerevisiae* for the production of n-butanol," *Microb. Cell Fact.* 7:36 (provided electronically by publisher as pp. 1-8) (2008).
Steffan and McAlister-Henn, "Isolation and characterization of the yeast gene encoding the MDH3 isozyme of malate dehydrogenase," *J. Biol. Chem.* 267:24708-24715 (1992).
Steinbüchel and Schlegel, "NAD-linked L(+)-lactate dehydrogenase from the strict aerobe *alcaligenes eutrophus*. 2. Kinetic properties and inhibition by oxaloacetate," *Eur. J. Biochem.* 130(2):329-334 (1983).
Steinbuchel and Schlegel, "A multifunctional fermentative alcohol dehydrogenase from the strict aerobe *Alcaligenes eutrophus*: purification and properties," *Eur. J. Biochem.* 141:555-564 (1984).
Stim-Herndon et al., "Characterization of an acetyl-CoA C-acetyltransferase (thiolase) gene from *Clostridium acetobutylicum* ATCC 824," *Gene* 154(1):81-85 (1995).
Stirling and Perry, "Purification and Properties of a Nicotinamide Adenine Dinucleotide-Linked Cyclohexanol Dehydrogenase from a cocardia Species," *Curr. Microbiol.* 4:37-40 (1980).
Stokell et al., "Probing the roles of key residues in the unique regulatory NADH binding site of type II citrate synthase of *Escherichia coli*," *J. Biol. Chem.* 278:35435-35443 (2003).
Stols and Donnelly, "Production of succinic acid through overexpression of $NAD^+$-dependent malic enzyme in an *Escherichia coli* mutant," *Appl. Environ. Microbiol.* 63(7):2695-2701 (1997).
Stols et al., "Expression of *Ascaris suum* malic enzyme in a mutant *Escherichia coli* allows production of succinic acid from glucose," *Appl. Biochem. Biotechnol.* 63-65: 153-158 (1997).
Stols et al., "New vectors for co-expression of proteins: Structure of *Bacillus subtilis* ScoAB obtained by High-throughput protocols," *Protein Expr. Purif.* 53:396-403 (2007).
Stoyan et al., "Cloning, sequencing and overexpression of the leucine dehydrogenase gene from *Bacillus cereus*," J. Biotechnol. 54:77-80 (1997).
Straathof et al., "Feasibility of acrylic acid production by fermentation," *Appl. Microbiol. Biotechnol.* 67:727-734 (2005).
Strauss and Fuchs, "Enzymes of a novel autotrophic $CO_2$ fixation pathway in the phototrophic bacterium *Chloroflexus aurantiacus*, the 3-hydroxypropionate cycle," *Eur. J. Biochem.* 215:633-643 (1993).
Stringfellow et al., "Sequence of the *Escherichia coli* C homoprotocatechuic acid degradative operon completed with that of the 2,4-dihydroxyhept-2-ene-1,7-dioicic acide aldolase-encoding gene (hpdH)," Gene 166:73-76 (1995).
Suarez De Mata et al., "Propionyl-CoA condensing enzyme from *Ascaris* muscle mitochondria. I. Isolation and characterization of multiple forms," *Arch. Biochem. Biophys.* 285(1):158-165 (1991).

(56) References Cited

OTHER PUBLICATIONS

Suarez De Mata et al., "Propionyl-CoA condensing enzyme from *Ascaris* muscle mitochondria. II. Coenzyme A modulation," *Arch. Biochem. Biophys.* 285:166-171 (1991).

Suda et al., "Purification and properties of α-ketoadipate reductase, a newly discovered enzyme from human placenta," *Arch. Biochem. Biophys.* 176(2):610-620 (1976).

Suda et al., "Subcellular localization and tissue distribution of α-ketoadipate reduction and oxidation in the rat," *Biochem. Biophys. Res. Commun.* 77(2):586-591 (1977).

Suematsu et al., "Molecular cloning and functional expression of rat liver cytosolic acetyl-CoA hydrolase," *Eur. J. Biochem.* 268(9):2700-2709 (2001).

Sulzenbacher et al., "Crystal structure of *E.coli* alcohol dehydrogenase YqhD: evidence of a covalently modified NADP Coenzyme," *J. Mol. Biol.* 342(2):489-502 (2004).

Suzuki et al., "Properties and metabolic role of mesaconate hydratase of an aerobic bacterium," *J. Biochem.* 81:1917-1925 (1977).

Suzuki, "Phospotransacetylase of *Escherichia coli* B., activation by pyruvate and inhibition by NADH and certain nucleotides," *Biochem. Biophys. Acta* 191:559-569 (1969).

Svensson et al., "Characterization and isolation of enzymes that hydrolyze short-chain acyl-CoA in rat-liver mitochondria," *Eur. J. Biochem.* 238(2):526-531 (1996).

Svetlitchnyi et al., "A functional Ni-Ni-[4Fe-4S] cluster in the monomeric acetyl-CoA synthase from *Carboxydothermus hydrogenoformans*," *Proc. Natl. Acad. Sci. U.S.A.* 101(2):446-451 (2004).

Switzer, "Glutamate mutase," in Dolphin, D. ed., *Vitamin B$_{12}$ (Vol. 2: Biochemistry and Medicine)*, Wiley-Interscience: New York, p. 289-305 (1982).

Tae-Kang et al., "Purification and characterization of a cyclohexanol dehydrogenase from *Rhodococcus* sp. TK6," *J. Microbiol. Biotechnol.* 12:39-45 (2002).

Tahlan et al., "Two sets of paralogous genes encode the enzymes involved in the early stages of clavulanic acid and clavam metabolite biosynthesis in *Streptomyces clavuligerus*," *Antimicrob. Agents Chemother.* 48(3):930-939 (2004).

Takacs et al., "Formate hydrogenlyase in the hyperthermophilic archaeon, *Thermococcus litoralis*," *BMC Microbiol.* 8:88 (2008).

Takagi et al, "Purification, crystallization, and molecular properties of aspartase from *Pseudomonas fluorescens*," *J. Biochem.* 96(2):545-552 (1984).

Takagi et al., "Isolation of a versatile *Serratia marcescens* mutant as a host and molecular cloning of the aspartase gene," *J. Bacteriol.* 161:1-6 (1985).

Takagi et al., "Cloning and nucleotide sequence of the aspartase gene of *Pseudomonas fluorescens*," *J. Biochem.* 100(3):697-705 (1986).

Takahashi and Yamada, "Metabolic pathways for cytoxic and end product formation from glutamate- and aspartate-containing peptides by *Porphyromonas gingivalis*," *J. Bacteriol.* 182:4704-4710 (2000).

Takahashi-Abbe et al., "Biochemical and functional properties of a pyruvate formate-lyase (PFL)-activating system in *Streptococcus mutans*," *Oral Microbiol. Immunol.* 18:293-297 (2003).

Takanashi et al., "Characterization of a novel 3-hydroxybutyrate dehydrogenase from *Ralstonia pickettii* T1," *Antonie van Leeuwnhoek* 95(3):249-262 (2009).

Takatsuka et al., "Gene cloning and molecular characterization of lysine decarboxylase from *Selenomonas ruminantium* delineate its evolutionary relationship to ornithine decarboxylases from eukaryotes," *J. Bacteriol.* 182:6732-6741 (2000).

Takatsuka et al., "Identification of the amino acid residues conferring substrate specificity upon *Selenomonas ruminantium* lysine decarboxylase," *Bioxci. Biotechnol. Biochem.* 63:1843-1846 (1999).

Tallant and Krzycki, "Coenzyme M methylase activity of the 480-kilodalton corrinoid protein from *Methanosarcina barkeri*," *J. Bacteriol.* 178(5):1295-1301 (1996).

Tallant and Krzycki, "Methylthiol:Coenzyme M Methyltransferase from *Methanosarcina barkeri*, an enzyme of methanogenesis from dimethylsulfide and methylmercaptopropionate," *J. Bacteriol.* 179(22):6902-6911 (1997).

Tallant et al., "The MtsA subunit of the methylthiol:Coenzyme M methyltransferase of *Methanosarcina barkeri* catalyses both half-reactions of corrinoid-dependent dimethylsulfide: Coenzyme M methyl transfer," *J. Biol. Chem.* 276(6):4485-4493 (2001).

Tamaki et al., "Purification, properties, and sequencing of aminoisobutyrate aminotransferases from rat liver," *Methods Enzymol.* 324:376-389 (2000).

Tanaka et al., "Cloning and characterization of a human orthologue of testis-specific succinyl CoA: 3-oxo acid CoA transferase (Scot-t) cDNA," *Mol. Hum. Reprod.* 8:16-23 (2002).

Tanaka et al., "Lysine decarboxylase of *Vibrio parahaemolyticus*: kinetics of transcription and role in acid resistance," *J. Appl. Microbiol.* 104:1283-1293 (2008).

Tang et al., "Identification of a novel pyridoxal 5'-phosphaste binding site in adenosylcobalamin-dependent lysine 5,6-aminomutase from *Porphyromonas gingivalis*," *Biochemistry* 41(27):8767-8776 (2002).

Tani et al., "Thermostable NADP$^+$-dependent medium-chain alcohol dehydrogenase from *Acinetobacter* sp. strain M-1: purification and characterization and gene expression in *Escherichia coli*," *Appl. Environ. Microbiol.* 66(12):5231-5235 (2000).

Tanizawa et al., "The primary structure of thermostable D-amino acid aminotransferase from a thermophilic *Bacillus* species and its correlation with L-amino acid aminotransferases," *J. Biol. Chem.* 264(5):2450-2454 (1989).

Tanous et al., "Glutamate dehydrogenase activity can be transmitted naturally to *Lactococcus lactis* strains to stimulate amino acid conversion to aroma compounds," *Appl. Environ. Microbiol.* 72(2):1402-1409 (2006).

Teipel et al., "The substrate specificity of fumarase," *J. Biol. Chem.* 243:5684-5694 (1968).

Ter Schure et al., "Pyruvate decarboxylase catalyzes decarboxylation of branched-chain 2-oxo acids but is not essential for fusel alcohol production by *Saccharomyces cerevisiae*," *Appl. Environ. Microbiol.* 64:1303-1307 (1998).

Teufel et al., "3-hydroxypropionyl-Coenzyme A dehydratase and acryloyl-Coenzyme A reductase, enzymes of the autotrophic 3-hydroxypropionate/4-hydroxybutyrate cycle in the Sulfolbales," *J. Bacteriol.* 191:4572-4581 (2009).

Thanos and Simon, "Electro-enzymic viologen-mediated stereospecific reduction of 2-enoates with free and immobilized enoate reductase on cellulose filters or modified carbon electrodes," *J. Biotechnol.* 6:13-29 (1987).

Thornton et al., "Primary structure of the monomer of the 12S subunit of transcarboxylase as deduced from DNA and characterizatio nof the product expressed in *Escherichia coli*," J. Bacteriol. 175:5301-5308 (1993).

Tian et al., "Variant tricarboxylic acid cycle in *Mycobacterium tuberculosis*: identification of α-ketoglutarate decarboxylase," *Proc. Natl. Acad. Sci. U.S.A.* 102:10670-10675 (2005).

Tischer et al., "Purification and Some Properties of a Hitherto-Unknown Enzyme Reducing the Carbon-Carbon Double Bond of α,β-Unsaturated Carboxylate Anions," *Eur. J. Biochem.* 97(1):103-112 (1979).

Tobimatsu et al., "Molecular cloning, Sequencing and Characterization of the Genes for Adenosylcobalamin-deptendent Diol Dehydratase of *Klebsiella pneumoniae*," *Biosci. Biotechnol. Biochem.* 62(9):1744-1777 (1998).

Tobimatsu et al., "Molecular cloning, Sequencing and Expression of the Genes Encoding Adenosylcobalamin-dependent Diol Dehydrase of *Klebsiella oxytoca*," *J. Biol. Chem.* 270(13):7142-7148 (1995).

Tobin et al., "Localization of the Lysine ε-Aminotransferase (lat) and δ-Aminoadipyl)-L-Cysteinyl-D-Valine Synthetase (pcbAB) Genes from *Streptomyces clavuligerus* and Production of Lysine ε-Aminotransferase Activity in *Escherichia coli*," *J. Bacteriol.* 173(19):6223-6229 (1991).

Toraya et al., "Substrate Specificity of Coenzyme B$_{12}$-Dependent Diol Dehydrase: Glycerol as Both a Good Substrate and a Potent Inactivator," *Biochem. Biophys. Res. Commun.* 69:475-480 (1976).

(56) References Cited

OTHER PUBLICATIONS

Toth et al., "The ald Gene, Encoding a Coenzyme A-Acylating Aldehyde Dehydrogenase, Distinguishes *Clostridium beijerinckii* and Two Other Solvent-Producing Clostridia from *Clostridium acetobutylicum*," *App. Environ. Microbiol.* 65(11):4973-4980 (1999).

Tretter and Adam-Vizi, "Alpha-ketoglutarate dehydrogenase: a target and generator of oxidative stress," *Philos. Trans. R. Soc. B* 360:2335-2345 (2006).

Tsao et al., "Production of multifunctional organic acids from renewable resources," *Adv. Biochem. Eng. Biotechnol.* 65:243-280 (1999).

Tseng et al., "Metabolic Engineering of *Escherichia coli* for Enhanced Production of (R)-and (S)-3-Hydroxybutyrate," *App. Environ. Microbiol.* 75(10):3137-3145 (2009).

Tseng et al., "Oxygen- and growth rate-dependent regulation of *Escherichia coli* fumarase (FumA, FumB, and BumC) activity," *J. Bacteriol.* 183(2):461-467 (2001).

Tucci and Martin, "A novel prokaryotic trans-2-enoyl-CoA reductase from the spirochete *Treponema denticola*," *FEBS Lett.* 581(8):1561-1566 (2007).

Twarog and Wolfe, "Role of butyryl phosphate in the energy metabolism of *Clostridium* tetanomorphum," *J. Bacteriol.* 86:112-117 (1963).

Two pages from URL: toxnet.nlm.nih.gov/cgi-bin/sis/search/f?./temp/~FwAsma:1:BASIC (printed Feb. 17, 2010).

Uchiyama et al., "Identification of the 4-Hydroxycinnamate Decarboxylase (PAD) Gene of *Klebsiella oxytoca*," Biosci. Biotechnol. Biochem. 72: 116-123 (2008).

Ulaganathan et al., "Structure of *Staphylococcus aureus*1,4-dihydroxy-2-naphthoyl-CoA synthase (MenB) in complex with acetoacetyl-CoA," *Acta. Crystallogr. Sect. F. Struct. Biol. Cryst. Commun.* 63(Pt 11):908-913 (2007).

Umbarger and Brown, "Threonine deamination in *Escherichia coli*. II. Evidence fro two L-threonine deaminases," *J. Bacteriol.* 73(1):105-112 (1957).

Underwood et al., "Genetic Changes to Optimize Carbon Partitioning between Ethanol and Biosynthesis in Ethanologenic *Escherichia coli*," *App. Environ. Microbiol.* 68(12):6263-6272 (2002).

Urbance et al., "Evaluation of succinic acid continuous and repeat-batch biofilm fermentation by *Actinobacillus succinogenes* using plastic composite support bioreactors," *Appl. Microbiol. Biotechnol.* 65(6):664-670 (2004).

Uttaro and Opperdoes, "Purification and characterisation of a novel isopropanol dehydrogenase from Phytomonas sp.," *Mol. Biochem. Parasitol.* 85:213-219 (1997).

Vadali et al., "Enhanced Isoamyl Acetate Production upon Manipulation of the Acetyl-CoA node in *Escherichia coli*," *Biotech. Prog.* 20:692-697 (2004).

Vadali et al., "Production of isoamyl acetate in ackA-pta and/or ldh mutants of *E. coli* with overexpression of yeast ATF2," *Appl. Microbiol. Biotechnol.* 63:698-704 (2004).

Vadali et al., "Cofactor engineering of intercellular CoA/acetyl-CoA and its effect on metabolic flux redistribution in *Escherichia coli*," *Metab Eng.* 6(2): 133-139 (2004).

Valdes-Hevia and Gancedo, "Isolation and characterization of the gene encoding phosphoenolpyruvate carboxykinase from *Saccharomyces cerevisiae*," *FEBS Lett.* 258:313-316 (1989).

Valentin et al., "Metabolic pathway for biosynthesis of poly(3-hydroxybutyrate-co-4-hydroxybutyrate) from 4-hydroxybutyrate by *Alcaligenes eutrophus*," Eur. J. Biochem. 227(1-2):43-60 (1995).

Valentine and Wolfe, "Purification and role of phosphotransbutyrylase," *J. Biol. Chem.* 235:1948-1952 (1960).

Vamecq et al., "The microsomal dicarboxylyl-CoA synthetase," *Biochem. J.* 230(3):683-693 (1985).

Van Der Voorhorst et al., "Genetic and biochemcial characterization of a short-chain alcohol dehydrogenase from the hyperthermophilic archaeon *Pyrococcus furiosus*," *Eur. J. Biochem.* 268:3062-3068 (2001).

Van Der Westhuizen, et al., "Autolytic Activity and Butanol tolerance of *Clostridium acetobutylicum*," *Appl. Environ. Microbiol.* 44:1277-1281 (1982).

Van Grinsven et al., "Acetate:succinate CoA-transferase in the hydrogenosomes of *Trichomonas vaginalis*: identification and characterization," *J. Biol. Chem.* 283:1411-1418 (2008).

Van Loon and Young, "Intracellular sorting of alcohol dehydregenase isoenzymes in yeast: a cytosolic location oreflects absence of an amino-terminal targeting sequence for the mitochondrion," *EMBO J.* 5:161-165 (1986).

Van Maris et al., "Directed evolution of pyruvate decarboxylase-negative *Saccharomyces cerevisiae*, yielding a $C_2$-independent, glucose-tolerant, and pyruvate-hyperproducing yeast," *Appl. Environ. Microbiol.* 7:159-166 (2004).

Vanderwinkel et al., "Growth of *Escherichia coli* on fatty acids: requirement for Coenzyme A transferase activity," *Biochem. Biophys. Res. Commun.* 33(6):902-908 (1968).

Vanrolleghem et al., "Validation of a Metabolic Network for *Saccharomyces cerevisiae* Using Mixed Substrate Studies," *Biotechnol. Prog.* 12(4):434-448 (1996).

Varadarajan and Miller, "Catalytic Upgrading of Fermentation-Derived Organic Acids," *Biotechnol. Prog.* 15:845-854 (1999).

Varma and Palsson, "Metabolic Flux Balancing: Basic Concepts, Scientific and Practical Use," *Biotechnology* 12:994-998 (1994).

Vazquez et al., "Phosphtransbutyrylase expression in *Bacillus megaterium*," *Curr. Microbiol.* 42:345-349 (2001).

Vega et al., "The Biological Production of Ethanol from Synthesis Gas," *Appl. Biochem. Biotechnol.* 20/21:781-797 (1989).

Vellanki et al., "Expression of hepatitis B surface antigen in *Saccharomyces cerevisiae* utilizing glyceraldehyde-3-phosphate dehydrogenase promoter of *Pichia pastoris*," *Biotechnol. Lett.* 29(2):313-318 (2007).

Vemuri et al. "Succinate production in dual-phase *Escherichia coli* fermentations depends on the time of transition from aerobic to anaerobic conditions," J. Ind. Microbiol. Biotechnol. 28:325-332 (2002).

Vemuri et al., "Effects of growth mode and pyruvate carboxylase on succinic acid production by metabolically engineered strains of *Escherichia coli*," Appl. Environ. Microbiol. 68(4):1715-1727 (2002).

Vemuri, et al. "Succinate production in dual-phase *Escherichia coli* fermentations depends on the time of transition from aerobic to anaerobic conditions," *J. Ind. Microbiol. Biotechnol.* 28:325-332 (2002).

Verhaert et al., "Enzyme kinetics in reversed micelles. 2. Behaviour of enoate reductase," *Eur. J. Biochem.* 187:73-79 (1990).

Vernal et al., "Cloning and heterologous expression of a broad specificity aminotransferase of *Leishmania mexicana* promastigotes," *FEMS Microbiol. Lett.* 229:217-222 (2003).

Vernal et al., "Isolation partial characterization of a broad specificity aminotransferase from *leishmania mexicana* promastigotes," *Mol. Biochem. Parasitol.* 96:83-92 (1998).

Vey et al., "Structural basis for glycyl radical formation by pyruvate formate-lyase activating enzyme," *Proc. Natl. Acad. Sci. U.S.A.* 105:16137-16141 (2008).

Vrijbloed et al., "Insertional inactivation of methylmalonyl Coenzyme A (CoA) mutase and isobutyryl-CoA mutase genes in *Streptomyces* cinnamonensis: influence on polyketide antibiotic biosynthesis," *J. Bacteriol.* 181(18):5600-5605 (1999).

Wakil et al., "Studies on the fatty acid oxidizing system of animal tissues. VI. β-Hydroxyacyl Coenzyme A dehydrogenase," *J. Biol. Chem.* 207(2):631-638 (1954).

Walker et al., "Yeast pyruvate carboxylase: identification of two genes encoding isoenzymes," *Biochem. Biophys. Res. Commun.* 176:1210-1217 (2007).

Walter et al., "Molecular characterization of two *Clostridium acetobutylicum* ATCC 824 butanol dehydrogenase isozyme genes," *J. Bacteriol.* 174(22):7149-7158 (1992).

Walter et al., "Sequence and arrangement of two genes of the butyrate-synthesis pathway of *Clostridium acetobutylicum* ATCC 824," *Gene* 134(1):107-111 (1993).

Wang and Barker, "Purification and Properties of L-citramalate hydrolase," *J. Biol. Chem.* 244(10):2516-2526 (1969).

(56) References Cited

OTHER PUBLICATIONS

Wang and Seah, "Determination of the metal ion dependence and substrate specificty of a hydratase involve din the degradation pathway of biphenyl/chlorobiphenyl," *FEBS J.* 272: 966-974 (2005).
Wang et al, "Molecular cloning and functional identification of a novel phenylacetyl-CoA ligase gene from *Penicillium chrysogenum*," *Biochem. Biopyhs. Res. Commun.* 360(2):453-458 (2007).
Wang et al., "The primary structure of branched-chain α-oxo acid dehydrogenase from *Bacillus subtilis* and its similarity to other α-oxo acid dehydrogenases," *Eur. J. Biochem.* 213:1091-1099 (1993).
Wang et al., "Bioconversion of fumaric acid to succinic acid by recombinant *E. coli*," *App. Biochem. Biotechnol.* 70-72: 919-928 (1998).
Wang et al., "Cloning, Sequencing, and Expression of the Pyruvate Carboxylase Gene in *Lactococcus lactis* subsp. lactis C2," *App. Environ. Microbiol.* 66(3):1223-1227 (2000).
Wang et al., "Expression of galactose permease and pyruvate carboxylase in *Escherichia coli* ptsG mutant increases the growth rate and succinate yield under anaerobic conditions," *Biotechnol. Lett.* 28(2):89-93 (2006).
Wang et al., "Site-directed mutagenesis of the phosphorylatable serine ($Ser^8$) in $C_4$ phosphoenolpyruvate carboxylase from sorghum. The effect of negative charge at position 8," *J. Biol. Chem.* 267:16759-16762. (1992).
Wanner and Tressl, "Purification and characterization of two enone reductases from *Saccharomyces* cerevisia," *Eur. J. Biochem.* 255(1):271-278 (1998).
Ward et al., "Molecular analysis of the rele of two aromatic aminotransferases and a broad-specificity aminotransferase in the aromatic amino acid metabolism of *Pyococcus furiosus*," *Archaea* 1:133-141 (2002).
Weaver, "Structure of free fumarase C from *Escherichia coli*," *Acta. Crystallogr. D. Biol. Crystallogr.* 61(Pt 10):1395-1401 (2005).
Weidner and Sawers, "Molecular characterization of the Genes Encoding Pyruvate Formate-Lyase and Its Activating enzyme of *clostridium* pasteruianum," *J. Bacteriol.* 178(8):2440-2444 (1996).
Welch et al., "Purification and Characterization of the NADH-Dependent Butanol Dehydrogenase from *Clostridium acetobutylicum* (ATCC 824)," *Arch. Biochem. Biophys.* 273(2):309-318 (1989).
Westin et al., "The identification of a succinyl-CoA thioesterase suggests a novel pathway for succinate production in peroxisomes," *J. Biol. Chem.* 280(46):38125-38132 (2005).
Wexler et al., "A wide host-range metagenomic library from a waste water treatment plant yields a novel alcohol/aldehyde dehdrogenase," *Environ. Microbiol.* 7:1917-1926 (2006).
Whalen and Berg, "Analysis of an avtA::Mu d1(Ap lac) Mutant: Metabolic Role of Transaminase C," *J. Bacteriol.* 150(2):739-746 (1982).
Whalen and Berg, "Gratuitous repression of avtA in *Escherichia coli* and *Salmonella* typhimurium," *J. Bacteriol.* 158(2):571-574 (1984).
White et al., "Long-chain alcohol production by yeasts," *7th Int. Symp. Yeasts* S465-S470 (1989).
White et al., "The structural biology of type II fatty acid biosynthesis," *Ann. Rev. Biochem.* 74:791-831 (2005).
Wiesenborn et al., "Coenzyme A Transferase from *clostridium acetobutylicum* ATCC 824 and Its Role in the Uptake of Acids," *Appl. Environ. Microbiol.* 55(2):323-329 (1989).
Wiesenborn et al., "Phosphotransbutyrylase from *clostridium acetobutylicum* ATCC 824 and its role in acidogenesis," *Appl. Environ. Microbiol.* 55:317-322 (1989).
Wilkie and Warren, "Recombinant expression, purification, and characterization of three isoenzymes of aspartate aminotransferase from *Arabidopsis thaliana*," *Protein Expr. Purif.* 12:381-389 (1998).
Wilks et al., "A specific, Highly Active Malate Dehydrogenase by Redesign of a Lactate Dehydrogenase Framework," *Science* 242:1541-1544 (1988).
Wilks et al., "Design of a Specific Phenyllactate Dehydrogenase by Peptide Loop Exchange on the *Bacillus stearothermophilus* Lactate Dehydrogenase Framework," *Biochemistry* 31:7802-7806 (1992).
Wilks et al., "Designs for a Broad Substrate Specificity Keto Acid Dehydrogenase," *Biochemistry* 29:8587-8591 (1990).
Willke and Vorlop, "Biotechnological production of itaconic acid," *Appl. Microbiol. Biotechnol.* 56(3-4):289-295 (2001).
Willke and Vorlop, "Industrial bioconversion of renewable resources as an alternative to conventional chemistry," *Appl. Microbiol. Biotechnol.* 66:131-142 (2004).
Winkler et al., "A new type of a multifunctional β-oxidation enzyme in *euglena*," *Plant. Physiol.* 131(2):753-762 (2003).
Winzer et al., "Differential regulation of two thiolase genes from *Clostridium acetobutylicum* DSM 792," *J. Mol. Microbiol. Biotechnol.* 2(4):531-541 (2000).
Witkowski et al., "Conversion of β-ketoacyl synthase to a Malonyl Decarboxylase by replacement of the active cysteine with glutamine," *Biochemistry* 38:11643-11650 (1999).
Wolff and Kenealy, "Purification and characterization of the oxygen-sensitive 4-hydroxybutanoate dehydrogenase from *Clostridium kluyveri*," *Protein Expr. Purif.* 6:206-212 (1995).
Wong et al., "Molecular Properties of Pyruvate Formate-Lyase Activating Enzyme," *Biochemistry* 32:14102-14110 (1993).
Woods, "Two biochemically distinct classes of fumarase in *Escherichia coli*," Biochim. Biophys. Acta 954(1):14-26 (1988).
Wynn et al., "Chaperonins GroEL and GroES promote assembly of heterotetramers ($α_2β_2$) of mammalian mitochondrial branched-chain α-keto acid decarboxylase in *Escherichia coli*," *J. Biol. Chem.* 267:12400-12403 (1992).
Wynn et al., "Cloning and expression in *Escherichia coli* of mature E1 β subunit of bovine mitochondrial branched-chain α-keto acid dehydrogenase complex. Mapping of the E1 β-binding region on E2," *J. Biol. Chem.* 267:1881-1887 (1992).
Yabutani et al., "Analysis of β-ketothiolase and acetoacetyl-CoA reductase genes of a methylotrophic bacterium, *Paracoccus denitrificans*, and their expression in *Escherichia coli*," *FEMS Microbiol. Lett.* 133:85-90 (1995).
Yagi et al., "Aspartate: 2-oxoglutarate aminotransferase from bakers' yeast: crystallization and characterization," *J. Biochem.* 92(1):35-43 (1982).
Yagi et al., "Crystallization and properties of aspartate aminotransferase from *Escherichia coli* B," *FEBS Lett.* 100(1):81-84 (1979).
Yagi et al., "Glutamate-aspartate transaminase from microorganisms," *Methods Enzymol.* 113:83-89 (1985).
Yamamoto et al., "Carboxylation reaction catalyzed by 2-oxoglutarate:ferredoxin oxidoreductases from *Hydrogenobacter thermophilus*," *Extremophiles* 14:79-85 (2010).
Yamamoto et al., "Purification and Properties of NADP-dependent Formate Dehydrogenase from *Clostridium* thermoaceticum, a tungsten-Selenium-Iron Protein," *J. Biol. Chem.* 258(3):1826-1832 (1983).
Yamano et al., "Construction of a brewer's yeast having α-acetolactate decarboxylase gene from *acetobacter aceti* ssp. xylinum integrated in the genome," *J. Biotechnol.* 32:173-178 (1994).
Yan and Chen, "Coenzyme A-acylating aldehyde dehydrogenase from *Clostridium beijerinckii* NRRL B592," *Appl. Environ. Microbiol.* 56:2591-2599 (1990).
Yang et al., "Aspartate Dehydrogenase, a Novel Enzyme Identified from Structural and Functional Studies of TM1643," *J. Biol. Chem.* 278(10):8804-8808 (2003).
Yang et al., "Effect of Variation of *Klebsiella pneumoniae* Acetolactate Synthase Expression on Metabolic Flux Redistribution in *Escherichia coli*," *Biotechnol. Bioeng.* 69(2)150-159 (2000).
Yang et al., "Metabolic Flux Analysis of *Escherichia coli* Deficient in the Acetate Production Pathway and Expressing the *Bacillus subtilis* Acetolactate Synthase," *Metab. Eng.* 1(1):26-34 (1999).
Yang et al., "Nucleotide sequence of the fadA gene. Primary structure of 3-ketoacyl-Coenzyme A thiolase from *Escherichia coli* and the structural organization of the fadAB operon," *J. Biol. Chem.* 265(18):10424-10429 (1990).
Yang et al., "Nucleotide sequence of the fadA gene. Primary structure of 3-ketoacyl-Coenzyme A thiolase from *Escherichia coli* and the structural organization of the fadAB operon," *J. Biol. Chem.* 266(24):16255 (1991).

(56) References Cited

OTHER PUBLICATIONS

Yang et al., "Nucleotide sequence of the promoter and fadB gene of the fadBA operon and primary structure of the multifunctional fatty acid oxidation protein from *Escherichia coli*," *Biochemistry* 30(27):6788-6795 (1991).
Yang et al., "Redistribution of Metabolic Fluxes in *Escherichia coli* with Fermentative Lactate Dehydrogenase Overexpression and Deletion," *Metab. Eng.* 1:141-152 (1999).
Yang et al., "The effects of feed and intracellular pyruvate levels on the redistribution of metabolic fluxes in *Escherichia coli*," *Metab Eng.* 3(2):115-123 (2001).
Yang, "Location of the fadBA operon on the physical map of *Escherichia coli*," *J. Bacteriol.* 173(23):7405-7406 (1991).
Yano et al., "Directed evolution of an aspartate aminotransferase with new substrate specificities," *Proc. Natl. Acad. Sci U.S.A.* 95:5511-5515 (1998).
Yarlett et al., "*Trichomonas vaginalis*: characterization of ornithine decarboxylase," *Biochem. J.* 293(Pt2):487-493 (1993).
Yeh and Ornston, Evolutionarily Homologous $\alpha_2\beta_2$ Oligomeric Structures in β-Ketoadipate Succinyl-CoA Transferases from *Acinetobacter calcoaceticus* and *Pseudomonas putida, J. Biol. Chem.* 256(4):1565-1569 (1981).
Ylianttila et al., "Crystal Structure of Yeast Peroxisomal Multifunctional Enzyme: Structural Basis for Substrate Specificity of (3R)-hydroxyacyl-CoA Dehydrogenase Units," *J. Mol. Biol.* 258:1286-1295 (2006).
Ylianttila et al., "Site-directed mutagenesis to enable and improve crystallizability of *candida tropicalis* (3R)-hydroxyacyl-CoA dehydrogenase," *Biochem. Biophys. Res. Commun.* 324:25-30 (2004).
Yoshida et al., "The Structures of L-Rhamnose Isomerase from *Pseudomonas stutzeri* in Complexes with L-Rhamnose and D-Allose Provide Insights into Broad Substrate Specificity," *J. Mol. Biol.* 365:1505-1516 (2007).
Yoshimoto, et al., "Isolation and Characterization of the ATF2 Gene Encoding Alcohol Acetyltransferase II in the Bottom Fermenting Yeast *Saccharomyces pastorianus*," *Yeast* 15:409-417 (1999).
Yoshioka and Hashimoto, "Ester formation by Alcohol Acetyltransferase from Brewers' Yeast," *Agric. Biol. Chem.* 45:2183-2190 (1981).
Youngleson et al., "Homology between hydroxybutyryl and hydroxyacyl Coenzyme A dehydrogenase enzymes from *Clostridium acetobutylicum* fermentation and vertebrate fatty acid β-oxidation pathways," *J. Bacteriol.* 171(12):6800-6807 (1989).
Yun et al., "The genes for anabolic 2-oxoglutarate: ferredoxin oxidoreductse from *hydrogenobacter thermophilus* TK-6," *Biochem. Biophys. Res. Commun.* 282(2):589-594 (2001).
Yun et al., "ω-Amino acid:pyruvate transaminase from *Alcaligenes denitrificans* Y2k-2: a new catalyst for kinetic resolution of β-amino acids and amines," *Appl. Environ. Microbiol.* 70(4):2529-2534 (2004).
Yun et al., "Enhancement of lactate and succinate formation in adhE or pta-ackA mutants of NADH dehydrogenase-deficient *Escherichia coli*," *J. Appl. Microbiol.* 99(6):1404-1412 (2005).
Zeiher and Randall, "Identification and characterization of Mitochondrial Acetyl-Coenzyme A Hydrolase from *Pisum sativum* L. Seedlings," *Plant. Physiol.* 94:20-27 (1990).
Zeikus et al., "Biotechnology of succinic acid production and markets for derived industrial products," *Appl. Microbiol. Biotechnol.* 51:545-552 (1999).
Zelle et al., "Malic acid production by *Saccharomyces cerevisiae*: engineering of pyruvate carboxylation, oxaloacetate reduction, and malate export," *Appl. Environ. Microbiol.* 74(9):2766-2777 (2008).
Zerbe-Burkhardt et al., "Cloning, sequencing, expression, and insertional inactivation of the gene for the large subunit of the Coenzyme B12-dependent isobutyryl-CoA mutase from *Streptomyces cinnamonensis*," *J. Biol. Chem.* 273(11):6508-6517 (1998).
Zhang et al., "2-Oxoacid:Ferredoxin Oxidoreductase from the thermoacidophilic Archaeon, *sulfolobus* sp. Strain 7," *J. Biochem.* 120:587-599 (1996).
Zhang et al., "Genes encoding acyl-CoA dehydrogenase (AcdH) homologues from *Streptomyces* coelicolor and *Streptomyces avermitilis* provide insights into the metabolism of small branched-chain fayy acids and marcrolide antibiotic production," *Microbiol.* 145 (Pt 9):2323-2334 (1999).
Zhang et al., "Isolation and properties of a levo-lactonase from *Fusarium proliferatum* ECU2002: a robust biocatalyst for production of chiral lactones," *Appl. Microbiol. Biotechnol.* 75:1087-1094 (2007).
Zhang et al., "Molecular basis for the inhibition of the carboxyltransferase domain of acetyl-Coenzyme-A carboxylase by haloxfop and dicofop," *Proc. Natl. Acad. Sci. U.S.A.* 101:5910-5915 (2004).
Zhao and Winkler, "A novel α-ketoglutarate reductase activity of the serA-encoded 3-phosphoglycerate dehydrogenase of *Escherichia coli* K-12 and its possible implications for human 2-hydroxyglutaric aciduria," *J. Bacteriol.* 178(1):232-239 (1996).
Zhou et al., "Comparison of fumaric acid production by *Rhizopus oryzae* using different neutralizing agents," *Bioproc. Biosyst. Eng.* 25(3):179-181 (2002).
Zhou et al., "Engineering a native homoethanol pathway in *Escherichia coli* B for ethanol production," *Biotechnol. Lett.* 30:335-342 (2008).
Zhou et al., "The remarkable structural and functional organization of the eukaryotic pyruvate dehydrogenase complexes," Proc. Natl. Acad. Sci. U.S.A. 98:14802-14807 (2001).
Zhuang et al., "The YbgC protein encoded by the ybgC gene of the tol-pal gene cluster of *Haemophilus influenzae* catalyzes acyl-Coenzyme A thioester hydrolysis," *FEBS Lett.* 516(1-3):161-163 (2002).
Zou et al., "Metabolic engineering for microbial production and applications of copolyesters consisting of 3-hydroxybutyrate and medium-chain-length 3-hydroxyalkanoates," *Macromol. Biosci.* 7:174-182 (2007).

* cited by examiner

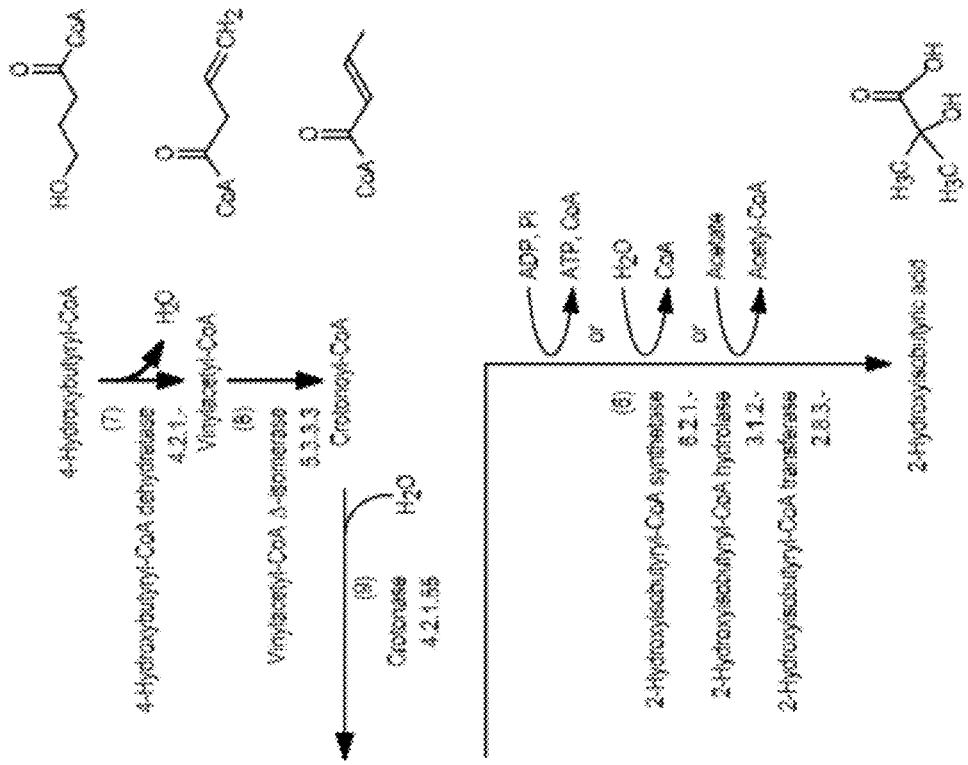
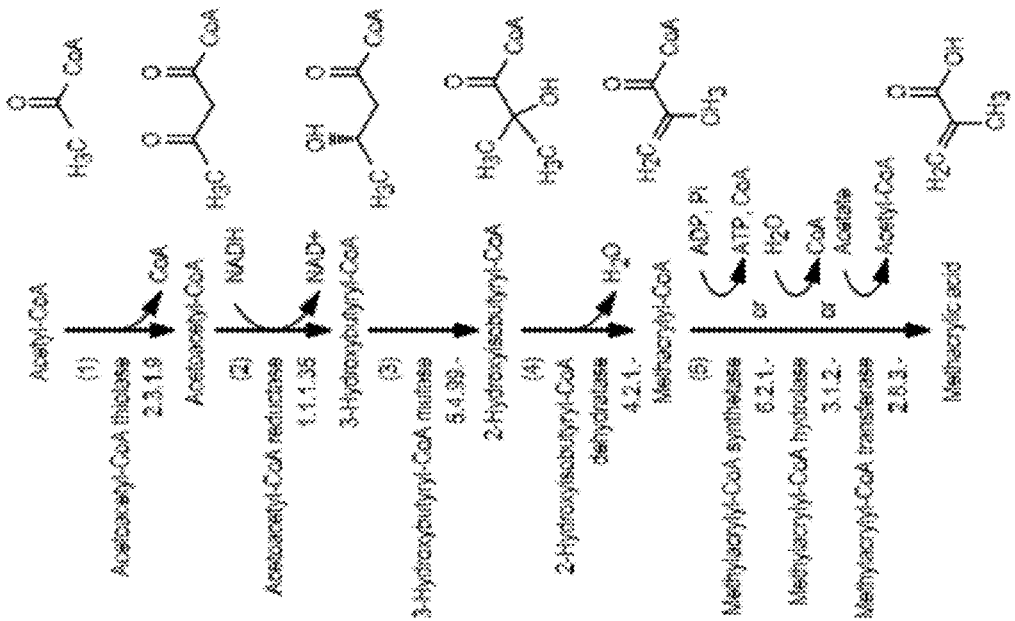
FIGURE 12

MICROORGANISMS FOR THE PRODUCTION OF METHACRYLIC ACID

This application is a continuation of application Ser. No. 12/433,829, filed Apr. 30, 2009, which claims the benefit of priority of U.S. Provisional application Ser. No. 61/049,730, filed May 1, 2008, each of which the entire contents are incorporated herein by reference.

BACKGROUND OF THE INVENTION

The present invention relates generally to biosynthetic processes, and more specifically to organisms having methacrylic acid, 2-hydroxyisobutyrate and 3-hydroxyisobutyrate biosynthetic capabilities.

Methyl methacrylate is an organic compound with the formula $CH_2=C(CH_3)CO_2CH_3$. This colourless liquid is the methyl ester of methacrylic acid (MMA) and is the monomer for the production of the transparent plastic polymethyl methacrylate (PMMA). Methyl methacrylate (MMA) is a key intermediate chemical with a global demand in excess of 4.5 billion pounds per year, much of which is converted to polyacrylates.

Most commercial producers apply an acetone cyanohydrin (ACH) route to produce methacrylic acid (MAA), with acetone and hydrogen cyanide as raw materials. The intermediate cyanohydrin is converted with sulfuric acid to a sulfate ester of the methacrylamide, hydrolysis of which gives ammonium bisulfate and MAA. Some producers start with an isobutylene or, equivalently, tert-butanol, which is oxidized to methacrolein, and again oxidized to methacrylic acid. MAA is then esterified with methanol to MMA.

The conventional production process, using the acetone cyanohydrin route, involves the conversion of hydrogen cyanide (HCN) and acetone to acetone cyanohydrin, which then undergoes acid assisted hydrolysis and esterification with methanol to give MMA. Difficulties in handling potentially deadly HCN along with the high costs of byproduct disposal (1.2 tons of ammonium bisulfate are formed per ton of MMA) have sparked a great deal of research aimed at cleaner and more economical processes. A number of new processes have been commercialized over the last two decades and many more are close to commercialization. The Asahi "Direct Metha" route, which involves the oxidation of isobutylene to methacrolein, which is then mixed with methanol, oxidized with air, and esterified to MMA, has been described as an economical process.

The principal application of methyl methacrylate is the production of polymethyl methacrylate acrylic plastics. Also, methyl methacrylate is used for the production of the co-polymer methyl methacrylate-butadiene-styrene (MBS), used as a modifier for PVC. Methyl methacrylate polymers and co-polymers are used for waterborne coatings, such as latex paint. Uses are also found in adhesive formulations. Contemporary applications include the use in plates that keep light spread evenly across liquid crystal display (LCD) computer and TV screens. Methyl methacrylate is also used to prepare corrosion casts of anatomical organs, such as coronary arteries of the heart.

Methacrylic acid, or 2-methyl-2-propenoic acid, is a low molecular weight carboxylic acid that occurs naturally in small amounts in the oil of Roman chamomile. It is a corrosive liquid with an acrid unpleasant odor. It is soluble in warm water and miscible with most organic solvents.

Methacrylic acid polymerizes readily upon heating or treatment with a catalytic amount of strong acid, such as HCl. The resulting polymer is a ceramic-looking plastic. Methacrylic acid is used industrially in the preparation of its esters, known collectively as methacrylates, such as methyl methacrylate, as discussed above. The methacrylates have numerous uses, most notably in the manufacture of polymers with trade names such as Lucite™ and Plexiglas™.

Other than MMA polymers, the other major product of this industry is crude methacrylic acid (crude MAA, FIG. 1), which accounts for about 20 percent of the total production of MMA. Crude MAA is processed into butyl methacrylates and/or "glacial" MAA, which is highly purified crude MAA. Glacial MAA can be used directly as a comonomer in various polymers and is also used to make a variety of small volume methacrylates. On the other hand, MAA can also be converted into MMA via esterification with methanol.

Thus, there exists a need for alternative methods for effectively producing commercial quantities of compounds such as methacrylic acid, 2-hydroxyisobutyrate or 3-hydroxyisobutyrate. The present invention satisfies this need and provides related advantages as well.

SUMMARY OF INVENTION

The invention provides a non-naturally occurring microbial organism having a methacrylic acid pathway. The microbial organism contains at least one exogenous nucleic acid encoding an enzyme in a methacrylic acid pathway. The invention additionally provides a method for producing methacrylic acid. The method can include culturing methacrylic acid producing microbial organism, where the microbial organism expresses at least one exogenous nucleic acid encoding a methacrylic acid pathway enzyme in a sufficient amount to produce methacrylic acid, under conditions and for a sufficient period of time to produce methacrylic acid. The invention also describes organisms and production methods for the methacrylic acid precursors 3-hydroxyisobutyrate and 2-hydroxyisobutyrate.

BRIEF DESCRIPTION OF THE DRAWINGS

FIG. 3A shows conversion of 2-hydroxymethyl glutarate by 2-(hydroxymethyl)glutarate dehydratase (EC 4.2.1.-). FIG. 3B shows dehydration of malate to fumarate by fumarate hydratase (EC 4.2.1.2). FIG. 3C shows the predicted dehydration of 3-hydroxyisobutyrate to MAA.

FIG. 7A, methylmalonyl-CoA mutase (MCM, EC 5.4.99.2); FIG. 7B, isobutyryl-CoA mutase (ICM, EC 5.4.99.13); and FIG. 7C, predicted transformation proposed in FIG. 6 step 1.

FIG. 9A shows transformation from aconitate to iconitate catalyzed by aconitate decarboxylase (EC 4.1.1.6). FIG. 9B shows decarboxylation of 4-oxalocrotonate to 2-oxopentenoate by 4-oxalocrotonate decarboxylase (EC 4.1.1.77). FIG. 9C shows the predicted decarboxylation of mesaconate to form MAA.

FIG. 11A shows transformation from 2-methylmalate to mesaconate catalyzed by 2-methylmalate dehydratase (EC 4.2.1.34). FIG. 11B shows dehydration of malate to fumarate by fumarate hydratase (EC 4.2.1.2). FIG. 11C shows the predicted dehydration of 3-methylmalate to mesaconate.

FIG. 12 shows exemplary metabolic pathways for the conversion of acetyl-CoA or 4-hydroxybutyryl-CoA into MAA or 2-hydroxyisobutyrate.

DETAILED DESCRIPTION OF THE INVENTION

The present invention is directed to the design and production of cells and organisms having biosynthetic production capabilities for methacrylic acid. The results described herein indicate that metabolic pathways can be designed and recombinantly engineered to achieve the biosynthesis of methacrylic acid in *Escherichia coli* and other cells or organisms. Biosynthetic production of methacrylic acid can be confirmed by construction of strains having the designed metabolic genotype. These metabolically engineered cells or organisms also can be subjected to adaptive evolution to further augment methacrylic acid biosynthesis, including under conditions approaching theoretical maximum growth.

As disclosed herein, organisms and methods are provided for producing 2-methacrylic acid via fermentation from a renewable sugar feedstock. Described herein are high-yielding metabolic pathways for producing MAA from succinyl-CoA, alpha-ketoglutarate, acetyl-CoA, or other central metabolic precursors. Disclosed herein are pathways, their maximum product and ATP yields, and candidate genes for implementation of fermentative MAA production.

Figure 2:
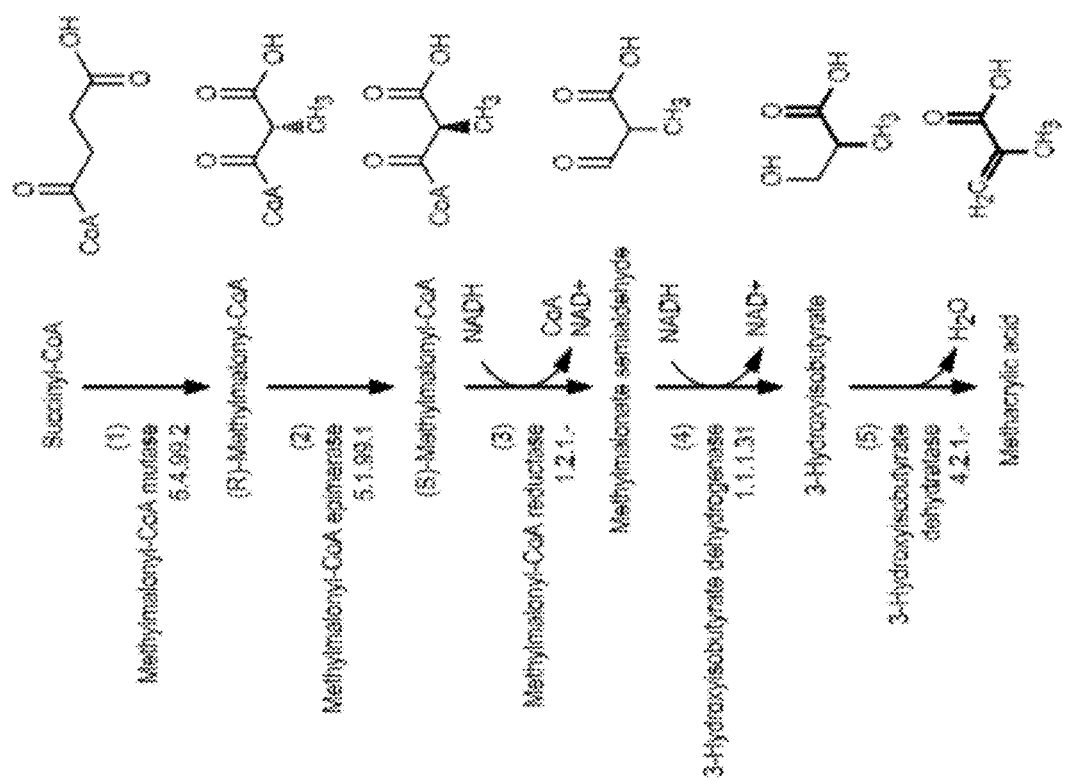
FIG. 2 shows an exemplary metabolic pathway from succinyl-CoA to MMA via 3-hydroxyisobutyrate.
Figure 6:
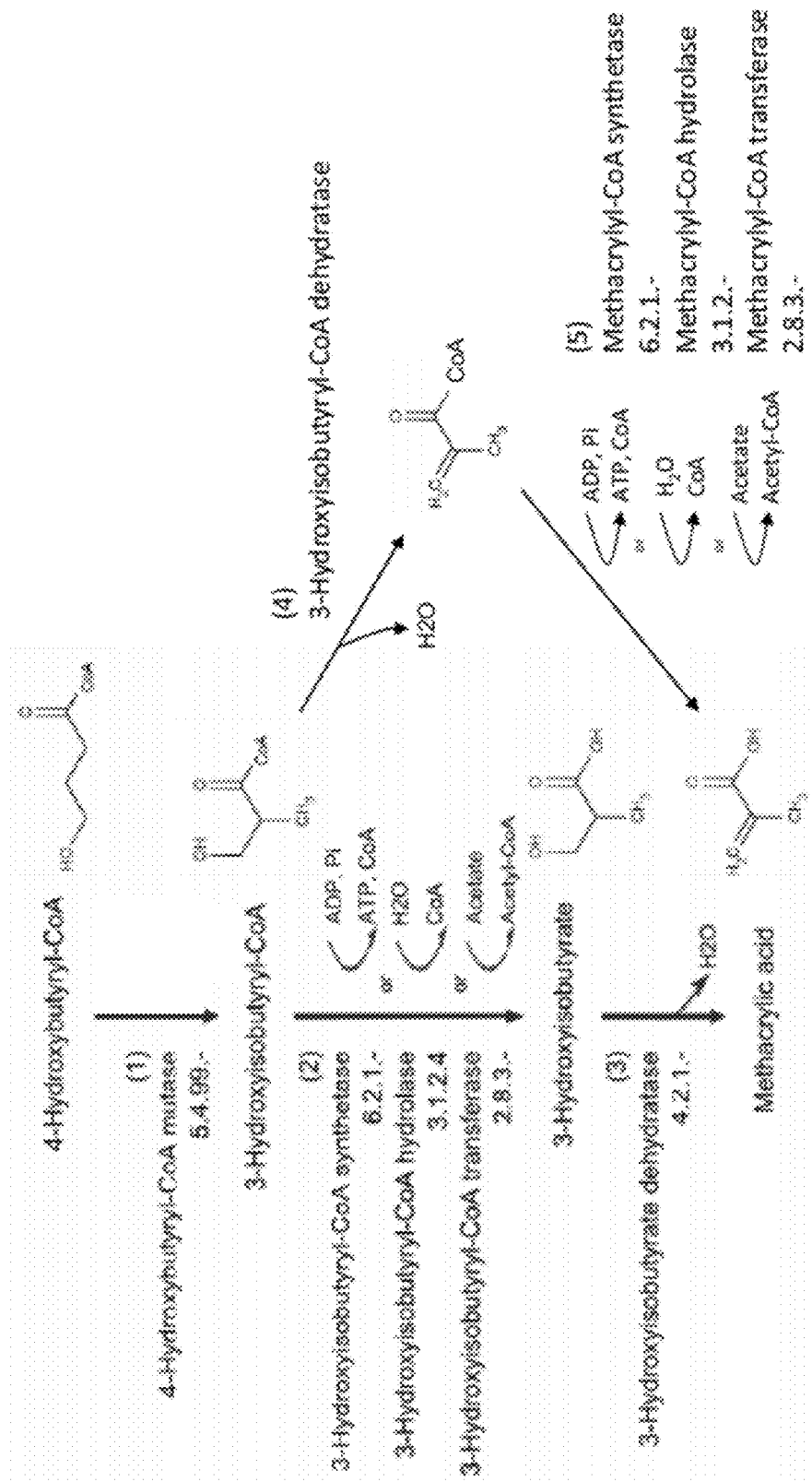
FIG. 6 shows an exemplary 4-hydroxybutyryl-CoA to MAA pathway that proceeds via 3-hydroxyisobutyrate or methacrylyl-CoA. Step 2 can be catalyzed by three alternative enzymes: 3-hydroxyisobutyryl-CoA synthetase, 3-hydroxyisobutyryl-CoA hydrolase or 3-hydroxyisobutyryl-CoA transferase. Similarly, step 5 can be catalyzed by three alternative enzymes: methacrylyl-CoA synthetase, methacrylyl-CoA hydrolase or methacrylyl-CoA transferase.

It is understood that pathways passing through a 3-hydroxyisobutyrate intermediate can be applied for 3-hydroxyisobutyrate production as opposed to methacrylate production if the downstream enzyme, that is, a dehydratase, is omitted (see FIGS. 2 and 6). In this case, the non-naturally occurring organism would produce 3-hydroxyisobutyrate instead of methacrylate. The non-naturally occurring organism could alternatively produce a mixture of 3-hydroxyisobutyate and methacrylate. The maximum molar yields of ATP and product will be unchanged regardless of whether methacrylate or 3-hydroxyisobutyrate is produced. It is also understood that the pathway passing through a 2-hydroxyisobutyryl-CoA intermediate can be applied for 2-hydroxyisobutyrate production as opposed to methacrylate production if the downstream enzyme, that is, a dehydratase, is omitted and a 2-hydroxyisobutyryl-CoA transferase, synthetase, or hydrolase is applied (see FIG. 12). In this case, the non-naturally occurring organism would produce 2-hydroxyisobutyrate instead of methacrylate. The non-naturally occurring organism could alternatively produce a mixture of 2-hydroxyisobutyate and methacrylate. The maximum molar yields of ATP and production will be unchanged regardless of whether methacrylate or 2-hydroxyisobutyrate is produced.

It is further understood that, if desired, 3-hydroxyisobutyric acid or 2-hydroxyisobutyric acid expressed by a microbial organism of the invention can be chemically converted to methacrylic acid. For example, 3-hydroxyisobutyric acid, or β-hydroxyisobutyricacid, can be dehydrated to form methacrylic acid as described, for example, in U.S. Pat. No. 7,186,856. 2-Hydroxyisobutyric acid, or α-hydroxyisobutyric acid, can also be dehydrated to form methacrylic acid as described in U.S. Pat. No. 3,666,805 and U.S. Pat. No. 5,225,594.

Two pathways originating from succinyl-CoA, described in Examples I and III, and two pathways originating from 4-hydroxybutyryl-CoA, described in Example V and XIX, provide high yields under anaerobic conditions (1.33 mol/mol glucose), favorable energetics and the availability of suitable enzyme candidates. The maximum theoretical yield of methacrylate starting from glucose as a raw material is 1.33 mol/mol glucose as shown below:

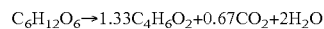

$$C_6H_{12}O_6 \rightarrow 1.33 C_4H_6O_2 + 0.67 CO_2 + 2H_2O$$

Three additional pathways, described in Examples VII, IX and XI, are high-yielding and energetically favorable under aerobic conditions. These pathways originate from alpha-ketoglutarate (Examples VII and IX) or acetyl-CoA (Example XI) as a starting material.

Three additional pathways, described in Examples XIII-XV, provide lower yields. The alternate acetyl-CoA pathway (Example XIII) is high-yielding under aerobic conditions but is lengthy, involving a minimum of seven enzymatic steps.

The acrylyl-CoA pathway (Example XIV) is high-yielding under anaerobic and aerobic conditions, but has the disadvantages of unfavorable energetics, formation of a toxic intermediate (acrylyl-CoA), and a high susceptibility to the secretion of fermentation byproducts. The 2-ketoisovalerate pathway is high-yielding under aerobic conditions but also has the disadvantage of producing a potentially toxic intermediate (MAA-CoA) (Example XV).

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes within a methacrylic acid biosynthetic pathway.

A metabolic modification refers to a biochemical reaction that is altered from its naturally occurring state. Therefore, non-naturally occurring microorganisms can have genetic modifications to nucleic acids encoding metabolic polypeptides or, functional fragments thereof. Exemplary metabolic modifications are disclosed herein.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" is intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

Figure 1:
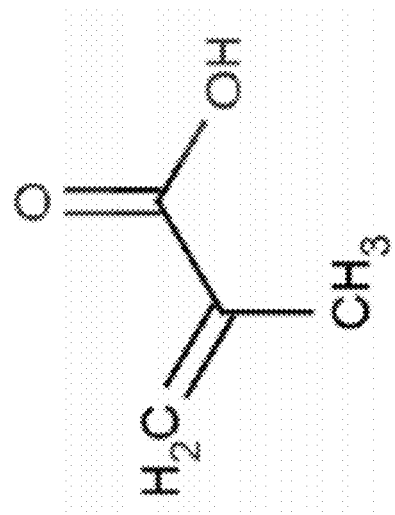
FIG. 1 shows the structure of methacrylic acid (MAA).

As used herein, "methacrylic acid," having the chemical formula $CH_2=C(CH_3)CO_2$ (see FIG. 1) (IUPAC name 2-methyl-2-propenoic acid), is the acid form of methacrylate, and it is understood that methacrylic acid and methacrylate can be used interchangebly throughout to refer to the compound in any of its neutral or ionized forms, including any salt forms thereof. It is understood by those skilled understand that the specific form will depend on the pH. Similarly, it is understood that 2-hydroxyisobutyrate and 2-hydroxyisobutyric acid can be used interchangebly throughout to refer to the compound in any of its neutral or ionized forms, including any salt forms thereof. Further, 3-hydroxyisobutyrate and 3-hydroxyisobutyric acid can be used interchangebly throughout to refer to the compound in any of its neutral or ionized forms, including any salt forms thereof.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

The non-naturally occurring microbal organisms of the invention can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

Those skilled in the art will understand that the genetic alterations, including metabolic modifications exemplified herein, are described with reference to a suitable host organism such as *E. coli* and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the *E. coli* metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of mycoplasma 5'-3' exonuclease and *Drosophila* DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the non-naturally occurring microbial organisms of the invention having methacrylic acid biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionally related genes.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; word-size: 11; filter: off. Those skilled in the art will know what modifications can be made to the above parameters to either increase or decrease the stringency of the comparison, for example, and determine the relatedness of two or more sequences.

As disclosed herein, high-yielding metabolic pathways for 2-methacrylic acid (MAA) synthesis using glucose/sucrose as a carbon substrate are described. The two principal criteria for analyzing and ranking these pathways were the maximum theoretical yields of MAA and the associated energetics under both aerobic and anaerobic conditions. Product and energy yields were calculated by adding the pathways in question to an *E. coli* stoichiometric network in SimPheny™ that is similar to the one described in Reed et al (Reed et al., *Genome Biol.* 4:R54 (2003)). As MAA is a charged molecule under physiological conditions, product export is assumed to be mediated by a proton-symport mechanism. This transport mechanism is not expected to encounter a thermodynamic limitation at near neutral fermentation conditions, although it will become less thermodynamically favorable under acidic fermentation conditions. The reactions in the pathways and the required enzymatic activities are discussed in the Examples.

The invention provides a non-naturally occurring microbial organism capable of producing methacrylic acid. For example, a methacrylic acid pathway is provided in which succinyl-CoA is a precursor (see Examples I-IV, FIGS. 2 and 4). In one embodiment, the invention provides a non-naturally occurring microbial organism having a methacrylic acid pathway comprising at least one exogenous nucleic acid encoding a methacrylic acid pathway enzyme expressed in a sufficient amount to produce methacrylic acid, the methacrylic acid pathway comprising methylmalonyl-CoA mutase, methylmalonyl-CoA epimerase, methylmalonyl-CoA reductase, 3-hydroxyisobutyrate dehydrogenase and 3-hydroxyisobutyrate dehydratase (see Examples I and II and FIG. 2). In another embodiment, the invention provides a non-naturally occurring microbial organism having a methacrylic acid pathway comprising at least one exogenous nucleic acid encoding a methacrylic acid pathway enzyme expressed in a sufficient amount to produce methacrylic acid, the methacrylic acid pathway comprising methylmalonyl-CoA mutase, methylmalonyl-CoA epimerase, alcohol/aldehyde dehydrogenase, and 3-hydroxyisobutyrate dehydratase (see Example I). The invention additionally provides a non-naturally occurring microbial organism having a methacrylic acid pathway comprising at least one exogenous nucleic acid encoding a methacrylic acid pathway enzyme expressed in a sufficient amount to produce methacrylic acid, the methacrylic acid pathway comprising methylmalonyl-CoA mutase, methylmalonyl-CoA epimerase, methylmalonyl-CoA reductase, 3-amino-2-methylpropionate transaminase, and 3-amino-2-methylpropionate ammonia lyase (see Examples III and IV and FIG. 4).

Additionally provided is a non-naturally occurring microbial organism containing a methacrylic acid pathway having 4-hydroxybutyryl-CoA as a precursor. One such embodiment is a non-naturally occurring microbial organism having a methacrylic acid pathway comprising at least one exogenous nucleic acid encoding a methacrylic acid pathway enzyme expressed in a sufficient amount to produce methacrylic acid, the methacrylic acid pathway comprising 4-hydroxybutyryl-CoA mutase, 3-hydroxyisobutyryl-CoA synthetase or 3-hydroxyisobutyryl-CoA hydrolase or 3-hydroxyisobutyryl-CoA transferase, and 3-hydroxyisobutyrate dehydratase (see Examples V and VI and FIG. 6). Alternatively, the pathway could include 4-hydroxybutyryl-CoA mutase, 3-hydroxyisobutyryl-CoA dehydratase; and methacrylyl-CoA synthetase or methacrylyl-CoA hydrolase or methacrylyl-CoA transferase.

Further, the present invention provides a non-naturally occurring microbial organism containing a 3-hydroxyisobutyric acid pathway having 4-hydroxybutyryl-CoA as a precursor. One such embodiment is a non-naturally occurring microbial organism having a 3-hydroxyisobutyric acid pathway comprising at least one exogenous nucleic acid encoding a 3-hydroxyisobutyric acid pathway enzyme expressed in a sufficient amount to produce 3-hydroxyisobutyric acid, the 3-hydroxyisobutyric acid pathway comprising 4-hydroxybutyryl-CoA mutase; and 3-hydroxyisobutyryl-CoA synthetase or 3-hydroxyisobutyryl-CoA hydrolase or 3-hydroxyisobutyryl-CoA transferase (see Example V and FIG. 6).

The invention further provides a non-naturally occurring microbial organism containing a methacrylic acid pathway having alpha-ketoglutarate as a precursor. One such embodiment is a non-naturally occurring microbial organism having a methacrylic acid pathway comprising at least one exogenous nucleic acid encoding a methacrylic acid pathway enzyme expressed in a sufficient amount to produce methacrylic acid, the methacrylic acid pathway comprising aspartate aminotransferase, glutamate mutase, 3-methylaspartase, and mesaconate decarboxylase (see Examples VII and VIII and FIG. 8). In yet another embodiment, the invention provides a non-naturally occurring microbial organism, comprising a microbial organism having a methacrylic acid pathway comprising at least one exogenous nucleic acid encoding a methacrylic acid pathway enzyme expressed in a sufficient amount to produce methacrylic acid, the methacrylic acid pathway comprising alpha-ketoglutarate reductase, 2-hydroxyglutamate mutase, 3-methylmalate dehydratase, and mesaconate decarboxylase (see Examples IX and X and FIG. 10).

In still another embodiment, the invention provides a non-naturally occurring microbial organism containing a methacrylic acid pathway having acetyl-CoA as a precursor. For example, the invention provides a non-naturally occurring microbial organism having a methacrylic acid pathway comprising at least one exogenous nucleic acid encoding a methacrylic acid pathway enzyme expressed in a sufficient amount to produce methacrylic acid, the methacrylic acid pathway comprising acetoacetyl-CoA thiolase, acetoacetyl-CoA reductase, 3-hydroxybutyryl-CoA mutase, 2-hydroxyisobutyryl-CoA dehydratase, and methacrylyl-CoA transferase or methacrylyl-CoA hydrolase or methacrylyl-CoA synthetase (see Examples XI and XII and FIG. 12). In another embodiment, the invention provides a non-naturally occurring microbial organism having a methacrylic acid pathway comprising at least one exogenous nucleic acid encoding a methacrylic acid pathway enzyme expressed in a sufficient amount to produce methacrylic acid, the methacrylic acid pathway comprising acetoacetyl-CoA thiolase, acetoacetyl-CoA reductase, 3-hydroxybutyryl-CoA mutase, 2-hydroxyisobutyryl-CoA dehydratase, enoyl-CoA hydratase, and 3-hydroxyisobutyryl-CoA hydrolase or 3-hydroxyisobutyryl-CoA synthetase or 3-hydroxyisobutyryl-CoA transferase, and 3-hydroxyisobutyrate dehydratase (see Example XI and XII).

In still another embodiment, the invention provides a non-naturally occurring microbial organism containing a 2-hydroxyisobutyric acid pathway having acetyl-CoA as a precursor. For example, the invention provides a non-naturally occurring microbial organism having a 2-hydroxyisobutyric acid pathway comprising at least one exogenous nucleic acid encoding a 2-hydroxyisobutyric acid pathway enzyme expressed in a sufficient amount to produce 2-hydroxyisobutyric acid, the 2-hydroxyisobutyric acid pathway comprising acetoacetyl-CoA thiolase; acetoacetyl-CoA reductase; 3-hydroxybutyryl-CoA mutase; and 2-hydroxyisobutyryl-CoA hydrolase or 2-hydroxyisobutyryl-CoA synthetase or 2-hydroxyisobutyryl-CoA transferase (see Examples XI and FIG. 12).

In further embodiments, the invention provides non-naturally occurring microbial organisms containing a methacrylic acid or 2-hydroxyisobutyric acid pathway having 4-hydroxybutyryl-CoA as a precursor. For example, the invention provides a non-naturally occurring microbial organism having a methacrylic acid pathway comprising at least one exogenous nucleic acid encoding a methacrylic acid pathway enzyme expressed in a sufficient amount to produce methacrylic acid, the methacrylic acid pathway comprising 4-hydroxybutyryl-CoA dehydratase; vinylacetyl-CoA Δ-isomerase; crotonase; 3-hydroxybutyryl-CoA mutase; 2-hydroxyisobutyryl-CoA dehydratase; and methacrylyl-CoA hydrolase or methacrylyl-CoA synthetase or methacrylyl-CoA transferase (see Example XVIII and FIG. 12). Further, the invention provides a non-naturally occurring microbial organism having a 2-hydroxyisobutyric acid pathway comprising at least one exogenous nucleic acid encoding a 2-hydroxyisobutyric acid pathway enzyme expressed in a sufficient amount to produce 2-hydroxyisobutyric acid, the 2-hydroxyisobutyric acid pathway comprising 4-hydroxybutyryl-CoA dehydratase; vinylacetyl-CoA Δ-isomerase; crotonase; 3-hydroxybutyryl-CoA mutase; and 2-hydroxyisobutyryl-CoA hydrolase or 2-hydroxyisobutyryl-CoA synthetase or 2-hydroxyisobutyryl-CoA transferase (see Examples XVIII and FIG. 12).

Figure 13:
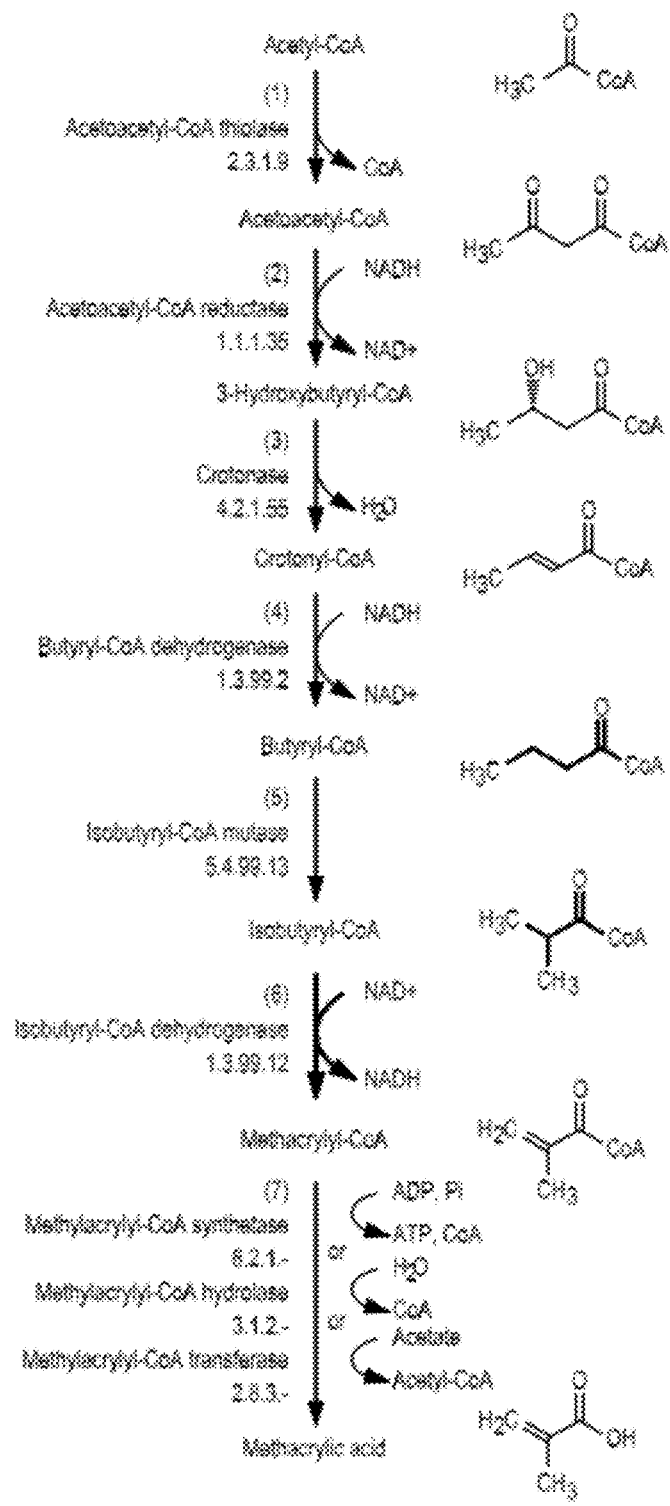
FIG. 13 shows an exemplary pathway from acetyl-CoA to MAA.

In yet another embodiment, the invention provides a non-naturally occurring microbial organism having a methacrylic acid pathway comprising at least one exogenous nucleic acid encoding a methacrylic acid pathway enzyme expressed in a sufficient amount to produce methacrylic acid, the methacrylic acid pathway comprising acetoacetyl-CoA thiolase, acetoacetyl-CoA reductase, crotonase, butyryl-CoA dehydrogenase, isobutyryl-CoA mutase, isobutyryl-CoA dehydrogenase, and methacrylyl-CoA synthetase or methacrylyl-CoA hydrolase or methacrylyl-CoA transferase (see Example XIII and FIG. 13).

The invention further provides a non-naturally occurring microbial organism containing a methacrylic acid pathway having pyruvate as a precursor. For example, the invention provides a non-naturally occurring microbial organism having a methacrylic acid pathway comprising at least one exogenous nucleic acid encoding a methacrylic acid pathway enzyme expressed in a sufficient amount to produce methacrylic acid, the methacrylic acid pathway comprising lactate dehydrogenase, lactate-CoA transferase, lactoyl-CoA dehydratase, acyl-CoA dehydrogenase, propionyl-CoA carboxylase, methylmalonyl-CoA reductase, 3-hydroxyisobutyrate dehydrogenase, and 3-hydroxyisobutyrate dehydratase (see Example XIV and FIG. 14).

Figure 15:
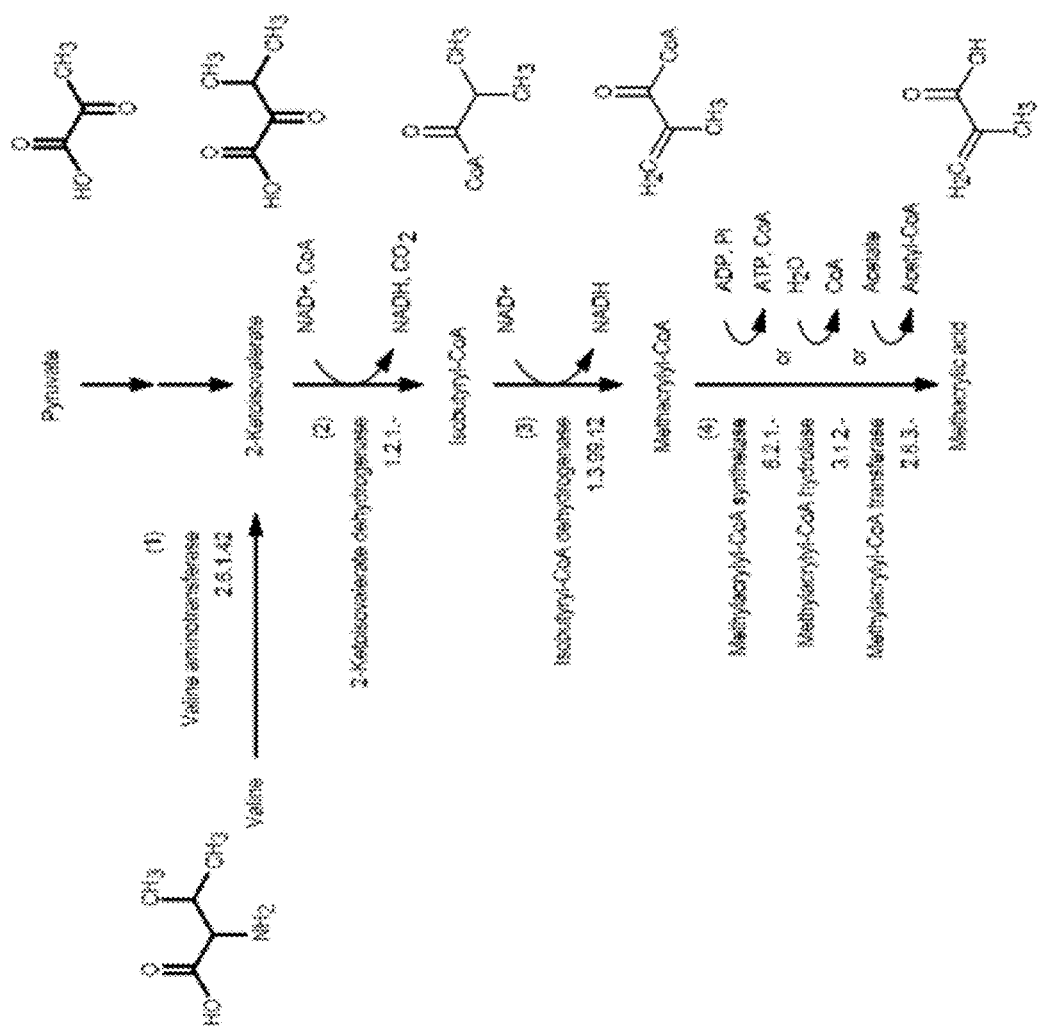
FIG. 15 shows an exemplary 2-ketovalerate to MAA pathway. 2-Ketoisovalerate can be produced either from valine or pyruvate. An exemplary set of enzymes for pyruvate conversion to 2-ketoisovalerate is comprised of acetolactate synthase, acetohydroxy acid isomeroreductase, and dihydroxyacid dehydratase.

Also provided by the invention is a non-naturally occurring microbial organism containing a methacrylic acid pathway having 2-ketoisovalerate as a precursor. For example, the invention provides a non-naturally occurring microbial organism having a methacrylic acid pathway comprising at least one exogenous nucleic acid encoding a methacrylic acid pathway enzyme expressed in a sufficient amount to produce methacrylic acid, the methacrylic acid pathway comprising valine aminotransferase, 2-ketoisovalerate dehydrogenase, isobutyryl-CoA dehydrogenase, and methacrylyl-CoA synthetase or methacrylyl-CoA hydrolase or methacrylyl-CoA transferase (see Example XV and FIG. 15). Such a methacrylic acid pathway can further contain valine aminotransferase, which converst valine to 2-ketoisovalerate (FIG. 15). In addition, such a methacrylic acid pathway can further contain enzymes that convert pyruvate to 2-ketoisovalerate (FIG. 15), such as acetolactate synthase, acetohydroxy acid isomeroreductase and dihydroxy-acid dehydratase (see Example XV).

In an additional embodiment, the invention provides a non-naturally occurring microbial organism having a 2-hydroxyisobutyric acid, 3-hydroxyisobutyric acid or methacrylic acid pathway, wherein the non-naturally occurring microbial organism comprises at least one exogenous nucleic acid encoding a protein or enzyme that converts a substrate to a product. Such a pathway can be, for example, succinyl-CoA to methylmalonyl-CoA, methylmalonyl-CoA to methylmalonate semialdehyde, methylmalonate semialdehyde to 3-hydroxyisobutyrate for a succinyl-CoA to 3-hydroxyisobutyrate pathway, and additionally 3-hydroxyisobutyrate to methacrylic acid for a succinyl-CoA to methacrylic acid pathway (see FIG. 2). Additionally, such a pathway can be, for example, succinyl-CoA to methylmalonyl-CoA, methylmalonyl-CoA to methylmalonate semialdehyde, methylmalonate semialdehyde to 3-amino-2-methylpriopionate, and 3-amino-2-methylpriopionate to methacrylic acid for an alternative succinyl-CoA to methacrylic acid pathway (see FIG. 4).

Figure 8:
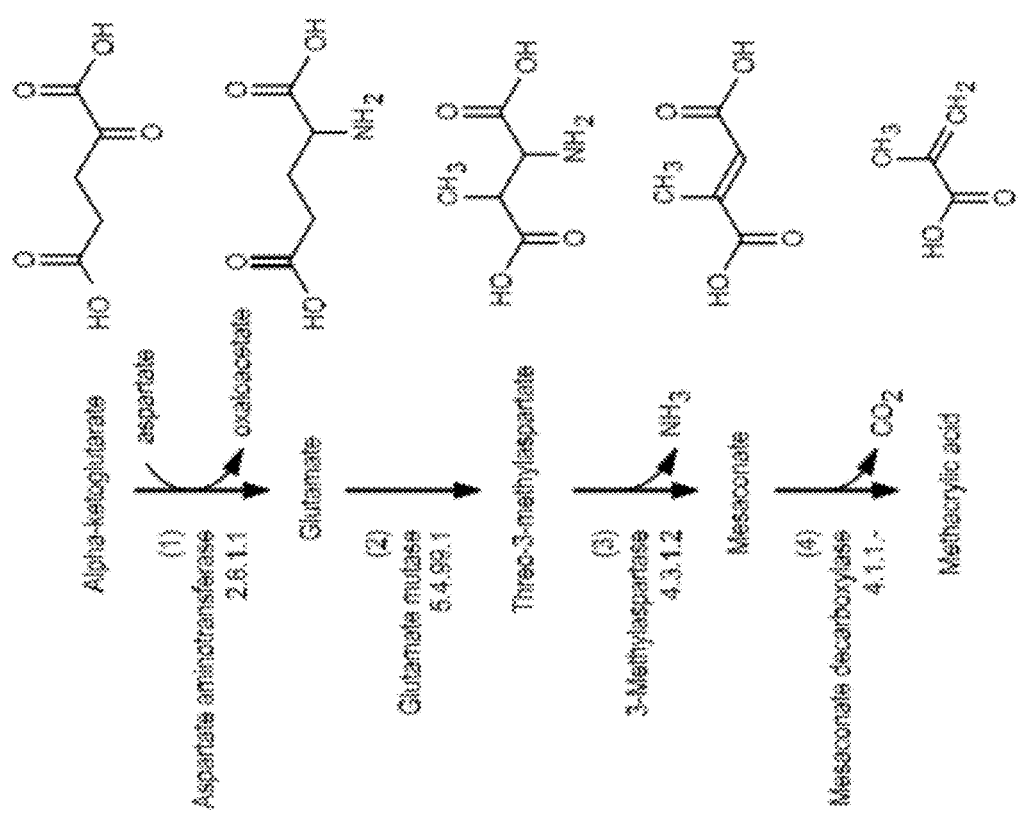
FIG. 8 shows an exemplary alpha-ketoglutarate to MAA pathway via threo-3-methylaspartate.
Figure 10:
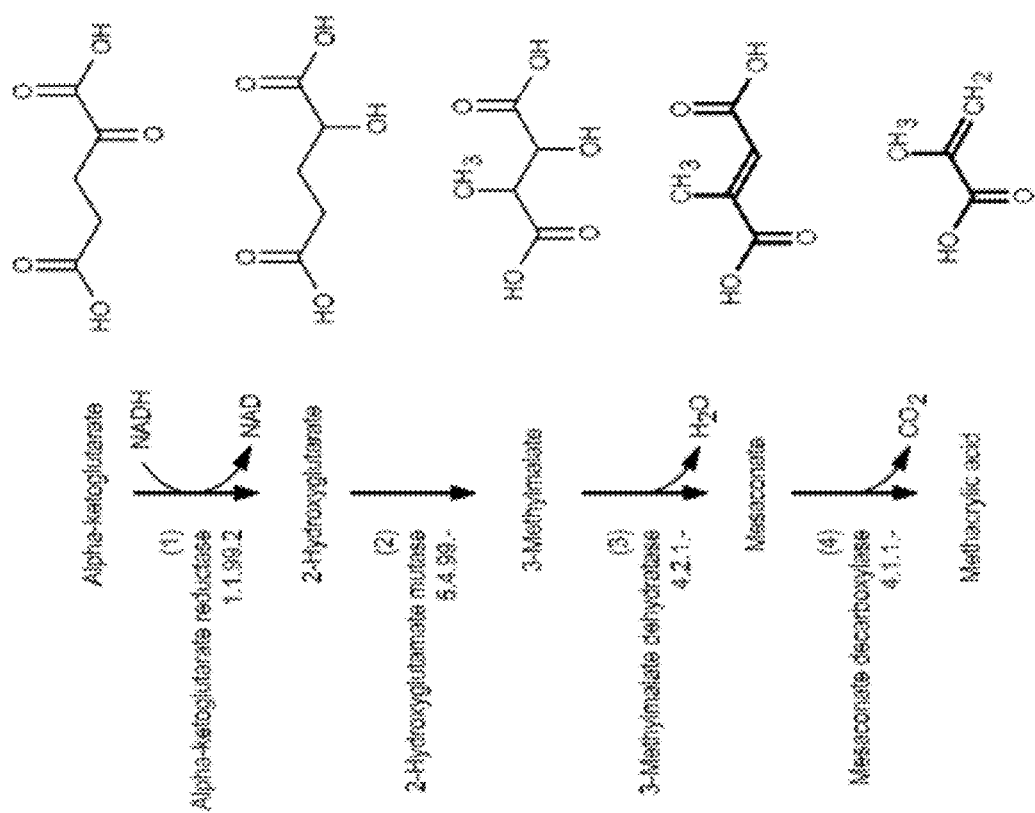
FIG. 10 shows an exemplary alpha-ketoglutarate to MAA pathway via 2-hydroxyglutarate.

In another embodiment, such a pathway can be, for example, 4-hydroxybutyryl-CoA to 3-hydroxyisobutyryl-CoA, 3-hydroxyisobutyryl-CoA to 3-hydroxisobutyrate for a 4-hydroxybutyryl-CoA to 3-hydroxisobutyrate pathway, and additionally 3-hydroxyisobutyrate to methacrylic acid for a 4-hydroxybutyryl-CoA to methacrylic acid pathway (see FIG. 6). Further, such a pathway can be, for example, alpha-ketoglutarate to glutamate, glutamate to threo-3-methylaspartate, threo-3-methylaspartate to mesaconate, mesaconate to methacrylic acid for an alpha-ketoglutarate to methacrylic acid pathway (FIG. 8). Also, such a pathway can be, for example, alpha-ketoglutarate to 2-hydroxyglutarate, 2-hydroxyglutarate to 3-methylmalate, 3-methylmalate to mesaconate, and mesaconate to methacrylic acid for an alpha-ketoglutarate to methacrylic acid pathway (FIG. 10).

In still another embodiment, such a pathway can be, for example, acetyl-CoA to acetoacetyl-CoA, acetoacetyl-CoA to 3-hydroxybutyryl-CoA, 3-hydroxybutyryl-CoA to 2-hydroxyisobutyryl-CoA, 2-hydroxyisobutyryl-CoA to methacrylyl-CoA, and methacrylyl-CoA to methacrylic acid for an acetyl-CoA to methacrylic acid pathway (FIG. 12). Also, such a pathway can be, for example, 4-hydroxybutyryl-CoA to vinylacetyl-CoA, vinylacetyl-CoA to crotonyl-CoA, crotonyl-CoA to 3-hydroxybutyryl-CoA, 3-hydroxybutyryl-CoA to 2-hydroxyisobutyryl-CoA, 2-hydroxyisobutyryl-CoA to methacrylyl-CoA, and methacrylyl-CoA to methacrylic acid for a 4-hydroxybutyryl-CoA to methacrylic acid pathway (FIG. 12).

In yet another embodiment, such a pathway can be, for example, acetyl-CoA to acetoacetyl-CoA, acetoacetyl-CoA to 3-hydroxybutyryl-CoA, 3-hydroxybutyryl-CoA to 2-hydroxyisobutyryl-CoA, 2-hydroxyisobutyryl-CoA to 2-hydroxyisobutyric acid for an acetyl-CoA to 2-hydroxyisobutyric acid pathway (FIG. 12). Also, such a pathway can be, for example, 4-hydroxybutyryl-CoA to vinylacetyl-CoA, vinylacetyl-CoA to crotonyl-CoA, crotonyl-CoA to 3-hydroxybutyryl-CoA, 3-hydroxybutyryl-CoA to 2-hydroxyisobutyryl-CoA, and 2-hydroxyisobutyryl-CoA to 2-hydroxyisobutyric acid for 4-hydroxybutyryl-CoA to 2-hydroxyisobutyric acid pathway (FIG. 12).

Figure 14:
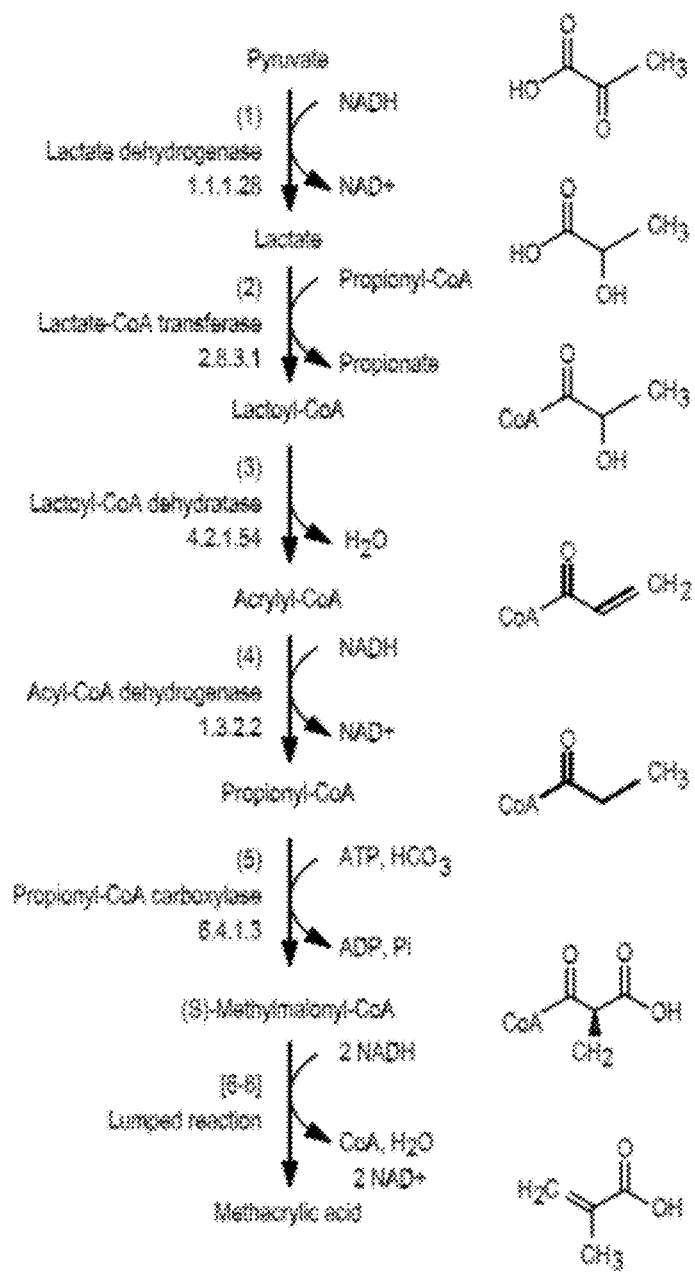
FIG. 14 shows an exemplary acrylyl-CoA to MAA pathway.

In another embodiment, such a pathway can be, for example, acetyl-CoA to acetoactyl-CoA, acetoactyl-CoA to 3-hydroxybutyryl-CoA, 3-hydroxybutyryl-CoA to crotonyl-CoA, crotonyl-CoA to butyryl-CoA, butyryl-CoA to isobutyryl-CoA, isobutyryl-CoA to methacrylyl-CoA, and methacrylyl-CoA to methacrylic acid (FIG. 13). Additionally, such a pathway can be, for example, pyruvate to lactate, lactate to lactoyl-CoA, lactoyl-CoA to acrylyl-CoA, acrylyl-CoA to propionyl-CoA, propionyl-CoA to methylmalonyl-CoA, and methylmalonyl-CoA to methacrylic acid (FIG. 14). Also, such a pathway can be, for example, pyruvate to 2-ketoisovalerate, 2-ketoisovalerate to isobutyryl-CoA, isobutyryl-CoA to methacrylyl-CoA, and methacrylyl-CoA to methacrylic acid for a pyruvate to methacrylic acid pathway (FIG. 15). Alternatively, such a pathway can be, for example, valine to 2-ketoisovalerate, 2-ketoisovalerate to isobutyryl-CoA, isobutyryl-CoA to methacrylyl-CoA, and methacrylyl-CoA to methacrylic acid for a valine to methacrylic acid pathway (FIG. 15). Thus, the invention provides a non-naturally occurring microbial organism containing at least one exogenous nucleic acid encoding an enzyme or protein that converts the substrates and products of a 2-hydroxyisobutyric acid, 3-hydroxyisobutyric acid or methacryl acid pathway, such as that shown in FIGS. 2, 4, 6, 8, 10, and 12-15.

The invention is described herein with general reference to the metabolic reaction, reactant or product thereof, or with specific reference to one or more nucleic acids or genes encoding an enzyme associated with or catalyzing the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes as well as the reactants and products of the reaction.

The non-naturally occurring microbial organisms of the invention can be produced by introducing expressible nucleic acids encoding one or more of the enzymes participating in one or more methacrylic acid biosynthetic pathways. Similarly, non-naturally occurring organisms of the invention can be produced by introducing expressible nucleic acids encoding one or more of the enzymes participating in one or more 3-hydroxyisobutyric acid or 2-hydroxyisobutyric acid pathways. Depending on the host microbial organism chosen for biosynthesis, nucleic acids for some or all of a particular methacrylic acid, 3-hydroxyisobutyric acid or 2-hydroxyisobutyric acid biosynthetic pathway can be expressed. For example, if a chosen host is deficient in one or more enzymes for a desired biosynthetic pathway, then expressible nucleic acids for the deficient enzyme(s) are introduced into the host for subsequent exogenous expression. Alternatively, if the chosen host exhibits endogenous expression of some pathway genes, but is deficient in others, then an encoding nucleic acid is needed for the deficient enzyme(s) to achieve methacrylic acid, 3-hydroxyisobutyric acid, or 2-hydroxyisobutyric acid biosynthesis. Thus, a non-naturally occurring microbial organism of the invention can be produced by introducing exogenous enzyme activities to obtain a desired biosynthetic pathway or a desired biosynthetic pathway can be obtained by introducing one or more exogenous enzyme activities that, together with one or more endogenous enzymes, produces a desired product such as methacrylic acid, 3-hydroxyisobutyric acid or 2-hydroxyisobutyric acid.

Depending on the methacrylic acid biosynthetic pathway constituents of a selected host microbial organism, the non-naturally occurring microbial organisms of the invention will include at least one exogenously expressed methacrylic acid pathway-encoding nucleic acid and up to all encoding nucleic acids for one or more methacrylic acid biosynthetic pathways. For example, methacrylic acid biosynthesis can be established in a host deficient in a pathway enzyme through exogenous expression of the corresponding encoding nucleic acid. In a host deficient in all enzymes of a methacrylic acid pathway, exogenous expression of all enzyme in the pathway can be included, although it is understood that all enzymes of a pathway can be expressed even if the host contains at least one of the pathway enzymes. Similarly, depending on the 3-hydroxyisobutyric acid or 2-hydroxyisobutyric acid biosynthetic pathway constituents of a selected host microbial organism, the non-naturally occurring microbial organisms of the invention will include at least one exogenously expressed 3-hydroxyisobutyric acid or 2-hydroxyisobutyric acid pathway-encoding nucleic acid and up to all encoding nucleic acids for one or more 3-hydroxyisobutyric acid or 2-hydroxyisobutyric acid biosynthetic pathways, respectively.

For example, exogenous expression of all enzymes in a pathway for production of methacrylic acid can be included. For example, all enzymes in a pathway for production of methacrylic acid can be included, such as methylmalonyl-CoA mutase, methylmalonyl-CoA epimerase, methylmalonyl-CoA reductase, 3-hydroxyisobutyrate dehydrogenase and 3-hydroxyisobutyrate dehydratase. Another example of enzymes in a methacrylic acid pathway includes methylmalonyl-CoA mutase, methylmalonyl-CoA epimerase, alcohol/aldehyde dehydrogenase, and 3-hydroxyisobutyrate dehydratase. A further example of enzymes in a methacrylic acid pathway includes methylmalonyl-CoA mutase, methylmalonyl-CoA epimerase, methylmalonyl-CoA reductase, 3-amino-2-methylpropionate transaminase, and 3-amino-2-methylpropionate ammonia lyase. In still another example of enzymes in a methacrylic acid pathway includes 4-hydroxybutyryl-CoA mutase, 3-hydroxyisobutyryl-CoA synthetase or 3-hydroxyisobutyryl-CoA hydrolase or 3-hydroxyisobutyryl-CoA transferase, and 3-hydroxyisobutyrate dehydratase. Also, an example of enzymes in a methacrylic acid pathway includes aspartate aminotransferase, glutamate mutase, 3-methylaspartase, and mesaconate decarboxylase. Yet another example of enzymes in a methacrylic acid pathway includes alpha-ketoglutarate reductase, 2-hydroxyglutamate mutase, 3-methylmalate dehydratase, and mesaconate decarboxylase. A further example of enzymes in a methacrylic acid pathway includes acetoacetyl-CoA thiolase, acetoacetyl-CoA reductase, 3-hydroxybutyryl-CoA mutase, 2-hydroxyisobutyryl-CoA dehydratase, and methacrylyl-CoA transferase or methacrylyl-CoA hydrolase or methacrylyl-CoA synthetase. Still another example of enzymes in a methacrylic acid pathway includes acetoacetyl-CoA thiolase, acetoacetyl-CoA reductase, 3-hydroxybutyryl-CoA mutase, 2-hydroxyisobutyryl-CoA dehydratase, enoyl-CoA hydratase, and 3-hydroxyisobutyryl-CoA hydrolase or 3-hydroxyisobutyryl-CoA synthetase or 3-hydroxyisobutyryl-CoA transferase, and 3-hydroxyisobutyrate dehydratase. It is understood that these and any of the methacrylic acid pathways disclosed herein can be utilized in a microbial organism to generate a methacrylic acid producing microbial organism.

Given the teachings and guidance provided herein, those skilled in the art will understand that the number of encoding nucleic acids to introduce in an expressible form will, at least, parallel the methacrylic acid pathway deficiencies of the selected host microbial organism. Therefore, a non-naturally occurring microbial organism of the invention can have one, two, three, four, and so forth, up to all nucleic acids encoding the above enzymes constituting a methacrylic acid biosynthetic pathway, as disclosed herein. In some embodiments, the non-naturally occurring microbial organisms also can include other genetic modifications that facilitate or optimize methacrylic acid biosynthesis or that confer other useful functions onto the host microbial organism. One such other functionality can include, for example, augmentation of the synthesis of one or more of the methacrylic acid, 3-hydroxyisobutyric acid or 2-hydroxyisobutyric acid pathway precursors. Exemplary methacrylic acid pathway precursors include, but are not limited to, succinyl-CoA, 4-hydroxybutyryl-CoA, alpha-ketoglutarate, acetyl-CoA, pyruvate, and 2-ketoisovalerate.

Generally, a host microbial organism is selected such that it produces the precursor of a methacrylic acid, 3-hydroxyisobutyric acid or 2-hydroxyisobutyric acid pathway, either as a naturally produced molecule or as an engineered product that either provides de novo production of a desired precursor or increased production of a precursor naturally produced by the host microbial organism. For example, succinyl-CoA, alpha-ketoglutarate, acetyl-CoA, and pyruvate are produced naturally in a host organism such as *E. coli* during glucose, fatty acid and amino acid metabolism and as components of the TCA cycle. A host organism can be engineered to increase production of a precursor, as disclosed herein. Such engineered microorganisms have been described previously (see, for example, U.S. publication 2007/0111294). In addition, a microbial organism that has been engineered to produce a desired precursor can be used as a host organism, for example, a microorganism engineered to produce 4-hydroxybutyryl-CoA (see, for example, U.S. application Ser. No. 12/049,256, filed Mar. 14, 2008), as disclosed herein. Such host organisms can be further engineered to express enzymes of a methacrylic acid 3-hydroxyisobutyric acid or 2-hydroxyisobutyric acid pathway.

In some embodiments, a non-naturally occurring microbial organism of the invention is generated from a host that contains the enzymatic capability to synthesize methacrylic acid, 3-hydroxyisobutyric acid or 2-hydroxyisobutyric acid. In this specific embodiment it can be useful to increase the synthesis or accumulation of a methacrylic acid, 3-hydroxyisobutyric acid or 2-hydroxyisobutyric acid pathway product to, for example, drive methacrylic acid, 3-hydroxyisobutyric acid or 2-hydroxyisobutyric acid pathway reactions toward methacrylic acid, 3-hydroxyisobutyric acid or 2-hydroxyisobutyric acid production. Increased synthesis or accumulation can be accomplished by, for example, overexpression of nucleic acids encoding one or more of the above-described methacrylic acid, 3-hydroxyisobutyric acid or 2-hydroxyisobutyric acid pathway enzymes. Over expression of the methacrylic acid, 3-hydroxyisobutyric acid or 2-hydroxyisobutyric acid pathway enzyme or enzymes can occur, for example, through exogenous expression of the endogenous gene or genes, or through exogenous expression of the heterologous gene or genes. Therefore, naturally occurring organisms can be readily generated to be non-naturally occurring microbial organisms of the invention, for example, producing methacrylic acid, 3-hydroxyisobutyric acid or 2-hydroxyisobutyric acid, through overexpression of one, two, three, four, five, and so forth, depending on the methacrylic acid, 3-hydroxyisobutyric acid or 2-hydroxyisobutyric acid pathway, that is, up to including all nucleic acids encoding methacrylic acid, 3-hydroxyisobutyric acid or 2-hydroxyisobutyric acid biosynthetic pathway enzymes. In addition, a non-naturally occurring organism can be generated by mutagenesis of an endogenous gene that results in an increase in activity of an enzyme in the methacrylic acid, 3-hydroxyisobutyric acid or 2-hydroxyisobutyric acid biosynthetic pathway.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism.

It is understood that, in methods of the invention, any of the one or more exogenous nucleic acids can be introduced into a microbial organism to produce a non-naturally occurring microbial organism of the invention. The nucleic acids can be introduced so as to confer, for example, a methacrylic acid, 3-hydroxyisobutyric acid or 2-hydroxyisobutyric acid biosynthetic pathway onto the microbial organism. Alternatively, encoding nucleic acids can be introduced to produce an intermediate microbial organism having the biosynthetic capability to catalyze some of the required reactions to confer methacrylic acid, 3-hydroxyisobutyric acid or 2-hydroxyisobutyric acid biosynthetic capability. For example, a non-naturally occurring microbial organism having a methacrylic acid biosynthetic pathway can comprise at least two exogenous nucleic acids encoding desired enzymes. One exemplary combination includes the combination of methylmalonyl-CoA mutase and methylmalonyl-CoA epimerase; or methylmalonyl-CoA mutase and methylmalonyl-CoA reductase; 3-hydroxyisobutyrate dehydrogenase and 3-hydroxyisobutyrate dehydratase, and the like. In another exemplary pathway, a combination can include 4-hydroxybutyryl-CoA mutase and 3-hydroxyisobutyryl-CoA transferase; 3-hydroxyisobutyryl-CoA synthetase and 3-hydroxyisobutyrate dehydratase; 4-hydroxybutyryl-CoA mutase and 3-hydroxyisobutyryl-CoA synthetase, and so forth. Thus, it is understood that any combination of two or more enzymes of a biosynthetic pathway can be included in a non-naturally occurring microbial organism of the invention.

Similarly, it is understood that any combination of three or more enzymes of a biosynthetic pathway can be included in a non-naturally occurring microbial organism of the invention, for example, methylmalonyl-CoA mutase, methylmalonyl-CoA epimerase, and methylmalonyl-CoA reductase; methylmalonyl-CoA epimerase, 3-amino-2-methylpropionate transaminase, and 3-amino-2-methylpropionate ammonia lyase, and so forth. In another example, the combination can be alpha-ketoglutarate reductase, 3-methylmalate dehydratase, and mesaconate decarboxylase; 2-hydroxyglutamate mutase, 3-methylmalate dehydratase, and mesaconate decarboxylase, and so forth, as desired, so long as the combination of enzymes of the desired biosynthetic pathway results in production of the corresponding desired product. Similarly, any combination of four, five, six or more enzymes, depending on the desired pathway, of a biosynthetic pathway as disclosed herein can be included in a non-naturally occurring microbial organism of the invention, as desired, so long as the combination of enzymes of the desired biosynthetic pathway results in production of the corresponding desired product.

In addition to the biosynthesis of methacrylic acid, 3-hydroxyisobutyric acid or 2-hydroxyisobutyric acid as described herein, the non-naturally occurring microbial organisms and methods of the invention also can be utilized in various combinations with each other and with other microbial organisms and methods well known in the art to achieve product biosynthesis by other routes. For example, one alternative to produce methacrylic acid other than use of the methacrylic acid producers is through addition of another microbial organism capable of converting a methacrylic acid pathway intermediate to methacrylic acid. One such procedure includes, for example, the fermentation of a microbial organism that produces a methacrylic acid pathway intermediate. The methacrylic acid pathway intermediate can then be used as a substrate for a second microbial organism that converts the methacrylic acid pathway intermediate to methacrylic acid. The methacrylic acid pathway intermediate can be added directly to another culture of the second organism or the original culture of the methacrylic acid pathway intermediate producers can be depleted of these microbial organisms by, for example, cell separation, and then subsequent addition of the second organism to the fermentation broth can be utilized to produce the final product without intermediate purification steps.

In other embodiments, the non-naturally occurring microbial organisms and methods of the invention can be assembled in a wide variety of subpathways to achieve biosynthesis of, for example, methacrylic acid, 3-hydroxyisobutyric acid or 2-hydroxyisobutyric acid. In these embodiments, biosynthetic pathways for a desired product of the invention can be segregated into different microbial organisms, and the different microbial organisms can be co-cultured to produce the final product. In such a biosynthetic scheme, the product of one microbial organism is the substrate for a second microbial organism until the final product is synthesized. For example, the biosynthesis of methacrylic acid, 3-hydroxyisobutyric acid or 2-hydroxyisobutyric acid can be accomplished by constructing a microbial organism that contains biosynthetic pathways for conversion of one pathway intermediate to another pathway intermediate or the product. Alternatively, methacrylic acid, 3-hydroxyisobutyric acid or 2-hydroxyisobutyric acid also can be biosynthetically produced from microbial organisms through co-culture or co-fermentation using two organisms in the same vessel, where the first microbial organism produces a methacrylic acid, 3-hydroxyisobutyric acid or 2-hydroxyisobutyric acid pathway intermediate and the second microbial organism converts the intermediate to methacrylic acid, 3-hydroxyisobutyric acid or 2-hydroxyisobutyric acid.

Given the teachings and guidance provided herein, those skilled in the art will understand that a wide variety of combinations and permutations exist for the non-naturally occurring microbial organisms and methods of the invention together with other microbial organisms, with the co-culture of other non-naturally occurring microbial organisms having subpathways and with combinations of other chemical and/or biochemical procedures well known in the art to produce methacrylic acid, 3-hydroxyisobutyric acid or 2-hydroxyisobutyric acid. For example, fermentation to form 3-hydroxyisobutyric acid can be combined with a purification scheme to yield methyl methacrylate (see WO 2002/090312).

Sources of encoding nucleic acids for a methacrylic acid, 3-hydroxyisobutyric acid or 2-hydroxyisobutyric acid pathway enzyme can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli, Homo sapiens, Propionibacterium fredenreichii, Methylobacterium extorquens, Shigella flexneri, Salmonella enterica, Yersinia frederiksenii, Propionibacterium acnes, Rattus norvegicus, Caenorhabditis elegans, Bacillus cereus, Acinetobacter calcoaceticus, Acinetobacter baylyi, Acinetobacter sp., Clostridium kluyveri, Pseudomonas sp., Thermus thermophilus, Pseudomonas aeruginosa, Pseudomonas putida, Oryctolagus cuniculus, Clostridium acetobutylicum, Leuconostoc mesenteroides, Eubacterium barkeri, Bacteroides capillosus, Anaerotruncus colihominis, Natranaerobius thermophilus, Campylobacter jejuni, Arabidopsis thaliana, Corynebacterium glutamicum, Sus scrofa, Bacillus subtilus, Pseudomonas fluorescens, Serratia marcescens, Streptomyces coelicolor, Methylibium petroleiphilum, Streptomyces cinnamonensis, Streptomyces avermitilis, Archaeoglobus fulgidus, Haloarcula marismortui, Pyrobaculum aerophilum, Saccharomyces cerevisiae, Clostridium cochlearium, Clostridium tetanomorphum, Clostridium tetani, Citrobacter amalonaticus, Ralstonia eutropha, Mus musculus, Bos taurus, Fusobacterium nucleatum, Morganella morganii, Clostridium pasteurianum, Rhodobacter sphaeroides, Xanthobacter autotrophicus, Clostridium propionicum, Megasphaera elsdenii, Aspergillus terreus, Candida, Sulfolobus tokodaii, Metallosphaera sedula, Chloroflexus aurantiacus, Clostridium saccharoperbutylacetonicum, Acidaminococcus fermentans, Helicobacter pylori*, as well as other exemplary species disclosed herein or available as source organisms for corresponding genes. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite methacrylic acid, 3-hydroxyisobutyric acid or 2-hydroxyisobutyric acid biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations enabling biosynthesis of methacrylic acid, 3-hydroxyisobutyric acid or 2-hydroxyisobutyric acid described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative methacrylic acid, 3-hydroxyisobutyric acid or 2-hydroxyisobutyric acid biosynthetic pathway exists in an unrelated species, methacrylic acid, 3-hydroxyisobutyric acid or 2-hydroxyisobutyric acid biosynthesis can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms may differ. However, given the teachings and guidance provided herein, those skilled in the art also will understand that the teachings and methods of the invention can be applied to all microbial organisms using the cognate metabolic alterations to those exemplified herein to construct a microbial organism in a species of interest that will synthesize methacrylic acid, 3-hydroxyisobutyric acid or 2-hydroxyisobutyric acid.

Host microbial organisms can be selected from, and the non-naturally occurring microbial organisms generated in, for example, bacteria, yeast, fungus or any of a variety of other microorganisms applicable to fermentation processes. Exemplary bacteria include species selected from *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens*, and *Pseudomonas putida*. Exemplary yeasts or fungi include species selected from *Saccharomyces cerevisiae, Schizosaccharomyces pombe, Kluyveromyces lactis, Kluyveromyces marxianus, Aspergillus terreus, Aspergillus niger* and *Pichia pastoris. E. coli* is a particularly useful host organisms since it is a well characterized microbial organism suitable for genetic engineering. Other particularly useful host organisms include yeast such as *Saccharomyces cerevisiae*.

Methods for constructing and testing the expression levels of a non-naturally occurring methacrylic acid, 3-hydroxyisobutyric acid or 2-hydroxyisobutyric acid-producing host can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

Exogenous nucleic acid sequences involved in a pathway for production of methacrylic acid, 3-hydroxyisobutyric acid or 2-hydroxyisobutyric acid can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280: 4329-4338 (2005). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include one or more methacrylic acid biosynthetic pathway encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration in to a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

The invention additionally provides methods for producing a desired product such as methacrylic acid. In one embodiment, the invention provides a method for producing methacrylic acid, comprising culturing a non-naturally occurring microbial organism having a methacrylic acid pathway, the pathway comprising at least one exogenous nucleic acid encoding a methacrylic acid pathway enzyme expressed in a sufficient amount to produce methacrylic acid, under conditions and for a sufficient period of time to produce methacrylic acid, the methacrylic acid pathway comprising methylmalonyl-CoA mutase, methylmalonyl-CoA epimerase, methylmalonyl-CoA reductase, 3-hydroxyisobutyrate dehydrogenase and 3-hydroxyisobutyrate dehydratase (see Examples I and II and FIG. 2). In another embodiment, the invention provides a method for producing methacrylic acid, comprising culturing a non-naturally occurring microbial organism having a methacrylic acid pathway, the pathway comprising at least one exogenous nucleic acid encoding a methacrylic acid pathway enzyme expressed in a sufficient amount to produce methacrylic acid, under conditions and for a sufficient period of time to produce methacrylic acid, the methacrylic acid pathway comprising methylmalonyl-CoA mutase, methylmalonyl-CoA epimerase, alcohol/aldehyde dehydrogenase, and 3-hydroxyisobutyrate dehydratase (see Example I).

Figure 4:
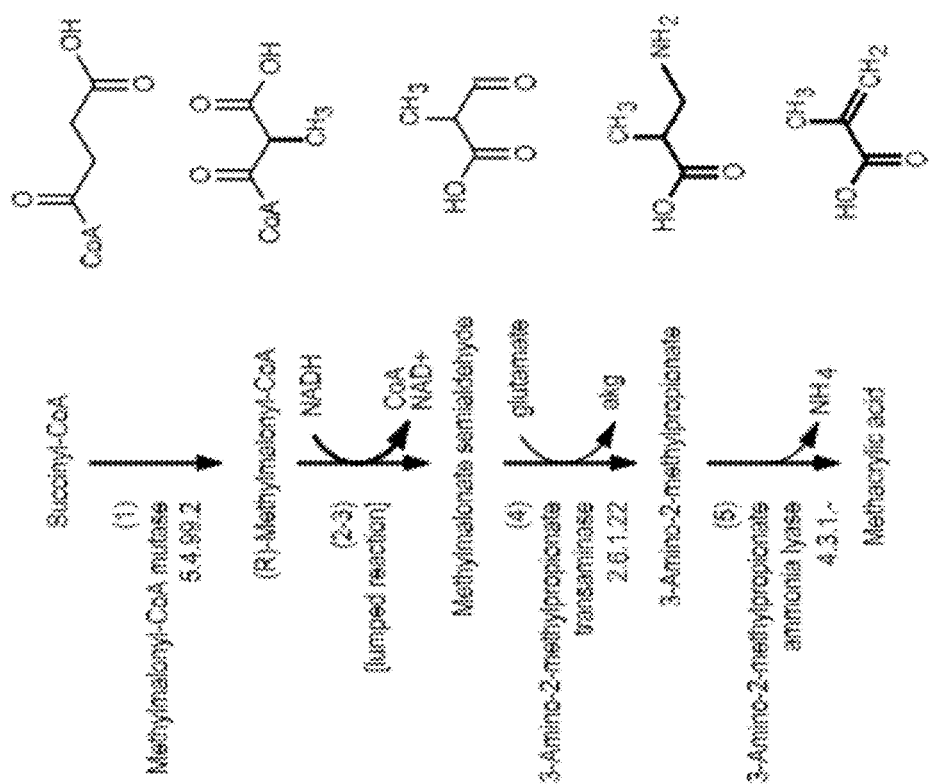
FIG. 4 shows an exemplary succinyl-CoA to MAA pathway via 3-amino-2-methylpropionate. The "lumped reaction" (steps 2-3) is catalyzed by 1) methylmalonyl-CoA epimerase and 2) methylmalonyl-CoA reductase.

In yet another embodiment, the invention provides a method for producing methacrylic acid, comprising culturing a non-naturally occurring microbial organism having a methacrylic acid pathway, the pathway comprising at least one exogenous nucleic acid encoding a methacrylic acid pathway enzyme expressed in a sufficient amount to produce methacrylic acid, under conditions and for a sufficient period of time to produce methacrylic acid, the methacrylic acid pathway comprising methylmalonyl-CoA mutase, methylmalonyl-CoA epimerase, methylmalonyl-CoA reductase, 3-amino-2-methylpropionate transaminase, and 3-amino-2-methylpropionate ammonia lyase (see Examples III and IV and FIG. 4). Additionally provided is a method for producing methacrylic acid, comprising culturing a non-naturally occurring microbial organism having a methacrylic acid pathway, the pathway comprising at least one exogenous nucleic acid encoding a methacrylic acid pathway enzyme expressed in a sufficient amount to produce methacrylic acid, under conditions and for a sufficient period of time to produce methacrylic acid, the methacrylic acid pathway comprising 4-hydroxybutyryl-CoA mutase, 3-hydroxyisobutyryl-CoA synthetase or 3-hydroxyisobutyryl-CoA hydrolase or 3-hydroxyisobutyryl-CoA transferase, and 3-hydroxyisobutyrate dehydratase (see Examples V and VI and FIG. 6).

Also provided is a method for producing methacrylic acid, comprising culturing a non-naturally occurring microbial organism having a methacrylic acid pathway, the pathway comprising at least one exogenous nucleic acid encoding a methacrylic acid pathway enzyme expressed in a sufficient amount to produce methacrylic acid, under conditions and for a sufficient period of time to produce methacrylic acid, the methacrylic acid pathway comprising aspartate aminotransferase, glutamate mutase, 3-methylaspartase, and mesaconate decarboxylase (see Examples VII and VIII and FIG. 8). Another embodiment provides a method for producing methacrylic acid, comprising culturing a non-naturally occurring microbial organism having a methacrylic acid pathway, the pathway comprising at least one exogenous nucleic acid encoding a methacrylic acid pathway enzyme expressed in a sufficient amount to produce methacrylic acid, under conditions and for a sufficient period of time to produce methacrylic acid, the methacrylic acid pathway comprising alpha-ketoglutarate reductase, 2-hydroxyglutamate mutase, 3-methylmalate dehydratase, and mesaconate decarboxylase (see Examples IX and X and FIG. 10).

In yet a further embodiment, the invention provides a method for producing methacrylic acid, comprising culturing a non-naturally occurring microbial organism having a methacrylic acid pathway, the pathway comprising at least one exogenous nucleic acid encoding a methacrylic acid pathway enzyme expressed in a sufficient amount to produce methacrylic acid, under conditions and for a sufficient period of time to produce methacrylic acid, the methacrylic acid pathway comprising acetoacetyl-CoA thiolase, acetoacetyl-CoA reductase, 3-hydroxybutyryl-CoA mutase, 2-hydroxyisobutyryl-CoA dehydratase, and methacrylyl-CoA transferase or methacrylyl-CoA hydrolase or methacrylyl-CoA synthetase (see Example XI and XII and FIG. 12). A still further embodiment provides a method for producing methacrylic acid, comprising culturing a non-naturally occurring microbial organism having a methacrylic acid pathway, the pathway comprising at least one exogenous nucleic acid encoding a methacrylic acid pathway enzyme expressed in a sufficient amount to produce methacrylic acid, under conditions and for a sufficient period of time to produce methacrylic acid, the methacrylic acid pathway comprising acetoacetyl-CoA thiolase, acetoacetyl-CoA reductase, 3-hydroxybutyryl-CoA mutase, 2-hydroxyisobutyryl-CoA dehydratase, enoyl-CoA hydratase, and 3-hydroxyisobutyryl-CoA hydrolase or 3-hydroxyisobutyryl-CoA synthetase or 3-hydroxyisobutyryl-CoA transferase, and 3-hydroxyisobutyrate dehydratase (see Example XI and XII).

The invention additional provides a method for producing methacrylic acid, comprising culturing a non-naturally occurring microbial organism having a methacrylic acid pathway, the pathway comprising at least one exogenous nucleic acid encoding a methacrylic acid pathway enzyme expressed in a sufficient amount to produce methacrylic acid, under conditions and for a sufficient period of time to produce methacrylic acid, the methacrylic acid pathway comprising acetoacetyl-CoA thiolase, acetoacetyl-CoA reductase, crotonase, butyryl-CoA dehydrogenase, isobutyryl-CoA mutase, isobutyryl-CoA dehydrogenase, and methacrylyl-CoA synthetase or methacrylyl-CoA hydrolase or methacrylyl-CoA transferase (see Example XIII and FIG. 13). Also provided method for producing methacrylic acid, comprising culturing a non-naturally occurring microbial organism having a methacrylic acid pathway, the pathway comprising at least one exogenous nucleic acid encoding a methacrylic acid pathway enzyme expressed in a sufficient amount to produce methacrylic acid, under conditions and for a sufficient period of time to produce methacrylic acid, the methacrylic acid pathway comprising lactate dehydrogenase, lactate-CoA transferase, lactoyl-CoA dehydratase, acyl-CoA dehydrogenase, propionyl-CoA carboxylase, methylmalonyl-CoA reductase, 3-hydroxyisobutyrate dehydrogenase, and 3-hydroxyisobutyrate dehydratase (see Example XIV and FIG. 14). Yet a further embodiment provides a method for producing methacrylic acid, comprising culturing a non-naturally occurring microbial organism having a methacrylic acid pathway, the pathway comprising at least one exogenous nucleic acid encoding a methacrylic acid pathway enzyme expressed in a sufficient amount to produce methacrylic acid, under conditions and for a sufficient period of time to produce methacrylic acid, the methacrylic acid pathway comprising valine aminotransferase, 2-ketoisovalerate dehydrogenase, isobutyryl-CoA dehydrogenase, and methacrylyl-CoA synthetase or methacrylyl-CoA hydrolase or methacrylyl-CoA transferase (see Example XV and FIG. 15). Such a pathway can further comprise acetolactate synthase, acetohydroxy acid isomeroreductase and dihydroxy-acid dehydratase.

The invention additionally provides a method for producing 3-hydroxyisobutyric acid, comprising culturing a non-naturally occurring microbial organism having a 3-hydroxyisobutyric acid pathway, the pathway comprising at least one exogenous nucleic acid encoding a 3-hydroxyisobutyric acid pathway enzyme expressed in a sufficient amount to produce 3-hydroxyisobutyric acid, under conditions and for a sufficient period of time to produce 3-hydroxyisobutyric acid, the 3-hydroxyisobutyric acid pathway comprising 4-hydroxybutyryl-CoA mutase; and 3-hydroxyisobutyryl-CoA synthetase or 3-hydroxyisobutyryl-CoA hydrolase or 3-hydroxyisobutyryl-CoA transferase (see Example V and FIG. 6). Also provided is a method for producing 2-hydroxyisobutyric acid, comprising culturing a non-naturally occurring microbial organism having a 2-hydroxyisobutyric acid pathway, the pathway comprising at least one exogenous nucleic acid encoding a 2-hydroxyisobutyric acid pathway enzyme expressed in a sufficient amount to produce 2-hydroxyisobutyric acid, under conditions and for a sufficient period of time to produce 2-hydroxyisobutyric acid, the 2-hydroxyisobutyric acid pathway comprising acetoacetyl-CoA thiolase; acetoacetyl-CoA reductase; 3-hydroxybutyryl-CoA mutase; and 2-hydroxyisobutyryl-CoA transferase or 2-hydroxyisobutyryl-CoA hydrolase or 2-hydroxyisobutyryl-CoA synthetase (see Example XI and FIG. 12).

In another embodiment, the invention provides a method for producing methacrylic acid comprising culturing a non-naturally occurring microbial organism having a methacrylic acid pathway, the pathway comprising at least one exogenous nucleic acid encoding a methacrylic acid pathway enzyme expressed in a sufficient amount to produce methacrylic acid, under conditions and for a sufficient period of time to produce methacrylic acid, the methacrylic acid pathway comprising 4-hydroxybutyryl-CoA dehydratase; vinylacetyl-CoA Δ-isomerase; crotonase; 3-hydroxybutyryl-CoA mutase; 2-hydroxyisobutyryl-CoA dehydratase; and methacrylyl-CoA hydrolase or methacrylyl-CoA synthetase or methacrylyl-CoA transferase (see Example XVIII and FIG. 12). Also provided is a method for producing 2-hydroxyisobutyric acid, comprising culturing a non-naturally occurring microbial organism having a 2-hydroxyisobutyric acid pathway, the pathway comprising at least one exogenous nucleic acid encoding a 2-hydroxyisobutyric acid pathway enzyme expressed in a sufficient amount to produce 2-hydroxyisobutyric acid, under conditions and for a sufficient period of time to produce 2-hydroxyisobutyric acid, the 2-hydroxyisobutyric acid pathway comprising 4-hydroxybutyryl-CoA dehydratase; vinylacetyl-CoA Δ-isomerase; crotonase; 3-hydroxybutyryl-CoA mutase; and 2-hydroxyisobutyryl-CoA hydrolase or 2-hydroxyisobutyryl-CoA synthetase or 2-hydroxyisobutyryl-CoA transferase (see Examples XVIII and FIG. 12).

Suitable purification and/or assays to test for the production of methacrylic acid can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy), or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., *Biotechnol. Bioeng.* 90:775-779 (2005)), or other suitable assay and detection methods well known in the art. The individual enzyme activities from the exogenous DNA sequences can also be assayed using methods well known in the art.

The methacrylic acid, 2-hydroxyisobutyric acid or 3-hydroxyisobutyric acid products can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the non-naturally occurring microbial organisms described herein can be cultured to produce and/or secrete the biosynthetic products of the invention. For example, the methacrylic acid producers can be cultured for the biosynthetic production of methacrylic acid.

For the production of methacrylic acid, 2-hydroxyisobutyric acid or 3-hydroxyisobutyric acid, the recombinant strains are cultured in a medium with carbon source and other essential nutrients. It is highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic conditions can be applied by perforating the septum with a small hole for limited aeration. Exemplary anaerobic conditions have been described previously and are well-known in the art. Exemplary aerobic and anaerobic conditions are described, for example, in United State patent application Ser. No. 11/891,602, filed Aug. 10, 2007. Fermentations can be performed in a batch, fed-batch or continuous manner, as disclosed herein.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The growth medium can be, for example, any carbohydrate source which can supply a source of carbon to the non-naturally occurring microorganism. Such sources include, for example, sugars such as glucose, xylose, arabinose, galactose, mannose, fructose and starch. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms of the invention for the production of methacrylic acid.

In addition to renewable feedstocks such as those exemplified above, the methacrylic acid microbial organisms of the invention also can be modified for growth on syngas as its source of carbon. In this specific embodiment, one or more proteins or enzymes are expressed in the methacrylic acid producing organisms to provide a metabolic pathway for utilization of syngas or other gaseous carbon source.

Synthesis gas, also known as syngas or producer gas, is the major product of gasification of coal and of carbonaceous materials such as biomass materials, including agricultural crops and residues. Syngas is a mixture primarily of $H_2$ and CO and can be obtained from the gasification of any organic feedstock, including but not limited to coal, coal oil, natural gas, biomass, and waste organic matter. Gasification is generally carried out under a high fuel to oxygen ratio. Although largely $H_2$ and CO, syngas can also include $CO_2$ and other gases in smaller quantities. Thus, synthesis gas provides a cost effective source of gaseous carbon such as CO and, additionally, $CO_2$.

The Wood-Ljungdahl pathway catalyzes the conversion of CO and $H_2$ to acetyl-CoA and other products such as acetate. Organisms capable of utilizing CO and syngas also generally have the capability of utilizing $CO_2$ and $CO_2/H_2$ mixtures through the same basic set of enzymes and transformations encompassed by the Wood-Ljungdahl pathway. $H_2$-dependent conversion of $CO_2$ to acetate by microorganisms was recognized long before it was revealed that CO also could be used by the same organisms and that the same pathways were involved. Many acetogens have been shown to grow in the presence of $CO_2$ and produce compounds such as acetate as long as hydrogen is present to supply the necessary reducing equivalents (see for example, Drake, *Acetogenesis*, pp. 3-60 Chapman and Hall, New York, (1994)). This can be summarized by the following equation:

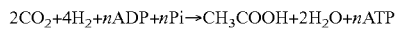

$$2CO_2+4H_2+nADP+nPi \rightarrow CH_3COOH+2H_2O+nATP$$

Hence, non-naturally occurring microorganisms possessing the Wood-Ljungdahl pathway can utilize $CO_2$ and $H_2$ mixtures as well for the production of acetyl-CoA and other desired products.

The Wood-Ljungdahl pathway is well known in the art and consists of 12 reactions which can be separated into two branches: (1) methyl branch and (2) carbonyl branch. The methyl branch converts syngas to methyl-tetrahydrofolate (methyl-THF) whereas the carbonyl branch converts methyl-THF to acetyl-CoA. The reactions in the methyl branch are catalyzed in order by the following enzymes: ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase. The reactions in the carbonyl branch are catalyzed in order by the following enzymes: cobalamide corrinoid/iron-sulfur protein, methyltransferase, carbon monoxide dehydrogenase, acetyl-CoA synthase, acetyl-CoA synthase disulfide reductase and hydrogenase. Following the teachings and guidance provided herein for introducing a sufficient number of encoding nucleic acids to generate a methacrylic acid, 3-hydroxyisobutyric acid or 2-hydroxyisobutyric acid pathway, those skilled in the art will understand that the same engineering design also can be performed with respect to introducing at least the nucleic acids encoding the Wood-Ljungdahl enzymes absent in the host organism. Therefore, introduction of one or more encoding nucleic acids into the microbial organisms of the invention such that the modified organism contains the complete Wood-Ljungdahl pathway will confer syngas utilization ability.

Accordingly, given the teachings and guidance provided herein, those skilled in the art will understand that a non-naturally occurring microbial organism can be produced that secretes the biosynthesized compounds of the invention when grown on a carbon source such as a carbohydrate. Such compounds include, for example, methacrylic acid and any of the intermediate metabolites in the methacrylic acid pathway. All that is required is to engineer in one or more of the required enzyme activities to achieve biosynthesis of the desired compound or intermediate including, for example, inclusion of some or all of the methacrylic acid biosynthetic pathways. Accordingly, the invention provides a non-naturally occurring microbial organism that produces and/or secretes methacrylic acid when grown on a carbohydrate and produces and/or secretes any of the intermediate metabolites shown in the methacrylic acid pathway when grown on a carbohydrate. Intermediate metabolites that can be produced and/or excreted include 3-hydroxyisobutyric acid and 2-hydroxyisobutyric acid.

The methacrylic acid producing microbial organisms of the invention can initiate synthesis from an intermediate. For example, in addition to initiating synthesis from succinyl-CoA as a precursor, synthesis can be initiated from an intermediate such as (R)-methylmalonyl-CoA, (S)-methylmalonyl-CoA, methylmalonate semialdehyde or 3-hydroxyisobutyrate (see Example I and FIG. 2). Alternatively, synthesis can be initiated from an intermediate such as (R)-methylmalonyl-CoA, (S)-methylmalonyl-CoA, methylmalonate semialdehyde, or 3-amino-2-methylpropionate (see Example III and FIG. 4). In a pathway having 4-hydroxybutyryl-CoA as a precursor, synthesis can be initiated from an intermediate such as 3-hydroxyisobutyryl-CoA, methacrylyl-CoA or 3-hydroxyisobutyrate (see Example V and FIG. 6).

In a methacrylic acid pathway utilizing alpha-ketoglutarate as a precursor, synthesis can be initiated, for example, from glutamate, threo-3-methylaspartate or mesaconate (see Example VII and FIG. 8). Alternatively, synthesis can initiate from an intermediate such as 2-hydroxyglutarate, 3-methylmalate or mesaconate (see Example IX and FIG. 10). In a pathway utilizing acetyl-CoA as a precursor, synthesis can initiate, for example, from an intermediate such as acetoacetyl-CoA, 3-hydroxybutyryl-CoA, 2-hydroxyisobutyryl-CoA, or methacrylyl-CoA (see Example XI and FIG. 12). Alternatively, synthesis can be initiated from an intermediate such as acetoacetyl-CoA, 3-hydroxybutyryl-CoA, crotonyl-CoA, butyryl-CoA, isobutyryl-CoA and methacrylyl-CoA (see Example XIII and FIG. 13).

In a methacrylic acid pathway utilizing pyruvate as a precursor, synthesis can initiate from an intermediate such as lactate, lactoyl-CoA, acrylyl-CoA, propionyl-CoA, (S)-methylmalonyl-CoA, methylmalonate semialdehyde or 3-hydroxyisobutyrate (see Example XIV and FIG. 14). In a pathway utilizing 2-ketoisovalerate as precursor, synthesis can initiate from an intermediate such as isobutyryl-CoA or methacrylyl-CoA (see Example XV and FIG. 15). In addition, synthesis can initiate from an intermediate in the conversion of pyruvate to 2-ketoisovalerate.

In a 3-hydroxyisobutyric acid pathway utilizing 4-hydroxybutyryl-CoA as a precursor, synthesis can initiate from an intermediate such as 3-hydroxyisobutyryl-CoA (see Example V and FIG. 6). In a 2-hydroxyisobutyric acid pathway utilizing acetyl-CoA as a precursor, synthesis can initiate, for example, from an intermediate such as acetoacetyl-CoA, 3-hydroxybutyryl-CoA, or 2-hydroxyisobutyryl-CoA (see Example XI and FIG. 12).

Furthermore, it is understood that additional modifications can be to a microbial organism of the invention to increase product yield. For example, metabolic modeling can be employed to determine any additional modifications that can be made to a microbial organism having a 2-hydroxyisobutyric acid, 3-hydroxyisobutyric acid or methacrylic acid pathway to increase product yield (see Example XXV). In one embodiment, modifications can be employed to increase the production of a precursor or intermediate of a 2-hydroxyisobutyric acid, 3-hydroxyisobutyric acid or methacrylic acid pathway. As disclosed herein, modifications of metabolic pathways can be employed, including modification of central metabolic reactions and their corresponding enzymes, to increase the yield of a desired precursor, intermediate or product. For example, it has been found that increasing the expression of several enzymes by various mechanisms can be utilized to increase the yield of MAA or 3-hydroxyisobutyrate. Such enzymes include, but are not limited to, 1) citrate synthase and aconitase; 2) isocitrate lyase and malate synthase; 3) pyruvate dehydrogenase and/or pyruvate ferredoxin oxidoreductase; and 4) phosphoenolpyruvate (PEP) carboxykinase (see Example XXV). Expression of these enzymes can be used to increase the yields of MAA or 3-hydroxyisobutyrate using the pathways from succinyl-CoA or 4-hydroxybutyryl-CoA.

Thus, the invention additionally provides a non-naturally occurring microbial organism which, in addition to containing a 2-hydroxisobutyric acid, 3-hydroxyisobutyric acid or methacrylic acid pathway, further is genetically modified to increase the activity of at least one protein or enzyme that increases production of a precursor or intermediate of the 2-hydroxisobutyric acid, 3-hydroxyisobutyric acid or methacrylic acid product, wherein the increase in activity is relative to the absence of the genetic modification that increases the activity of the at least one protein or enzyme. For example, the non-naturally occurring microbial organism can be genetically modified to increase the activity of at least one of an enzyme selected from citrate synthase, aconitase, isocitrate lyase, malate synthase, pyruvate dehydrogenase, pyruvate ferredoxin oxidoreductase and phosphoenolpyruvate carboxykinase (see Example XXV). It is understood that the increase in activity is relative to a microbial organism that has not been genetically modified to increase the activity of such enzymes. For example, if the genetic modification to increase the activity of an enzyme is introduced into a microbial organism having a methacrylic acid pathway, then the increase in activity of the enzyme is relative to the host organism having a methacrylic acid pathway but in the absence of the genetic modification. It is understood that such genetic modifications include, but are not limited to, introducing an exogenous nucleic acid encoding a homologous (native) or heterologous sequence of a protein or enzyme whose activity is to be increased, either by chromosomal integration or contained on a plasmid. For example, a heterologous sequence from an organism having a desirable property that increases the activity of the protein or enzyme can be introduced, or an increased copy number of the endogenous gene can be introduced into the organism. In addition, the promoter of the endogenous gene can be replaced with a more active promoter or the native promoter can be genetically modified with mutations to increase expression and therefore activity of the protein or enzyme. Such a replacement or other genetic modification of the promoter can result in either a constitutive or inducible promoter. Additionally, a repressor of the endogenous gene can be decreased, for example, by knocking out the repressor with a gene disruption or genetically modifying its promoter to decrease expression. Thus, these and other genetic modifications disclosed herein and known in the art can be used to increase the activity of a desired protein or enzyme.

The non-naturally occurring microbial organisms of the invention are constructed using methods well known in the art as exemplified herein to exogenously express at least one nucleic acid encoding a methacrylic acid pathway enzyme in sufficient amounts to produce methacrylic acid, 3-hydroxyisobutyric acid or 2-hydroxyisobutyric acid. It is understood that the microbial organisms of the invention are cultured under conditions sufficient to produce methacrylic acid, 3-hydroxyisobutyric acid or 2-hydroxyisobutyric acid. Following the teachings and guidance provided herein, the non-naturally occurring microbial organisms of the invention can achieve biosynthesis of methacrylic acid, 3-hydroxyisobutyric acid or 2-hydroxyisobutyric acid resulting in intracellular concentrations between about 0.1-200 mM or more. Generally, the intracellular concentration of methacrylic acid, 3-hydroxyisobutyric acid or 2-hydroxyisobutyric acid is between about 3-150 mM, particularly between about 5-125 mM and more particularly between about 8-100 mM, including about 10 mM, 20 mM, 50 mM, 80 mM, or more. Intracellular concentrations between and above each of these exemplary ranges also can be achieved from the non-naturally occurring microbial organisms of the invention.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. patent application Ser. No. 11/891,602, filed Aug. 10, 2007. Any of these conditions can be employed with the non-naturally occurring microbial organisms as well as other anaerobic conditions well known in the art. Under such anaerobic conditions, the methacrylic acid, 3-hydroxyisobutyric acid or 2-hydroxyisobutyric acid producers can synthesize methacrylic acid, 3-hydroxyisobutyric acid or 2-hydroxyisobutyric acid, respectively, at intracellular concentrations of 5-10 mM or more as well as all other concentrations exemplified herein. It is understood that, even though the above description refers to intracellular concentrations, methacrylic acid, 3-hydroxyisobutyric acid or 2-hydroxyisobutyric acid producing microbial organisms can produce methacrylic acid, 3-hydroxyisobutyric acid or 2-hydroxyisobutyric acid intracellularly and/or secrete the product into the culture medium.

The culture conditions can include, for example, liquid culture procedures as well as fermentation and other large scale culture procedures. As described herein, particularly useful yields of the biosynthetic products of the invention can be obtained under anaerobic or substantially anaerobic culture conditions.

As described herein, one exemplary growth condition for achieving biosynthesis of methacrylic acid, 3-hydroxyisobutyric acid or 2-hydroxyisobutyric acid includes anaerobic culture or fermentation conditions. In certain embodiments, the non-naturally occurring microbial organisms of the invention can be sustained, cultured or fermented under anaerobic or substantially anaerobic conditions. Briefly, anaerobic conditions refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions described herein can be scaled up and grown continuously for manufacturing of methacrylic acid. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of methacrylic acid, 3-hydroxyisobutyric acid or 2-hydroxyisobutyric acid. Generally, and as with non-continuous culture procedures, the continuous and/or near-continuous production of methacrylic acid, 3-hydroxyisobutyric acid or 2-hydroxyisobutyric acid will include culturing a non-naturally occurring methacrylic acid, 3-hydroxyisobutyric acid or 2-hydroxyisobutyric acid producing organism of the invention in sufficient nutrients and medium to sustain and/or nearly sustain growth in an exponential phase. Continuous culture under such conditions can be include, for example, 1 day, 2, 3, 4, 5, 6 or 7 days or more. Additionally, continuous culture can include 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods. It is further understood that the time of culturing the microbial organism of the invention is for a sufficient period of time to produce a sufficient amount of product for a desired purpose.

Fermentation procedures are well known in the art. Briefly, fermentation for the biosynthetic production of methacrylic acid, 3-hydroxyisobutyric acid or 2-hydroxyisobutyric acid can be utilized in, for example, fed-batch fermentation and batch separation; fed-batch fermentation and continuous separation, or continuous fermentation and continuous separation. Examples of batch and continuous fermentation procedures are well known in the art.

In addition to the above fermentation procedures using the methacrylic acid producers of the invention for continuous production of substantial quantities of methacrylic acid, the methacrylic acid producers also can be, for example, simultaneously subjected to chemical synthesis procedures to convert the product to other compounds or the product can be separated from the fermentation culture and sequentially subjected to chemical conversion to convert the product to other compounds, if desired. Furthermore, in addition to the above fermentation procedures using the 3-hydroxyisobutyrate or 2-hydroxyisobutyrate producers of the invention for continuous production of substantial quantities of 3-hydroxyisobutyrate or 2-hydroxyisobutyrate, respectively, the 3-hydroxyisobutyrate or 2-hydroxyisobutyrate producers also can be, for example, simultaneously subjected to chemical synthesis procedures to convert the product to other compounds or the product can be separated from the fermentation culture and sequentially subjected to chemical conversion to convert the product to other compounds, if desired.

One consideration for bioprocessing is whether to use a batch or continuous fermentation scheme. One difference between the two schemes that will influence the amount of product produced is the presence of a preparation, lag, and stationary phase for the batch scheme in addition to the exponential growth phase. In contrast, continuous processes are kept in a state of constant exponential growth and, if properly operated, can run for many months at a time. For growth-associated and mixed-growth-associated product formation, continuous processes provide much higher productivities (i.e., dilution rate times cell mass) due to the elimination of the preparation, lag, and stationary phases.

Despite advantages in productivity, many more batch processes are in operation than continuous processes for a number of reasons. First, for non-growth associated product formation, the productivity of a batch system can significantly exceed that of a continuous process because the latter would have to operate at very low dilution rates. Next, production strains generally have undergone modifications to their genetic material to improve their biochemical or protein production capabilities. These specialized strains are likely to grow less rapidly than their parental complements whereas continuous processes such as those employing chemostats (fermenters operated in continuous mode) impose large selection pressures for the fastest growing cells. Cells containing recombinant DNA or carrying point mutations leading to the desired overproduction phenotype are susceptible to back-mutation into the original less productive parental strain. It also is possible for strains having single gene deletions to develop compensatory mutations that will tend to restore the wild-type growth phenotype. The faster growing cells usually out-compete their more productive counterparts for limiting nutrients, drastically reducing productivity. Batch processes, on the other hand, limit the number of generations available by not reusing cells at the end of each cycle, thus decreasing the probability of the production strain reverting back to its wild-type phenotype. Finally, continuous processes are more difficult to operate long-term due to potential engineering obstacles such as equipment failure and foreign organism contamination. The consequences of such failures also are much more considerable for a continuous process than with a batch culture.

For small-volume production of specialty chemicals and/or proteins, the productivity increases of continuous processes rarely outweigh the risks associated with strain stability and reliability. However, for the production of large-volume, growth-associated products such as 3-hydroxyisobutyric acid or methacrylic acid, the increases in productivity for a continuous process can result in significant economic gains when compared to a batch process. Although the engineering obstacles associated with continuous bioprocess operation would always be present, the strain stability concerns can be overcome through metabolic engineering strategies that reroute metabolic pathways to reduce or avoid negative selective pressures and favor production of the target product during the exponential growth phase.

To generate better producers, metabolic modeling can be utilized to optimize growth conditions. Modeling can also be used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of methacrylic acid, 3-hydroxyisobutyric acid or 2-hydroxyisobutyric acid.

One computational method for identifying and designing metabolic alterations favoring biosynthesis of a desired product is the OptKnock computational framework, Burgard et al., *Biotechnol. Bioeng.* 84:647-657 (2003). OptKnock is a metabolic modeling and simulation program that suggests gene deletion strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of a desired product or used in connection with the non-naturally occurring microbial organisms for further optimization of biosynthesis of a desired product.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. Opt- Knock computational framework allows the construction of model formulations that enable an effective query of the performance limits of metabolic networks and provides methods for solving the resulting mixed-integer linear programming problems. The metabolic modeling and simulation methods referred to herein as OptKnock are described in, for example, U.S. publication 2002/0168654, filed Jan. 10, 2002, in International Patent No. PCT/US02/00660, filed Jan. 10, 2002, and U.S. publication 2009/0047719, filed Aug. 10, 2007.

Another computational method for identifying and designing metabolic alterations favoring biosynthetic production of a product is a metabolic modeling and simulation system termed SimPheny®. This computational method and system is described in, for example, U.S. publication 2003/0233218, filed Jun. 14, 2002, and in International Patent Application No. PCT/US03/18838, filed Jun. 13, 2003. SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components. Analysis methods such as convex analysis, linear programming and the calculation of extreme pathways as described, for example, in Schilling et al., *J. Theor. Biol.* 203:229-248 (2000); Schilling et al., *Biotech. Bioeng.* 71:286-306 (2000) and Schilling et al., *Biotech. Prog.* 15:288-295 (1999), can be used to determine such phenotypic capabilities.

As described above, one constraints-based method used in the computational programs applicable to the invention is flux balance analysis. Flux balance analysis is based on flux balancing in a steady state condition and can be performed as described in, for example, Varma and Palsson, *Biotech. Bioeng.* 12:994-998 (1994). Flux balance approaches have been applied to reaction networks to simulate or predict systemic properties of, for example, adipocyte metabolism as described in Fell and Small, *J. Biochem.* 138:781-786 (1986), acetate secretion from *E. coli* under ATP maximization conditions as described in Majewski and Domach, *Biotech. Bioeng.* 35:732-738 (1990) or ethanol secretion by yeast as described in Vanrolleghem et al., *Biotech. Prog.* 12:434-448 (1996). Additionally, this approach can be used to predict or simulate the growth of *S. cerevisiae* on a variety of single-carbon sources as well as the metabolism of *H. influenzae* as described in Edwards and Palsson, *Proc. Natl. Acad. Sci.* 97:5528-5533 (2000), Edwards and Palsson, *J. Bio. Chem.* 274:17410-17416 (1999) and Edwards et al., *Nature Biotech.* 19:125-130 (2001).

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host microbial organisms. Such metabolic modeling and simulation methods include, for example, the computational systems exemplified above as SimPheny® and OptKnock. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

Figure 16:
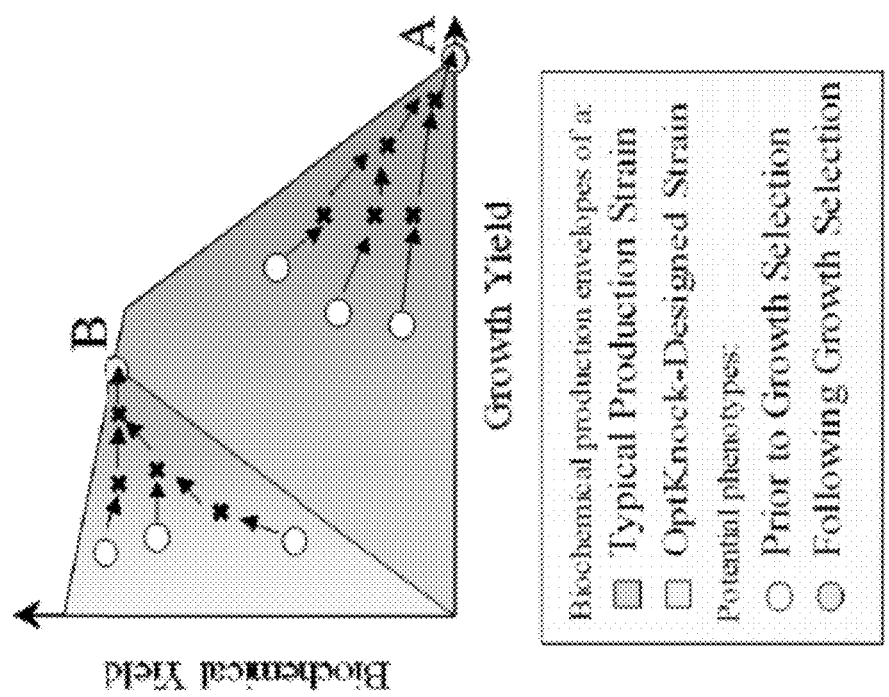
FIG. 16 shows hypothetical production envelopes of an OptKnock-designed strain compared to a typical non-growth-coupled production strain. The area to the right of the diagonal relates to a typical production strain, whereas the left of the diagonal represents an Optknock-designed strain. The potential evolutionary trajectories of the OptKnock strain are fundamentally different in that they lead to a high producing phenotype. The open circles within the shaded areas represent prior to growth selection. The circles at the apex of the shaded areas (B for Optknock, A for typical production strain) represent phenotypes following growth selection.

The ability of a cell or organism to obligatory couple growth to the production of a biochemical product can be illustrated in the context of the biochemical production limits of a typical metabolic network calculated using an in silico model. These limits are obtained by fixing the uptake rate(s) of the limiting substrate(s) to their experimentally measured value(s) and calculating the maximum and minimum rates of biochemical production at each attainable level of growth. As shown in FIG. 16, the production of a desired biochemical generally is in direct competition with biomass formation for intracellular resources. Under these circumstances, enhanced rates of biochemical production will necessarily result in sub-maximal growth rates. The knockouts suggested by the metabolic modeling and simulation programs such as OptKnock, as disclosed herein, are designed to restrict the allowable solution boundaries forcing a change in metabolic behavior from the wild-type strain as depicted in FIG. 16. Although the actual solution boundaries for a given strain will expand or contract as the substrate uptake rate(s) increase or decrease, each experimental point will lie within its calculated solution boundary. Plots such as these allow accurate predictions of how close the designed strains are to their performance limits which also indicates how much room is available for improvement.

The OptKnock mathematical framework is exemplified herein for pinpointing gene deletions leading to growth-coupled biochemical production as illustrated in FIG. 16. The procedure builds upon constraint-based metabolic modeling which narrows the range of possible phenotypes that a cellular system can display through the successive imposition of governing physico-chemical constraints (Price et al., *Nat Rev Microbiol*, 2: 886-97 (2004)). As described above, constraint-based models and simulations are well known in the art and generally invoke the optimization of a particular cellular objective, subject to network stoichiometry, to suggest a likely flux distribution.

Briefly, the maximization of a cellular objective quantified as an aggregate reaction flux for a steady state metabolic network comprising a set $N=\{1, \ldots, N\}$ of metabolites and a set $M=\{1, \ldots, M\}$ of metabolic reactions is expressed mathematically as follows:

$$\text{maximize} \quad v_{cellular\ objective}$$

$$\text{subject to} \quad \sum_{j=1}^{M} S_{ij} v_j = 0, \quad \forall\ i \in N$$

$$v_{substrate} = v_{substrate\_uptake}\ \text{mmol/gDW} \cdot \text{hr}$$

$$\forall\ i \in \{\text{limiting substrate(s)}\}$$

$$v_{atp} \geq v_{atp\_main}\ \text{mmol/gDW} \cdot \text{hr}$$

$$v_j \geq 0, \quad \forall\ j \in \{irrev.\ \text{reactions}\}$$

where $S_{ij}$ is the stoichiometric coefficient of metabolite i in reaction j, $v_j$ is the flux of reaction j, $v_{substrate\_uptake}$ represents the assumed or measured uptake rate(s) of the limiting substrate(s), and $v_{atp\_main}$ is the non-growth associated ATP maintenance requirement. The vector v includes both internal and external fluxes. In this study, the cellular objective is often assumed to be a drain of biosynthetic precursors in the ratios required for biomass formation, Neidhardt, F. C. et al., 2nd ed. 1996, Washington, D.C.: ASM Press. 2 v. (xx, 2822, lxxvi). The fluxes are generally reported per 1 gDW·hr (gram of dry weight times hour) such that biomass formation is expressed as g biomass produced/gDW·hr or 1/hr.

The modeling of gene deletions, and thus reaction elimination, first employs the incorporation of binary variables into the constraint-based approach framework, Burgard et al., *Biotechnol Bioeng*, 74: 364-375 (2001), Burgard et al., *Biotechnol Prog*, 17: 791-797 (2001). These binary variables, $$y_j = \begin{cases} 1, & \text{if reaction flux } v_j \text{ is active} \\ 0, & \text{if reaction flux } v_j \text{ is not active} \end{cases} \forall\ j \in M$$

assume a value of 1 if reaction j is active and a value of 0 if it is inactive. The following constraint, $$v_j^{min} \cdot y_j \leq v_j \leq v_j^{max} \cdot y_j, \quad \forall j \in M$$

ensures that reaction flux $v_j$ is set to zero only if variable $y_j$ is equal to zero. Alternatively, when $y_j$ is equal to one, $v_j$ is free to assume any value between a lower $v_j^{min}$ and an upper $v_j^{max}$ bound. Here, $v_j^{min}$ and $v_j^{max}$ are identified by minimizing and maximizing, respectively, every reaction flux subject to the network constraints described above, Mahadevan et al., *Metab Eng*, 5: 264-76 (2003).

Optimal gene/reaction knockouts are identified by solving a bilevel optimization problem that chooses the set of active reactions ($y_j=1$) such that an optimal growth solution for the resulting network overproduces the chemical of interest. Schematically, this bilevel optimization problem is illustrated in FIG. 2. Mathematically, this bilevel optimization problem is expressed as the following bilevel mixed-integer optimization problem:

$$\text{maximize}\ v_{chemical} \quad (OptKnock)$$

$$\left( \begin{array}{l} \text{subject to} \underset{v_j}{\text{ maximize}} \quad v_{biomass} \\ \qquad \text{subject to} \quad \sum_{j=1}^{M} S_{ij} v_j = 0, \quad \forall\ i \in N \\ \qquad \qquad v_{substrate} = v_{substrate\_uptake} \quad \forall\ i \in \{\text{limiting substrate(s)}\} \\ \qquad \qquad v_{atp} \geq v_{atp\_main} \\ \qquad \qquad v_{biomass} \geq v_{biomass}^{target} \end{array} \right)$$

$$v_j^{min} \cdot y_j \leq v_j \leq v_j^{max} \cdot y_j,\ \forall\ j \in M$$

$$\sum_{j \in M^{forward}} (1 - y_j) = K$$

$$y_j \in \{0, 1\},\ \forall\ j \in M$$

where $v_{chemical}$ is the production of the desired target product, for example 2-hydroxyisobutyric acid, 3-hydroxyisobutyric acid, methacrylic acid, or other biochemical product, and K is the number of allowable knockouts. Note that setting K equal to zero returns the maximum biomass solution of the complete network, while setting K equal to one identifies the single gene/reaction knockout ($y_j=0$) such that the resulting network involves the maximum overproduction given its maximum biomass yield. The final constraint ensures that the resulting network meets a minimum biomass yield. Burgard et al., *Biotechnol Bioeng*, 84: 647-57 (2003), provide a more detailed description of the model formulation and solution procedure. Problems containing hundreds of binary variables can be solved in the order of minutes to hours using CPLEX 8.0, *GAMS: The Solver Manuals*. 2003: GAMS Development Corporation, accessed via the GAMS, Brooke et al., *GAMS Development Corporation* (1998), modeling environment on an IBM RS6000-270 workstation. The OptKnock framework has already been able to identify promising gene deletion strategies for biochemical overproduction, Burgard et al., *Biotechnol Bioeng*, 84: 647-57 (2003), Pharkya et al., *Bio-*

*technol Bioeng,* 84: 887-899 (2003), and establishes a systematic framework that will naturally encompass future improvements in metabolic and regulatory modeling frameworks.

The methods described above will provide one set of metabolic reactions to disrupt. Elimination of each reaction within the set or metabolic modification can result in a desired product as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., *Biotechnol. Prog.* 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny®.

Constraints of the above form preclude identification of larger reaction sets that include previously identified sets. For example, employing the integer cut optimization method above in a further iteration would preclude identifying a quadruple reaction set that specified reactions 1, 2, and 3 for disruption since these reactions had been previously identified. To ensure identification of all possible reaction sets leading to growth-coupled production of a product, a modification of the integer cut method was employed.

Briefly, the modified integer cut procedure begins with iteration 'zero' which calculates the maximum production of the desired biochemical at optimal growth for a wild-type network. This calculation corresponds to an OptKnock solution with K equaling 0. Next, single knockouts are considered and the two parameter sets, objstore$_{iter}$ and ystore$_{iter,j}$, are introduced to store the objective function ($v_{chemical}$) and reaction on-off information ($y_j$), respectively, at each iteration, iter. The following constraints are then successively added to the OptKnock formulation at each iteration.

$$v_{chemical} \geq \text{objstore}_{iter} + \epsilon - M \cdot \Sigma_{j \in \text{ystore}_{iter,j}=0} y_j$$

In the above equation, $\epsilon$ and M are a small and a large numbers, respectively. In general, $\epsilon$ can be set at about 0.01 and M can be set at about 1000. However, numbers smaller and/or larger then these numbers also can be used. M ensures that the constraint can be binding only for previously identified knockout strategies, while $\epsilon$ ensures that adding knockouts to a previously identified strategy must lead to an increase of at least $\epsilon$ in biochemical production at optimal growth. The approach moves onto double deletions whenever a single deletion strategy fails to improve upon the wild-type strain. Triple deletions are then considered when no double deletion strategy improves upon the wild-type strain, and so on. The end result is a ranked list, represented as desired biochemical production at optimal growth, of distinct deletion strategies that differ from each other by at least one knockout. This optimization procedure as well as the identification of a wide variety of reaction sets that, when disrupted, lead to the growth-coupled production of a biochemical product are exemplified in detail further below. Given the teachings and guidance provided herein, those skilled in the art will understand that the methods and metabolic engineering designs exemplified herein are applicable to the obligatory coupling of cell or microorganism growth to any biochemical product.

The methods exemplified herein allow the construction of cells and organisms that biosynthetically produce a desired product, including the obligatory coupling of production of a target biochemical product to growth of the cell or organism engineered to harbor the identified genetic alterations. Therefore, the computational methods described herein allow the identification and implementation of metabolic modifications that are identified by an in silico method selected from OptKnock or SimPheny®. The set of metabolic modifications can include, for example, addition of one or more biosynthetic pathway enzymes and/or functional disruption of one or more metabolic reactions including, for example, disruption by gene deletion.

As discussed above, the OptKnock methodology was developed on the premise that mutant microbial networks can be evolved towards their computationally predicted maximum-growth phenotypes when subjected to long periods of growth selection. In other words, the approach leverages an organism's ability to self-optimize under selective pressures. The OptKnock framework allows for the exhaustive enumeration of gene deletion combinations that force a coupling between biochemical production and cell growth based on network stoichiometry. The identification of optimal gene/reaction knockouts requires the solution of a bilevel optimization problem that chooses the set of active reactions such that an optimal growth solution for the resulting network overproduces the biochemical of interest (Burgard et al., *Biotechnol. Bioeng.* 84:647-657 (2003)).

An in silico stoichiometric model of *E. coli* metabolism can be employed to identify essential genes for metabolic pathways as exemplified previously and described in, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379. As disclosed herein, the OptKnock mathematical framework can be applied to pinpoint gene deletions leading to the growth-coupled production of a desired product. Further, the solution of the bilevel OptKnock problem provides only one set of deletions. To enumerate all meaningful solutions, that is, all sets of knockouts leading to growth-coupled production formation, an optimization technique, termed integer cuts, can be implemented. This entails iteratively solving the OptKnock problem with the incorporation of an additional constraint referred to as an integer cut at each iteration, as discussed above.

As disclosed herein, an OptKnock strategy was used to identify gene knockouts to couple growth with production of a desired product such as 3-hydroxyisobutyric acid or methacrylic acid (see Examples XXI to XXIII). While identified using an OptKnock strategy, it is understood that any suitable modeling system, including a system such as SimPheny™ can be used to identify gene knockouts to develop strains able to couple production of a desired product to growth, as disclosed herein. Any of the gene deletion strategies disclosed herein can be combined, as appropriate, with any of the non-naturally occurring microbial organisms disclosed herein having a pathway for production of 2-hydroxyisobutyric acid, 3-hydroxyisobutyric acid or methacrylic acid to increase production of 2-hydroxyisobutyric acid, 3-hydroxyisobutyric acid or methacrylic acid.

Thus the invention additionally provides a non-naturally occurring microbial organism, comprising one or more gene disruptions, the one or more gene disruptions occurring in genes encoding proteins or enzymes where the one or more gene disruptions confer increased production of 3-hydroxyisobutyric acid or methacrylic acid in said organism. As disclosed herein, the gene disruptions can confer production of 3-hydroxyisobutyric acid or methacrylic acid that is growth-coupled or not growth-coupled. For example, the one or more gene disruptions can encode a protein or enzyme listed in Tables 10 or 11 (see Examples XXII and XXIII). In a particular embodiment, the one or more gene disruptions can encode proteins or enzymes selected from the group consisting of malate dehydrogenase, lactate dehydrogenase and acetaldehyde-CoA dehydrogenase. In an additional embodiment, the organism can further comprise one or more gene disruptions encoding proteins or enzymes selected from the group consisting of aspartase, pyruvate formate lyase, NAD(P) transhydrogenase, glutamate dehydrogenase, ATP synthase, phosphoenolpyruvate:pyruvate phosphotransferase system, glutamate dehydrogenase, phosphotransacetylase, acetate kinase, 6-phosphogluconolactonase, glucose 6-phosphate dehydrogenase and NADH dehydrogenase.

Thus, the invention provides an organism with an improved yield of MAA or 3-HIB (see Examples XXII and XXIII) that contains functional disruptions in alcohol dehydrogenase, malate dehydrogenase, and lactate dehydrogenase (Tables 6 and 8, Design 1). Additionally provided is an organism with an additional functional disruption in any of glutamate dehydrogenase, aspartase, NAD(P) transhydrogenase or NADH dehydrogenase (Table 6, Designs 2, 7, 10, 13; Table 8, Designs 2, 8). Further provided is an organism with an additional functional disruption in aspartase and any of NAD(P) transhydrogenase, glutamate dehydrogenase, ATP synthase or pyruvate formate lyase (Table 6, Designs 3, 5; Table 8, Designs 3, 5). Also provided is an organism with an additional functional disruption in pyruvate formate lyase and any of NAD(P) transhydrogenase or glutamate dehydrogenase (Table 6, Design 4; Table 8, Design 4). Additionally provided is an organism with an additional functional disruption in ATP synthase and in any of pyruvate formate lyase, D-glucose transport via PEP:Pyr PTS, 6-phosphogluconolactonase or glucose-6-phosphate dehydrogenase (Table 6, Design 6; Table 8, Design 6, 7). Also provided is an organism with an additional functional disruption in glutamate dehydrogenase and pyruvate formate lyase (Table 6 Design 8). Further provided is an organism with an additional functional disruption in any of acetate kinase or phosphotransacetylase (Table 6, Design 9). Additionally provided is an organism with an additional functional disruption in NAD(P) transhydrogenase and in any of 6-phosphogluconolactonase or glucose-6-phosphate dehydrogenase (Table 6, Design 11; Table 8, Design 9 w/THD2). Further provided is an organism with an additional functional disruption in glutamate dehydrogenase and in any of 6-phosphogluconolactonase or glucose-6-phosphate dehydrogenase (Table 8, Design 9 w/GLUDy). Also provided is an organism with an additional functional disruption in pyruvate formate lyase (Table 6, Design 12). Additionally provided is an organism with an additional functional disruption in NADH dehydrogenase and in any of acetate kinase or phosphotransacetylase (Table 6, Design 14).

As disclosed herein, the one or more gene disruptions can comprises a deletion of the one or more genes. Such methods for gene disruptions, including gene deletions, are well known to those skilled in the art, as disclosed herein. If desired, the cells can be cultured in a substantially anaerobic culture medium.

Also provided are methods for producing 3-hydroxyisobutyric acid or methacrylic acid using the organisms disclosed herein and discussed above and in Examples XXII and XXIII having one or more gene disruptions. Thus, the invention provides a method for producing 3-hydroxyisobutyric acid or methacrylic acid comprising culturing a non-naturally occurring microbial organism, comprising one or more gene disruptions, the one or more gene disruptions occurring in genes encoding a protein or enzyme wherein the one or more gene disruptions confer obligatory coupling of 3-hydroxyisobutyric acid or methacrylic acid production to growth of the organism when the gene disruption reduces an activity of the protein or enzyme, whereby said one or more gene disruptions confers stable growth-coupled production of 3-hydroxyisobutyric acid or methacrylic acid onto the organism.

Given the teachings and guidance provided herein, those skilled in the art will understand that to disrupt an enzymatic reaction it is necessary to disrupt the catalytic activity of the one or more enzymes involved in the reaction. Disruption can occur by a variety of means including, for example, deletion of an encoding gene or incorporation of a genetic alteration in one or more of the encoding gene sequences. The encoding genes targeted for disruption can be one, some, or all of the genes encoding enzymes involved in the catalytic activity. For example, where a single enzyme is involved in a targeted catalytic activity disruption can occur by a genetic alteration that reduces or destroys the catalytic activity of the encoded gene product. Similarly, where the single enzyme is multimeric, including heteromeric, disruption can occur by a genetic alteration that reduces or destroys the function of one or all subunits of the encoded gene products. Destruction of activity can be accomplished by loss of the binding activity of one or more subunits in order to form an active complex, by destruction of the catalytic subunit of the multimeric complex or by both. Other functions of multimeric protein association and activity also can be targeted in order to disrupt a metabolic reaction of the invention. Such other functions are well known to those skilled in the art. Further, some or all of the functions of a single polypeptide or multimeric complex can be disrupted according to the invention in order to reduce or abolish the catalytic activity of one or more enzymes involved in a reaction or metabolic modification of the invention. Similarly, some or all of enzymes involved in a reaction or metabolic modification of the invention can be disrupted so long as the targeted reaction is destroyed.

Given the teachings and guidance provided herein, those skilled in the art also will understand that an enzymatic reaction can be disrupted by reducing or eliminating reactions encoded by a common gene and/or by one or more orthologs of that gene exhibiting similar or substantially the same activity. Reduction of both the common gene and all orthologs can lead to complete abolishment of any catalytic activity of a targeted reaction. However, disruption of either the common gene or one or more orthologs can lead to a reduction in the catalytic activity of the targeted reaction sufficient to promote coupling of growth to product biosynthesis. Exemplified herein are both the common genes encoding catalytic activities for a variety of metabolic modifications as well as their orthologs. Those skilled in the art will understand that disruption of some or all of the genes encoding a enzyme of a targeted metabolic reaction can be practiced in the methods of the invention and incorporated into the non-naturally occurring microbial organisms of the invention in order to achieve the growth-coupled product production.

In some embodiments, the gene disruption can include a complete gene deletion. In some embodiments other means to disrupt a gene include, for example, frameshifting by omission or addition of oligonucleotides or by mutations that render the gene inoperable. One skilled in the art will recognize the advantages of gene deletions, however, because of the stability it may confer to the non-naturally occurring organism from reverting to its wild-type. In particular, the gene disruptions are selected from the gene set that includes genes detailed herein.

Each of the proposed strains can be supplemented with additional deletions if it is determined that the predicted strain designs do not sufficiently couple the formation of the product with biomass formation. Alternatively, some other enzymes not known to possess significant activity under the growth conditions can become active due to adaptive evolution or random mutagenesis and can also be knocked out. However, the list of gene deletion sets provided here serves as a starting point for construction of high-yielding growth-coupled 3-hydroxyisobutyric acid or methacrylic acid production strains.

One skilled in the art will recognize the ability to also produce MAA, 2-hydroxyisobutyrate, or 3-hydroxyisobutyrate, by non-growth-coupled production by providing a non-producing growth phase, followed by a non-growth production phase, for example. The results described herein indicate that combinations of gene deletions or functional disruptions of genes significantly improve the MAA, 2-hydroxyisobutyrate, or 3-hydroxyisobutyrate production capabilities of E. coli and other organisms. The strain design pathways are equally applicable if a microbial organism other than E. coli is chosen as the production host, even if the organism naturally lacks the activity or exhibits low activity of a subset of the gene products marked for disruption. In the latter case, disruptions can be introduced to eliminate or lessen the enzymatic activities of the gene products that are naturally present in the chosen production host. In some embodiments, growth-coupled production of MAA, 2-hydroxyisobutyrate, or 3-hydroxyisobutyrate for the in silico determined metabolic pathways is confirmed by construction of strains having the designed metabolic genotype. These metabolically engineered cells or organisms can also be subjected to adaptive evolution to further augment growth-coupled product production. In some embodiments, the engineered cells or organisms can also incorporate additional copies of beneficial genes to increase flux through a particular metabolic pathway. Alternatively, exogenous gene insertions from another organism can be used to install functionality that is not present in the host organism.

The design strategies described herein are useful not only for enhancing growth coupled production, but they are also well-suited for enhancing non-growth coupled production because they link the production of 2-hydroxyisobutyric acid, 3-hydroxyisobutyric acid or methacrylic acid to energy generation and/or redox balance. Exemplary non-growth coupled production methods include implementing an aerobic growth phase followed by an anaerobic production phase. For example, Vemuri et al., (*J. Ind. Microbiol. Biotechnol.* 28(6): 325-332 (2002)) describe a dual-phase process for the production of succinate in *E. Coli*. Okino et al. *Appl. Microbiol. Biotechnol.* 81(3):459-464 (2008)) describe a similar non-growth coupled production process in a strain of *Corynebacterium glutamicum* strain.

Another such method involves withholding an essential nutrient from a propagated cell culture, thereby limiting growth, but not precluding production as described in Durner et al., *Appl. Environ. Microbiol.* 66(8):3408-3414 (2000). Yet another strategy aimed at decoupling growth from production involves replacing the growth substrate with another compound that is more slowly metabolizable as described in Altamirano et al., *Biotechnol. Bioeng.* 76:351-360 (2001). Growth decoupled-product formation can also be brought about by specific genetic modifications as described in Blombach et al., *Appl. Microbiol. Biotechnol.* 79:471-479 (2008).

It is understood that modifications which do not substantially affect the activity of the various embodiments of this invention are also provided within the definition of the invention provided herein. Accordingly, the following examples are intended to illustrate but not limit the present invention.

Example I

Pathway for Conversion of Succinyl-CoA to MAA Via 3-Hydroxyisobutyrate

This example describes an exemplary MAA synthesis pathway from succinyl-CoA to methacrylic acid via 3-hydroxyisobutyrate.

One exemplary pathway for MAA synthesis proceeds from succinyl-CoA (see FIG. 2). This pathway uses at least three and at most five enzymatic steps to form MAA from succinyl-CoA. The pathway is redox-balanced, indicating that it can potentially lead to the maximum MAA yield of 1.33 mol per mol of glucose under anaerobic conditions with no byproduct formation. Moreover, the pathway is energetically efficient and can generate 0.5 ATP per mole of glucose metabolized to MAA if phosphoenolpyruvate (PEP) carboxykinase (PEPCK) activity is assumed irreversible (that is, cannot catalyze the ATP-generating carboxylation of PEP to oxaloacetate) or 1.72 ATP if PEPCK is assumed reversible. The latter ATP yield is comparable to the ATP yield from the formation of lactate or ethanol from glucose, that is, 2 ATP per glucose metabolized, indicating that methacrylate fermentation can generate sufficient energy for cell growth and maintenance.

In this pathway (see FIG. 2), succinyl-CoA is first converted to (R)-methylmalonyl-CoA, which is potentially converted to (S)-methylmalonyl-CoA by an epimerase. Either the (R)- or (S)-stereoisomer of methylmalonyl-CoA is then reduced to (R)- or (S)-3-hydroxyisobutyrate, respectively, by either a pair of enzymes (as shown in FIG. 2) or a single enzyme that exhibits acyl-CoA reductase and alcohol dehydrogenase activities. The pathway from succinyl-CoA to 3-hydroxyisobutyrate has also been described in WO 2007/141208. In the final step, 3-hydroxyisobutyrate is dehydrated to form MAA.

Successfully engineering this pathway involves identifying an appropriate set of enzymes with sufficient activity and specificity. This entails identifying an appropriate set of enzymes, cloning their corresponding genes into a production host, optimizing fermentation conditions, and assaying for product formation following fermentation. To engineer a production host for the production of methacrylic acid, one or more exogenous DNA sequence(s) are expressed in microorganisms. In addition, the microorganisms can have endogenous gene(s) functionally deleted. These modifications allow the production of methacrylic acid using renewable feedstock.

Below is described a number of biochemically characterized candidate genes capable of encoding enzymes that catalyze each step of the desired pathway. Although described using E. coli as a host organism to engineer the pathway, essentially any suitable host organism can be used. Specifically listed are genes that are native to E. coli as well as genes in other organisms that can be applied to catalyze the appropriate transformations when properly cloned and expressed.

Referring to FIG. 2, step 1 involves methylmalonyl-CoA mutase (EC 5.4.99.2). In the first step, succinyl-CoA is converted into methylmalonyl-CoA by methylmalonyl-CoA mutase (MCM). In E. coli, the reversible adenosylcobalamin-dependant mutase participates in a three-step pathway leading to the conversion of succinate to propionate (Haller et al., Biochemistry 39:4622-4629 (2000)). Overexpression of the MCM gene candidate along with the deletion of YgfG can be used to prevent the decarboxylation of methylmalonyl-CoA to propionyl-CoA and to maximize the methylmalonyl-CoA available for MAA synthesis. MCM is encoded by genes scpA in Escherichia coli (Bobik and Rasche, Anal. Bioanal. Chem. 375:344-349 (2003); Haller et al., Biochemistry 39:4622-4629 (2000)) and mutA in Homo sapiens (Padovani and Banerjee, Biochemistry 45:9300-9306 (2006)). In several other organisms MCM contains alpha and beta subunits and is encoded by two genes. Exemplary gene candidates encoding the two-subunit protein are Propionibacterium fredenreichii sp. shermani mutA and mutB (Korotkova and Lidstrom, J. Biol. Chem. 279:13652-13658 (2004)) and Methylobacterium extorquens mcmA and mcmB (Korotkova and Lidstrom, supra, 2004). The protein sequences of these genes can be identified by their corresponding GenBank accession numbers.

| Gene | GenBank ID | Organism |
| --- | --- | --- |
| scpA | NP_417392.1 | Escherichia coli K12 |
| mutA | P22033.3 | Homo sapiens |
| mutA | P11652.3 | Propionibacterium fredenreichii sp. shermanii |
| mutB | P11653.3 | Propionibacterium fredenreichii sp. shermanii |
| mcmA | Q84FZ1 | Methylobacterium extorquens |
| mcmB | Q6TMA2 | Methylobacterium extorquens |

These sequences can be used to identify homologue proteins in GenBank or other databases through sequence similarity searches (for example, BLASTp). The resulting homologue proteins and their corresponding gene sequences provide additional exogenous DNA sequences for transformation into E. coli or other suitable host microorganisms to generate production hosts. Additional gene candidates include the following, which were identified based on high homology to the E. coli spcA gene product.

| Gene | GenBank ID | Organism |
| --- | --- | --- |
| sbm | NP_838397.1 | Shigella flexneri |
| SARI_04585 | ABX24358.1 | Salmonella enterica |
| YfreA_01000861 | ZP_00830776.1 | Yersinia frederiksenii |

There exists evidence that genes adjacent to the methylmalonyl-CoA mutase catalytic genes contribute to maximum activity. For example, it has been demonstrated that the meaB gene from M. extorquens forms a complex with methylmalonyl-CoA mutase, stimulates in vitro mutase activity, and possibly protects it from irreversible inactivation (Korotkova and Lidstrom, J. Biol. Chem. 279:13652-13658 (2004)). The M. extorquens meaB gene product is highly similar to the product of the E. coli argK gene (BLASTp: 45% identity, e-value: 4e-67), which is adjacent to scpA on the chromosome. No sequence for a meaB homolog in P. freudenreichii is catalogued in GenBank. However, the Propionibacterium acnes KPA171202 gene product, YP_055310.1, is 51% identical to the M. extorquens meaB protein and its gene is also adjacent to the methylmalonyl-CoA mutase gene on the chromosome.

| Gene | GenBank ID | Organism |
| --- | --- | --- |
| argK | AAC75955.1 | Escherichia coli K12 |
|  | YP_055310.1 | Propionibacterium acnes KPA171202 |
| meaB | 2QM8_B | Methylobacterium extorquens |

E. coli can synthesize adenosylcobalamin, a necessary cofactor for this reaction, only when supplied with the intermediates cobinamide or cobalamin (Lawrence and Roth. J. Bacteriol. 177:6371-6380 (1995); Lawrence and Roth, Genetics 142:11-24 (1996)). Alternatively, the ability to synthesize cobalamins de novo has been conferred upon E. coli following the expression of heterologous genes (Raux et al., J. Bacteriol. 178:753-767 (1996)).

Referring to FIG. 2, step 2 involves methylmalonyl-CoA epimerase (EC 5.1.99.1). The second enzyme in the pathway, methylmalonyl-CoA epimerase (MMCE), converts (R)-methylmalonyl-CoA to (S)-methylmalonyl-CoA. MMCE is an essential enzyme in the breakdown of odd-numbered fatty acids and of the amino acids valine, isoleucine, and methionine. Methylmalonyl-CoA epimerase activity is not believed to be encoded in the E. coli genome (Boynton et al., J. Bacteriol. 178:3015-3024 (1996)), but is present in other organisms such as Homo sapiens (YqjC) (Fuller and Leadlay, Biochem. J. 213:643-650 (1983)), Rattus norvegicus (Mcee) (Bobik and Rasche, J. Biol. Chem. 276:37194-37198 (2001)), Propionibacterium shermanii (AF454511) (Fuller. and Leadlay, Biochem. J. 213:643-650 (1983); Haller et al., Biochemistry 39:4622-4629 (2000); McCarthy et al., Structure 9:637-646.2001)) and Caenorhabditis elegans (mmce) (Kuhnl et al., FEBS J. 272:1465-1477 (2005)). This enzymatic step may or may not be necessary depending upon the stereospecificity of the enzyme or enzymes used for the conversion of methylmalonyl-CoA to 3-hydroxyisobutyrate (steps 3-4 in FIG. 2). Additional gene candidates in microorganisms, such as AE016877 in Bacillus cereus, have high sequence homology but have not been experimentally verified.

| Gene | GenBank ID | Organism |
| --- | --- | --- |
| MCEE | Q96PE7.1 | Homo sapiens |
| Mcee_predicted | NP_001099811.1 | Rattus norvegicus |
| AF454511 | AAL57846.1 | Propionibacterium fredenreichii sp. shermanii |
| mmce | AAT92095.1 | Caenorhabditis elegans |
| AE016877 | AAP08811.1 | Bacillus cereus ATCC 14579 |

Referring to FIG. 2, step 3 involves methylmalonyl-CoA reductase (EC 1.2.1.-). As shown in FIG. 2, the reduction of methylmalonyl-CoA to its corresponding alcohol, 3-hydroxyisobutyrate, can proceed by two enzymatic steps. The first step, conversion of methylmalonyl-CoA to methylmalonic semialdehyde, is accomplished by a CoA-dependent aldehyde dehydrogenase. An enzyme encoded by a malonyl-CoA reductase gene from Sulfolobus tokodaii (Alber et. al., J. Bacteriol. 188(24):8551-8559 (2006)), has been shown to catalyze the conversion of methylmalonyl-CoA to its corresponding aldehyde (WO2007141208). A similar enzyme exists in Metallosphaera sedula (Alber et. al., J. Bacteriol. 188(24):8551-8559 (2006)). Several additional CoA dehydrogenases are capable also of reducing an acyl-CoA to its corresponding aldehyde. Exemplary genes that encode such enzymes include the Acinetobacter calcoaceticus acr1 encoding a fatty acyl-CoA reductase (Reiser and Somerville. J. Bacteriol. 179:2969-2975 (1997)), the Acinetobacter sp. M-1 fatty acyl-CoA reductase (Ishige et al., Appl. Environ. Microbiol. 68:1192-1195 (2002)), and a CoA- and NADP-dependent succinate semialdehyde dehydrogenase encoded by the sucD gene in Clostridium kluyveri (Sohling and Gottschalk, J. Bacteriol. 178:871-880 (1996); Sohling and Gottschalk, J. Bacteriol. 178:871-880 (1996)). The enzyme acylating acetaldehyde dehydrogenase in Pseudomonas sp, encoded by bphG, is also a good candidate as it has been demonstrated to oxidize and acylate the branched-chain compound isobutyraldehyde (Powlowski et al., J. Bacteriol. 175: 377-385 (1993)).

| Gene | GenBank ID | Organism |
| --- | --- | --- |
| mcr | NP_378167 | Sulfolobus tokodaii |
| mcr | YP_001190808.1 | Metallosphaera sedula |
| acr1 | YP_047869.1 | Acinetobacter calcoaceticus |
| acr1 | AAC45217 | Acinetobacter baylyi |
| acr1 | BAB85476.1 | Acinetobacter sp. Strain M-1 |
| sucD | P38947.1 | Clostridium kluyveri |
| bphG | BAA03892.1 | Pseudomonas sp |

Referring to FIG. 2, step 4 involves 3-hydroxyisobutyrate dehydrogenase (EC 1.1.1.31). 3-hydroxyisobutyrate dehydrogenase catalyzes the reversible oxidation of 3-hydroxyisobutyrate to methylmalonate semialdehyde. This enzyme participates in valine, leucine and isoleucine degradation and has been identified in bacteria, eukaryotes, and mammals. The enzyme encoded by P84067 from Thermus thermophilus HB8 has been structurally characterized (Lokanath et al., J. Mol. Biol. 352:905-917 (2005)). The reversibility of the human 3-hydroxyisobutyrate dehydrogenase was demonstrated using isotopically-labeled substrate (Manning and Pollitt, Biochem. J. 231:481-484 (1985)). Additional genes encoding this enzyme include 3hidh in Homo sapiens (Hawes et al., Methods Enzymol. 324:218-228 (2000)) and Oryctolagus cuniculus (Chowdhury et al., Biosci. Biotechnol. Biochem. 60:2043-2047 (1996); Hawes et al., Methods Enzymol. 324:218-228 (2000)), mmsb in Pseudomonas aeruginosa, and dhat in Pseudomonas putida (Aberhart and Hsu. J Chem. Soc. [Perkin 1] 6:1404-1406 (1979); Chowdhury et al., Biosci. Biotechnol. Biochem. 67:438-441 (2003); Chowdhury et al., Biosci. Biotechnol. Biochem. 60:2043-2047 (1996)).

| Gene | GenBank ID | Organism |
| --- | --- | --- |
| P84067 | P84067 | Thermus thermophilus |
| mmsb | P28811.1 | Pseudomonas aeruginosa |
| dhat | Q59477.1 | Pseudomonas putida |
| 3hidh | P31937.2 | Homo sapiens |
| 3hidh | P32185.1 | Oryctolagus cuniculus |

Referring to FIG. 2, as an alternative, steps 3 and 4 can involve a combined Alcohol/Aldehyde dehydrogenase (EC 1.2.1.-). Methylmalonyl-CoA can be reduced to 3-hydroxyisobutyrate in one step by a multifunctional enzyme with dual acyl-CoA reductase and alcohol dehydrogenase activity. No evidence for the direct conversion of methylmalonyl-CoA to 3-hydroxyisobutyrate has been reported. However, this reaction is similar to the common conversions such as acetyl-CoA to ethanol and butyryl-CoA to butanol, which are catalyzed by CoA-dependant enzymes with both alcohol and aldehyde dehydrogenase activities. Gene candidates include the E. coli adhE (Kessler et al., FEBS Lett. 281:59-63 (1991)) and C. acetobutylicum bdh I and bdh II (Walter, et al., J. Bacteriol. 174:7149-7158 (1992)), which can reduce acetyl-CoA and butyryl-CoA to ethanol and butanol, respectively. In addition to reducing acetyl-CoA to ethanol, the enzyme encoded by adhE in Leuconostoc mesenteroides has been shown to oxide the branched chain compound isobutyraldehyde to isobutyryl-CoA (Kazahaya et al., J. Gen. Appl. Microbiol. 18:43-55 (1972); Koo et al., Biotechnol. Lett. 27:505-510 (2005)). An additional candidate enzyme for converting methylmalonyl-CoA directly to 3-hydroxyisobutyrate is encoded by a malonyl-CoA reductase from Chloroflexus aurantiacus (Hügler, et al., J. Bacteriol. 184(9):2404-2410 (2002).

| Gene | GenBank ID | Organism |
| --- | --- | --- |
| mcr | YP_001636209.1 | Chloroflexus aurantiacus |
| adhE | NP_415757.1 | Escherichia coli |
| bdh I | NP_349892.1 | Clostridium acetobutylicum |
| bdh II | NP_349891.1 | Clostridium acetobutylicum |
| adhE | AAV66076.1 | Leuconostoc mesenteroides |

Figure 3:
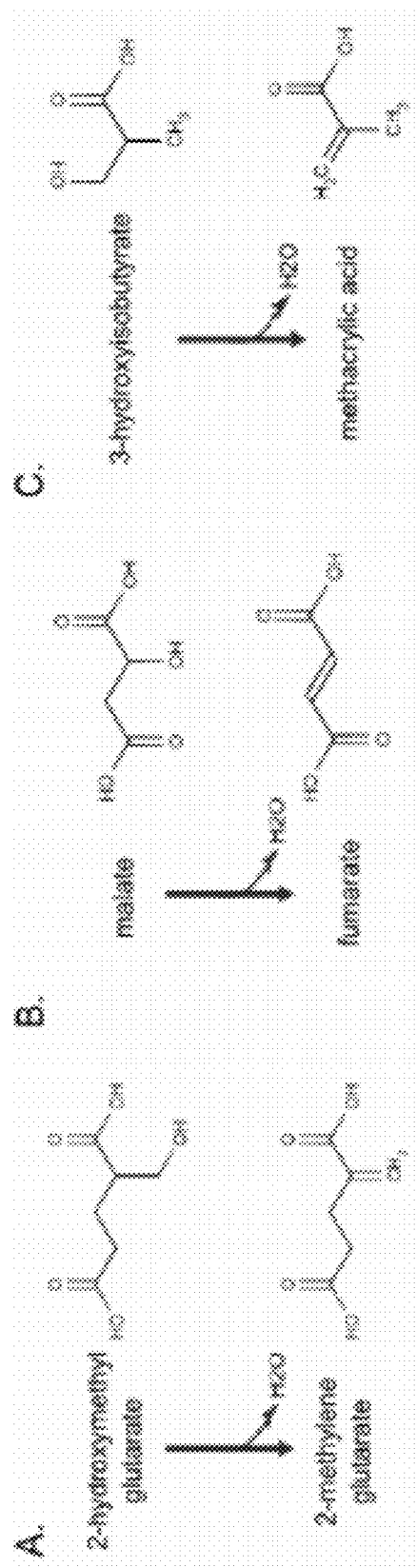
FIG. 3 shows a comparison of known enzyme-catalyzed dehydrations with a predicted transformation for the dehydration of 3-hydroxyisobutyrate.

Referring to FIG. 2, step 5 involves 3-hydroxyisobutyrate dehydratase (EC 4.2.1.-). The final step involves the dehydration of 3-hydroxyisobutyrate to methacrylic acid. No direct evidence for this specific enzymatic transformation has been identified. However, most dehydratases catalyze the α,β-elimination of water, which involves activation of the α-hydrogen by an electron-withdrawing carbonyl, carboxylate, or CoA-thiol ester group and removal of the hydroxyl group from the β-position (Buckel and Barker, J Bacteriol. 117: 1248-1260 (1974); Martins et al, Proc. Natl. Acad. Sci. USA 101:15645-15649 (2004)). This is the exact type of transformation proposed for the final step in the methacrylate pathway. In addition, the proposed transformation is highly similar to the 2-(hydroxymethyl)glutarate dehydratase of Eubacterium barkeri (FIG. 3A). This enzyme has been studied in the context of nicotinate catabolism and is encoded by hmd (Alhapel et al., Proc. Natl. Acad. Sci. USA 103:12341-12346 (2006)). Similar enzymes with high sequence homology are found in Bacteroides capillosus, Anaerotruncus colihominis, and Natranaerobius thermophilus. These enzymes are also homologous to the α- and β-subunits of [4Fe-4S]- containing bacterial serine dehydratases, for example, *E. coli* enzymes encoded by tdcG, sdhB, and sdaA).

| Gene | GenBank ID | Organism |
|---|---|---|
| hmd | ABC88407.1 | *Eubacterium barkeri* |
| BACCAP_02294 | ZP_02036683.1 | *Bacteroides capillosus* ATCC 29799 |
| ANACOL_02527 | ZP_02443222.1 | *Anaerotruncus colihominis* DSM 17241 |
| NtherDRAFT_2368 | ZP_02852366.1 | *Natranaerobius thermophilus* JW/NM-WN-LF |

Fumarate hydratase enzymes, which naturally catalyze the dehydration of malate to fumarate, represent an additional set of candidates (FIG. 3B). Although the ability of fumarate hydratase to react on branched substrates has not been described, a wealth of structural information is available for this enzyme and other researchers have successfully engineered the enzyme to alter activity, inhibition and localization (Weaver, *Acta Crystallogr. D Biol. Crystallogr.* 61:1395-1401 (2005)). Exemplary enzyme candidates include those encoded by fumC from *Escherichia coli* (Estevez et al., *Protein Sci.* 11:1552-1557 (2002); Hong and Lee, *Biotechnol. Bioprocess Eng.* 9:252-255 (2004); Rose and Weaver, *Proc. Natl. Acad. Sci. USA* 101:3393-3397 (2004)), *Campylobacter jejuni* (Smith et al., *Int. J. Biochem. Cell Biol.* 31:961-975 (1999)) and *Thermus thermophilus* (Mizobata et al., *Arch. Biochem. Biophys.* 355:49-55 (1998)), and fumH from *Rattus norvegicus* (Kobayashi et al., *J. Biochem.* 89:1923-1931 (1981)). Similar enzymes with high sequence homology include fum1 from *Arabidopsis thaliana* and fumC from *Corynebacterium glutamicum*.

| Gene | GenBankID | Organism |
|---|---|---|
| fumC | P05042.1 | *Escherichia coli* K12 |
| fumC | O69294.1 | *Campylobacter jejuni* |
| fumC | P84127 | *Thermus thermophilus* |
| fumH | P14408.1 | *Rattus norvegicus* |
| fum1 | P93033.2 | *Arabidopsis thaliana* |
| fumC | Q8NRN8.1 | *Corynebacterium glutamicum* |

This example describes a biosynthetic pathway for production of MMA from succinyl-CoA.

Example II

Preparation of an MAA Producing Microbial Organism Having a Pathway for Converting Succinyl-CoA to MAA Via 3-Hydroxyisobutyrate This example describes the generation of a microbial organism capable of producing MAA from succinyl-CoA via 3-hydroxyisobutyrate.

*Escherichia coli* is used as a target organism to engineer the MAA pathway shown in FIG. 2. *E. coli* provides a good host for generating a non-naturally occurring microorganism capable of producing MAA. *E. coli* is amenable to genetic manipulation and is known to be capable of producing various products, like ethanol, acetic acid, formic acid, lactic acid, and succinic acid, effectively under anaerobic or microaerobic conditions.

To generate an *E. coli* strain engineered to produce MAA, nucleic acids encoding the enzymes utilized in the pathway are expressed in *E. coli* using well known molecular biology techniques (see, for example, Sambrook, supra, 2001; Ausubel supra, 1999). In particular, the scpA (NP_417392.1), argK (AAC75955.1), and AF454511 (AAL57846.1) genes encoding the methylmalonyl-CoA mutase, its stabilizer protein, and methylmalonyl-CoA epimerase activities, respectively, are cloned into the pZE13 vector (Expressys, Ruelzheim, Germany) under the PA1/lacO promoter. In addition, mcr (NP_378167), dhat (Q59477.1), and hmd (ABC88407.1) genes encoding methylmalonyl-CoA reductase, 3-hydroxyisobutyrate dehydrogenase, and 3-hydroxyisobutyrate dehydratase activities, respectively, are cloned into the pZA33 vector (Expressys, Ruelzheim, Germany) under the PA1/lacO promoter. The two sets of plasmids are transformed into *E. coli* strain MG1655 to express the proteins and enzymes required for MAA synthesis via the succinyl-CoA to 3-hydroxyisobutyrate pathway.

The resulting genetically engineered organism is cultured in glucose-containing medium following procedures well known in the art (see, for example, Sambrook et al., supra, 2001). Cobalamin is also supplied to the medium to ensure activity of the mutase enzyme unless the host strain of *E. coli* is engineered to synthesize cobalamin de novo (see, for example, Raux et al., *J. Bacteriol.* 178:753-767 (1996)). The expression of the MAA synthesis genes is corroborated using methods well known in the art for determining polypeptide expression or enzymatic activity, including for example, Northern blots, PCR amplification of mRNA, immunoblotting, and the like. Enzymatic activities of the expressed enzymes are confirmed using assays specific for the individual activities. The ability of the engineered *E. coli* strain to produce MAA is confirmed using HPLC, gas chromatography-mass spectrometry (GCMS) and/or liquid chromatography-mass spectrometry (LCMS).

Microbial strains engineered to have a functional MAA synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of MAA. One modeling method is the bilevel optimization approach, OptKnock (Burgard et al., *Biotechnol. Bioengineer.* 84:647-657 (2003)), which is applied to select gene knockouts that collectively result in better production of MAA. Adaptive evolution also can be used to generate better producers of, for example, the succinyl-CoA intermediate of the MAA product. Adaptive evolution is performed to improve both growth and production characteristics (Fong and Palsson, *Nat. Genet.* 36:1056-1058 (2004); Alper et al., *Science* 314:1565-1568 (2006)). Based on the results, subsequent rounds of modeling, genetic engineering and adaptive evolution can be applied to the MAA producer to further increase production.

For large-scale production of MAA, the above organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing the culture vessel, for example, flasks can be sealed with a septum and crimp-cap. Microaerobic conditions also can be utilized by providing a small hole in the septum for limited aeration. The pH of the medium is maintained at a pH of around 7 by addition of an acid, such as $H_2SO_4$. The growth rate is determined by measuring optical density using a spectrophotometer (600 nm) and the glucose uptake rate by monitoring carbon source depletion over time. Byproducts such as undesirable alcohols, organic acids, and residual glucose can be quantified by HPLC (Shimadzu, Columbia Md.), for example, using an Aminex® series of HPLC columns (for example, HPX-87 series) (BioRad, Hercules Calif.), using a refractive index detector for glucose and alcohols, and a UV detector for organic acids (Lin et al., *Biotechnol. Bioeng.* 775-779 (2005)).

This example describes the preparation of a microbial organism that can produce MAA from succinyl-CoA via 3-hydroxyisobutyrate.

Example III

Pathway for Conversion of Succinyl-CoA to MAA Via 3-Amino-2-Methylpropanoate

This example describes an exemplary MAA synthesis pathway from succinyl-CoA to MAA via 3-amino-methylpropanoate.

Another exemplary pathway for MAA biosynthesis proceeds from succinyl-CoA through 3-amino-2-methylpropanoate (see FIG. 4). This pathway is high-yielding under anaerobic conditions with a maximum theoretical yield of 1.33 mol MAA/mol glucose. The pathway is also energetically efficient, capable of generating 1.55 mol ATP/mol glucose at maximum product yield, under the assumption that PEP carboxykinase can operate reversibly.

The first three steps of this pathway, involving the conversion of succinyl-CoA to methylmalonate semialdehyde, are identical to the succinyl-CoA to MAA pathway described in Example I (see FIG. 2). The pathway diverges at step 4, where methylmalonate semialdehyde is converted to 3-amino-2-methylpropionate by a transaminase. The final pathway step entails deamination of 3-amino-2-methylpropionate to methacrylic acid.

Enzyme and gene candidates for catalyzing the first three pathway steps are described in Example I. Gene candidates for steps 4 and 5 are discussed below.

Referring to FIG. 4, step 4 involves 3-amino-2-methylpropionate transaminase (EC 2.6.1.22). 3-amino-2-methylpropionate transaminase catalyzes the transformation from methylmalonate semialdehyde to 3-amino-2-methylpropionate. The enzyme, characterized in *Rattus norvegicus* and *Sus scrofa* and encoded by Abat, has been shown to catalyze this transformation in the direction of interest in the pathway (Kakimoto et al., *Biochim. Biophys. Acta* 156:374-380 (1968); Tamaki et al., *Methods Enzymol.* 324:376-389 (2000)). Enzyme candidates in other organisms with high sequence homology to 3-amino-2-methylpropionate transaminase include Gta-1 in *C. elegans* and gabT in *Bacillus subtilus*. Additionally, one of the native GABA aminotransferases in *E. coli*, encoded by gene gabT, has been shown to have broad substrate specificity and may utilize 3-amino-2-methylpropionate as a substrate (Liu et al., *Biochemistry* 43:10896-10905 (2004); Schulz et al., *Appl. Environ. Microbiol.* 56:1-6 (1990)).

| Gene | GenBankID | Organism |
|------|-----------|----------|
| Abat | P50554.3 | *Rattus norvegicus* |
| Abat | P80147.2 | *Sus scrofa* |
| Gta-1 | Q21217.1 | *Caenorhabditis elegans* |
| gabT | P94427.1 | *Bacillus subtilus* |
| gabT | P22256.1 | *Escherichia coli* K12 |

Figure 5:
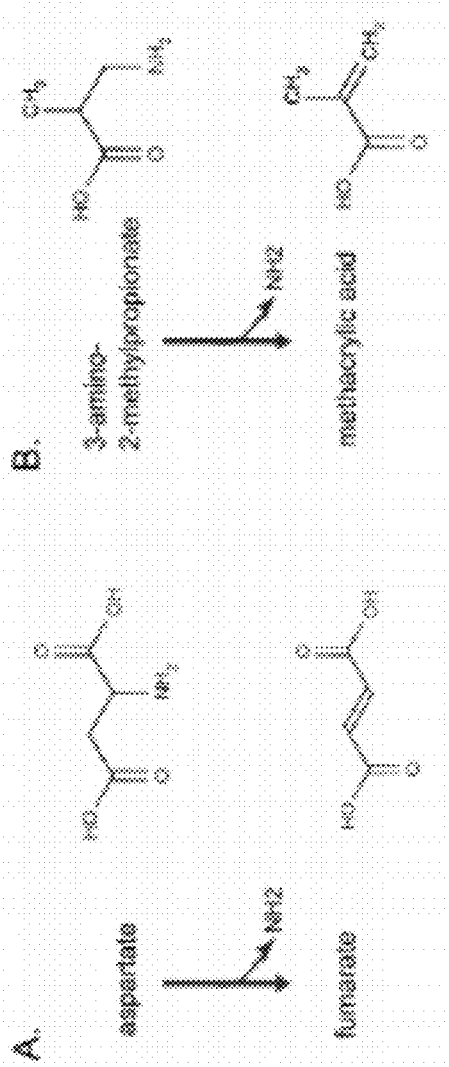
FIG. 5 shows a comparison of the known enzyme-catalyzed deamination of aspartate to form fumarate (FIG. 5A, EC 4.3.1.1) with the predicted deamination of 3-amino-2-methylpropionate to MAA (FIG. 5B).

Referring to FIG. 4, step 5 involves 3-amino-2-methylpropionate ammonia lyase (EC 4.3.1.-). In the final step of this pathway, 3-amino-2-methylpropionate is deaminated to methacrylic acid. An enzyme catalyzing this exact transformation has not been demonstrated experimentally; however the native *E. coli* enzyme, aspartate ammonia lyase (EC 4.3.1.1), may be able to catalyze this reaction (see FIG. 5A). Encoded by aspA in *E. coli*, aspartate ammonia lyase deaminates asparatate to form fumarate but can also react with alternate substrates aspartatephenylmethylester, asparagine, benzyl-aspartate and malate (Ma et al., *Ann. N.Y. Acad. Sci.* 672:60-65 (1992)). In a separate study, directed evolution was been employed on this enzyme to alter substrate specificity (Asano et al., *Biomol. Eng.* 22:95-101 (2005)). Genes encoding aspartase in other organisms include ansB in *Bacillus subtilus* (Sjostrom et al., *Biochim. Biophys. Acta* 1324:182-190 (1997)) and aspA in *Pseudomonas fluorescens* (Takagi et al., *J. Biochem.* 96:545-552 (1984); Takagi et al., *J. Biochem.* 100:697-705 (1986)) and *Serratia marcescens* (Takagi et al., *J. Bacteriol.* 161:1-6 (1985)).

| Gene | GenBankID | Organism |
|------|-----------|----------|
| aspA | P0AC38.1 | *Escherichia coli* K12 |
| ansB | P26899.1 | *Bacillus subtilus* |
| aspA | P07346.1 | *Pseudomonas fluorescens* |
| aspA | P33109.1 | *Serratia marcescens* |

This example describes an MAA biosynthetic pathway from succinyl-CoA.

Example IV

Preparation of an MAA Producing Microbial Organism Having a Pathway for Converting Succinyl-CoA to MAA Via 3-Amino-2-Methylpropanoate This example describes the generation of a microbial organism capable of producing MAA from succinyl-CoA via 3-amino-2-methylpropanoate.

*Escherichia coli* is used as a target organism to engineer the MAA pathway shown in FIG. 4. *E. coli* provides a good host for generating a non-naturally occurring microorganism capable of producing MAA. *E. coli* is amenable to genetic manipulation and is known to be capable of producing various products, like ethanol, acetic acid, formic acid, lactic acid, and succinic acid, effectively under anaerobic or microaerobic conditions.

To generate an *E. coli* strain engineered to produce MAA, nucleic acids encoding the enzymes utilized in the pathway are expressed in *E. coli* using well known molecular biology techniques (see, for example, Sambrook, supra, 2001; Ausubel supra, 1999). In particular, the scpA (NP_417392.1), argK (AAC75955.1), and AF454511 (AAL57846.1) genes encoding the methylmalonyl-CoA mutase, its stabilizer protein, and methylmalonyl-CoA epimerase activities, respectively, are cloned into the pZE13 vector (Expressys, Ruelzheim, Germany) under the PA1/lacO promoter. In addition, the bphG (BAA03892.1), gabT (P22256.1), and aspA (P0AC38.1) genes encoding methylmalonyl-CoA reductase, 3-amino-2-methylpropionate transaminase, and 3-amino-2-methylpropionate ammonia lyase activities, respectively, are cloned into the pZA33 vector (Expressys, Ruelzheim, Germany) under the PA1/lacO promoter. The two sets of plasmids are transformed into E. coli strain MG1655 to express the proteins and enzymes required for MAA synthesis via the succinyl-CoA to 3-amino-2-methylpropanoate pathway.

The resulting genetically engineered organism is cultured in glucose-containing medium following procedures well known in the art (see, for example, Sambrook et al., supra, 2001). Cobalamin is also supplied to the medium to ensure activity of the mutase enzyme unless the host strain of E. coli is engineered to synthesize cobalamin de novo (see, for example, Raux et al., *J. Bacteriol.* 178:753-767 (1996)). The expression of the MAA synthesis genes is corroborated using methods well known in the art for determining polypeptide expression or enzymatic activity, including for example, Northern blots, PCR amplification of mRNA, immunoblotting, and the like. Enzymatic activities of the expressed enzymes are confirmed using assays specific for the individual activities. The ability of the engineered E. coli strain to produce MAA is confirmed using HPLC, gas chromatography-mass spectrometry (GCMS) and/or liquid chromatography-mass spectrometry (LCMS).

Microbial strains engineered to have a functional MAA synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of MAA. One modeling method is the bilevel optimization approach, OptKnock (Burgard et al., *Biotechnol. Bioengineer.* 84:647-657 (2003)), which is applied to select gene knockouts that collectively result in better production of MAA. Adaptive evolution also can be used to generate better producers of, for example, the succinyl-CoA intermediate of the MAA product. Adaptive evolution is performed to improve both growth and production characteristics (Fong and Palsson, *Nat. Genet.* 36:1056-1058 (2004); Alper et al., *Science* 314:1565-1568 (2006)). Based on the results, subsequent rounds of modeling, genetic engineering and adaptive evolution can be applied to the MAA producer to further increase production.

For large-scale production of MAA, the above organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing the culture vessel, for example, flasks can be sealed with a septum and crimp-cap. Microaerobic conditions also can be utilized by providing a small hole in the septum for limited aeration. The pH of the medium is maintained at a pH of around 7 by addition of an acid, such as $H_2SO_4$. The growth rate is determined by measuring optical density using a spectrophotometer (600 nm) and the glucose uptake rate by monitoring carbon source depletion over time. Byproducts such as undesirable alcohols, organic acids, and residual glucose can be quantified by HPLC (Shimadzu, Columbia Md.), for example, using an Aminex® series of HPLC columns (for example, HPX-87 series) (BioRad, Hercules Calif.), using a refractive index detector for glucose and alcohols, and a UV detector for organic acids (Lin et al., *Biotechnol. Bioeng.* 775-779 (2005)).

This example describes the preparation of a microbial organism that can produce MAA from succinyl-CoA via 3-amino-2-methylpropanoate.

Example V

Pathway for Conversion of 4-Hydroxybutyryl-CoA to 3-Hydroxyisobutyric Acid or MAA This example describes an exemplary 3-hydroxyisobutyric acid or MAA synthesis pathway from 4-hydroxybutyryl-CoA.

An additional exemplary pathway entails the conversion of 4HB-CoA to MAA (see FIG. 6). In the first step, 4HB-CoA is converted to 3-hydroxyisobutyryl-CoA (3-Hib-CoA) by a methylmutase. 3-Hib-CoA can then be converted to 3-hydroxyisobutyrate by a CoA hydrolase, synthase or transferase. 3-hydroxyisobutyrate can be secreted and recovered as a product or as a final step in the production of methacrylic acid. 3-Hydroxybutyrate can be dehydrated to form methacrylic acid. Alternatively, 3-Hib-CoA can be dehydrated to methacrylyl-CoA which is then converted to MAA by a hydrolase, synthase, or transferase. The enzymes required for converting the tricarboxylic acid cycle intermediates, alpha-ketoglutarate, succinate, or succinyl-CoA, into 4HB-CoA, are well-documented (Burk et al., U.S. application Ser. No. 12/049,256, filed Mar. 14, 2008; Lutke-Eversloh and Steinbuchel. *FEMS Microbiol. Lett.* 181:63-71 (1999); Sohling and Gottschalk, *Eur. J. Biochem.* 212:121-127 (1993); Sohling and Gottschalk, *J. Bacteriol.* 178:871-880 (1996); Valentin et al., *Eur. J. Biochem.* 227:43-60 (1995); Wolff and Kenealy, *Protein Expr. Purif.* 6:206-212. (1995)).

Under anaerobic conditions, the maximum theoretical product yield is 1.33 moles MAA per mol glucose if a CoA-transferase or synthetase is employed to convert 3-hydroxyisobutyryl-CoA to 3-hydroxybutyrate in step 2 of the pathway (Table 1). If a hydrolase is employed, the maximum theoretical yield drops to 1.13 mol/mol unless PEP carboxykinase is assumed to reversibly operate in the ATP-generating direction towards oxaloacetate. Likewise, the energetic yields are dependent on the type of enzyme utilized in step 2 of the pathway. The highest ATP yields are obtained when a CoA-synthetase is utilized in step 2 and PEP carboxykinase is assumed to be reversible. The product and energetic yields under aerobic conditions are also dependent on the type of enzyme utilized in the conversion of 3-hydroxyisobutyryl-CoA to 3-hydroxybutyrate. It is understood that the maximum molar yields of ATP and product will be unchanged regardless of whether methacrylate or 3-hydroxyisobutyrate is produced. Additionally, it is understood that the maximum molar yields of ATP and MAA will be unchanged if the pathway proceeds through methacryl-CoA as depicted in FIG. 6.

TABLE 1

The maximum theoretical yield of MAA using the biosynthetic pathway through 4-hydroxybutyryl-CoA (4HB-CoA). All yields are expressed as mole/mole glucose.

|  | MAA biosynthetic pathway via 4HB-CoA | |
| --- | --- | --- |
|  | Anaerobic | Aerobic |
| MAA Yield (hydrolase for step 2 and/or 5) | 1.13 | 1.28 |
| MAA Yield (PEPCK reversible) | 1.33 | 1.33 |
| Max ATP yield @ max MAA yield (PEPCK reversible, hydrolase for step 2 and/or 5) | 0.39 | 0.43 |
| Max ATP yield @ max MAA yield (PEPCK reversible, transferase for step 2 and/or 5) | 1.39 | 1.43 |
| Max ATP yield @ max MAA yield (PEPCK reversible, synthetase for step 2 and/or 5) | 1.72 | 1.76 |

Figure 7:
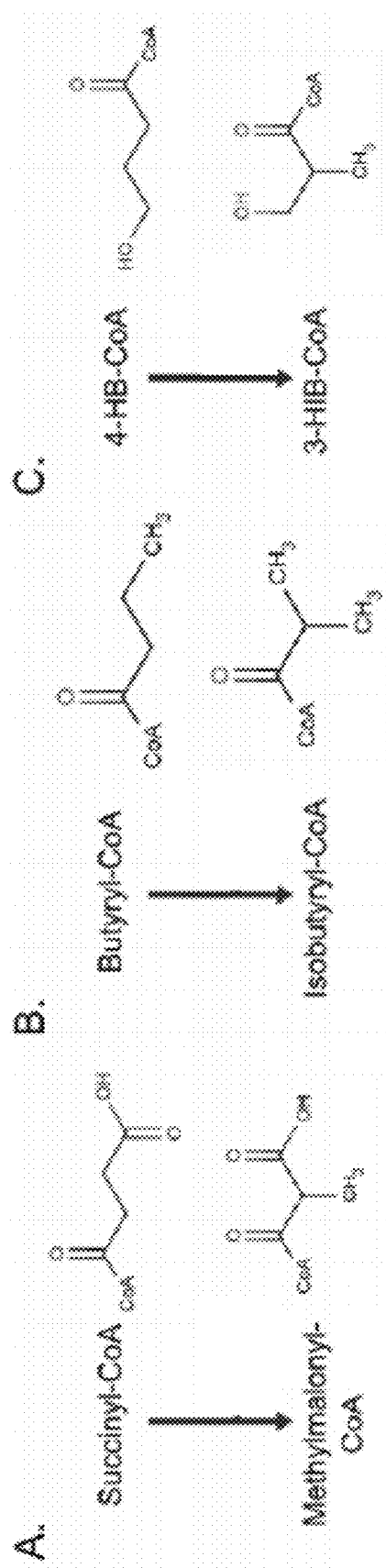
FIG. 7 shows a comparison of enzyme candidates for catalyzing the conversion of 4-hydroxybutyryl-CoA to 3-hydroxyisobutyryl-CoA. Pathways encoded by candidate methylmutases.

Referring to FIG. 6, step 1 involves 4-hydroxybutyryl-CoA mutase (EC 5.4.99.-). The conversion of 4HB-CoA to 3-hydroxyisobutyryl-CoA has yet to be demonstrated experimentally. However, two methylmutases, that is, isobutyryl-CoA mutase (ICM) and methylmalonyl-CoA mutase (MCM), which catalyze similar reactions, are good candidates given the structural similarity of their corresponding substrates (FIG. 7). Methylmalonyl-CoA mutase is a cobalamin-dependent enzyme that converts succinyl-CoA to methylmalonyl-CoA (FIG. 7A). This enzyme and suitable gene candidates were discussed in the succinyl-CoA to MAA pathway (see Example I).

Alternatively, ICM could catalyze the proposed transformation. ICM is a cobalamin-dependent methylmutase in the MCM family that reversibly rearranges the carbon backbone of butyryl-CoA into isobutyryl-CoA (FIG. 7B) (Ratnatilleke et al., J. Biol. Chem. 274:31679-31685 (1999)). A recent study of a novel ICM in Methylibium petroleiphilum, along with previous work, provides evidence that changing a single amino acid near the active site alters the substrate specificity of the enzyme (Ratnatilleke et al., J. Biol. Chem. 274:31679-31685 (1999); Rohwerder et al., Appl. Environ. Microbiol. 72:4128-4135. (2006)). This implies that if a native enzyme is unable to catalyze the conversion of 4HB-CoA to 3HIB-CoA, the enzyme could undergo rational engineering. Exemplary ICM genes encoding homodimeric enzymes include icmA in Streptomyces coelicolor A3 (Alhapel et al., Proc. Natl. Acad. Sci. USA 103:12341-12346 (2006)) and Mpe_B0541 in Methylibium petroleiphilum PM1 (Ratnatilleke et al., J. Biol. Chem. 274:31679-31685 (1999); Rohwerder et al., Appl. Environ. Microbiol. 72:4128-4135 (2006)). Genes encoding heterodimeric enzymes include icm and icmB in Streptomyces cinnamonensis (Ratnatilleke et al., J. Biol. Chem. 274: 31679-31685 (1999); Vrijbloed et al., J. Bacteriol. 181:5600-5605. (1999); Zerbe-Burkhardt et al., J. Biol. Chem. 273: 6508-6517 (1998)). Genes icmA and icmB in Streptomyces avermitilis MA-4680 show high sequence similarity to known ICMs.

| Gene | GenBankID | Organism |
| --- | --- | --- |
| icmA | CAB40912.1 | Streptomyces coelicolor A3(2) |
| Mpe_B0541 | YP_001023546.1 | Methylibium petroleiphilum PM1 |
| icm | AAC08713.1 | Streptomyces cinnamonensis |
| icmB | CAB59633.1 | Streptomyces cinnamonensis |
| icmA | NP_824008.1 | Streptomyces avermitilis MA-4680 |
| icmB | NP_824637.1 | Streptomyces avermitilis MA-4680 |

Referring to FIG. 6, step 2 involves 3-hydroxyisobutyryl-CoA hydrolase (EC 3.1.2.4), synthetase (EC 6.2.1.-) or 3-hydroxyisobutyryl-CoA transferase (EC 2.8.3.-). Step 5 involves methacrylyl-CoA hydrolase, synthetase, or transferase. These transformations can be performed by different classes of enzymes including CoA hydrolases (EC 3.1.2.-), CoA transferases (EC 2.8.3.-), and CoA synthetases (EC 6.1.2.-). As discussed earlier, pathway energetics are most favorable if a CoA transferase or a CoA synthetase is employed to accomplish this transformation (Table 1).

In the CoA-transferase family, E. coli enzyme acyl-CoA: acetate-CoA transferase, also known as acetate-CoA transferase (EC 2.8.3.8), has been shown to transfer the CoA moiety to acetate from a variety of branched and linear acyl-CoA substrates, including isobutyrate (Matthies and Schink, Appl. Environ. Microbiol. 58:1435-1439 (1992)), valerate (Vanderwinkel et al., Biochem. Biophys. Res. Commun. 33:902-908 (1968)) and butanoate (Vanderwinkel et al. supra, 1968). This enzyme is encoded by atoA (alpha subunit) and atoD (beta subunit) in E. coli sp. K12 (Korolev et al., Acta Crystallogr. D Biol. Crystallogr. 58:2116-2121 (2002); Vanderwinkel et al., supra, 1968) and actA and cg0592 in Corynebacterium glutamicum ATCC 13032 (Duncan et al., Appl. Environ. Microbiol. 68:5186-5190 (2002)) and represents an ideal candidate to catalyze the desired 3-hydroxyisobutyryl-CoA transferase or methacrylyl-CoA transferase biotransformations shown in FIG. 6, steps 2 and 5. Candidate genes by sequence homology include atoD and atoA in Escherichia coli UT189. Similar enzymes also exist in Clostridium acetobutylicum and Clostridium saccharoperbutylacetonicum.

| Gene | GenBankID | Organism |
| --- | --- | --- |
| atoA | P76459.1 | Escherichia coli K12 |
| atoD | P76458.1 | Escherichia coli K12 |
| actA | YP_226809.1 | Corynebacterium glutamicum ATCC 13032 |
| cg0592 | YP_224801.1 | Corynebacterium glutamicum ATCC 13032 |
| atoA | ABE07971.1 | Escherichia coli UT189 |
| atoD | ABE07970.1 | Escherichia coli UT189 |
| ctfA | NP_149326.1 | Clostridium acetobutylicum |
| ctfB | NP_149327.1 | Clostridium acetobutylicum |
| ctfA | AAP42564.1 | Clostridium saccharoperbutylacetonicum |
| ctfB | AAP42565.1 | Clostridium saccharoperbutylacetonicum |

Additional exemplary transferase transformations are catalyzed by the gene products of cat1, cat2, and cat3 of Clostridium kluyveri which have been shown to exhibit succinyl-CoA, 4-hydroxybutyryl-CoA, and butyryl-CoA acetyltransferase activity, respectively (Sohling and Gottschalk, J. Bacteriol. 178(3): 871-880 (1996); Seedorf et al., Proc. Natl. Acad. Sci. USA, 105(6):2128-2133 (2008)).

| Gene | GenBankID | Organism |
| --- | --- | --- |
| cat1 | P38946.1 | Clostridium kluyveri |
| cat2 | P38942.2 | Clostridium kluyveri |
| cat3 | EDK35586.1 | Clostridium kluyveri |

The glutaconate-CoA-transferase (EC 2.8.3.12) enzyme from anaerobic bacterium Acidaminococcus fermentans reacts with diacid glutaconyl-CoA and 3-butenoyl-CoA (Mack and Buckel, FEBS Lett. 405:209-212 (1997)). The genes encoding this enzyme are gctA and gctB. This enzyme has reduced but detectable activity with other CoA derivatives including glutaryl-CoA, 2-hydroxyglutaryl-CoA, adipyl-CoA and acrylyl-CoA (Buckel et al., *Eur. J. Biochem.* 118: 315-321 (1981)). The enzyme has been cloned and expressed in *E. coli* (Mack et al., *Eur. J. Biochem.* 226:41-51 (1994)).

| Gene name | GenBankID | Organism |
|---|---|---|
| gctA | CAA57199.1 | *Acidaminococcus fermentans* |
| gctB | CAA57200.1 | *Acidaminococcus fermentans* |

Additional enzyme candidates include succinyl-CoA:3-ketoacid CoA transferases which utilize succinate as the CoA acceptor. Exemplary succinyl-CoA:3:ketoacid-CoA transferases are present in *Helicobacter pylori* (Corthesy-Theulaz et al., *J. Biol. Chem.* 272:25659-25667 (1997)) and *Bacillus subtilis* (Stols et al., *Protein Expr. Purif.* 53:396-403 (2007)).

| Gene name | GenBankID | Organism |
|---|---|---|
| HPAG1_0676 | YP_627417 | *Helicobacter pylori* |
| HPAG1_0677 | YP_627418 | *Helicobacter pylori* |
| ScoA | NP_391778 | *Bacillus subtilis* |
| ScoB | NP_391777 | *Bacillus subtilis* |

A candidate ATP synthase is ADP-forming acetyl-CoA synthetase (ACD, EC 6.2.1.13), an enzyme that couples the conversion of acyl-CoA esters to their corresponding acids with the concurrent synthesis of ATP. Although this enzyme has not been shown to react with 3-hydroxyisobutyryl-CoA or methacrylyl-CoA as a substrate, several enzymes with broad substrate specificities have been described in the literature. ACD I from *Archaeoglobus fulgidus*, encoded by AF1211, was shown to operate on a variety of linear and branched-chain substrates including isobutyrate, isopentanoate, and fumarate (Musfeldt and Schonheit, *J. Bacteriol.* 184:636-644 (2002)). The enzyme from *Haloarcula marismortui* (annotated as a succinyl-CoA synthetase) accepts priopionate, butyrate, and branched-chain acids (isovalerate and isobutyrate) as substrates, and was shown to operate in the forward and reverse directions (Brasen and Schonheit, *Arch. Microbiol.* 182:277-287 (2004)). The ACD encoded by PAE3250 from hyperthermophilic crenarchaeon *Pyrobaculum aerophilum* showed the broadest substrate range of all characterized ACDs, reacting with acetyl-CoA, isobutyryl-CoA (preferred substrate) and phenylacetyl-CoA (Brasen and Schonheit, supra, 2004). However, directed evolution or engineering can be used to modify this enzyme to operate at the physiological temperature of the host organism. The enzymes from *A. fulgidus, H. marismortui* and *P. aerophilum* have all been cloned, functionally expressed, and characterized in *E. coli* (Brasen and Schonheit, supra, 2004; Musfeldt and Schonheit, *J. Bacteriol.* 184:636-644 (2002)).

| Gene name | GenBankID | Organism |
|---|---|---|
| AF1211 | NP_070039.1 | *Archaeoglobus fulgidus* DSM 4304 |
| scs | YP_135572.1 | *Haloarcula marismortui* ATCC 43049 |
| PAE3250 | NP_560604.1 | *Pyrobaculum aerophilum* str. IM2 |

In the CoA hydrolase family, the enzyme 3-hydroxyisobutyryl-CoA hydrolase is specific for 3-HIBCoA and has been described to efficiently catalyze the desired transformation during valine degradation (Shimomura et al., *J. Biol. Chem.* 269:14248-14253 (1994)). Genes encoding this enzyme include hibch of *Rattus norvegicus* (Shimomura et al., *J. Biol. Chem.* 269:14248-14253 (1994); Shimomura et al., *Methods Enzymol.* 324:229-240 (2000)) and *Homo sapiens* (Shimomura et al., supra, 2000). Candidate genes by sequence homology include hibch of *Saccharomyces cerevisiae* and BC_2292 of *Bacillus cereus*.

| Gene name | GenBankID | Organism |
|---|---|---|
| hibch | Q5XIE6.2 | *Rattus norvegicus* |
| hibch | Q6NVY1.2 | *Homo sapiens* |
| hibch | P28817.2 | *Saccharomyces cerevisiae* |
| BC_2292 | Q81DR3 | *Bacillus cereus* |

Referring to FIG. 6, step 3 involves 3-hydroxyisobutyrate dehydratase (EC 4.2.1.-). The entails dehydration of 3-hydroxyisobutyrate to MAA by 3-hydroxyisobutyrate dehydratase. Gene candidates for this enzyme are described in the succinyl-CoA to MAA pathway (see Example I). Also referring to FIG. 6, step 4 involves 3-hydroxyisobutyryl-CoA dehydratase (EC 4.2.1.-). Dehydration of 3-hydroxyisobutyryl-CoA to methacrylyl-CoA can be accomplished by a reversible 3-hydroxyacyl-CoA dehydratase such as crotonase (also called 3-hydroxybutyryl-CoA dehydratase, EC 4.2.1.55) or enoyl-CoA hydratase (also called 3-hydroxyacyl-CoA dehydratase, EC 4.2.1.17). These enzymes are generally reversible (Moskowitz and Merrick, *Biochemistry* 8:2748-2755 (1969); Dune et al., *FEMS Microbiol. Rev.* 17:251-262 (1995)). Exemplary genes encoding crotonase enzymes can be found in *C. acetobutylicum* (Boynton, et al., *J. Bacteriol.* 178(11):3015-3024 (1996)), *C. kluyveri* (Hillmer and Gottschalk, *FEBS Lett.* 21(3):351-354 (1972)), and *Metallosphaera sedula* (Berg et al., *Science* 318(5857) 1782-1786 (2007)) though the sequence of the latter gene is not known. Enoyl-CoA hydratases, which are involved in fatty acid beta-oxidation and/or the metabolism of various amino acids, can also catalyze the hydration of crotonyl-CoA to form 3-hydroxybutyryl-CoA (Agnihotri and Liu, *Bioorg. Med. Chem.* 11(1):9-20 (2003); Roberts et al., *Arch. Microbiol.* 117(1):99-108 (1978); Conrad et al., *J. Bacteriol.* 118 (1):103-111 (1974)). The enoyl-CoA hydratases, phaA and phaB, of *P. putida* are believed to carry out the hydroxylation of double bonds during phenylacetate catabolism (Olivera et al., *Proc. Natl. Acad. Sci. USA* 95:6419-6424 (1998)). The paaA and paaB from *P. fluorescens* catalyze analogous transformations (Olivera et al., supra, 1998). Lastly, a number of *Escherichia coli* genes have been shown to demonstrate enoyl-CoA hydratase functionality including maoC (Park and Lee, *J. Bacteriol.* 185:5391-5397 (2003)), paaF (Ismail et al., *Eur. J. Biochem.* 270:3047-3054 (2003); Park and Lee, *Appl. Biochem. Biotechnol.* 113-116:335-346 (2004); Park and Yup, *Biotechnol. Bioeng.* 86:681-686. (2004)), and paaG (Ismail et al., *Eur. J. Biochem.* 270:3047-3054 (2003); Park and Lee, *Appl. Biochem. Biotechnol.* 113-116:335-346 (2004); Park and Yup, *Biotechnol. Bioeng.* 86:681-686 (2004)).

| Gene name | GenBankID | Organism |
|---|---|---|
| crt | NP_349318.1 | *Clostridium acetobutylicum* |
| crt1 | YP_001393856 | *Clostridium kluyveri* DSM 555 |
| paaA | NP_745427.1 | *Pseudomonas fluorescens* |
| paaB | NP_745426.1 | *Pseudomonas fluorescens* |
| phaA | ABF82233.1 | *Pseudomonas putida* |
| phaB | ABF82234.1 | *Pseudomonas putida* |
| maoC | NP_415905.1 | *Escherichia coli* |

-continued

| Gene name | GenBankID | Organism |
|---|---|---|
| paaF | NP_415911.1 | Escherichia coli |
| paaG | NP_415912.1 | Escherichia coli |

This example describes a biosynthetic pathway for production of 3-hydroxyisobutyric acid or methacrylic acid from 4-hydroxybutyryl-CoA.

Example VI

Preparation of an MAA Producing Microbial Organism Having a Pathway for Converting 4-Hydroxybutyryl-CoA to MAA This example describes the generation of a microbial organism capable of producing MAA from 4-hydroxybutyryl-CoA.

Escherichia coli is used as a target organism to engineer the MAA pathway shown in FIG. 6. E. coli provides a good host for generating a non-naturally occurring microorganism capable of producing MAA. E. coli is amenable to genetic manipulation and is known to be capable of producing various products, like ethanol, acetic acid, formic acid, lactic acid, and succinic acid, effectively under anaerobic or microaerobic conditions.

To generate an E. coli strain engineered to produce MAA, nucleic acids encoding the enzymes utilized in the pathway are expressed in E. coli using well known molecular biology techniques (see, for example, Sambrook, supra, 2001; Ausubel supra, 1999). In particular, the sucD (YP_001396394), 4hbd (YP_001396393), buk1 (Q45829), and ptb (NP_349676) genes encoding succinic semialdehyde dehydrogenase (CoA-dependent), 4-hydroxybutyrate dehydrogenase, 4-hydroxybutyrate kinase, and phosphotransbutyrylase activities, respectively, are cloned into the pZE13 vector (Expressys, Ruelzheim, Germany) under the PA1/lacO promoter. This construct allows the production of 4HB-CoA from succinyl-CoA as described in Burk et al. (U.S. application Ser. No. 12/049,256, filed Mar. 14, 2008). In addition, the icmA (CAB40912.1), hibch (Q5XIE6.2), and hmd (ABC88407.1) genes encoding 4-hydroxybutyryl-CoA mutase, 3-hydroxyisobutyryl-CoA hydrolase, and 3-hydroxyisobutyrate dehydratase activities, respectively, are cloned into the pZA33 vector (Expressys, Ruelzheim, Germany) under the PA1/lacO promoter. The two sets of plasmids are transformed into E. coli strain MG1655 to express the proteins and enzymes required for MAA synthesis via the 4-hydroxybutyryl-CoA pathway.

The resulting genetically engineered organism is cultured in glucose-containing medium following procedures well known in the art (see, for example, Sambrook et al., supra, 2001). Cobalamin is also supplied to the medium to ensure activity of the mutase enzyme unless the host strain of E. coli is engineered to synthesize cobalamin de novo (see, for example, Raux et al., J. Bacteriol. 178:753-767 (1996)). The expression of the MAA synthesis genes is corroborated using methods well known in the art for determining polypeptide expression or enzymatic activity, including for example, Northern blots, PCR amplification of mRNA, immunoblotting, and the like. Enzymatic activities of the expressed enzymes are confirmed using assays specific for the individual activities. The ability of the engineered E. coli strain to produce MAA is confirmed using HPLC, gas chromatography-mass spectrometry (GCMS) and/or liquid chromatography-mass spectrometry (LCMS).

Microbial strains engineered to have a functional MAA synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of MAA. One modeling method is the bilevel optimization approach, OptKnock (Burgard et al., Biotechnol. Bioengineer. 84:647-657 (2003)), which is applied to select gene knockouts that collectively result in better production of MAA. Adaptive evolution also can be used to generate better producers of, for example, the succinyl-CoA or 4-hydroxybutyryl-CoA intermediates of the MAA product. Adaptive evolution is performed to improve both growth and production characteristics (Fong and Palsson, Nat. Genet. 36:1056-1058 (2004); Alper et al., Science 314:1565-1568 (2006)). Based on the results, subsequent rounds of modeling, genetic engineering and adaptive evolution can be applied to the MAA producer to further increase production.

For large-scale production of MAA, the above organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing the culture vessel, for example, flasks can be sealed with a septum and crimp-cap. Microaerobic conditions also can be utilized by providing a small hole in the septum for limited aeration. The pH of the medium is maintained at a pH of around 7 by addition of an acid, such as $H_2SO_4$. The growth rate is determined by measuring optical density using a spectrophotometer (600 nm) and the glucose uptake rate by monitoring carbon source depletion over time. Byproducts such as undesirable alcohols, organic acids, and residual glucose can be quantified by HPLC (Shimadzu, Columbia Md.), for example, using an Aminex® series of HPLC columns (for example, HPX-87 series) (BioRad, Hercules Calif.), using a refractive index detector for glucose and alcohols, and a UV detector for organic acids (Lin et al., Biotechnol. Bioeng. 775-779 (2005)).

This example describes the preparation of a microbial organism that can produce MAA from 4-hydroxybutyryl-CoA.

Example VII

Pathway for Conversion of Alpha-Ketoglutarate to MAA Via Threo-3-Methylaspartate This example describes an exemplary MAA synthesis pathway from alpha-ketoglutarate to threo-3-methylaspartate.

Another exemplary pathway for MAA biosynthesis proceeds through alpha-ketoglutarate, a metabolite in E. coli produced in the TCA cycle (see FIG. 8). This pathway is high-yielding under aerobic conditions with a maximum theoretical yield of 1.2 mol MAA/mol glucose (Table 2). The yields under anaerobic conditions are lower, as the pathway is redox imbalanced and MAA synthesis requires the formation of fermentation byproducts such as formate and ethanol.

TABLE 2

The maximum theoretical yield of MAA using the alpha-ketoglutarate biosynthetic pathway.

|  | MAA biosynthetic pathway via alpha-ketoglutarate | |
| --- | --- | --- |
|  | Anaerobic | Aerobic |
| MAA Yield | 0.69 | 1.2 |
| MAA Yield (PEPCK reversible) | 0.82 | 1.2 |
| ATP Yield @ max MAA yield (PEPCK reversible) | 0 | 0.95 |

All yields are expressed as mole/mole glucose.

The first step of the pathway, catalyzed by the enzyme aspartate aminotransferase, transfers an amino group from aspartate to alpha-ketoglutarate, forming glutamate and oxaloacetate. The subsequent two steps include rearrangement of the carbon backbone and subsequent deamination to form mesaconate. Enzymes catalyzing these conversions are found in the energy-yielding fermentation of glutamate in soil Clostridia and other organisms capable of fermenting amino acids (Buckel and Barker, *J. Bacteriol.* 117:1248-1260 (1974)). The directionality of the pathway in these organisms is in agreement with the direction required for MAA synthesis in the biopathway. The final pathway step entails decarboxylation of mesaconate to yield methacrylic acid.

Referring to FIG. 8, step 1 involves aspartate aminotransferase (EC 2.6.1.1). The first step of the pathway transfers an amino group from aspartate to alpha-ketoglutarate, forming glutamate and oxaloacetate. The genes aspC from *Escherichia coli* (Yagi et al., *FEBS Lett.* 100:81-84 (1979); Yagi et al., *Methods Enzymol.* 113:83-89 (1985)), AAT2 from *Saccharomyces cerevisiae* (Yagi et al., *J. Biochem.* 92:35-43 (1982)) and ASP5 from *Arabidopsis thaliana* (de la Torre et al., *Plant J.* 46:414-425 (2006); Kwok and Hanson, *J. Exp. Bot.* 55:595-604 (2004); Wilkie and Warren, *Protein Expr. Purif.* 12:381-389 (1998)), encode the enzyme that catalyzes this conversion, aspartate aminotransferase.

| Gene name | GenBank Accession # | Organism |
| --- | --- | --- |
| aspC | NP_415448.1 | *Escherichia coli* |
| AAT2 | P23542.3 | *Saccharomyces cerevisiae* |
| ASP5 | P46248.2 | *Arabidopsis thaliana* |

Referring to FIG. 8, step 2 involves glutamate mutase (EC 5.4.99.1). In step 2, the linear carbon chain of glutamate is rearranged to the branched structure of threo-3-methylaspartate. This transformation is catalyzed by glutamate mutase, a cobalamin-dependent enzyme composed of two subunits. Two glutamate mutases, from *Clostridium cochlearium* and *Clostridium tetanomorphum*, have been cloned and functionally expressed in *E. coli* (Holloway and Marsh, *J. Biol. Chem.* 269:20425-20430 (1994); Reitzer et al., *Acta Crystallogr. D Biol. Crystallogr.* 54:1039-1042 (1998)). The genes encoding this two-subunit protein are glmE and glmS from *Clostridium cochlearium*, mamA and glmE from *Clostridium tetanomor-phum*, and mutE and mutS from *Clostridium tetani* (Switzer, Glutamate mutase, pp. 289-305 Wiley, New York (1982)).

| Gene name | GenBankID | Organism |
| --- | --- | --- |
| glmE | P80077.2 | *Clostridium cochlearium* |
| glmS | P80078.2 | *Clostridium cochlearium* |
| mamA | Q05488.1 | *Clostridium tetanomorphum* |
| glmE | Q05509.1 | *Clostridium tetanomorphum* |
| mutE | NP_783086.1 | *Clostridium tetani* E88 |
| mutS | NP_783088.1 | *Clostridium tetani* E88 |

Referring to FIG. 8, step 3 involves 3-methylaspartase (EC 4.3.1.2). 3-methylaspartase, also referred to as beta-methylaspartase or 3-methylaspartate ammonia-lyase, catalyzes the deamination of threo-3-methylasparatate to mesaconate. The 3-methylaspartase from *Clostridium tetanomorphum* has been cloned, functionally expressed in *E. coli*, and crystallized (Asuncion et al., *Acta Crystallogr. D Biol. Crystallogr.* 57:731-733 (2001); Asuncion et al., *J. Biol. Chem.* 277:8306-8311 (2002); Botting et al., *Biochemistry* 27:2953-2955 (1988); Goda et al., *Biochemistry* 31:10747-10756 (1992)). In *Citrobacter amalonaticus*, this enzyme is encoded by BAA28709 (Kato and Asano, *Arch. Microbiol.* 168:457-463 (1997)). 3-methylaspartase has also been crystallized from *E. coli* YG1002 (Asano and Kato, *FEMS Microbiol. Lett.* 118: 255-258 (1994)), although the protein sequence is not listed in public databases such as GenBank. Sequence homology can be used to identify additional candidate genes, including CTC_02563 in *C. tetani* and ECs0761 in *Escherichia coli* O157:H7.

| Gene name | GenBankID | Organism |
| --- | --- | --- |
| MAL | AAB24070.1 | *Clostridium tetanomorphum* |
| BAA28709 | BAA28709.1 | *Citrobacter amalonaticus* |
| CTC_02563 | NP_783085.1 | *Clostridium tetani* |
| ECs0761 | BAB34184.1 | *Escherichia coli* O157:H7 str. Sakai |

Figure 9:
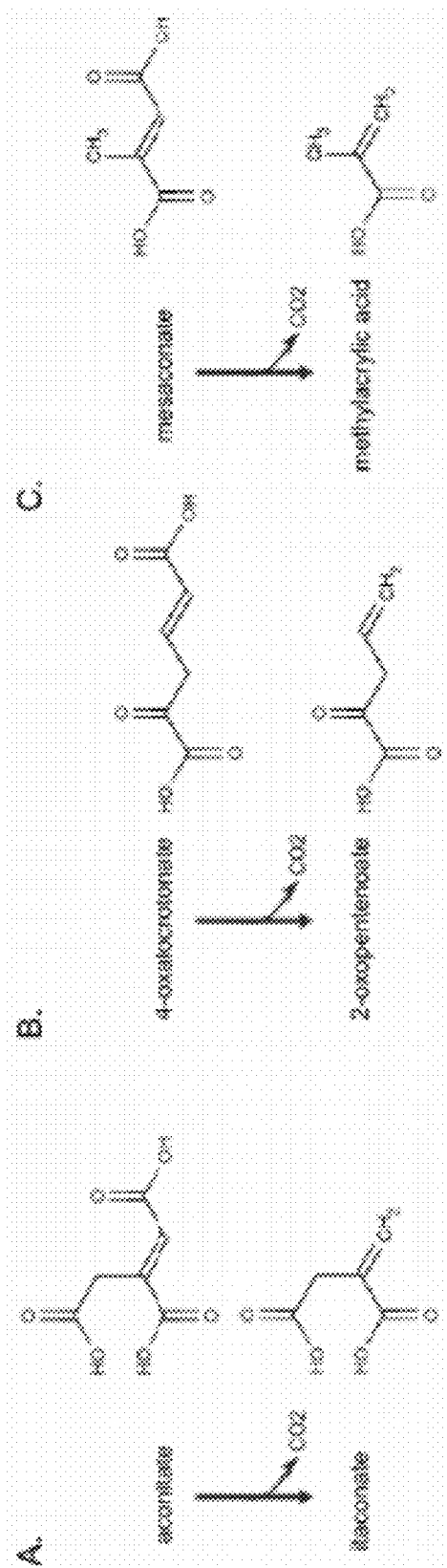
FIG. 9 shows a comparison of known enzyme-catalyzed decarboxylations with the predicted decarboxylation of mesaconate.

Referring to FIG. 8, step 4 involves mesaconate decarboxylase (EC 4.1.1.-). The final step of the pathway entails the decarboxylation of mesaconate to methacrylic acid. An enzyme catalyzing this exact reaction has not been demonstrated experimentally. However, several enzymes catalyzing highly similar reactions exist (FIG. 9). One enzyme with closely related function is aconitate decarboxylase (FIG. 9A). This enzyme catalyzes the final step in itaconate biosynthesis in a strain of *Candida* and the filamentous fungi *Aspergillus terreus* (Bonnarme et al., *J. Bacteriol.* 177:3573-3578 (1995); Willke and Vorlop, *Appl. Microbiol. Biotechnol.* 56:289-295 (2001)). Although itaconate is a compound of biotechnological interest, no efforts have been made thus far to identify or clone the aconitate decarboxylase gene.

A second enzyme with similar function is 4-oxalocronate decarboxylase (FIG. 9B). This enzyme is common in a variety of organisms and the genes encoding the enzyme from *Pseudomonas* sp. (strain 600) have been cloned and expressed in *E. coli* (Shingler et al., *J. Bacteriol.* 174:711-724 (1992)). The methyl group in mesaconate may cause steric hindrance, but this problem could likely be overcome with directed evolution or protein engineering. 4-oxalocronate decarboxylase is composed of two subunits. Genes encoding this enzyme include dmpH and dmpE in *Pseudomonas* sp. (strain 600) (Shingler et al., *J. Bacteriol.* 174:711-724 (1992)), xylII and xylIII from *Pseudomonas putida* (Kato and Asano, *Arch. Microbiol.* 168:457-463 (1997); Stanley et al., *Biochemistry* 39:718-726 (2000)), and Reut_B5691 and Reut_B5692 from *Ralstonia eutropha* JMP134 (Hughes et al., *J. Bacteriol.* 158:79-83 (1984)).

| Gene name | GenBankID | Organism |
|---|---|---|
| dmpH | CAA43228.1 | *Pseudomonas* sp. CF600 |
| dmpE | CAA43225.1 | *Pseudomonas* sp. CF600 |
| xylII | YP_709328.1 | *Pseudomonas putida* |
| xylIII | YP_709353.1 | *Pseudomonas putida* |
| Reut_B5691 | YP_299880.1 | *Ralstonia eutropha* JMP134 |
| Reut_B5692 | YP_299881.1 | *Ralstonia eutropha* JMP134 |

This example describes a biosynthetic pathway for production of MMA from alpha-ketoglutarate.

Example VIII

Preparation of an MAA Producing Microbial Organism Having a Pathway for Converting Alpha-Ketoglutarate to MAA Via Threo-3-Methylaspartate This example describes the generation of a microbial organism capable of producing MAA from alpha-ketoglutarate via threo-3-methylaspartate.

*Escherichia coli* is used as a target organism to engineer the MAA pathway shown in FIG. 8. *E. coli* provides a good host for generating a non-naturally occurring microorganism capable of producing MAA. *E. coli* is amenable to genetic manipulation and is known to be capable of producing various products, like ethanol, acetic acid, formic acid, lactic acid, and succinic acid, effectively under anaerobic or microaerobic conditions.

To generate an *E. coli* strain engineered to produce MAA, nucleic acids encoding the enzymes utilized in the pathway are expressed in *E. coli* using well known molecular biology techniques (see, for example, Sambrook, supra, 2001; Ausubel supra, 1999). In particular, the aspC (NP_415448.1), glmE (P80077.2), and glmS (P80078.2) genes encoding the aspartate aminotransferase and glutamate mutase activities are cloned into the pZE13 vector (Expressys, Ruelzheim, Germany) under the PA1/lacO promoter. In addition, the MAL (AAB24070.1), dmpH (CAA43228.1), and dmpE (CAA43225.1) genes encoding 3-methylaspartase and mesaconate decarboxylase activities are cloned into the pZA33 vector (Expressys, Ruelzheim, Germany) under the PA1/lacO promoter. The two sets of plasmids are transformed into *E. coli* strain MG1655 to express the proteins and enzymes required for MAA synthesis via the alpha-ketoglutarate to threo-3-methylaspartate pathway.

The resulting genetically engineered organism is cultured in glucose-containing medium following procedures well known in the art (see, for example, Sambrook et al., supra, 2001). Cobalamin is also supplied to the medium to ensure activity of the mutase enzyme unless the host strain of *E. coli* is engineered to synthesize cobalamin de novo (see, for example, Raux et al., *J. Bacteriol.* 178:753-767 (1996)). The expression of the MAA synthesis genes is corroborated using methods well known in the art for determining polypeptide expression or enzymatic activity, including for example, Northern blots, PCR amplification of mRNA, immunoblotting, and the like. Enzymatic activities of the expressed enzymes are confirmed using assays specific for the individual activities. The ability of the engineered *E. coli* strain to produce MAA is confirmed using HPLC, gas chromatography-mass spectrometry (GCMS) and/or liquid chromatography-mass spectrometry (LCMS).

Microbial strains engineered to have a functional MAA synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of MAA. One modeling method is the bilevel optimization approach, OptKnock (Burgard et al., *Biotechnol. Bioengineer.* 84:647-657 (2003)), which is applied to select gene knockouts that collectively result in better production of MAA. Adaptive evolution also can be used to generate better producers of, for example, the alpha-ketoglutarate intermediate of the MAA product. Adaptive evolution is performed to improve both growth and production characteristics (Fong and Palsson, *Nat. Genet.* 36:1056-1058 (2004); Alper et al., *Science* 314:1565-1568 (2006)). Based on the results, subsequent rounds of modeling, genetic engineering and adaptive evolution can be applied to the MAA producer to further increase production.

For large-scale production of MAA, the above organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing the culture vessel, for example, flasks can be sealed with a septum and crimp-cap. Microaerobic conditions also can be utilized by providing a small hole in the septum for limited aeration. The pH of the medium is maintained at a pH of around 7 by addition of an acid, such as $H_2SO_4$. The growth rate is determined by measuring optical density using a spectrophotometer (600 nm) and the glucose uptake rate by monitoring carbon source depletion over time. Byproducts such as undesirable alcohols, organic acids, and residual glucose can be quantified by HPLC (Shimadzu, Columbia Md.), for example, using an Aminex® series of HPLC columns (for example, HPX-87 series) (BioRad, Hercules Calif.), using a refractive index detector for glucose and alcohols, and a UV detector for organic acids (Lin et al., *Biotechnol. Bioeng.* 775-779 (2005)).

This example describes the preparation of a microbial organism that can produce MAA from alpha-ketoglutarate via threo-3-methylaspartate.

Example IX

Pathway for Conversion of Alpha-Ketoglutarate to MAA Via 2-Hydroxyglutarate

This example describes an exemplary MAA synthesis pathway from alph-ketoglutarate to MAA via 2-hydroxyglutarate.

Another exemplary pathway for MAA biosynthesis has a scheme similar to the pathway described in Example VII, but it passes through the hydroxylated intermediates 2-hydroxyglutarate and 3-methylmalate (see FIG. 10), rather than amine-substituted intermediates (see FIG. 8). Like the pathway described in Example VII, this pathway is high-yielding under aerobic conditions with a maximum theoretical yield of 1.2 mol MAA/mol glucose (Table 3). Under anaerobic conditions, the pathway is not redox-balanced and MAA synthesis requires formation of fermentation byproducts such as ethanol, formate and succinate.

TABLE 3

The maximum theoretical yield of MAA using the alpha-ketoglutarate biosynthetic pathway via 2-hydroxyglutarate.

| | MAA biosynthetic pathway via alpha-ketoglutarate (alt) | |
|---|---|---|
| | Anaerobic | Aerobic |
| MAA Yield | 0.74 | 1.20 |
| MAA Yield (PEPCK reversible) | 0.87 | 1.20 |
| ATP Yield @ max MAA yield (PEPCK reversible) | 0 | 1.55 |

All yields are expressed as mole/mole glucose.

Referring to FIG. 10, step 1 involves alpha-ketoglutarate reductase (EC 1.1.99.2). The first step of this pathway entails the reduction of alpha-ketoglutarate to 2-hydroxyglutarate by native enzyme alpha-ketoglutarate reductase. This enzyme is encoded by serA, a multifunctional enzyme which also catalyzes the reduction of 3-phosphoglycerate in central metabolism (Zhao and Winkler, *J. Bacteriol.* 178:232-239 (1996)). Genes L2HGDH in *Homo sapiens* (Jansen and Wanders, *Biochim. Biophys. Acta* 1225:53-56 (1993)), FN0487 in L2hgdh in *Fusobacterium nucleatum* (Hayashi et al., *J. Nihon Univ. Sch. Dent.* 28:12-21 (1986)), and L2hgdh_predicted in *Rattus norvegicus* (Jansen and Wanders, *Biochim. Biophys. Acta* 1225:53-56 (1993)) encode this enzyme. Gene candidates with high sequence homology include L2hgdh in *Mus musculus* and L2HGDH in *Bos taurus*. At high concentrations, 2-hydroxyglutarate has been shown to feed back on alpha-ketoglutarate reductase activity by competitive inhibition (Zhao and Winkler, *J. Bacteriol.* 178:232-239. (1996)).

| Gene name | GenBankID | Organism |
|---|---|---|
| serA | CAA01762.1 | *Escherichia coli* |
| L2HGDH | Q9H9P8.2 | *Homo sapiens* |
| L2hgdh | NP_663418.1 | *Mus musculus* |
| L2hgdh_predicted | NP_001101498.1 | *Rattus norvegicus* |
| L2HGDH | NP_001094560.1 | *Bos taurus* |
| FN0487 | Q8RG31 | *Fusobacterium nucleatum* subsp. *Nucleatum* |

Referring to FIG. 10, step 2 involves 2-hydroxyglutamate mutase (EC 5.4.99.-). In the second step of the pathway, the carbon backbone undergoes rearrangement by a glutamate mutase enzyme. The most common reaction catalyzed by such an enzyme is the conversion of glutamate to threo-3-methylasparate, shown in step 2 of FIG. 8. The adenosylcobalamin-dependent glutamate mutase from *Clostridium cochlearium* has also been shown to react with 2-hydroxyglutarate as an alternate substrate (Roymoulik et al., *Biochemistry* 39:10340-10346 (2000)), although the rate of this reaction is two orders of magnitude lower with 2-hydroxyglutarate compared to the rate with native substrate glutamate. Directed evolution of the enzyme can be used to increase glutamate mutase affinity for 2-hydroxyglutarate. GenBank accession numbers of protein sequences encoding glutamate mutases are found in Example VII, step 2 of the pathway.

Figure 11:
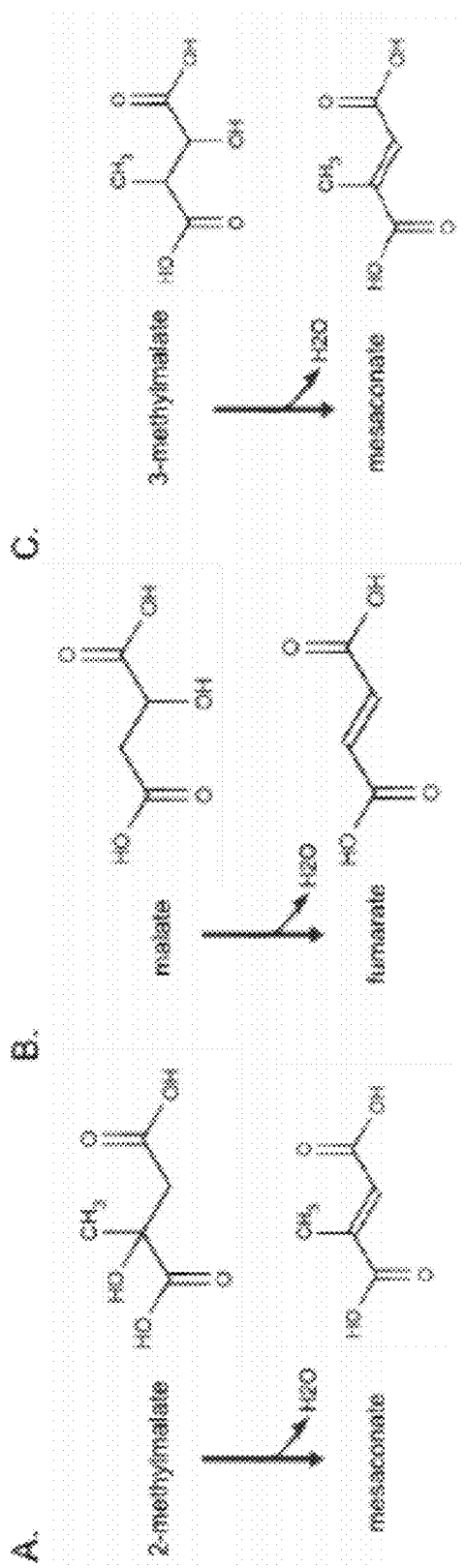
FIG. 11 shows enzyme candidates for 3-methylmalate conversion to mesaconate.

Referring to FIG. 10, step 3 involves 3-methylmalate dehydratase (EC 4.2.1.-). In the third step, 3-methylmalate is dehydrated to form mesaconate. Although an enzyme catalyzing this exact transformation has not been described in the literature, several enzymes are able to catalyze a similar reaction (FIG. 11). One such enzyme is 2-methylmalate dehydratase, also called citramalate hydrolyase, which converts 2-methylmalate to mesaconate (FIG. 11A). 2-Methylmalate and 3-methylmalate are closely related, with the only difference in structure being the location of the hydroxyl group. 2-Methylmalate dehydratase activity was detected in *Clostridium tetanomorphum, Morganella morganii, Citrobacter amalonaticus* in the context of the glutamate degradation VI pathway (Kato and Asano, *Arch. Microbiol.* 168:457-463 (1997)); however the genes encoding this enzyme have not been sequenced to date.

A second candidate enzyme is fumarate hydratase, which catalyzes the dehydration of malate to fumarate (FIG. 11B). As described in Example I (step 5), a wealth of structural information is available for this enzyme and other studies have successfully engineered the enzyme to alter activity, inhibition and localization (Weaver, *Acta Crystallogr. D Biol. Crystallogr.* 61:1395-1401 (2005)). Gene candidates are discussed in Example I, step 5 of the pathway.

Referring to FIG. 10, step 4 involves mesaconate decarboxylase (EC 4.1.1.-). The final pathway step involves the decarboxylation of mesaconate to methacrylic acid. This reaction is identical to the final step of the pathway described in Example VII.

This example describes a biosynthetic pathway for production of MMA from alpha-ketoglutarate.

Example X

Preparation of an MAA Producing Microbial Organism Having a Pathway for Converting Alpha-Ketoglutarate to MAA Via 2-Hydroxyglutarate This example describes the generation of a microbial organism capable of producing MAA from alpha-ketoglutarate via 2-hydroxyglutarate.

*Escherichia coli* is used as a target organism to engineer the MAA pathway shown in FIG. 10. *E. coli* provides a good host for generating a non-naturally occurring microorganism capable of producing MAA. *E. coli* is amenable to genetic manipulation and is known to be capable of producing various products, like ethanol, acetic acid, formic acid, lactic acid, and succinic acid, effectively under anaerobic or microaerobic conditions.

To generate an *E. coli* strain engineered to produce MAA, nucleic acids encoding the enzymes utilized in the pathway are expressed in *E. coli* using well known molecular biology techniques (see, for example, Sambrook, supra, 2001; Ausubel supra, 1999). In particular, the serA (CAA01762.1), glmE (P80077.2), and glmS (P80078.2) genes encoding the alpha-ketoglutarate reductase and 2-hydroxyglutamate mutase activities are cloned into the pZE13 vector (Expressys, Ruelzheim, Germany) under the PA1/lacO promoter. In addition, the fumC (P05042.1), dmpH (CAA43228.1), and dmpE (CAA43225.1) genes encoding 3-methylmalate dehydratase and mesaconate decarboxylase activities are cloned into the pZA33 vector (Expressys, Ruelzheim, Germany) under the PA1/lacO promoter. The two sets of plasmids are transformed into *E. coli* strain MG1655 to express the proteins and enzymes required for MAA synthesis via the alpha-ketoglutarate to 2-hydroxyglutarate pathway.

The resulting genetically engineered organism is cultured in glucose-containing medium following procedures well known in the art (see, for example, Sambrook et al., supra, 2001). Cobalamin is also supplied to the medium to ensure activity of the mutase enzyme unless the host strain of E. coli is engineered to synthesize cobalamin de novo (see, for example, Raux et al., J. Bacteriol. 178:753-767 (1996)). The expression of the MAA synthesis genes is corroborated using methods well known in the art for determining polypeptide expression or enzymatic activity, including for example, Northern blots, PCR amplification of mRNA, immunoblotting, and the like. Enzymatic activities of the expressed enzymes are confirmed using assays specific for the individual activities. The ability of the engineered E. coli strain to produce MAA is confirmed using HPLC, gas chromatography-mass spectrometry (GCMS) and/or liquid chromatography-mass spectrometry (LCMS).

Microbial strains engineered to have a functional MAA synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of MAA. One modeling method is the bilevel optimization approach, OptKnock (Burgard et al., Biotechnol. Bioengineer. 84:647-657 (2003)), which is applied to select gene knockouts that collectively result in better production of MAA. Adaptive evolution also can be used to generate better producers of, for example, the alpha-ketoglutarate intermediate of the MAA product. Adaptive evolution is performed to improve both growth and production characteristics (Fong and Palsson, Nat. Genet. 36:1056-1058 (2004); Alper et al., Science 314:1565-1568 (2006)). Based on the results, subsequent rounds of modeling, genetic engineering and adaptive evolution can be applied to the MAA producer to further increase production.

For large-scale production of MAA, the above organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing the culture vessel, for example, flasks can be sealed with a septum and crimp-cap. Microaerobic conditions also can be utilized by providing a small hole in the septum for limited aeration. The pH of the medium is maintained at a pH of around 7 by addition of an acid, such as $H_2SO_4$. The growth rate is determined by measuring optical density using a spectrophotometer (600 nm) and the glucose uptake rate by monitoring carbon source depletion over time. Byproducts such as undesirable alcohols, organic acids, and residual glucose can be quantified by HPLC (Shimadzu, Columbia Md.), for example, using an Aminex® series of HPLC columns (for example, HPX-87 series) (BioRad, Hercules Calif.), using a refractive index detector for glucose and alcohols, and a UV detector for organic acids (Lin et al., Biotechnol. Bioeng. 775-779 (2005)).

This example describes the preparation of a microbial organism that can produce MAA from alpha-ketoglutarate via 2-hydroxyglutarate.

Example XI

Pathway for Conversion of Acetyl-CoA to 2-Hydroxyisobutyric Acid or MAA

This example describes an exemplary 2-hydroxyisobutyric acid or MAA synthesis pathway from acetyl-CoA.

MAA biosynthesis can proceed from acetyl-CoA in a minimum of five enzymatic steps (see FIG. 12). In this pathway, two molecules of acetyl-CoA are combined to form acetoacetyl-coA, which is then reduced to 3-hydroxybutyryl-CoA. Alternatively, 4-hydroxybutyryl-CoA can be converted to 3-hydroxybutyryl-CoA by way of 4-hydroxybutyryl-CoA dehydratase and crotonase (Martins et al., Proc. Nat. Acad. Sci. USA 101(44) 15645-15649 (2004); Jones and Woods, Microbiol. Rev. 50:484-524 (1986); Berg et al., Science 318 (5857) 1782-1786 (2007)). A methylmutase then rearranges the carbon backbone of 3-hydroxybutyryl-CoA to 2-hydroxyisobutyryl-CoA, which is then dehydrated to form methacrylyl-CoA. Alternatively, 2-hydroxyisobutyryl-CoA can be converted to 2-hydroxyisobutyrate, secreted, and recovered as product. The final step converting methacrylyl-CoA to MAA can be performed by a single enzyme (shown in FIG. 12) or a series of enzymes.

The pathway shown in FIG. 12 has a maximum theoretical product yield of 1.25 mol/mol glucose under aerobic conditions which also requires the utilization of 0.4 moles of oxygen (Table 4). In the absence of oxygen uptake, the maximum theoretical yield drops to 1.01 mol/mol glucose and the fermentation byproducts such as ethanol and formate must be formed to maintain redox balance. The assumption that PEP carboxykinase (PEPCK) can operate in the ATP generating direction increases the MAA yield under anaerobic conditions to 1.09 mol/mol, but does not prevent the formation of byproducts. The energetics of MAA formation are favorable if a CoA transferase or synthetase is utilized in step 5 of the pathway. Equivalent maximum yields of product and ATP are obtain if 2-hydroxyisobutyric acid is produced as opposed to methacrylic acid via the pathways described herein.

TABLE 4

MAA and ATP yields for Acetyl-CoA pathway.

| | MAA biosynthetic pathway via Acetyl-CoA | |
|---|---|---|
| | Anaerobic | Aerobic |
| MAA Yield | 1.01 | 1.25 |
| MAA Yield (PEPCK reversible) | 1.09 | 1.25 |
| Max ATP yield @ max MAA yield (PEPCK reversible, hydrolase for step 5) | 0 | 0.03 |
| Max ATP yield @ max MAA yield (PEPCK reversible, transferase or synthetase for step 5) | 1.09 | 1.28 |

Referring to FIG. 12, step 1 involves acetoacetyl-CoA thiolase (EC 2.3.1.9). The formation of acetoacetyl-CoA from two acetyl-CoA units is catalyzed by acetyl-CoA thiolase. This enzyme is native to E. coli, encoded by gene atoB, and typically operates in the acetoacetate-degrading direction during fatty acid oxidation (Duncombe and Frerman, *Arch. Biochem. Biophys.* 176:159-170 (1976); Frerman and Duncombe, *Biochim. Biophys. Acta* 580:289-297 (1979)). The gene thlA from *Clostridium acetobutylicum* was engineered into an isopropanol-producing strain of *E. coli* and was shown to function in the direction of acetoacetate synthesis (Hanai et al., *Appl. Environ. Microbiol.* 73:7814-7818 (2007); Stim-Herndon et al., *Gene* 154:81-85 (1995)). An additional gene candidate is thl from *Clostridium pasteurianum* (Meng and Li. Cloning, *Biotechnol. Lett.* 28:1227-1232 (2006)).

| Gene name | GenBankID | Organism |
| --- | --- | --- |
| atoB | P76461.1 | *Escherichia coli* |
| thlA | P45359.1 | *Clostridium acetobutylicum* |
| thl | ABA18857.1 | *Clostridium pasteurianum* |

Referring to FIG. 12, step 2 involves acetoacetyl-CoA reductase (EC#: 1.1.1.35). The second step entails the reduction of acetoacetyl-CoA to 3-hydroxybutyryl-CoA by acetoacetyl-CoA reductase. This enzyme participates in the acetyl-CoA fermentation pathway to butyrate in several species of Clostridia and has been studied in detail (Jones and Woods, *Microbiol. Rev.* 50:484-524 (1986)). The enzyme from *Clostridium acetobutylicum*, encoded by hbd, has been cloned and functionally expressed in *E. coli* (Youngleson et al., *J. Bacteriol.* 171:6800-6807 (1989)). Additionally, subunits of two fatty acid oxidation complexes in *E. coli*, encoded by fadB and fadJ, function as 3-hydroxyacyl-CoA dehydrogenases (Binstock and Schulz, *Methods Enzymol.* 71 Pt C:403-411 (1981)). Additional gene candidates include Hbd1 (C-terminal domain) and Hbd2 (N-terminal domain) in *Clostridium kluyveri* (Hillmer and Gottschalk, *Biochim. Biophys. Acta* 3334:12-23 (1974)) and HSD17B10 in *Bos taurus* (Wakil et al., *J. Biol. Chem.* 207:631-638 (1954)).

| Gene name | GenBankID | Organism |
| --- | --- | --- |
| fadB | P21177.2 | *Escherichia coli* |
| fadJ | P77399.1 | *Escherichia coli* |
| Hbd2 | EDK34807.1 | *Clostridium kluyveri* |
| Hbd1 | EDK32512.1 | *Clostridium kluyveri* |
| hbd | P52041.2 | *Clostridium acetobutylicum* |
| HSD17B10 | O02691.3 | *Bos taurus* |

Referring to FIG. 12, step 3 involves 3-hydroxybutyryl-CoA mutase (EC 5.4.99.-). In the next step, 3-hydroxybutyryl-CoA, is rearranged to form 2-HIBCoA by 3-hydroxybutyryl-CoA mutase. This enzyme is a novel ICM-like methylmutase recently discovered and characterized in *Methylibium petroleiphilum* (Ratnatilleke et al., *J. Biol. Chem.* 274:31679-31685 (1999); Rohwerder et al., *Appl. Environ. Microbiol.* 72:4128-4135 (2006)). This enzyme, encoded by Mpe_B0541 in *Methylibium petroleiphilum* PM1, has high sequence homology to the large subunit of methylmalonyl-CoA mutase in other organisms including Rsph17029_3657 in *Rhodobacter sphaeroides* and Xaut_5021 in *Xanthobacter autotrophicus*. As discussed in Example V (step 1), changes to a single amino acid near the active site alters the substrate specificity of the enzyme (Ratnatilleke et al., supra, 1999; Rohwerder et al., supra, 2006), so alternate gene candidates for this enzyme can be engineered at this site to achieve the appropriate reactivity.

| Gene name | GenBankID | Organism |
| --- | --- | --- |
| Mpe_B0541 | YP_001023546.1 | *Methylibium petroleiphilum* PM1 |
| Rsph17029_3657 | YP_001045519.1 | *Rhodobacter sphaeroides* ATCC 17029 |
| Xaut_5021 | YP_001409455.1 | *Xanthobacter autotrophicus* Py2 |

Referring to FIG. 12, step 4 involves 2-hydroxyisobutyryl-CoA dehydratase. The dehydration of 2-hydroxyacyl-CoA can be catalyzed by a special class of oxygen-sensitive enzymes that operate via a radical-mechanism (Buckel and Golding, *Annu. Rev. Microbiol.* 60:27-49 (2006); Buckel et al., *Curr. Opin. Chem. Biol.* 8:462-467 (2004); Buckel et al., *Biol. Chem.* 386:951-959 (2005); Kim et al., *FEBS J.* 272:550-561 (2005); Kim et al., *FEMS Microbiol. Rev.* 28:455-468 (2004); Zhang et al., *Microbiology* 145 (Pt 9):2323-2334 (1999)). One example of such an enzyme is the lactyl-CoA dehydratase from *Clostridium propionicum*, which catalyzes the dehydration of lactoyl-CoA to form acryl-CoA (Kuchta and Abeles, *J. Biol. Chem.* 260:13181-13189 (1985); Hofmeister and Buckel, *Eur. J. Biochem.* 206:547-552 (1992)). An additional example is 2-hydroxyglutaryl-CoA dehydratase encoded by hgdABC from *Acidaminococcus fermentans* (Mueller and Buckel, *Eur. J. Biochem.* 230:698-704 (1995); Schweiger et al., *Eur. J. Biochem.* 169:441-448 (1987)). Yet another example is the 2-hydroxyisocaproyl-CoA dehydratase from *Clostridium difficile* catalyzed by hadBC and activated by hadI (Darley et al., *FEBS J.* 272:550-61 (2005)). The corresponding sequences for *A. fermentans* and *C. difficile* can be found using the following GenBankIDs, while the sequences for *C. propionicum* are not yet listed in publicly available databases.

| Gene name | GenBankID | Organism |
| --- | --- | --- |
| hgdA | P11569 | *Acidaminococcus fermentans* |
| hgdB | P11570 | *Acidaminococcus fermentans* |
| hgdC | P11568 | *Acidaminococcus fermentans* |
| hadB | YP_001086863 | *Clostridium difficile* |
| hadC | YP_001086864 | *Clostridium difficile* |
| hadI | YP_001086862 | *Clostridium difficile* |

Referring to FIG. 12, steps 5 or 6 involve a transferase (EC 2.8.3.-), hydrolase (EC 3.1.2.-), or synthetase (EC 6.2.1.-) with activity on a methacrylic acid or 2-hydroxyisobutyric acid, respectively. Direct conversion of methacrylyl-CoA to MAA or 2-hydroxyisobutyryl-CoA to 2-hydrioxyisobutyrate can be accomplished by a CoA transferase, synthetase or hydrolase. As discussed in Example V, pathway energetics are most favorable if a CoA transferase or a CoA synthetase is employed to accomplish this transformation. In the transferase family, the enzyme acyl-CoA:acetate-CoA transferase, also known as acetate-CoA transferase, is a suitable candidate to catalyze the desired 2-hydroxyisobutyryl-CoA or methacryl-CoA transferase activity due to its broad substrate specificity that includes branched acyl-CoA substrates (Matthies and Schink, *Appl. Environ. Microbiol.* 58:1435-1439 (1992); Vanderwinkel et al., *Biochem. Biophys. Res. Commun.* 33:902-908 (1968)). ADP-forming acetyl-CoA synthetase (ACD) is a promising enzyme in the CoA synthetase family operating on structurally similar branched chain compounds (Brasen and Schonheit, *Arch. Microbiol.* 182:277-287 (2004); Musfeldt and Schonheit, *J. Bacteriol.* 184:636-644 (2002)). In the CoA-hydrolase family, the enzyme 3-hydroxyisobutyryl-CoA hydrolase has been shown to operate on a variety of branched chain acyl-CoA substrates including 3-hydroxyisobutyryl-CoA, methylmalonyl-CoA, and 3-hydroxy-2-methylbutanoyl-CoA (Hawes et al., *Methods Enzymol.* 324:218-228 (2000); Hawes et al., *J. Biol. Chem.* 271:26430-26434 (1996); Shimomura et al., *J. Biol. Chem.* 269:14248-14253 (1994)). Additional exemplary gene candidates for CoA transferases, synthetases, and hydrolases are discussed in Example V (step 2 and 5).

Referring to FIG. 12, an alternative step 5 involves indirect conversion to MAA. As an alternative to direct conversion of MAA-CoA to MAA, an alternate strategy for converting methacrylyl-CoA into MAA entails a multi-step process in which MAA-CoA is converted to MAA via 3-hydroxyisobutyrate. By this process, MAA-CoA is first converted to 3-hydroxyisobutyryl-CoA, which can subsequently be converted to MAA as described in Example V.

The first step of this indirect route entails the conversion of MAA-CoA to 3-hydroxyisobutyryl-CoA (3HIB-CoA) by enoyl-CoA hydratase (EC 4.2.1.17 and 4.2.1.74). In *E. coli*, the gene products of fadA and fadB encode a multienzyme complex involved in fatty acid oxidation that exhibits enoyl-CoA hydratase activity (Nakahigashi and Inokuchi, *Nucleic Acids Research* 18:4937 (1990); Yang, *J. Bacteriol.* 173: 7405-7406 (1991); Yang et al., *J. Biol. Chem.* 265:10424-10429 (1990); Yang et al., *Biochemistry* 30:6788-6795 (1991)). Knocking out a negative regulator encoded by fadR can be utilized to activate the fadB gene product (Sato et al., *J. Biosci. Bioengineer.* 103:38-44 (2007)). The fadI and fadJ genes encode similar functions and are naturally expressed under anaerobic conditions (Campbell et al., *Mol. Microbiol.* 47:793-805 (2003)).

| Gene name | GenBankID | Organism |
| --- | --- | --- |
| fadA | YP_026272.1 | *Escherichia coli* |
| fadB | NP_418288.1 | *Escherichia coli* |
| fadI | NP_416844.1 | *Escherichia coli* |
| fadJ | NP_416843.1 | *Escherichia coli* |
| fadR | NP_415705.1 | *Escherichia coli* |

Additional native gene candidates encoding an enoyl-CoA hydratase include maoC (Park and Lee, *J. Bacteriol.* 185: 5391-5397 (2003)), paaF (Ismail et al., *Eur. J. Biochem.* 270: 3047-3054 (2003); Park and Lee, *Appl. Biochem. Biotechnol.* 113-116:335-346 (2004); Park and Yup, *Biotechnol. Bioeng.* 86:681-686. (2004)), and paaG (Ismail et al., *Eur. J. Biochem.* 270:3047-3054 (2003); Park and Lee, *Appl. Biochem. Biotechnol.* 113-116:335-346 (2004); Park and Yup, *Biotechnol. Bioeng.* 86:681-686 (2004)). Non-native candidates include paaA, paaB, and paaN from *P. putida* (Olivera et al., *Proc. Natl. Acad. Sci. USA* 95:6419-6424 (1998)) and *P. fluorescens* (Di Gennaro et al., *Arch. Microbiol.* 188:117-125 (2007)). The gene product of crt from *C. acetobutylicum* is another candidate (Atsumi et al., *Metab. Eng.* epub Sep. 14, 2007; Boynton et al., *J. Bacteriol.* 178:3015-3024 (1996)).

| Gene name | GenBankID | Organism |
| --- | --- | --- |
| maoC | NP_415905.1 | *Escherichia coli* |
| paaF | NP_415911.1 | *Escherichia coli* |
| paaG | NP_415912.1 | *Escherichia coli* |
| paaA | NP_745427.1 | *Pseudomonas putida* |
| paaA | ABF82233.1 | *Pseudomonas fluorescens* |
| paaB | NP_745426.1 | *Pseudomonas putida* |
| paaB | ABF82234.1 | *Pseudomonas fluorescens* |
| paaN | NP_745413.1 | *Pseudomonas putida* |
| paaN | ABF82246.1 | *Pseudomonas fluorescens* |
| crt | NP_349318.1 | *Clostridium acetobutylicum* |

This example describes a biosynthetic pathway for production of 2-hydroxyisobutyrate or MAA from acetyl-CoA.

Example XII

Preparation of an MAA Producing Microbial Organism Having a Pathway for Converting Acetyl-CoA to MAA This example describes the generation of a microbial organism capable of producing MAA from acetyl-CoA.

*Escherichia coli* is used as a target organism to engineer the MAA pathway shown in FIG. 12. *E. coli* provides a good host for generating a non-naturally occurring microorganism capable of producing MAA. *E. coli* is amenable to genetic manipulation and is known to be capable of producing various products, like ethanol, acetic acid, formic acid, lactic acid, and succinic acid, effectively under anaerobic or microaerobic conditions.

To generate an *E. coli* strain engineered to produce MAA, nucleic acids encoding the enzymes utilized in the pathway are expressed in *E. coli* using well known molecular biology techniques (see, for example, Sambrook, supra, 2001; Ausubel supra, 1999). In particular, the atoB (P76461.1), hbd (P52041.2), and Mpe_B0541 (YP_001023546.1) genes encoding the acetoacetyl-CoA thiolase, acetoacetyl-CoA reductase, and 3-hydroxybutyryl-CoA mutase activities, respectively, are cloned into the pZE13 vector (Expressys, Ruelzheim, Germany) under the PA1/lacO promoter. In addition, the hgdA (P11569), hgdB (P11570), hgdC (P11568), and hibch (Q5XIE6.2) genes encoding 2-hydroxyisobutyryl-CoA dehydratase and methacrylyl-CoA hydrolase activities are cloned into the pZA33 vector (Expressys, Ruelzheim, Germany) under the PA1/lacO promoter. The two sets of plasmids are transformed into *E. coli* strain MG1655 to express the proteins and enzymes required for MAA synthesis via the acetyl-CoA pathway.

The resulting genetically engineered organism is cultured in glucose-containing medium following procedures well known in the art (see, for example, Sambrook et al., supra, 2001). Cobalamin is also supplied to the medium to ensure activity of the mutase enzyme unless the host strain of *E. coli* is engineered to synthesize cobalamin de novo (see, for example, Raux et al., *J. Bacteriol.* 178:753-767 (1996)). The expression of the MAA synthesis genes is corroborated using methods well known in the art for determining polypeptide expression or enzymatic activity, including for example, Northern blots, PCR amplification of mRNA, immunoblotting, and the like. Enzymatic activities of the expressed enzymes are confirmed using assays specific for the individual activities. The ability of the engineered *E. coli* strain to produce MAA is confirmed using HPLC, gas chromatography-mass spectrometry (GCMS) and/or liquid chromatography-mass spectrometry (LCMS).

Microbial strains engineered to have a functional MAA synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of MAA. One modeling method is the bilevel optimization approach, OptKnock (Burgard et al., *Biotechnol. Bioengineer.* 84:647-657 (2003)), which is applied to select gene knockouts that collectively result in better production of MAA. Adaptive evolution also can be used to generate better producers of, for example, the acetyl-CoA intermediate of the MAA product. Adaptive evolution is performed to improve both growth and production characteristics (Fong and Palsson, *Nat. Genet.* 36:1056-1058 (2004); Alper et al., *Science* 314:1565-1568 (2006)). Based on the results, subsequent rounds of modeling, genetic engineering and adaptive evolution can be applied to the MAA producer to further increase production.

For large-scale production of MAA, the above organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing the culture vessel, for example, flasks can be sealed with a septum and crimp-cap. Microaerobic conditions also can be utilized by providing a small hole in the septum for limited aeration. The pH of the medium is maintained at a pH of around 7 by addition of an acid, such as $H_2SO_4$. The growth rate is determined by measuring optical density using a spectrophotometer (600 nm) and the glucose uptake rate by monitoring carbon source depletion over time. Byproducts such as undesirable alcohols, organic acids, and residual glucose can be quantified by HPLC (Shimadzu, Columbia Md.), for example, using an Aminex® series of HPLC columns (for example, HPX-87 series) (BioRad, Hercules Calif.), using a refractive index detector for glucose and alcohols, and a UV detector for organic acids (Lin et al., *Biotechnol. Bioeng.* 775-779 (2005)).

This example describes the preparation of a microbial organism that can produce MAA from acetyl-CoA.

Example XIII

Pathway for Conversion of Acetyl-CoA to MAA Via Crotonoyl-CoA

This example describes an exemplary MAA synthetic pathway from acetyl-CoA via crotonoyl-CoA.

Another route for converting acetyl-CoA to MAA in a minimum of seven enzymatic steps is described (see FIG. 13). The yields of this pathway under aerobic and anaerobic conditions are similar to the pathway described in Example XI.

The first two steps of the pathway are identical to steps 1 and 2 in the pathway described in Example XI. In the third step, 3-HBCoA is dehydrated to form crotonyl-CoA by a crotonase (EC#: 4.2.1.55). The double bond in crotonyl-CoA is reduced by butyryl-CoA dehydrogenase (EC#: 1.3.99.2). Both of these enzymes, just like the acetoacetyl-CoA reductase, are a part of the acetyl-CoA fermentation pathway to butyrate in Clostridia species (Jones and Woods, *Microbiol. Rev.* 50:484-524 (1986)). In the subsequent step, butyryl-CoA is converted into isobutyryl-CoA by isobutyryl-CoA mutase (5.4.99.12), an enzyme that can reversibly convert butyryl-CoA into isobutyryl-CoA. This enzyme has been cloned and sequenced from *Streptomyces cinnamonensis*, and the recombinant enzyme has been characterized in *E. coli* (Ratnatilleke et al., *J. Biol. Chem.* 274:31679-31685 (1999)). The next step in the pathway entails the conversion of isobutyryl-CoA into methacrylyl-CoA via 2-methyl-acylCoA dehydrogenase (EC #: 1.3.99.12). This transformation towards methacrylyl-CoA has been observed in *Streptomyces* species, and the associated enzyme has been isolated and expressed in *E. coli* (Youngleson et al., *J. Bacteriol.* 171: 6800-6807 (1989)). In the final step, methacrylyl-CoA is converted to MAA by either a single enzyme or a series of enzymes, as described in Example XI (step 5).

This example describes a biosynthetic pathway for production of MAA from acetyl-CoA.

Example XIV

Pathway for Conversion of Acrylyl-CoA to MAA

This example describes an exemplary MAA synthesis pathway from acrylyl-CoA.

High yields of MAA can be obtained through the acrylyl-CoA pathway (see FIG. 14). This pathway requires the activation of lactate to lactoyl-CoA followed by five, or optionally six, more steps for the conversion of this activated CoA molecule into MAA. The MAA yield from glucose using this pathway is 1.28 mol/mol of glucose and oxygen uptake is required for attaining these yields. In the absence of oxygen, the expected yield decreases from 1.28 mol to 1.09 mol/mol glucose consumed. Both the aerobic and anaerobic pathways are energy limited at maximum MAA yield and do not generate any ATP.

MAA biosynthesis through the acrylyl-CoA pathway first requires the conversion of pyruvate into lactate via lactate dehydrogenase (EC 1.1.1.28), an enzyme native to *E. coli* and many other organisms. The three subsequent steps, converting lactate into propionyl-CoA, are catalyzed by enzymes in pyruvate fermentation pathways in several unrelated bacteria such as *Clostridium propionicum* and *Megasphaera elsdenii* (MetaCyc). Lactate-CoA transferase (EC 2.8.3.1), also known as propionate-CoA transferase, converts lactate into lactoyl-CoA and can use both propionate and lactate as substrates. This enzyme has been purified and characterized (Schweiger et al., *Eur. J. Biochem.* 169:441-448 (1987)). Lactoyl-CoA is dehydrated into acrylyl-CoA using lactoyl-CoA dehydratase (EC 4.2.1.54), an enzyme that has been a subject of numerous studies (Hofmeister and Buckel, *Eur. J. Biochem.* 206:547-552. (1992); Kuchta and Abeles, *J. Biol. Chem.* 260:13181-13189 (1985)). Subsequently, acrylyl-CoA is reduced to propionyl-CoA using the acryloyl-CoA reductase (EC 1.3.2.2, formerly 1.3.99.3) (Hetzel et al., *Eur. J Biochem.* 270:902-910 (2003); Kuchta and Abeles, supra, 1985).

Referring to FIG. 14, in step 5, propionyl-CoA is converted into S-methylmalonyl-CoA by propionyl-CoA carboxylase (6.4.1.3). Propionyl-CoA carboxylase has been purified from rat liver (Browner et al., *J. Biol. Chem.* 264:12680-12685 (1989); Kraus et al., *J. Biol. Chem.* 258:7245-7248 (1983)) and has been isolated and characterized from human liver as well (Kalousek et al., *J. Biol. Chem.* 255:60-65 (1980)). Carboxylation of propionyl-CoA into succinyl-CoA via this enzyme has been identified as one of the mechanisms of propionate metabolism in *E. coli* (Evans et al., *Biochem. J.* 291 (Pt 3):927-932 (1993)), but very little is known about the genetics of the pathway.

The final steps of the pathway entail conversion of methylmalonyl-CoA into MAA (lumped reaction in FIG. 14). Enzymes catalyzing these reactions are described in Example I.

This example describes a biosynthetic pathway for production of MAA from pyruvate.

Example XV

Pathway for Conversion of 2-Ketoisovalerate to MAA

This example describes an exemplary MAA synthetic pathway from 2-ketoisovalerate.

In this pathway, MMA biosynthesis occurs through 2-ketoisovalerate, a precursor for valine biosynthesis (see FIG. 15). Specifically, 2-ketoisovalerate can be formed from pyruvate following the action of three enzymes, acetolactate synthase, acetohydroxy acid isomeroreductase, and dihydroxyacid dehydratase. The conversion of 2-ketoisovalerate to MAA requires four enzymatic steps and leads to MAA yields of 1 mol/mol glucose under aerobic conditions and to yields of 0.4 mol/mol glucose under anaerobic conditions (Table 5). The pathway is not redox-balanced, and the secretion of fermentation products such as ethanol and formate will occur under anaerobic conditions. In spite of the relatively low yields of MAA through this pathway in the absence of oxygen, the energetics are very favorable and up to 2.2 moles of ATP are generated per mole of glucose consumed.

TABLE 5

Product and ATP yields for 2-ketoisovalerate pathway.

| | MAA biosynthetic pathway via 2-Ketoisovalerate | |
|---|---|---|
| | Anaerobic | Aerobic |
| MAA Yield | 0.4 | 1.0 |
| Max ATP yield @ max MAA yield | 2.2 | 7.0 |

The pathway exploits multiple steps of the valine degradation route described in several organisms, including *Bacillus subtilis, Arabidopsis thaliana*, and several species of *Pseuodomonas* but not known to be present in *E. coli* or in *S. cerevisiae*. In the first step of the valine degradation pathway, valine is converted into 2-ketoisovalerate by branched-chain amino acid aminotransferase (EC 2.6.1.24), an enzyme also native to *E. coli* (Matthies and Schink, *Appl. Environ. Microbiol.* 58:1435-1439 (1992); Rudman and Meister, *J. Biol. Chem.* 200:591-604 (1953)). The subsequent conversion of 2-ketoisovalerate into isobutyryl-CoA, catalyzed by a branched-chain keto-acid dehydrogenase complex (EC 1.2.1.25), is the committing step for MAA biosynthesis via this route. Next, isobutyryl-CoA is converted to methacrylyl-CoA via isobutyryl-CoA dehydrogenase (EC 1.3.99.12). Details for this step are described in Example XIII. The final step, conversion of MAA-CoA to MAA, is described in Example I.

This example describes a biosynthetic pathway for production of MMA from 2-ketoisovalerate.

Example XVI

Preparation of a 3-Hydroxyisobutyric Acid Producing Microbial Organism Having a Pathway for Converting 4-Hydroxybutyryl-CoA to 3-Hydroxyisobutyric Acid This example describes the generation of a microbial organism capable of producing 3-hydroxyisobutyric acid from 4-hydroxybutyryl-CoA.

*Escherichia coli* is used as a target organism to engineer the 3-hydroxyisobutyric acid pathway shown in FIG. 6. *E. coli* provides a good host for generating a non-naturally occurring microorganism capable of producing 3-hydroxyisobutyric acid. *E. coli* is amenable to genetic manipulation and is known to be capable of producing various products, like ethanol, acetic acid, formic acid, lactic acid, and succinic acid, effectively under anaerobic or microaerobic conditions.

To generate an *E. coli* strain engineered to produce 3-hydroxyisobutyric acid, nucleic acids encoding the enzymes utilized in the pathway are expressed in *E. coli* using well known molecular biology techniques (see, for example, Sambrook, supra, 2001; Ausubel supra, 1999). In particular, the sucD (YP_001396394), 4hbd (YP_001396393), buk1 (Q45829), and ptb (NP_349676) genes encoding succinic semialdehyde dehydrogenase (CoA-dependent), 4-hydroxybutyrate dehydrogenase, 4-hydroxybutyrate kinase, and phosphotransbutyrylase activities, respectively, are cloned into the pZE13 vector (Expressys, Ruelzheim, Germany) under the PA1/lacO promoter. This construct allows the production of 4HB-CoA from succinyl-CoA as described in Burk et al. (U.S. publication 2009/0075351). In addition, the icmA (CAB40912.1) and hibch (Q5XIE6.2) genes encoding 4-hydroxybutyryl-CoA mutase and 3-hydroxyisobutyryl-CoA hydrolase, respectively, are cloned into the pZA33 vector (Expressys, Ruelzheim, Germany) under the PA1/lacO promoter. The two sets of plasmids are transformed into *E. coli* strain MG1655 to express the proteins and enzymes required for 3-hydroxyisobutyric acid synthesis via the 4-hydroxybutyryl-CoA pathway.

The resulting genetically engineered organism is cultured in glucose-containing medium following procedures well known in the art (see, for example, Sambrook et al., supra, 2001). Cobalamin is also supplied to the medium to ensure activity of the mutase enzyme unless the host strain of *E. coli* is engineered to synthesize cobalamin de novo (see, for example, Raux et al., *J. Bacteriol.* 178:753-767 (1996)). The expression of the 3-hydroxyisobutyric acid synthesis genes is corroborated using methods well known in the art for determining polypeptide expression or enzymatic activity, including, for example, Northern blots, PCR amplification of mRNA, immunoblotting, and the like. Enzymatic activities of the expressed enzymes are confirmed using assays specific for the individual activities. The ability of the engineered *E. coli* strain to produce 3-hydroxyisobutyric acid is confirmed using HPLC, gas chromatography-mass spectrometry (GCMS) and/or liquid chromatography-mass spectrometry (LCMS).

Microbial strains engineered to have a functional 3-hydroxyisobutyric acid synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of 3-hydroxyisobutyric acid. One modeling method is the bilevel optimization approach, OptKnock (Burgard et al., Biotechnol. Bioengineer. 84:647-657 (2003)), which is applied to select gene knockouts that collectively result in better production of 3-hydroxyisobutyric acid. Adaptive evolution also can be used to generate better producers of, for example, the succinyl-CoA or 4-hydroxybutyryl-CoA intermediates of the 3-hydroxyisobutyric acid product. Adaptive evolution is performed to improve both growth and production characteristics (Fong and Palsson, Nat. Genet. 36:1056-1058 (2004); Alper et al., Science 314:1565-1568 (2006)). Based on the results, subsequent rounds of modeling, genetic engineering and adaptive evolution can be applied to the 3-hydroxyisobutyric acid producer to further increase production.

For large-scale production of 3-hydroxyisobutyric acid, the above organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing the culture vessel, for example, flasks can be sealed with a septum and crimp-cap. Microaerobic conditions also can be utilized by providing a small hole in the septum for limited aeration. The pH of the medium is maintained at a pH of around 7 by addition of an acid, such as $H_2SO_4$. The growth rate is determined by measuring optical density using a spectrophotometer (600 nm) and the glucose uptake rate by monitoring carbon source depletion over time. Byproducts such as undesirable alcohols, organic acids, and residual glucose can be quantified by HPLC (Shimadzu, Columbia Md.), for example, using an Aminex® series of HPLC columns (for example, HPX-87 series) (BioRad, Hercules Calif.), using a refractive index detector for glucose and alcohols, and a UV detector for organic acids (Lin et al., Biotechnol. Bioeng. 775-779 (2005)).

This example describes the preparation of a microbial organism that can produce 3-hydroxyisobutyric acid from 4-hydroxybutyryl-CoA.

Example XVII

Preparation of 2-Hydroxyisobutyric Acid Producing Microbial Organism Having a Pathway for Converting Acetyl-CoA to 2-Hydroxyisobutyric Acid This example describes the generation of a microbial organism capable of producing 2-hydroxyisobutyric acid from acetyl-CoA.

Escherichia coli is used as a target organism to engineer the 2-hydroxyisobutyric acid pathway shown in FIG. 12. E. coli provides a good host for generating a non-naturally occurring microorganism capable of producing 2-hydroxyisobutyric acid. E. coli is amenable to genetic manipulation and is known to be capable of producing various products, like ethanol, acetic acid, formic acid, lactic acid, and succinic acid, effectively under anaerobic or microaerobic conditions.

To generate an E. coli strain engineered to produce 2-hydroxyisobutyric acid, nucleic acids encoding the enzymes utilized in the pathway are expressed in E. coli using well known molecular biology techniques (see, for example, Sambrook, supra, 2001; Ausubel, supra, 1999). In particular, the atoB (P76461.1), hbd (P52041.2), and Mpe_B0541 (YP_001023546.1) genes encoding the acetoacetyl-CoA thiolase, acetoacetyl-CoA reductase, and 3-hydroxybutyryl-CoA mutase activities, respectively, are cloned into the pZE13 vector (Expressys, Ruelzheim, Germany) under the PA1/lacO promoter. In addition, hibch (Q5XIE6.2) encoding 2-hydroxyisobutyryl-CoA hydrolase activity is cloned into the pZA33 vector (Expressys, Ruelzheim, Germany) under the PA1/lacO promoter. The two sets of plasmids are transformed into E. coli strain MG1655 to express the proteins and enzymes required for 2-hydroxyisobutyric acid synthesis via the acetyl-CoA pathway.

The resulting genetically engineered organism is cultured in glucose-containing medium following procedures well known in the art (see, for example, Sambrook et al., supra, 2001). Cobalamin is also supplied to the medium to ensure activity of the mutase enzyme unless the host strain of E. coli is engineered to synthesize cobalamin de novo (see, for example, Raux et al., J. Bacteriol. 178:753-767 (1996)). The expression of the 2-hydroxyisobutyric acid synthesis genes is corroborated using methods well known in the art for determining polypeptide expression or enzymatic activity, including, for example, Northern blots, PCR amplification of mRNA, immunoblotting, and the like. Enzymatic activities of the expressed enzymes are confirmed using assays specific for the individual activities. The ability of the engineered E. coli strain to produce 2-hydroxyisobutyric acid is confirmed using HPLC, gas chromatography-mass spectrometry (GCMS) and/or liquid chromatography-mass spectrometry (LCMS).

Microbial strains engineered to have a functional 2-hydroxyisobutyric acid synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of 2-hydroxyisobutyric acid. One modeling method is the bilevel optimization approach, OptKnock (Burgard et al., Biotechnol. Bioengineer. 84:647-657 (2003)), which is applied to select gene knockouts that collectively result in better production of 2-hydroxyisobutyric acid. Adaptive evolution also can be used to generate better producers of, for example, the acetyl-CoA intermediate of the 2-hydroxyisobutyric acid product. Adaptive evolution is performed to improve both growth and production characteristics (Fong and Palsson, Nat. Genet. 36:1056-1058 (2004); Alper et al., Science 314:1565-1568 (2006)). Based on the results, subsequent rounds of modeling, genetic engineering and adaptive evolution can be applied to the 2-hydroxyisobutyric acid producer to further increase production.

For large-scale production of 2-hydroxyisobutyric acid, the above organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing the culture vessel, for example, flasks can be sealed with a septum and crimp-cap. Microaerobic conditions also can be utilized by providing a small hole in the septum for limited aeration. The pH of the medium is maintained at a pH of around 7 by addition of an acid, such as $H_2SO_4$. The growth rate is determined by measuring optical density using a spectrophotometer (600 nm) and the glucose uptake rate by monitoring carbon source depletion over time. Byproducts such as undesirable alcohols, organic acids, and residual glucose can be quantified by HPLC (Shimadzu, Columbia Md.), for example, using an Aminex® series of HPLC columns (for example, HPX-87 series) (BioRad, Hercules Calif.), using a refractive index detector for glucose and alcohols, and a UV detector for organic acids (Lin et al., *Biotechnol. Bioeng.* 775-779 (2005)).

This example describes the preparation of a microbial organism that can produce 2-hydroxyisobutyric acid from acetyl-CoA.

Example XVIII

Pathway for Conversion of 4-Hydroxybutyryl-CoA to 2-Hydroxyisobutyrate or MAA Via 2-Hydroxyisobutyryl-CoA This example describes an exemplary 2-hydroxyisobutyrate or MAA synthesis pathway proceeding from 4-hydroxybutyryl-CoA that passes through 2-hydroxyisobutyryl-CoA. The pathway, depicted in FIG. 12, is high-yielding under even under anaerobic conditions with a maximum theoretical yield of 1.33 moles of 2-hydroxybutyrate or MAA per mole of glucose. This is in contrast to the pathways originating from acetyl-CoA described in Example XI, which are limited to a maximum theoretical yield of one mole of product per mole of glucose.

The pathway first entails the dehydration of 4-hydroxybutyryl-CoA to vinylacetyl-CoA which is subsequently isomerized to crotonoyl-CoA. Crotonyl-CoA is hydrated to form 3-hydroxybutyryl-CoA, which is rearranged into 2-hydroxyisobutyryl-CoA. The final step of the 2-hydroxyisobutyrate pathway involves eliminating the CoA functional group from 2-hydroxyisobutyryl-CoA. The final steps in MAA synthesis involve the dehydration of 2-hydroxyisobutyryl-CoA followed by the removal of the CoA functional group from methacrylyl-CoA. Gene candidates for the first three pathway steps, steps 7, 8, and 9 of FIG. 12, are described below. Gene candidates for steps 3, 4, 5, and 6 of FIG. 12 are discussed in example XI.

Referring to FIG. 12, steps 8 and 9 are carried out by 4-hydroxybutyryl-CoA dehydratase enzymes. The enzymes from both *Clostridium aminobutyrium* and *C. kluyveri* catalyze the reversible conversion of 4-hydroxybutyryl-CoA to crotonyl-CoA and also possess an intrinsic vinylacetyl-CoA Δ-isomerase activity (Scherf and Buckel, *Eur. J. Biochem.* 215:421-429 (1993); Scherf et al., *Arch. Microbiol.* 161:239-245 (1994)). Both native enzymes have been purified and characterized, including the N-terminal amino acid sequences (Scherf and Buckel, supra, 1993; Scherf et al., supra, 1994). The abfD genes from *C. aminobutyrium* and *C. kluyveri* match exactly with these N-terminal amino acid sequences, thus are encoding the 4-hydroxybutyryl-CoA dehydratases/vinylacetyl-CoA Δ-isomerase. In addition, abfD from *Porphyromonas gingivalis* ATCC 33277 is another exemplary 4-hydroxybutyryl-CoA dehydratase that can be identified through homology.

| abfD | YP_001396399.1 | *Clostridium kluyveri* DSM 555 |
|---|---|---|
| abfD | P55792 | *Clostridium aminobutyricum* |
| abfD | YP_001928843 | *Porphyromonas gingivalis* ATCC 33277 |

Step 10 of FIG. 12 is carried out by a crotonase enzyme. Such enzymes are required for n-butanol formation in some organisms, particularly Clostridial species, and also comprise one step of the 3-hydroxypropionate/4-hydroxybutyrate cycle in thermoacidophilic Archaea of the genera *Sulfolobus*, *Acidianus*, and *Metallosphaera*. Exemplary genes encoding crotonase enzymes can be found in *C. acetobutylicum* (Boynton, et al., *J. Bacteriol.* 178(11):3015-3024 (1996)), *C. kluyveri* (Hillmer and Gottschalk, *FEBS Lett.* 21(3):351-354 (1972)), and *Metallosphaera sedula* (Berg et al., *Science* 318(5857):1782-1786 (2007)) though the sequence of the latter gene is not known. Enoyl-CoA hydratases, which are involved in fatty acid beta-oxidation and/or the metabolism of various amino acids, can also catalyze the hydration of crotonyl-CoA to form 3-hydroxybutyryl-CoA (Agnihotri and Liu, *Bioorg. Med. Chem.* 11(1):9-20 (2003); Roberts et al., *Arch. Microbiol.* 117(1):99-108 (1978); Conrad et al., *J. Bacteriol.* 118(1); 103-11 (1974)). The enoyl-CoA hydratases, phaA and phaB, of *P. putida* are believed to carry out the hydroxylation of double bonds during phenylacetate catabolism (Olivera et al., *Proc Natl Acad Sci USA* 95(11):6419-6424 (1998)). The paaA and paaB from *P. fluorescens* catalyze analogous transformations (Olivera et al., supra, 1998). Lastly, a number of *Escherichia coli* genes have been shown to demonstrate enoyl-CoA hydratase functionality including maoC (Park and Lee, *J. Bacteriol.* 185(18):5391-5397 (2003)), paaF (Park and Lee, *Biotechnol. Bioeng.* 86(6):681-686 (2004a)); Park and Lee, *Appl. Biochem. Biotechnol.* 113-116:335-346 (2004b)); Ismail et al. *Eur. J. Biochem.* 270(14): 3047-3054 (2003), and paaG (Park and Lee, supra, 2004; Park and Lee, supra, 2004b; Ismail et al., supra, 2003).

| crt | NP_349318.1 | *Clostridium acetobutylicum* |
|---|---|---|
| crt1 | YP_001393856 | *Clostridium kluyveri* DSM 555 |
| paaA | NP_745427.1 | *Pseudomonas putida* |
| paaB | NP_745426.1 | *Pseudomonas putida* |
| phaA | ABF82233.1 | *Pseudomonas fluorescens* |
| phaB | ABF82234.1 | *Pseudomonas fluorescens* |
| maoC | NP_415905.1 | *Escherichia coli* |
| paaF | NP_415911.1 | *Escherichia coli* |
| paaG | NP_415912.1 | *Escherichia coli* |

This example describes a biosynthesis pathway for 2-hydroxyisobutyrate or methacylic acid from 4-hydroxybutyryl-CoA.

Example XIX

Preparation of an MAA Producing Microbial Organism Having a Pathway for Converting 4-Hydroxybutyryl-CoA to MAA Via 2-Hydroxyisobutyryl-CoA This example describes the generation of a microbial organism capable of producing MAA from 4-hydroxybutyryl-CoA via 2-hydroxyisobutyryl-CoA.

*Escherichia coli* is used as a target organism to engineer the MAA pathway shown in FIG. 12 that starts from 4-hydroxybutyryl-CoA. *E. coli* provides a good host for generating a non-naturally occurring microorganism capable of producing MAA. *E. coli* is amenable to genetic manipulation and is known to be capable of producing various products, like ethanol, acetic acid, formic acid, lactic acid, and succinic acid, effectively under anaerobic or microaerobic conditions.

To generate an *E. coli* strain engineered to produce MAA, nucleic acids encoding the enzymes utilized in the pathway are expressed in *E. coli* using well known molecular biology techniques (see, for example, Sambrook, supra, 2001; Ausubel, supra, 1999). First, the sucD (YP_001396394), 4hbd (YP_001396393), buk1 (Q45829), and ptb (NP_349676) genes encoding succinic semialdehyde dehydrogenase (CoA-dependent), 4-hydroxybutyrate dehydrogenase, 4-hydroxybutyrate kinase, and phosphotransbutyrylase activities, respectively, are cloned into the pZE13 vector (Expressys, Ruelzheim, Germany) under the PA1/lacO promoter. This construct allows the production of 4HB-CoA from succinyl-CoA as described in Burk et al. (U.S. publication 2009/0075351). The abfD (YP_001396399.1) and crt1 (YP_001393856) encoding 4-hydroxybutyryl-CoA dehydratase, vinylacetyl-CoA Δ-isomerase, and enoyl-CoA hydratase activities, respectively, are cloned into the pZS23 vector (Expressys, Ruelzheim, Germany) under the PA1/lacO promoter. In addition, the hgdA (P11569), hgdB (P11570), hgdC (P11568), and hibch (Q5XIE6.2) genes encoding 2-hydroxyisobutyryl-CoA dehydratase and methacrylyl-CoA hydrolase activities are cloned into the pZS13 vector (Expressys, Ruelzheim, Germany) under the PA1/lacO promoter. pZS23 is obtained by replacing the ampicillin resistance module of the pZS13 vector (Expressys, Ruelzheim, Germany) with a kanamycin resistance module by well-known molecular biology techniques. The three sets of plasmids are transformed into E. coli strain MG1655 to express the proteins and enzymes required for MAA synthesis from 4-hydroxybutyryl-CoA via 2-hydroxyisobutyryl-CoA.

The resulting genetically engineered organism is cultured in glucose-containing medium following procedures well known in the art (see, for example, Sambrook et al., supra, 2001). Cobalamin is also supplied to the medium to ensure activity of the mutase enzyme unless the host strain of E. coli is engineered to synthesize cobalamin de novo (see, for example, Raux et al., J. Bacteriol. 178:753-767 (1996)). The expression of the MAA synthesis genes is corroborated using methods well known in the art for determining polypeptide expression or enzymatic activity, including for example, Northern blots, PCR amplification of mRNA, immunoblotting, and the like. Enzymatic activities of the expressed enzymes are confirmed using assays specific for the individual activities. The ability of the engineered E. coli strain to produce MAA is confirmed using HPLC, gas chromatography-mass spectrometry (GCMS) and/or liquid chromatography-mass spectrometry (LCMS).

Microbial strains engineered to have a functional MAA synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of MAA. One modeling method is the bilevel optimization approach, OptKnock (Burgard et al., Biotechnol. Bioengineer. 84:647-657 (2003)), which is applied to select gene knockouts that collectively result in better production of MAA. Adaptive evolution also can be used to generate better producers of, for example, the 4-hydroxybutyryl-CoA intermediate of the MAA product. Adaptive evolution is performed to improve both growth and production characteristics (Fong and Palsson, Nat. Genet. 36:1056-1058 (2004); Alper et al., Science 314:1565-1568 (2006)). Based on the results, subsequent rounds of modeling, genetic engineering and adaptive evolution can be applied to the MAA producer to further increase production.

For large-scale production of MAA, the above organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing the culture vessel, for example, flasks can be sealed with a septum and crimp-cap. Microaerobic conditions also can be utilized by providing a small hole in the septum for limited aeration. The pH of the medium is maintained at a pH of around 7 by addition of an acid, such as $H_2SO_4$. The growth rate is determined by measuring optical density using a spectrophotometer (600 nm) and the glucose uptake rate by monitoring carbon source depletion over time. Byproducts such as undesirable alcohols, organic acids, and residual glucose can be quantified by HPLC (Shimadzu, Columbia Md.), for example, using an Aminex® series of HPLC columns (for example, HPX-87 series) (BioRad, Hercules Calif.), using a refractive index detector for glucose and alcohols, and a UV detector for organic acids (Lin et al., Biotechnol. Bioeng. 775-779 (2005)).

This example describes the preparation of a microbial organism that can produce MAA from 4-hydroxybutyrl-CoA via 2-hydroxyisobutyryl-CoA.

Example XX

Preparation of a 2-Hydroxyisobutyrate Producing Microbial Organism Having a Pathway for Converting 4-Hydroxybutyryl-CoA to 2-Hydroxyisobutyrate Via 2-Hydroxyisobutyryl-CoA This example describes the generation of a microbial organism capable of producing 2-hydroxyisobutyrate from 4-hydroxybutyryl-CoA via 2-hydroxyisobutyryl-CoA.

Escherichia coli is used as a target organism to engineer the 2-hydroxyisobutyrate pathway shown in FIG. 12 that starts from 4-hydroxybutyryl-CoA. E. coli provides a good host for generating a non-naturally occurring microorganism capable of producing 2-hydroxyisobutyrate. E. coli is amenable to genetic manipulation and is known to be capable of producing various products, like ethanol, acetic acid, formic acid, lactic acid, and succinic acid, effectively under anaerobic or microaerobic conditions.

To generate an E. coli strain engineered to produce 2-hydroxyisobutyrate, nucleic acids encoding the enzymes utilized in the pathway are expressed in E. coli using well known molecular biology techniques (see, for example, Sambrook, supra, 2001; Ausubel supra, 1999). First, the sucD (YP_001396394), 4hbd (YP_001396393), buk1 (Q45829), and ptb (NP_349676) genes encoding succinic semialdehyde dehydrogenase (CoA-dependent), 4-hydroxybutyrate dehydrogenase, 4-hydroxybutyrate kinase, and phosphotransbutyrylase activities, respectively, are cloned into the pZE13 vector (Expressys, Ruelzheim, Germany) under the PA1/lacO promoter. This construct allows the production of 4HB-CoA from succinyl-CoA as described in Burk et al. (U.S. publication 2009/0075351). The abfD (YP_001396399.1), crt1 (YP_001393856), and hibch (Q5XIE6.2) genes encoding 4-hydroxybutyryl-CoA dehydratase, vinylacetyl-CoA Δ-isomerase, enoyl-CoA hydratase, and 2-hydroxyisobutyryl-CoA hydrolase activities, respectively, are cloned into the pZS23 vector (Expressys, Ruelzheim, Germany) under the PA1/lacO promoter. The two sets of plasmids are transformed into E. coli strain MG1655 to express the proteins and enzymes required for 2-hydroxyisobutyrate synthesis from 4-hydroxybutyryl-CoA via 2-hydroxyisobutyryl-CoA.

The resulting genetically engineered organism is cultured in glucose-containing medium following procedures well known in the art (see, for example, Sambrook et al., supra, 2001). Cobalamin is also supplied to the medium to ensure activity of the mutase enzyme unless the host strain of E. coli is engineered to synthesize cobalamin de novo (see, for example, Raux et al., J. Bacteriol. 178:753-767 (1996)). The expression of the 2-hydroxyisobutyrate synthesis genes is corroborated using methods well known in the art for determining polypeptide expression or enzymatic activity, including for example, Northern blots, PCR amplification of mRNA, immunoblotting, and the like. Enzymatic activities of the expressed enzymes are confirmed using assays specific for the individual activities. The ability of the engineered E. coli strain to produce 2-hydroxyisobutyrate is confirmed using HPLC, gas chromatography-mass spectrometry (GCMS) and/or liquid chromatography-mass spectrometry (LCMS).

Microbial strains engineered to have a functional 2-hydroxyisobutyrate synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of 2-hydroxyisobutyrate. One modeling method is the bilevel optimization approach, OptKnock (Burgard et al., Biotechnol. Bioengineer. 84:647-657 (2003)), which is applied to select gene knockouts that collectively result in better production of 2-hydroxyisobutyrate. Adaptive evolution also can be used to generate better producers of, for example, the 4-hydroxybutyryl-CoA intermediate of the 2-hydroxyisobutyrate product. Adaptive evolution is performed to improve both growth and production characteristics (Fong and Palsson, Nat. Genet. 36:1056-1058 (2004); Alper et al., Science 314:1565-1568 (2006)). Based on the results, subsequent rounds of modeling, genetic engineering and adaptive evolution can be applied to the 2-hydroxyisobutyrate producer to further increase production.

For large-scale production of 2-hydroxyisobutyrate, the above organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing the culture vessel, for example, flasks can be sealed with a septum and crimp-cap. Microaerobic conditions also can be utilized by providing a small hole in the septum for limited aeration. The pH of the medium is maintained at a pH of around 7 by addition of an acid, such as $H_2SO_4$. The growth rate is determined by measuring optical density using a spectrophotometer (600 nm) and the glucose uptake rate by monitoring carbon source depletion over time. Byproducts such as undesirable alcohols, organic acids, and residual glucose can be quantified by HPLC (Shimadzu, Columbia Md.), for example, using an Aminex® series of HPLC columns (for example, HPX-87 series) (BioRad, Hercules Calif.), using a refractive index detector for glucose and alcohols, and a UV detector for organic acids (Lin et al., Biotechnol. Bioeng. 775-779 (2005)).

This example describes the preparation of a microbial organism that can produce 2-hydroxyisobutyrate from 4-hydroxybutyrl-CoA via 2-hydroxyisobutyryl-CoA.

Example XXI

Design of Gene Knockout Strains for Increased Production of Methacrylic Acid or 3-Hydroxyisobutyric Acid This example describes the design of strains with gene knockouts for increased production of methacrylic acid or 3-hydroxyisobutyric acid.

OptKnock is a bilevel computational framework formulated with the overall objective of developing genetically stable overproducing microorganisms. Specifically, the framework examines the complete network of a microorganism in order to suggest genetic manipulations that force the desired biochemical to become an obligatory byproduct of cell growth. By coupling biochemical production with cell growth through strategically placed gene deletions, the growth selection pressures imposed on the engineered strains after long periods of time in a bioreactor lead to improvements in performance as a result of the compulsory growth-coupled biochemical production. Lastly, there is negligible possibility of the designed strains reverting to their wild-type states because the genes selected by OptKnock are to be completely removed from the genome by appropriate genetic manipulations using a complete deletion rather than an insertion.

The concept of growth-coupled biochemical production can be visualized in the context of the biochemical production envelopes of a typical metabolic network calculated using an in silico model. These limits are obtained by fixing the uptake rate(s) of the limiting substrate(s) to their experimentally measured value(s) and calculating the maximum and minimum rates of biochemical production at each attainable level of growth. Although exceptions exist, typically the production of a desired biochemical is in direct competition with biomass formation for intracellular resources (see FIG. 16). Thus, enhanced rates of biochemical production will necessarily result in sub-maximal growth rates. The knockouts suggested by OptKnock are designed to restrict the allowable solution boundaries, forcing a change in metabolic behavior from the wild-type strain. Although the actual solution boundaries for a given strain will expand or contract as the substrate uptake rate(s) increase or decrease, each experimental point should lie within its calculated solution boundary. Plots such as these allow the visualization of how close strains are to their performance limits or, in other words, how much room is available for improvement. The OptKnock framework has already been able to identify promising gene deletion strategies for biochemical overproduction (Burgard et al., Biotechnol. Bioeng. 84(6):647-657 (2003); Pharkya et al., Biotechnol. Bioeng. 84(7):887-899 (2003); Pharkya et al., Genome Res. 14(11):2367-2376 (2004)) and establishes a systematic framework that will naturally encompass future improvements in metabolic and regulatory modeling frameworks.

Described in more detail in Examples XXII and XXIII are sets of enzyme activities that should be absent, attenuated, or eliminated for creating host organisms that achieve growth-coupled MAA or 3-hydroxyisobutyric acid production upon the addition of the MAA or 3-hydroxyisobutyric acid biosynthetic pathways. To enumerate all potential strategies, an optimization technique, termed integer cuts, has been implemented which entails iteratively solving the OptKnock problem with the incorporation of an additional constraint referred to as an integer cut at each iteration.

The OptKnock algorithm identified growth-coupled strain designs for overproduction of MAA, or if desired the precursor 3-hydroxyisobutyrate (3-HIB), based on a stoichiometric model of *Escherichia coli* metabolism. Assumptions include (i) a glucose uptake rate of 10 mmol/gdw/hr; (ii) anaerobic or microaerobic conditions; and (iii) a minimum non-growth associated maintenance requirement of 4 mmol/gDCW/hr. Although the growth substrate was assumed to be glucose, it is understood that the strategies are applicable to any substrate including glucose, sucrose, xylose, arabinose, or glycerol. The complete set of growth-coupled production designs for the succinyl-CoA:MAA pathway (FIG. 2) and the 4-HB-CoA:MAA pathway (FIG. 6) are listed in Tables 10 and 11, respectively. Tables 10 and 11 show the reaction combinations targeted for removal by OptKnock to enhance production of MAA or 3-hydroxyisobutyric acid via a succinyl-CoA (Table 10) or 4-hydroxybutyryl-CoA (Table 11) intermediate. Attenuation of at least one, or any combination of the reactions, including up to most or all of the reactions, can be utilized to achieve a desired effect. The enzyme names, their abbreviations, and the corresponding reaction stoichiometries are listed in Table 12. Finally, metabolite names corresponding to the abbreviations in the reaction equations are listed in Table 13.

Although the designs were identified using a metabolic model of *E. coli* metabolism, and the gene names listed in Table 12 are specific to *E. coli*, the method of choosing the metabolic engineering strategies and also the designs themselves are applicable to any MAA or 3-hydroxyisobutyrate producing organism. Thus the designs are essentially lists of enzymatic transformations whose activity must be either eliminated, attenuated, or initially absent from a microorganism to enable growth coupled production.

The key criterion for prioritizing the final selection of designs was the growth-coupled yield of 3-hydroxyisobutyrate and/or methacrylic acid. To examine this, production cones were constructed for each strategy by first maximizing and subsequently minimizing product yields at different rates of biomass formation, as described above. Convergence of the rightmost boundary of all possible phenotypes of the mutant network at a single point implies that there is a unique optimum yield of the product at the maximum biomass formation rate. In other cases, the rightmost boundary of the feasible phenotypes is a vertical line, indicating that at the point of maximum biomass, the network can make any amount of MAA in the calculated range, including the lowest amount at the bottommost point of the vertical line. Such designs were given a lower priority. Short lists of the highest priority OptKnock designs for each pathway are provided in Tables 6 and 8 in Examples XXII and XXIII, respectively.

Although strain designs in the following Examples are characterized by their capacity to produce MAA coupled to biomass formation, it is understood that these strains can also be utilized to overproduce the MAA-pathway intermediate 3-hydroxyisobutyrate. In both pathways, the final enzymatic step for forming MAA entails the dehydration of 3-hydroxyisobutyrate by 3-hydroxyisobutyrate dehydratase (step 5 in FIG. 2, step 3 in FIG. 6). Since this reaction does not consume or produce reducing equivalents, protons, or energy it will not alter the energetics of the strain designs. Thus, in a strain lacking 3-hydroxyisobutyrate dehydratase activity, all designs described herein allow growth-coupled production of 3-HIB.

This example describes the design of gene knockouts for generating strains for growth coupled production of MAA and/or 3-HIB.

Example XXII

Knockout Designs for a Succinyl-CoA:MAA Pathway

This example describes knockout designs for a succinyl-CoA to MAA pathway. As discussed previously, it is understood that similar knockout designs can be used for a succinyl-CoA to 3-hydroxyisobutyrate pathway as well.

Table 6 shows growth coupled designs for the succinyl-CoA to MAA pathway, designed as described in Example XXI. Table 7 shows maximum theoretical yields of MAA and biomass formation rates of growth-coupled designs shown in Table 6.

TABLE 6

Sets of enzymatic transformations whose activity should be either eliminated, attenuated or initially absent from a microorganism to allow the growth coupled production of methyacrylic acid and/or 3-hydroxyisobutyrate.

| Design | Enzyme activity | Abbreviation | Notes |
|---|---|---|---|
| 1 | Acetaldehyde-CoA dehydrogenase | ADHEr | |
|   | malate dehydrogenase | MDH | |
|   | D-lactate dehydrogenase | LDH_D | |
| 2 | Acetaldehyde-CoA dehydrogenase | ADHEr | Design 1 + ASPT |
|   | malate dehydrogenase | MDH | |
|   | L-aspartase | ASPT | |
|   | D-lactate dehydrogenase | LDH_D | |
| 3 | Acetaldehyde-CoA dehydrogenase | ADHEr | Design 2 + PFLi |
|   | malate dehydrogenase | MDH | |
|   | L-aspartase | ASPT | |
|   | D-lactate dehydrogenase | LDH_D | |
|   | pyruvate formate lyase | PFLi | |

TABLE 6-continued

Sets of enzymatic transformations whose activity should be either eliminated, attenuated or initially absent from a microorganism to allow the growth coupled production of methyacrylic acid and/or 3-hydroxyisobutyrate.

| Design | Enzyme activity | Abbreviation | Notes |
|---|---|---|---|
| 4 | Acetaldehyde-CoA dehydrogenase | ADHEr | Design 3 + THD2 and/or GLUDy |
|  | malate dehydrogenase | MDH |  |
|  | L-aspartase | ASPT |  |
|  | D-lactate dehydrogenase | LDH_D |  |
|  | pyruvate formate lyase | PFLi |  |
|  | NAD(P) transhydrogenase | THD2 and/or |  |
|  | and/or glutamate dehydrogenase (NADP) | GLUDy |  |
| 5 | Acetaldehyde-CoA dehydrogenase | ADHEr | Design 2 + ATPS4r |
|  | malate dehydrogenase | MDH |  |
|  | L-aspartase | ASPT |  |
|  | D-lactate dehydrogenase | LDH_D |  |
|  | ATP synthase | ATPS4r |  |
| 6 | Acetaldehyde-CoA dehydrogenase | ADHEr | Design 5 + GLCpts |
|  | malate dehydrogenase | MDH |  |
|  | L-aspartase | ASPT |  |
|  | D-lactate dehydrogenase | LDH_D |  |
|  | ATP synthase | ATPS4r |  |
|  | D-glucose transport via PEP:Pyr PTS | GLCpts |  |
| 7 | Acetaldehyde-CoA dehydrogenase | ADHEr | Design 1 + GLUDy |
|  | malate dehydrogenase | MDH |  |
|  | D-lactate dehydrogenase | LDH_D |  |
|  | glutamate dehydrogenase (NADP) | GLUDy |  |
| 8 | Acetaldehyde-CoA dehydrogenase | ADHEr | Design 7 + PFLi |
|  | malate dehydrogenase | MDH |  |
|  | D-lactate dehydrogenase | LDH_D |  |
|  | glutamate dehydrogenase (NADP) | GLUDy |  |
|  | pyruvate formate lyase | PFLi |  |
| 9 | Acetaldehyde-CoA dehydrogenase | ADHEr | Design 8 + ACKr and/or PTAr |
|  | malate dehydrogenase | MDH |  |
|  | D-lactate dehydrogenase | LDH_D |  |
|  | pyruvate formate lyase | PFLi |  |
|  | glutamate dehydrogenase (NADP) | GLUDy |  |
|  | Phosphotransacetylase and/or acetate kinase | ACKr and/or PTAr |  |
| 10 | Acetaldehyde-CoA dehydrogenase | ADHEr | Design 1 + THD2 |
|  | malate dehydrogenase | MDH |  |
|  | D-lactate dehydrogenase | LDH_D |  |
|  | NAD(P) transhydrogenase | THD2 |  |
| 11 | Acetaldehyde-CoA dehydrogenase | ADHEr | Design 10 + PGL and/or G6PDHy |
|  | malate dehydrogenase | MDH |  |
|  | D-lactate dehydrogenase | LDH_D |  |
|  | NAD(P) transhydrogenase | THD2 |  |
|  | 6-phosphogluconolactonase and/or | PGL and/or |  |
|  | glucose 6-phosphate dehydrogenase | G6PDHy |  |
| 12 | Acetaldehyde-CoA dehydrogenase | ADHEr | Design 11 + PFLi |
|  | malate dehydrogenase | MDH |  |
|  | D-lactate dehydrogenase | LDH_D |  |
|  | NAD(P) transhydrogenase | THD2 |  |
|  | 6-phosphogluconolactonase and/or | PGL and/or |  |
|  | glucose 6-phosphate dehydrogenase | G6PDHy |  |
|  | pyruvate formate lyase | PFLi |  |
| 13 | Acetaldehyde-CoA dehydrogenase | ADHEr | Design 1 + NADH6 |
|  | malate dehydrogenase | MDH |  |
|  | D-lactate dehydrogenase | LDH_D |  |
|  | NADH dehydrogenase | NADH6 |  |
| 14 | Acetaldehyde-CoA dehydrogenase | ADHEr | Design 13 + ACKr/PTAr |
|  | malate dehydrogenase | MDH |  |
|  | D-lactate dehydrogenase | LDH_D |  |
|  | NADH dehydrogenase | NADH6 |  |
|  | Phosphotransacetylase and/or acetate kinase | ACKr and/or PTAr |  |

Figure 17:
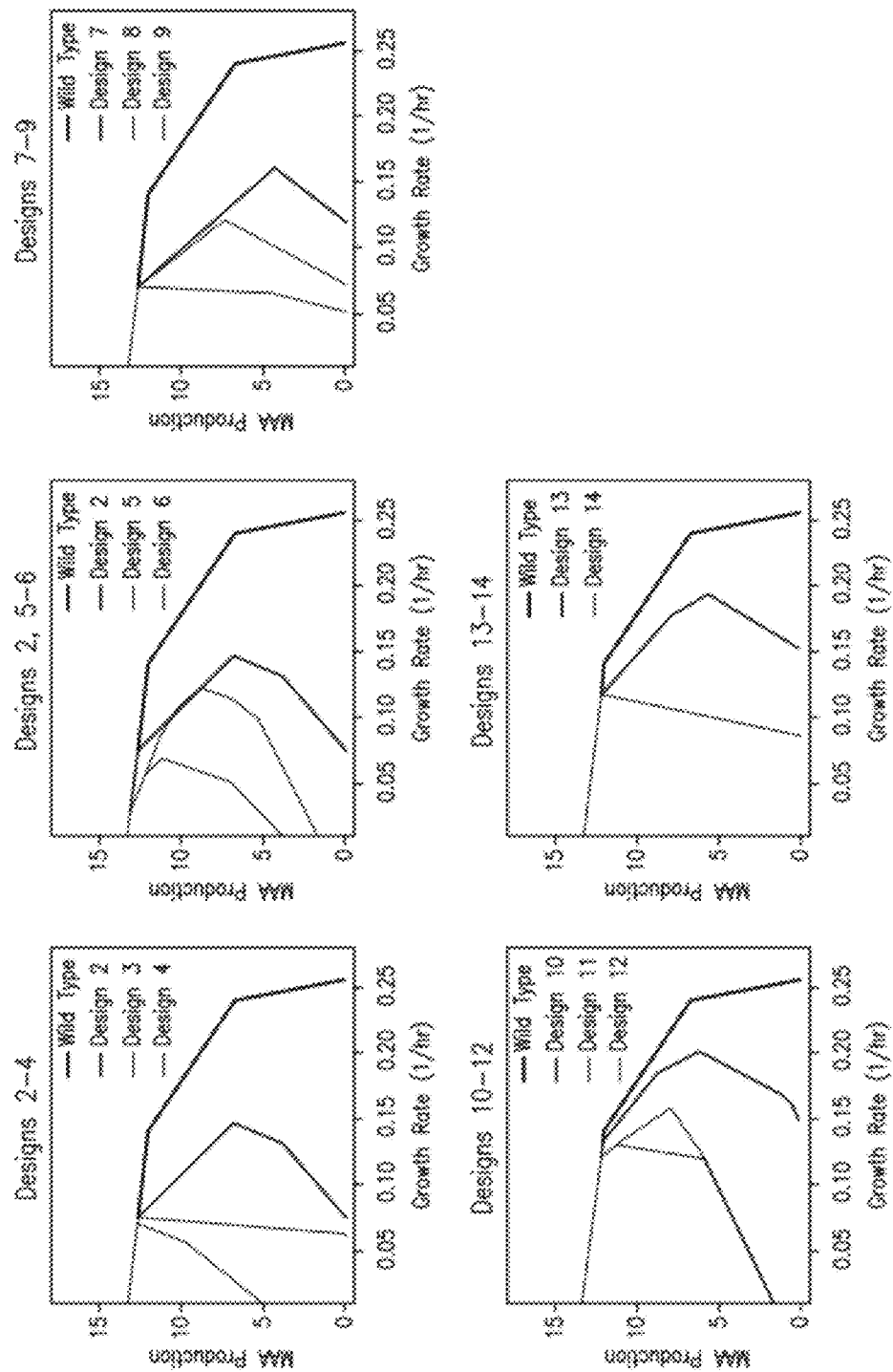
FIG. 17 shows growth-coupled MAA and 3-hydroxyisobutyrate production characteristics of the highest priority knockout strain designs (gray) compared with those of wild-type E. coli (black). A glucose uptake rate of 10 mmol/gDW/hr is assumed.

All high-priority growth coupled designs for the succinyl-CoA to MAA pathway (Table 6 and FIG. 17) build upon Design 1, which calls for the absence of acetylaldehyde-CoA dehydrogenase (ADHEr), malate dehydrogenase (MDH), and lactate dehydrogenase (LDH_D) activities to prevent the formation of fermentation byproducts. Design 2 builds upon this base design with the additional removal of L-aspartase (ASPT) functionality. This design is capable of reaching 54% of the theoretical maximum MAA yield (0.35 g/g) at the maximum biomass yield (Table 7).

TABLE 7

Maximum theoretical MAA yields and biomass formation rates of growth-coupled designs in Table 6.

| Design | MAA (g/g) | % Theoretical Yield | Biomass (1/hr) |
| --- | --- | --- | --- |
| 2 | 0.35 | 54% | 0.148 |
| 3 | 0.60 | 94% | 0.076 |
| 4 | 0.60 | 95% | 0.07 |
| 5 | 0.42 | 66% | 0.123 |
| 6 | 0.54 | 84% | 0.07 |
| 7 | 0.21 | 32% | 0.162 |
| 8 | 0.35 | 55% | 0.123 |
| 9 | 0.60 | 95% | 0.07 |
| 10 | 0.29 | 46% | 0.202 |
| 11 | 0.37 | 59% | 0.158 |
| 12 | 0.52 | 82% | 0.131 |
| 13 | 0.27 | 42% | 0.195 |
| 14 | 0.56 | 88% | 0.118 |

The maximum theoretical yield of MAA in a wild-type backround is 0.64 g/g (grams MAA produced per gram glucose utilized).

Designs 3 and 4 build on Design 2 as a base design. Design 3 entails the removal of pyruvate formate lyase (PFLi) activity to prevent secretion of formate as a byproduct. This design results in an MAA yield of 94% of the theoretical maximum. Further deletion of NAD(P) transhydrogenase (THD2) and/or glutamate dehydrogenase (GLUDy) in Design 4 serves to tightly couple cell growth to MAA production while achieving 95% of the theoretical maximum yield. This design also requires the formation of at least 0.24 g/g MAA for biomass formation.

Designs 5 and 6 also build on Design 2 as a base design. In Design 5, removal of ATP synthase (ATPS4r) results in a yield of 0.42 g/g MAA at the maximum biomass formation rate of 0.123 l/hr. This design tightly couples growth to product formation but requires secretion of acetate and formate as fermentation byproducts. Removing glucose transport via the phosphoenolpyruvate:pyruvate PTS system reduces byproduct formation and increases MAA production to 0.54 g/g (84% of the maximum theoretical yield).

Designs 7-14 build on Design 1, in which ADHEr, MDH and LDH_D functionality is removed. In Design 7, removal of glutamate dehydrogenase (GLUDy) functionality yields a mutant that produces 0.21 g/g MAA at 0.162 l/hr. Further deletion of pyruvate formate lyase (PFLi) in Design 8 yields 0.35 g/g MAA. Additional deletion of phosphotransacetylase (PTAr) and/or acetate kinase (ACKr) in Design 9 prevents formation of acetate and increases product yield to 0.60 g/g, 95% of the theoretical maximum. Further removal of transhydrogenase (THD2) functionality improves growth-coupling of this design.

Design 10 knocks out NAD(P) transhydrogenase (THD2) in addition to MDH, LDH, and ADHEr. This strain is predicted to achieve an MAA yield of 0.29 g/g at a maximum growth rate of 0.20 l/hr. Additional deletion of 6-phosphogluconolactonase (PGL) and/or glucose-6-phosphate dehydrogenase (G6PDHy) serves to increase flux through glycolysis, thereby improving the predicted MAA yield to 0.37 g/g with tightened coupling to biomass formation. Additional deletion of pyruvate formate lyase (PFLi), which forces flux through PDH and reduces byproduct formation, increases the predicted MAA yield to 0.52 g/g, 82% of the theoretical maximum. Additional deletions in ACKr and ASPT also improve the product yield of this design by reducing byproduct formation.

Design 13 builds on Design 1 with the additional knockout of NADH dehydrogenase (NADH6). This yields a strain with an MAA yield of 0.27 g/g at the maximum biomass formation rate. Further deletion of phosphotransacetylase (PTAr) and/or acetate kinase (ACKr) in Design 14 improves the yield to 0.56 g/g, 88% of the theoretical maximum. This design has the advantage of producing MAA as the sole fermentation byproduct.

All high-yielding strain designs involve deletion of at least one of the following reactions: alcohol dehydrogenase (ADHEr), malate dehydrogenase (MDH), lactate dehydrogenase (LDH_D), phosphogluconolactonase (PGL), glucose-6-phosphate dehydrogenase (G6PDHy), pyruvate formate lyase (PFLi), NAD(P) transhydrogenase (THD2), ATP synthetase (ATPS4r), glutamate dehydrogenase (GLUDy), aspartase (ASPT), acetate kinase (ACKr), phosphotransacetylase (PTAr) and NADH dehydrogenase (NADH6). Addition of any of these knockouts to the strain designs in Table 6 will further improve the yield of MAA or 3-hydroxyisobutryrate.

These results describe knockout design strategies to generate strains having growth-coupled production of MAA or 3-HIB.

Example XXIII

Knockout Designs for a 4-Hydroxybutyryl-CoA:MAA Pathway

This example describes knockout designs for a 4-hydroxybutyryl-CoA to MAA pathway. As discussed previously, it is understood that similar knockout designs can be used for a 4-hydroxybutyryl-CoA to 3-hydroxyisobutyrate pathway as well.

For the 4-hydroxybutyryl-CoA pathway, OptKnock designs were generated for strains that utilize either a hydrolase or a transferase to generate 3-hydroxyisobutyrate or MAA (FIG. 6, step 2). Designs generated for the two conditions were similar, although product yields and growth-coupling were significantly higher when a transferase is utilized. All designs are listed in Table 11. Table 8 shows growth coupled designs for the 4-hydroxybutyryl-CoA to MAA pathway, designed as described in Example XXI. Table 9 shows maximum theoretical yields of MAA and biomass formation rates of growth-coupled designs shown in Table 8.

TABLE 8

Sets of enzymatic transformations whose activity should be either eliminated, attenuated or initially absent from a microorganism to allow the growth coupled production of methacrylic acid and/or 3-hydroxyisobutyric acid.

| Design | Enzyme activity | Abbreviation | Notes |
| --- | --- | --- | --- |
| 1 | Acetaldehyde-CoA dehydrogenase | ADHEr | |
|  | malate dehydrogenase | MDH | |
|  | D-lactate dehydrogenase | LDH_D | |

TABLE 8-continued

Sets of enzymatic transformations whose activity should be either eliminated, attenuated or initially absent from a microorganism to allow the growth coupled production of methacrylic acid and/or 3-hydroxyisobutyric acid.

| Design | Enzyme activity | Abbreviation | Notes |
|---|---|---|---|
| 2 | Acetaldehyde-CoA dehydrogenase | ADHEr | Design 1 + ASPT |
|  | malate dehydrogenase | MDH |  |
|  | D-lactate dehydrogenase | LDH_D |  |
|  | L-aspartase | ASPT |  |
| 3 | Acetaldehyde-CoA dehydrogenase | ADHEr | Design 2 + THD2/GLUDy |
|  | malate dehydrogenase | MDH |  |
|  | D-lactate dehydrogenase | LDH_D |  |
|  | L-aspartase | ASPT |  |
|  | NAD(P) transhydrogenase | THD2 and/or |  |
|  | and/or glutamate dehydrogenase (NADP) | GLUDy |  |
| 4 | Acetaldehyde-CoA dehydrogenase | ADHEr | Design 3 + PFLi |
|  | malate dehydrogenase | MDH |  |
|  | L-aspartase | ASPT |  |
|  | D-lactate dehydrogenase | LDH_D |  |
|  | NAD(P) transhydrogenase | THD2 and/or |  |
|  | and/or glutamate dehydrogenase (NADP) | GLUDy |  |
|  | pyruvate formate lyase | PFLi |  |
| 5 | Acetaldehyde-CoA dehydrogenase | ADHEr | Design 2 + ATPS4r |
|  | malate dehydrogenase | MDH |  |
|  | D-lactate dehydrogenase | LDH_D |  |
|  | L-aspartase | ASPT |  |
|  | ATP synthase | ATPS4r |  |
| 6 | Acetaldehyde-CoA dehydrogenase | ADHEr | Design 5 + PGL and/or G6PDHy |
|  | malate dehydrogenase | MDH |  |
|  | D-lactate dehydrogenase | LDH_D |  |
|  | L-aspartase | ASPT |  |
|  | ATP synthase | ATPS4r |  |
|  | 6-phosphogluconolactonase and/or | PGL and/or |  |
|  | glucose 6-phosphate dehydrogenase | G6PDHy |  |
| 7 | Acetaldehyde-CoA dehydrogenase | ADHEr | Design 5 + PFLi |
|  | malate dehydrogenase | MDH |  |
|  | D-lactate dehydrogenase | LDH_D |  |
|  | L-aspartase | ASPT |  |
|  | ATP synthase | ATPS4r |  |
|  | Pyruvate formate lyase | PFLi |  |
| 8 | Acetaldehyde-CoA dehydrogenase | ADHEr | Design 1 + THD2 |
|  | malate dehydrogenase | MDH |  |
|  | D-lactate dehydrogenase | LDH_D |  |
|  | NAD(P) transhydrogenase | THD2 and/or |  |
|  | and/or glutamate dehydrogenase (NADP) | GLUDy |  |
| 9 | Acetaldehyde-CoA dehydrogenase | ADHEr | Design 8 + PGL and/or G6PDHy |
|  | malate dehydrogenase | MDH |  |
|  | D-lactate dehydrogenase | LDH_D |  |
|  | NAD(P) transhydrogenase | THD2 and/or |  |
|  | and/or glutamate dehydrogenase (NADP) | GLUDy |  |
|  | 6-phosphogluconolactonase and/or | PGL and/or |  |
|  | glucose 6-phosphate dehydrogenase | G6PDHy |  |

Figure 18:
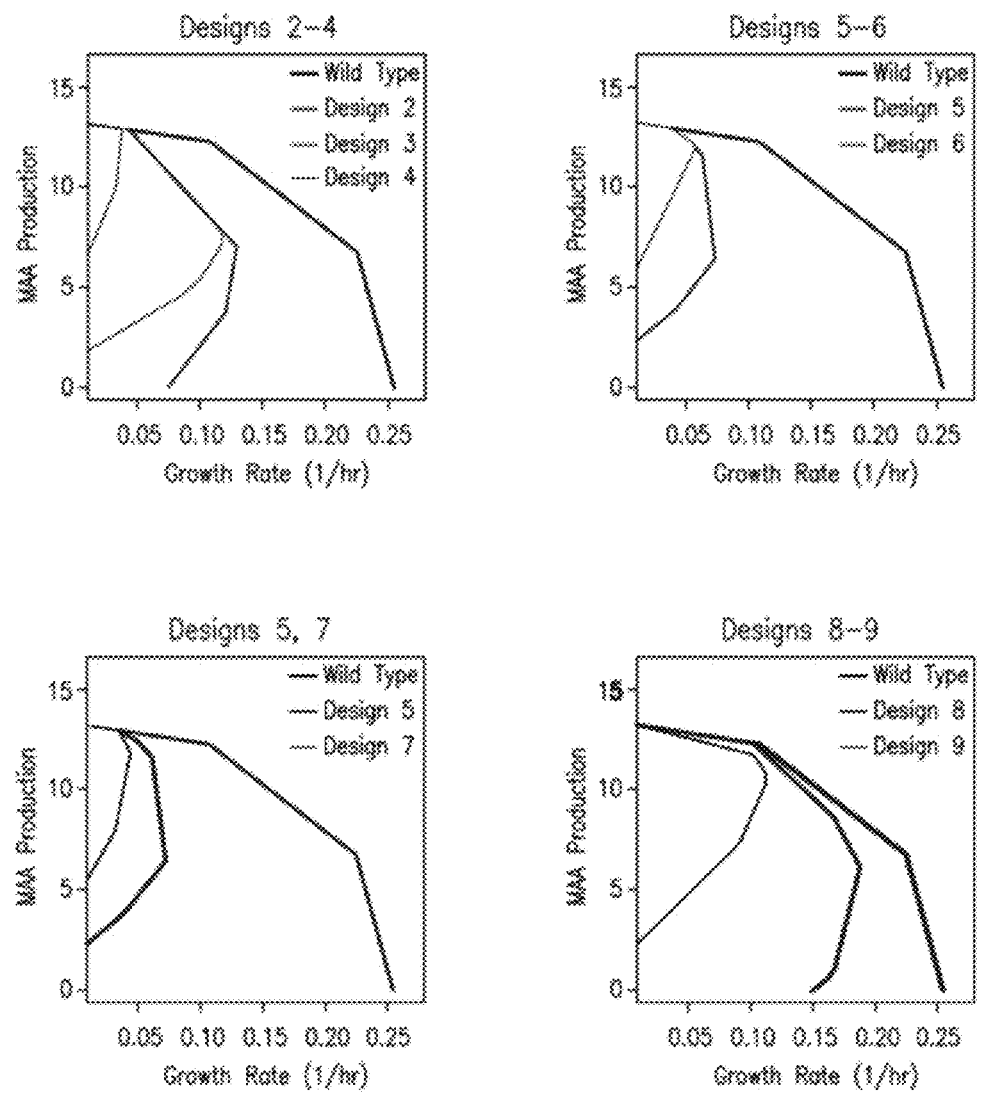
FIG. 18 shows growth-coupled MAA production characteristics of the highest priority knockout strains (gray) for a 4-hydroxybutyryl-CoA to MAA pathway compared to those of wild-type E. coli (black). A glucose uptake rate of 10 mmol/gDW/hr is assumed.

The highest priority growth-coupled strain designs (Table 8, FIG. 18) build upon Design 1, a base strain with removed, reduced or attenuated alcohol dehydrogenase (ADHEr), malate dehydrogenase (MDH) and lactate dehydrogenase (LDH_D) functionality. The additional removal of succinate semialdehyde dehydrogenase functionality may be beneficial for efficient channeling of flux through succinyl-CoA.

TABLE 9

Maximum theoretical MAA yields and biomass formation rates of growth-coupled designs in Table 8. MAA yields are calculated under the assumption that a transferase is utilized to convert 3-hydroxyisobutyrate. Identical yields are predicted if 3-hydroxyisobutyryl-CoA is first converted to methacryl-CoA which is then converted to MAA by a transferase.

| Design | MAA Yield (g/g) | % Theoretical Max | Biomass (1/hr) |
|---|---|---|---|
| 2 | 0.33 | 52% | 0.13 |
| 3 | 0.34 | 54% | 0.12 |
| 4 | 0.62 | 97% | 0.039 |
| 5 | 0.31 | 48% | 0.073 |
| 6 | 0.57 | 90% | 0.056 |
| 7 | 0.56 | 88% | 0.044 |
| 8 | 0.29 | 46% | 0.19 |
| 9 | 0.52 | 81% | 0.112 |

Additional assumptions: ATP maintenance energy = 4 mmol/gDCW/hr, SSALy knocked out.

Designs 2-7 build on Design 1 with the additional removal, reduction or attenuation of L-aspartase (ASPT) activity. Design 2 produces an MAA yield of 0.33 g/g at the maximum growth rate of 0.13 l/hr. The major fermentation byproducts of this strain are acetate and formate. Further deletion of genes involved in formate production and energy generation can reduce formation of these byproducts. Design 3 builds upon Design 2 with the additional deletion of NAD(P) transhydrogenase (THD2) and/or glutamate dehydrogenase (GLUDy), resulting in an MAA yield of 0.34 g/g at the maximum growth rate 0.12 l/hr. This strain does not eliminate byproduct formation, but it is tightly growth-coupled and is required to produce a minimum of 0.07 g MAA per gram glucose utilized for energy generation. Additional deletion of pyruvate formate lyase (PFLi) in Design 4 eliminates formate secretion and increases the MAA yield to 0.62 g/g (97% of the theoretical maximum) and also requires the production of at least 0.24 g/g MAA for energy generation.

Design 5 builds upon Design 4 with the additional deletion of ATP synthetase (ATPS4r). This strain achieves 0.31 g/g MAA at a maximum growth rate of 0.073 l/hr. Further deletion of 6-phosphogluconolactonase (PGL) and/or glucose-6-phosphate dehydrogenase (G6PDHy) functionality in Design 6 increases the product yield at maximum biomass (0.57 g/g at 0.056 l/hr maximum growth rate). Alternatively, deletion of pyruvate formate lyase also results in a high-yielding design with tight growth-coupling (Design 7).

Design 8 builds upon the Design 1 base strain (ADHEr, LDH_D, MDH) with the removal of NAD(P) transhydrogenase functionality. This strain design achieves 0.29 g/g MAA at biomass 0.19 l/hr. Further deletion of phosphogluconolactonase (PGL) and/or glucose-6-phosphate dehydrogenase (G6PDHy) in Design 9 increases MAA production at maximum biomass to 0.52 g/g at 0.112 l/hr.

All high-yielding strain designs involve deletion of at least one of the following reactions: alcohol dehydrogenase (ADHEr), malate dehydrogenase (MDH), lactate dehydrogenase (LDH_D), phosphogluconolactonase (PGL), glucose-6-phosphate dehydrogenase (G6PDHy), pyruvate formate lyase (PFLi), NAD(P) transhydrogenase (THD2), ATP synthetase (ATPS4r), glutamate dehydrogenase (GLUDy), and aspartase (ASPT). Addition of any of these knockouts to the strain designs in Table 8 will further improve the yield of MAA or 3-hydroxyisobutyrate.

These results describe knockout design strategies to generate strains having growth-coupled production of MAA or 3-HIB.

Example XXIV

Characterization of Engineered Strains

This example describes characterization of engineered strains.

Strain Construction:

*Escherichia coli* K-12 MG1655 housing the 3-hydroxyisobutyrate and/or MAA pathway is used as the strain into which the deletions are introduced. The strains are constructed by incorporating in-frame deletions using homologous recombination via the λ Red recombinase system of Datsenko and Wanner (*Proc. Natl. Acad. Sci. USA* 97(12): 6640-6645 2000)). The approach involves replacing a chromosomal sequence, that is, the gene targeted for removal, with a selectable antibiotic resistance gene, which itself is later removed. The knockouts are integrated one by one into the recipient strain. No antibiotic resistance markers remain after each deletion, allowing accumulation of multiple mutations in each target strain. The deletion technology completely removes the gene targeted for removal so as to substantially reduce the possibility of the constructed mutants reverting back to the wild-type.

Shake Flask Characterization:

As intermediate strains are constructed, strain performance is quantified by performing shake flask fermentations. Anaerobic conditions are obtained by sealing the flasks with a rubber septum and then sparging the medium with nitrogen. For strains where growth is not observed under strict anaerobic conditions, microaerobic conditions are applied by covering the flask with foil and poking a small hole for limited aeration. Experiments are performed using M9 minimal medium supplemented with glucose unless otherwise desired for a particular application. Pre-cultures are grown overnight and used as inoculum for a fresh batch culture for which measurements are taken during exponential growth. The growth rate is determined by measuring optical density using a spectrophotometer (600 nm), and the glucose uptake rate by monitoring carbon source depletion over time. Ethanol, MAA, 3-hydroxyisobutyric acid and organic acids are analyzed by GC-MS or HPLC using routine procedures. Triplicate cultures are grown for each strain.

Batch Fermenter Testing:

The performance of selected strains are tested in anaerobic, pH-controlled batch fermentations. This allows reliable quantification of the growth, glucose uptake, and formation rates of all products, as well as ensure that the accumulation of acidic fermentation products will not limit cell growth. In addition, it allows accurate determination of 3-hydryxoyisobutyric acid and/or MAA volumetric productivity and yield, two of the most important parameters in benchmarking strain performance. Fermentations are carried out in 1-L bioreactors with 600 mL working volume, equipped with temperature and pH control. The reactor is continuously sparged with $N_2$ at approximately 0.5 L/min to ensure that dissolved oxygen (DO) levels remain below detection levels. The culture medium is the same as described above, except that the glucose concentration is increased in accordance with the higher cell density achievable in a fermentation vessel.

Chemostat Testing:

Chemostat experiments are conducted to obtain a direct measure of how the switch in fermentation mode from batch to continuous affects 3-hydroxyisobutyric acid and/or MAA yield and volumetric productivity. The bioreactors described above using batch mode are operated in chemostat mode through continuous supply of medium and removal of spent culture. The inlet flow rate is set to maintain a constant dilution rate of 80% of the maximum growth rate observed for each strain in batch, and the outlet flow is controlled to maintain level. Glucose is the limiting nutrient in the medium and is set to achieve the desired optical density in the vessel.

Adaptive Evolution:

The knockout strains are expected initially to exhibit suboptimal growth rates until their metabolic networks have adjusted to their missing functionalities. To facilitate this adjustment, the strains are adaptively evolved. By subjecting the strains to adaptive evolution, cellular growth rate becomes the primary selection pressure and the mutant cells are compelled to reallocate their metabolic fluxes in order to enhance their rates of growth. This reprogramming of metabolism has been recently demonstrated for several *E. coli* mutants that had been adaptively evolved on various substrates to reach the growth rates predicted a priori by an in silico model (Fong and Palsson, *Nat. Genet.* 36(10):1056-1058 (2004)). The OptKnock-generated strains are adaptively evolved in triplicate (running in parallel) due to differences in the evolutionary patterns witnessed previously in *E. coli* (Fong and Palsson, *Nat Genet.* 36(10):1056-1058 (2004); Fong et al., *J. Bacteriol.* 185(21):6400-6408 (2003); Ibarra et al., *Nature* 420 (6912):186-189 (2002)) that could potentially result in one strain having superior production qualities over the others. Evolutions are run for a period of 2-6 weeks, depending upon the rate of growth improvement attained. In general, evolutions are stopped once a stable phenotype is obtained. The growth-coupled biochemical production concept behind the OptKnock approach results in the generation of genetically stable overproducers.

As described above and in previous examples, strain engineering strategies for coupling methacrylic acid (MAA) and 3-hydroxyisobutyrate (3-HIB) production to cell growth were calculated using OptKnock methodology. Two pathways were explored. The first pathway proceeds through methylmalonyl-CoA as an intermediate. The second pathway proceeds through 4-hydroxybutyryl-CoA and can utilize either a CoA transferase, hydrolase or synthetase to convert 3-hydroxyisobutyryl-CoA to 3-HIB. Alternatively, MAA can be produced directly by this pathway if 3-hydroxyisobutyryl-CoA is first converted to methacrylyl-CoA. Pathway selection, host background, and selection of enzymes for each particular step impact product yield and growth characteristics of the final production strain.

Assuming that 3-hydroxyisobutyric acid is produced as a precursor, the final step of both pathways entails dehydration of 3-HIB to MAA by 3-hydroxyisobutyrate dehydratase. As this conversion does not require energy or redox equivalents, it is understood that the strain design strategies described for MAA can also be applied for growth-coupled production of 3-HIB production if 3-hydroxyisobutyrate dehydratase activity is not present in the production organism. In this case, the non-naturally occurring organism would produce 3-HIB instead of MAA. The maximum theoretical product and energetic yields are unchanged regardless of whether MAA or 3-HIB is produced.

All high-priority strain designs are built on three central deletions: MDH, LDH_D and ADHEr. This analysis revealed that host strain design strategies are remarkably similar and involve the deletion of a small number of enzyme activities in the host organism. The main enzyme activities impacting MAA (or 3-HIB) production are: acetaldehyde-CoA dehydrogenase (ADHEr), malate dehydrogenase (MDH), lactate dehydrogenase (LDH_D), phosphogluconolactonase (PGL), glucose-6-phosphate dehydrogenase (G6PDHy), pyruvate formate lyase (PFLi), NAD(P) transhydrogenase (THD2), ATP synthetase (ATPS4r), glutamate dehydrogenase (GLUDy), aspartase (ASPT), acetate kinase (ACKr), phosphotransacetylase (PTAr) and NADH dehydrogenase (NADH6). Addition of any of these knockouts to the strain designs in Tables 6 and 8 or any of the non-naturally occurring microbial organisms disclosed herein will further improve the yield of MAA or 3-hydroxyisobutryate.

Example XXV

Central Metabolic Enzymes Providing Increased Theoretical Yields of MAA and/or 3-Hydroxyisobutyrate Via a Succinyl-CoA or 4-Hydroxybutyryl-CoA Precursor Pathway This example describes enzymes of central metabolic reactions that can be modulated to increase the theoretical yields of organisms engineered with a MAA and/or 3-hydroxyisobutyrate pathway utilizing succinyl-CoA or 4-hydroxybutyryl-CoA as a precursor.

In this example, we demonstrate the importance of several central metabolic reactions that allow high yields of MAA in an engineered microbe via a succinyl-CoA to MAA pathway or a 4-hydroxybutyryl-CoA to MAA pathway. The analysis described in this example equally applies if 3-hydroxyisobutyric acid is produced by the engineered microbe along with or instead of MAA. Specifically, a series of linear programming (LP) problems were solved that maximized the MAA, or 3-hydroxyisobutyric acid, yield from glucose for an *E. coli* metabolic network supplemented with either or both of the MAA production pathways, assuming that every reaction in central metabolism was individually deleted. As discussed above, the maximum MAA yield from glucose via either pathway is 1.33 mol/mol. Central metabolism includes all reactions in glycolysis, the pentose phosphate pathway, the tricarboxylic acid cycle, the glyoxylate shunt, and various anapleurotic reactions. Unless otherwise noted, it was assumed that PEP carboxykinase could operate only in the gluconeogenic, ATP-consuming direction towards phosphoenolpyruvate. Although *E. coli* was chosen as an exemplary microorganism, the analysis presented herein is applicable to virtually any prokaryotic or eukaryotic organism. Additionally, the conclusions described herein are valid independent of the exemplary carbohydrate feedstock, arbitrarily chosen in this example to be glucose.

Reactions whose deletion negatively affects the maximum MAA yield in the presence of an external electron acceptor (for example, oxygen, nitrate) are shown in Table 14 for three network assumptions: 1) undeleted wild-type network (that is, all reactions are present); 2) the wild-type network minus malate dehydrogenase (that is, a reaction targeted for attenuation in several OptKnock designs); and 3) the network minus both malate dehydrogenase and pyruvate formate lyase (that is, two reactions targeted for attenuation in several OptKnock designs). Similar results assuming that no external electron acceptor is present are provided in Table 15. This analysis led to three important observations, as discussed below in more detail.

TABLE 14

The maximum theoretical MAA molar yields on glucose are provided assuming that various central metabolic reactions are each individually inactivated. The analysis assumes that an external electron acceptor such as oxygen is present and that PEP carboxykinase is not used to produce oxaloacetate.

| | | WT | | ΔMDH | | ΔMDH, ΔPFL | |
|---|---|---|---|---|---|---|---|
| Abbreviation | Reaction Name | MAA Yield | % of Max Yield | MAA Yield | % of Max Yield | MAA Yield | % of Max Yield |
| ACONT | Aconitase | 1.067 | 80.0% | 0.954 | 71.6% | 0.954 | 71.6% |
| CS | Citrate Synthase | 1.067 | 80.0% | 0.954 | 71.6% | 0.954 | 71.6% |
| ENO | Enolase | 1.132 | 84.9% | 1.097 | 82.3% | 1.097 | 82.3% |
| FUM | Fumarase | 1.297 | 97.3% | 1.297 | 97.3% | 1.297 | 97.3% |
| GAPD | Glyceraldehyde-3-phosphate Dehydrogenase | 1.132 | 84.9% | 1.097 | 82.3% | 1.097 | 82.3% |
| ICL | Isocitrate Lyase | 1.333 | 100% | 1.284 | 96.3% | 1.284 | 96.3% |
| MALS | Malate synthase | 1.333 | 100% | 1.297 | 97.3% | 1.297 | 97.3% |
| PDH | Pyruvate dehydrogenase | 1.333 | 100% | 1.306 | 97.9% | 1.231 | 92.3% |
| PGI | Phosphoglucoisomerase | 1.330 | 99.8% | 1.296 | 97.2% | 1.296 | 97.2% |
| PGK | Phosphoglycerate Kinase | 1.132 | 84.9% | 1.097 | 82.3% | 1.097 | 82.3% |
| PGM | Phosphoglycerate Mutase | 1.132 | 84.9% | 1.097 | 82.3% | 1.097 | 82.3% |
| PPC | PEP carboxylase | 1.200 | 90.0% | 1.163 | 87.2% | 1.163 | 87.2% |
| TPI | Triose Phosphate Isomerase | 1.288 | 96.6% | 1.286 | 96.5% | 1.286 | 96.5% |

Three cases are explored:
1) WT   wild-type network including all *E.coli* central metabolic reactions;
2) ΔMDH   wild-type network minus malate dehydrogenase activity;
3) ΔMDH,ΔPFL   wild-type network minus malate dehydrogenase and pyruvate formate lyase activities.

TABLE 15

The maximum theoretical MAA molar yields on glucose are provided assuming that various central metabolic reactions are each individually inactivated. The analysis assumes that an external electron acceptor such as oxygen is present and that PEP carboxykinase is not used to produce oxaloacetate.

| | | WT | | ΔMDH | | ΔMDH, ΔPFL | |
|---|---|---|---|---|---|---|---|
| Abbreviation | Reaction Name | MAA Yield | % of Max Yield | MAA Yield | % of Max Yield | MAA Yield | % of Max Yield |
| ACONT | Aconitase | 1.067 | 80.0% | 0.845 | 63.4% | 0.845 | 63.4% |
| CS | Citrate Synthase | 1.067 | 80.0% | 0.845 | 63.4% | 0.845 | 63.4% |
| ENO | Enolase | 0.000 | 0.0% | 0.000 | 0.0% | 0.000 | 0.0% |
| FUM | Fumarase | 1.091 | 81.8% | 1.091 | 81.8% | 1.053 | 78.9% |
| GAPD | Glyceraldehyde-3-phosphate dehydrogenase | 0.000 | 0.0% | 0.000 | 0.0% | 0.000 | 0.0% |
| ICL | Isocitrate Lyase | 1.333 | 100% | 1.033 | 77.5% | 0.990 | 74.3% |
| MALS | Malate synthase | 1.333 | 100% | 1.091 | 81.8% | 1.053 | 78.9% |
| PDH | Pyruvate dehydrogenase | 1.333 | 100% | 1.277 | 95.7% | 0.770 | 57.8% |
| PGI | Phosphoglucoisomerase | 1.317 | 98.8% | 1.014 | 76.1% | 0.909 | 68.2% |
| PGK | Phosphoglycerate Kinase | 0.000 | 0.0% | 0.000 | 0.0% | 0.000 | 0.0% |
| PGM | Phosphoglycerate Mutase | 0.000 | 0.0% | 0.000 | 0.0% | 0.000 | 0.0% |
| PPC | PEP carboxylase | 0.839 | 62.9% | 0.000 | 0.0% | 0.000 | 0.0% |
| TPI | Triose Phosphate Isomerase | 1.108 | 83.1% | 0.988 | 74.1% | 0.909 | 68.2% |

Three cases are explored:
1) WT   wild-type network including all *E.coli* central metabolic reactions;
2) ΔMDH   wild-type network minus malate dehydrogenase activity;
3) ΔMDH,ΔPFL   wild-type network minus malate dehydrogenase and pyruvate formate lyase activities.

Observation 1.

Sufficient flux through citrate synthase and aconitase is required to achieve the greater than 80% of the theoretical yield of MAA in all cases. Though highly active under aerobic conditions, the oxidative branch of the tricarboxylic acid cycle is not highly active in the absence of an external electron acceptor such as oxygen or nitrate. In *E. coli*, for example, citrate synthase is inhibited by NADH, whose concentration is high in the absence of an external electron acceptor. Furthermore, under oxygen-limited conditions, the expression of the tricarboxylic acid cycle enzymes is repressed by product of the arcA gene (Alexeeva, et al., *J. Bacteriol.* 185(1):204-209 (2003)). An exemplary method for increasing citrate synthase and aconitase activity in *E. coli* under oxygen-limited conditions involves deleting the regulator arcA and/or replacing the native citrate synthase with an NADH-insensitive enzyme (Stokell et al., *J. Biol. Chem.* 278:35435-35443 (2003); Jin and Sonenshein, *J. Bacteriol.* 178(12):3658-3660 (1996).

Observation 2.

The glyoxylate shunt enzymes, isocitrate lysase, and malate synthase, are required to achieve the maximum theoretical yield of MAA when malate dehydrogenase activity is attenuated. The requirement for the glyoxylate shunt is exacerbated under oxygen-limited conditions as the maximum yield of MAA drops approximately 20% without isocitrate lysase or malate synthase activities. An exemplary method for increasing glyoxylate shunt activity in *E. coli* involves deleting the transcriptional repressor, iclR, as described in Sanchez, et al. (*Metab. Eng.* 7(3) 229-239 (2005).

Observation 3.

In a malate dehydrogenase and pyruvate formate lyase deficient background, pyruvate dehydrogenase is required to reach 93% of the maximum theoretical MAA yield in the presence of an external electron acceptor or 58% of the maximum theoretical yield in the absence of an external electron acceptor. Pyruvate dehydrogenase is inhibited by high NADH/NAD, ATP/ADP, and acetyl-CoA/CoA ratios. Thus the enzyme naturally exhibits very low activity under oxygen-limited or anaerobic conditions in organisms such as *E. coli* due in large part to the NADH sensitivity of the subunit E3, encoded by lpdA. Exemplary methods for obtaining pyruvate dehydrogenase activity in *E. coli* under oxygen-limited conditions include replacing the native promoter with an anaerobically-induced promoter (Zhou et al., *Biotechnol. Lett.* 30(2):335-342 (2008)), introducing a point mutation into lpdA to relieve the NADH sensitivity (Kim et al., *J. Bacteriol.* 190(11) 3851-3858 (2008), or inactivating the repressor, pdhR (Quail and Guest, *Mol. Microbiol.* 15(3) 519-529 (1995)). Net pyruvate dehydrogenase-like activity can alternatively be obtained from pyruvate ferredoxin oxidoreductase. To do so, a pyruvate ferredoxin oxidoreductase (PFOR) enzyme is used to convert pyruvate to acetyl-CoA with the concaminant reduction of a ferredoxin protein. The reduced ferredoxin then transfers its electrons to NAD+ or NADP+ by way of NAD(P)H/ferredoxin oxidoreductase. Heterologous and native PFOR genes have recently been demonstrated to improve hydrogen production in *E. coli* (Akhtar and Jones, *Metab. Eng.* 11:139-147 (2009); Do et al., *Appl. Biochem. Biotechnol.* 153:21-33 (2009)).

Lastly, the analysis was repeated assuming that PEP carboxykinase can operate in the ATP-forming, $CO_2$-fixing direction towards oxaloacetate. In organisms such as *E. coli*, the metabolic flux from phosphoenolpyruvate to oxaloacetate is carried by PEP carboxylase, an enzyme that does not generate an ATP equivalent. However, $CO_2$-fixing PEP carboxykinase activity can be enhanced in *E. coli* by overexpressing the native PEP carboxykinase under the appropriate conditions (Deok et al., *J. Microbiol. Biotechnol.* 16(9) 1448-1452 (2006)) or by expressing foreign genes encoding PEP carboxykinase enzymes with more favorable kinetic properties. The observed PEP carboxykinase activity might be more prevalent in a host organism with attenuated PEP carboxylase activity (Kim et al, *Appl. Env. Microbiol.* 70(2) 1238-1241 (2004)). Assuming that PEP carboxykinase can carry a significant net flux towards oxaloacetate eliminates the absolute requirement for isocitrate lyase and malate synthase activity to achieve the maximum yield of MAA in all cases. Furthermore, the requirement for pyruvate dehydrogenase is also eliminated in the wild-type and malate dehydrogenase negative backgrounds. Nevertheless, engineering PEP carboxykinase activity into the host organism chosen for MAA production will be useful due to its role in improving the maximum ATP yield of the MAA pathways from 0.47 mol/mol to 1.71 mol/mol.

TABLE 10

Growth-coupled production designs for the succinyl-CoA:MAA pathway (FIG. 2).

| Design ID | Metabolic Transformations Targeted for Removal | Predicted MAA Yield |
|---|---|---|
| 1 | FUM | 1.31393 |
| 2 | HEX1 | 0.81503 |
| 3 | MDH | 0.7159 |
| 4 | PFK and/or FBA and/or TPI | 0.32284 |
| 5 | MDH, THD2 and/or GLUDy | 6.09185 |
| 6 | FUM, PFLi | 5.98191 |
| 7 | HEX1, PFLi | 5.24339 |
| 8 | MDH, PFLi | 5.21195 |
| 9 | PFK and/or FBA and/or TPI, PFLi | 4.87678 |
| 10 | ADHEr, PPCK | 4.25091 |
| 11 | ADHEr, FRD and/or SUCD4 | 4.17475 |
| 12 | HEX1, THD2 and/or GLUDy | 3.09819 |
| 13 | FUM, HEX1 | 1.81756 |
| 14 | MDH, PFK and/or FBA and/or TPI | 1.36009 |
| 15 | FRD and/or SUCD4, PFLi | 1.07808 |
| 16 | PFLi, PPCK | 0.94993 |
| 17 | PPCK, PYK | 0.57249 |
| 18 | ADHEr, PFLi, PPCK | 6.93528 |
| 19 | ADHEr, FRD and/or SUCD4, PFLi | 6.8792 |
| 20 | HEX1, PFLi, THD2 and/or GLUDy | 6.71657 |
| 21 | MDH, PFK and/or FBA and/or TPI, PFLi | 6.3322 |
| 22 | MDH, PFLi, THD2 and/or GLUDy | 6.21103 |
| 23 | FUM, ME2, THD2 and/or GLUDy | 6.09185 |
| 24 | PFLi, PPCK, PYK | 5.16721 |
| 25 | ADHEr, PPCK, THD2 and/or GLUDy | 4.91251 |
| 26 | ADHEr, PFK and/or FBA and/or TPI, PPCK | 4.61324 |
| 27 | ADHEr, HEX1, PFK and/or FBA and/or TPI | 4.5815 |
| 28 | ADHEr, FRD and/or SUCD4, PFK and/or FBA and/or TPI | 4.57316 |
| 29 | ADHEr, MDH, THD2 and/or GLUDy | 4.35906 |
| 30 | ADHEr, FRD and/or SUCD4, MDH | 4.3526 |
| 31 | ADHEr, GLCpts, PPCK | 4.33751 |
| 32 | ADHEr, HEX1, THD2 and/or GLUDy | 4.32305 |
| 33 | ADHEr, MDH, PPCK | 4.3218 |
| 34 | ADHEr, FUM, PPCK | 4.3218 |
| 35 | ADHEr, FRD and/or SUCD4, ME2 | 4.27691 |

TABLE 10-continued

Growth-coupled production designs for the succinyl-CoA:MAA pathway (FIG. 2).

| Design ID | Metabolic Transformations Targeted for Removal | Predicted MAA Yield |
|---|---|---|
| 36 | ADHEr, FUM, THD2 and/or GLUDy | 4.26872 |
| 37 | ADHEr, FRD and/or SUCD4, THD2 and/or GLUDy | 4.26122 |
| 38 | ADHEr, FRD and/or SUCD4, GLCpts | 4.23155 |
| 39 | ADHEr, FUM, HEX1 | 4.07963 |
| 40 | GLUDy, HEX1, THD2 and/or GLUDy | 3.74821 |
| 41 | ME2, PGL and/or G6PDHy, THD2 and/or GLUDy | 3.74546 |
| 42 | HEX1, ME2, THD2 and/or GLUDy | 3.17934 |
| 43 | MDH, PYK, THD2 and/or GLUDy | 3.01298 |
| 44 | MDH, PPCK, PYK | 2.88966 |
| 45 | FUM, PPCK, PYK | 2.88966 |
| 46 | PPCK, PYK, THD2 and/or GLUDy | 2.28488 |
| 47 | PFLi, PPCK, THD2 and/or GLUDy | 1.92036 |
| 48 | ACKr and/or PTAr, FRD and/or SUCD4, PFLi | 1.19121 |
| 49 | ADHEr, MDH, PGL and/or G6PDHy, THD2 and/or GLUDy | 10.50357 |
| 50 | ADHEr, MDH, PFLi, THD2 and/or GLUDy | 8.26017 |
| 51 | ADHEr, PFK and/or FBA and/or TPI, PFLi, PPCK | 7.5749 |
| 52 | ADHEr, FRD and/or SUCD4, PFK and/or FBA and/or TPI, PFLi | 7.49524 |
| 53 | ADHEr, HEX1, PFK and/or FBA and/or TPI, PFLi | 7.47549 |
| 54 | ADHEr, PFLi, PPCK, THD2 and/or GLUDy | 7.32448 |
| 55 | HEX1, ME2, PGL and/or G6PDHy, THD2 and/or GLUDy | 7.30328 |
| 56 | ADHEr, GLCpts, PFLi, PPCK | 7.07538 |
| 57 | ADHEr, HEX1, PFLi, THD2 and/or GLUDy | 7.04634 |
| 58 | ADHEr, FRD and/or SUCD4, ME2, PFLi | 7.04349 |
| 59 | GLUDy, HEX1, PFLi, THD2 and/or GLUDy | 7.02387 |
| 60 | ADHEr, FRD and/or SUCD4, PFLi, THD2 and/or GLUDy | 6.99958 |
| 61 | ADHEr, ASPT, LDH_D, MDH | 6.91371 |
| 62 | PFLi, PPCK, PYK, THD2 and/or GLUDy | 6.78153 |
| 63 | ADHEr, FUM, HEX1, PFLi | 6.65795 |
| 64 | FUM, ME2, PFK and/or FBA and/or TPI, PFLi | 6.3322 |
| 65 | ADHEr, FRD and/or SUCD4, ME2, THD2 and/or GLUDy | 6.21914 |
| 66 | FUM, ME2, PFLi, THD2 and/or GLUDy | 6.21103 |
| 67 | ADHEr, GLUDy, MDH, THD2 and/or GLUDy | 6.18117 |
| 68 | ADHEr, MDH, PPCK, THD2 and/or GLUDy | 6.17362 |
| 69 | ADHEr, FUM, PPCK, THD2 and/or GLUDy | 6.17362 |
| 70 | ME2, PFLi, PGL and/or G6PDHy, THD2 and/or GLUDy | 6.01239 |
| 71 | ADHEr, ASPT, MDH, PYK | 5.92643 |
| 72 | ADHEr, FRD and/or SUCD4, PFK and/or FBA and/or TPI, PPCK | 4.76879 |
| 73 | ADHEr, HEX1, PFK and/or FBA and/or TPI, PPCK | 4.76303 |
| 74 | ADHEr, FRD and/or SUCD4, HEX1, PFK and/or FBA and/or TPI | 4.73051 |
| 75 | ADHEr, FUM, PFK and/or FBA and/or TPI, THD2 and/or GLUDy | 4.63551 |
| 76 | ADHEr, MDH, PFK and/or FBA and/or TPI, THD2 and/or GLUDy | 4.63551 |
| 77 | ADHEr, FRD and/or SUCD4, PPCK, PYK | 4.53921 |
| 78 | ADHEr, FRD and/or SUCD4, LDH_D, PPCK | 4.4635 |
| 79 | ADHEr, FRD and/or SUCD4, GLCpts, MDH | 4.44642 |
| 80 | ADHEr, GLCpts, MDH, THD2 and/or GLUDy | 4.44284 |
| 81 | ADHEr, MDH, PYK, THD2 and/or GLUDy | 4.42534 |
| 82 | ADHEr, FUM, GLCpts, PPCK | 4.41046 |
| 83 | ADHEr, GLCpts, MDH, PPCK | 4.41046 |
| 84 | ADHEr, GLCpts, PPCK, THD2 and/or GLUDy | 4.40279 |
| 85 | ASPT, MDH, PGL and/or G6PDHy, PYK | 4.3931 |
| 86 | ADHEr, MDH, PPCK, PYK | 4.39083 |
| 87 | ADHEr, FUM, PPCK, PYK | 4.39083 |
| 88 | ADHEr, FRD and/or SUCD4, GLCpts, ME2 | 4.36844 |
| 89 | ADHEr, FUM, ME2, THD2 and/or GLUDy | 4.35906 |
| 90 | ADHEr, FRD and/or SUCD4, FUM, ME2 | 4.3526 |
| 91 | ADHEr, FUM, GLCpts, THD2 and/or GLUDy | 4.32647 |
| 92 | ADHEr, FRD and/or SUCD4, GLCpts, THD2 and/or GLUDy | 4.31559 |
| 93 | FRD and/or SUCD4, FUM, PFK and/or FBA and/or TPI, THD5 | 4.08513 |
| 94 | FRD and/or SUCD4, MDH, PFK and/or FBA and/or TPI, THD5 | 4.08513 |
| 95 | ACKr and/or PTAr, ME2, PGL and/or G6PDHy, THD2 and/or GLUDy | 3.89111 |
| 96 | PGL and/or G6PDHy, PPCK, PYK, THD2 and/or GLUDy | 3.46752 |
| 97 | FUM, HEX1, PFK and/or FBA and/or TPI, THD5 | 3.35722 |
| 98 | HEX1, MDH, PFK and/or FBA and/or TPI, THD5 | 3.35722 |
| 99 | FRD and/or SUCD4, ME2, PFLi, THD2 and/or GLUDy | 2.78398 |
| 100 | FRD and/or SUCD4, ME1x, ME2, PYK | 2.6437 |
| 101 | ACKr and/or PTAr, PFLi, PPCK, THD2 and/or GLUDy | 2.01602 |
| 102 | FRD and/or SUCD4, FUM, MDH, PYK | 1.89207 |
| 103 | ACKr and/or PTAr, ME2, PGL and/or G6PDHy, SUCOAS | 1.83792 |
| 104 | FUM, GLYCL, ME2, PFK and/or FBA and/or TPI | 1.36495 |
| 105 | ACKr and/or PTAr, FRD and/or SUCD4, GLU5K, PFLi | 1.24122 |
| 106 | ACKr and/or PTAr, FRD and/or SUCD4, G5SD, PFLi | 1.24122 |
| 107 | ACKr and/or PTAr, GLU5K, PFLi, PPCK | 1.09336 |
| 108 | ACKr and/or PTAr, G5SD, PFLi, PPCK | 1.09336 |
| 109 | ACKr and/or PTAr, AKGD, PFLi, PPCK | 1.04907 |

TABLE 10-continued

Growth-coupled production designs for the succinyl-CoA:MAA pathway (FIG. 2).

| Design ID | Metabolic Transformations Targeted for Removal | Predicted MAA Yield |
|---|---|---|
| 110 | ACKr and/or PTAr, ME2, PFLi, PPCK | 1.04907 |
| 111 | ACKr and/or PTAr, LDH_D, PFLi, PPCK | 1.04907 |
| 112 | ACKr and/or PTAr, PFLi, PGL and/or G6PDHy, PPCK | 1.04907 |
| 113 | ACKr and/or PTAr, ASPT, PFLi, PPCK | 1.04907 |
| 114 | ACKr and/or PTAr, PFLi, PPCK | 1.04907 |
| 115 | ACKr and/or PTAr, ACS, PFLi, PPCK | 1.04907 |
| 116 | ACKr and/or PTAr, ADHEr, ASPT, MDH | 0.91363 |
| 117 | FRD and/or SUCD4, PFK and/or FBA and/or TPI, THD2 and/or GLUDy, THD5 | 0.79247 |
| 118 | ADHEr, AKGD, ASPT, MDH | 0.7853 |
| 119 | ADHEr, ASPT, MDH, P5CD | 0.7853 |
| 120 | ADHEr, ASPT, MDH, PGL and/or G6PDHy | 0.7853 |
| 121 | ADHEr, ASPT, MDH, PDH | 0.7853 |
| 122 | ADHEr, ASPT, MDH, VALTA | 0.7853 |
| 123 | ADHEr, ASPT, MDH, ME2 | 0.7853 |
| 124 | ADHEr, ASPT, MDH, PPS | 0.7853 |
| 125 | ADHEr, ASPT, MDH, NACODA | 0.7853 |
| 126 | ADHEr, ASPT, MDH | 0.7853 |
| 127 | ADHEr, ASPT, LDH_D, MDH, PFLi | 11.64516 |
| 128 | ACKr and/or PTAr, ADHEr, FRD and/or SUCD4, LDH_D, ME2 | 10.90737 |
| 129 | ADHEr, FUM, ME2, PGL and/or G6PDHy, THD2 and/or GLUDy | 10.88038 |
| 130 | ADHEr, ICL, MDH, PGL and/or G6PDHy, THD2 and/or GLUDy | 10.88038 |
| 131 | ADHEr, MALS, MDH, PGL and/or G6PDHy, THD2 and/or GLUDy | 10.88038 |
| 132 | ASPT, MDH, PGL and/or G6PDHy, PYK, SERD_L | 10.86679 |
| 133 | ADHEr, GLCpts, MDH, PGL and/or G6PDHy, THD2 and/or GLUDy | 10.79871 |
| 134 | ADHEr, ASPT, MDH, PGL and/or G6PDHy, PYK | 10.7622 |
| 135 | ADHEr, FRD and/or SUCD4, ME2, PGL and/or G6PDHy, THD2 and/or GLUDy | 10.51703 |
| 136 | ASPT, MDH, PGL and/or G6PDHy, PYK, THD2 and/or GLUDy | 10.0408 |
| 137 | ACKr and/or PTAr, ADHEr, FRD and/or SUCD4, LDH_D, MDH | 9.09361 |
| 138 | MDH, ME2, PGL and/or G6PDHy, PYK, THD2 and/or GLUDy | 8.70446 |
| 139 | ACKr and/or PTAr, ADHEr, ASPT, LDH_D, MDH | 8.58714 |
| 140 | ACKr and/or PTAr, ADHEr, LDH_D, MDH, THD2 and/or GLUDy | 8.35695 |
| 141 | FUM, MDH, PGL and/or G6PDHy, PYK, THD2 and/or GLUDy | 8.28079 |
| 142 | ADHEr, FUM, ME2, PFLi, THD2 and/or GLUDy | 8.26017 |
| 143 | HEX1, ME2, PFLi, PGL and/or G6PDHy, THD2 and/or GLUDy | 7.86496 |
| 144 | ADHEr, ASPT, LDH_D, MDH, THD2 and/or GLUDy | 7.77845 |
| 145 | ADHEr, FUM, PFK and/or FBA and/or TPI, PFLi, THD2 and/or GLUDy | 7.59996 |
| 146 | ADHEr, MDH, PFK and/or FBA and/or TPI, PFLi, THD2 and/or GLUDy | 7.59996 |
| 147 | ADHEr, FRD and/or SUCD4, PFK and/or FBA and/or TPI, PFLi, THD2 and/or GLUDy | 7.55146 |
| 148 | ADHEr, HEX1, PFK and/or FBA and/or TPI, PFLi, THD2 and/or GLUDy | 7.5299 |
| 149 | ADHEr, FRD and/or SUCD4, LDH_D, PFLi, PPCK | 7.51427 |
| 150 | ADHEr, GLCpts, PFLi, PPCK, THD2 and/or GLUDy | 7.41336 |
| 151 | ADHEr, GLUDy, PFLi, PPCK, THD2 and/or GLUDy | 7.39109 |
| 152 | ADHEr, ASPT, MDH, PYK, THD2 and/or GLUDy | 7.30613 |
| 153 | ADHEr, ASPT, FRD and/or SUCD4, LDH_D, MDH | 7.2706 |
| 154 | ADHEr, FRD and/or SUCD4, LDH_D, MDH, PFLi | 7.25565 |
| 155 | ADHEr, MDH, PFLi, PYK, THD2 and/or GLUDy | 7.21719 |
| 156 | ADHEr, ASPT, LDH_D, MDH, PPCK | 7.20783 |
| 157 | ADHEr, FRD and/or SUCD4, GLCpts, ME2, PFLi | 7.19295 |
| 158 | ADHEr, LDH_D, MDH, PFLi, THD2 and/or GLUDy | 7.17902 |
| 159 | ADHEr, FUM, PFLi, PPCK, PYK | 7.16927 |
| 160 | ADHEr, MDH, PFLi, PPCK, PYK | 7.16927 |
| 161 | ADHEr, FRD and/or SUCD4, ME2, PFLi, THD2 and/or GLUDy | 7.14501 |
| 162 | ADHEr, GLUDy, HEX1, PFLi, THD2 and/or GLUDy | 7.13398 |
| 163 | ADHEr, FUM, LDH_D, PFLi, PPCK | 7.12989 |
| 164 | ADHEr, LDH_D, MDH, PFLi, PPCK | 7.12989 |
| 165 | ADHEr, ASPT, GLCpts, LDH_D, MDH | 7.08892 |
| 166 | ADHEr, FRD and/or SUCD4, FUM, LDH_D, PFLi | 7.06106 |
| 167 | ADHEr, FUM, GLCpts, PFLi, THD2 and/or GLUDy | 7.05969 |
| 168 | ADHEr, FUM, LDH_D, PFLi, THD2 and/or GLUDy | 7.03327 |
| 169 | ADHEr, FRD and/or SUCD4, HEX1, LDH_D, PFLi | 7.00666 |
| 170 | ADHEr, NADH6 | 5.44845 |
| 171 | ADHEr, ATPS4r | 2.36532 |
| 172 | ADHEr, PGI | 1.80553 |
| 173 | ADHEr, FUM | 1.31393 |
| 174 | ADHEr, HEX1 | 0.81503 |
| 175 | ADHEr, MDH | 0.7159 |
| 176 | ADHEr, PFK and/or FBA and/or TPI | 0.32284 |
| 177 | ADHEr, HEX1, PGI | 8.63121 |

TABLE 10-continued

Growth-coupled production designs for the succinyl-CoA:MAA pathway (FIG. 2).

| Design ID | Metabolic Transformations Targeted for Removal | Predicted MAA Yield |
|---|---|---|
| 178 | ADHEr, NADH6, PFLi | 6.77656 |
| 179 | ADHEr, NADH6, PGI | 6.11877 |
| 180 | ADHEr, NADH6, PFK and/or FBA and/or TPI | 6.01968 |
| 181 | ADHEr, FUM, PFLi | 5.98191 |
| 182 | ADHEr, NADH6, PPCK | 5.82769 |
| 183 | ADHEr, MDH, NADH6 | 5.64458 |
| 184 | ADHEr, NADH6, THD2 and/or GLUDy | 5.57367 |
| 185 | ADHEr, FUM, NADH6 | 5.51162 |
| 186 | ADHEr, HEX1, PFLi | 5.24339 |
| 187 | ADHEr, MDH, PFLi | 5.21195 |
| 188 | ADHEr, PFK and/or FBA and/or TPI, PFLi | 4.87678 |
| 189 | ADHEr, ATPS4r, PPCK | 4.69887 |
| 190 | ADHEr, PGI, PPCK | 4.67315 |
| 191 | ADHEr, FRD and/or SUCD4, PGI | 4.63924 |
| 192 | ADHEr, ATPS4r, MDH | 3.93602 |
| 193 | ADHEr, ATPS4r, THD2 and/or GLUDy | 3.20207 |
| 194 | ADHEr, ATPS4r, FUM | 2.70933 |
| 195 | ADHEr, PFLi, PGI | 2.48299 |
| 196 | ADHEr, MDH, PFK and/or FBA and/or TPI | 1.36009 |
| 197 | ADHEr, HEX1, PFLi, PGI | 9.89317 |
| 198 | ADHEr, HEX1, PGI, THD2 and/or GLUDy | 8.685 |
| 199 | ADHEr, MDH, NADH6, THD2 and/or GLUDy | 8.42455 |
| 200 | ADHEr, PFLi, PGI, PPCK | 7.60434 |
| 201 | ADHEr, NADH6, PFLi, PGI | 7.53021 |
| 202 | ADHEr, FRD and/or SUCD4, PFLi, PGI | 7.53021 |
| 203 | ADHEr, NADH6, PFK and/or FBA and/or TPI, PFLi | 7.49524 |
| 204 | ADHEr, ATPS4r, MDH, NADH6 | 7.09625 |
| 205 | ADHEr, MDH, NADH6, PFLi | 7.03739 |
| 206 | ACKr and/or PTAr, ADHEr, NADH6, PGI | 7.02293 |
| 207 | ADHEr, NADH6, PFLi, THD2 and/or GLUDy | 6.90622 |
| 208 | ADHEr, GLCpts, NADH6, PFLi | 6.89924 |
| 209 | ADHEr, NADH12, NADH6, PFLi | 6.8792 |
| 210 | ADHEr, FUM, NADH6, PFLi | 6.87559 |
| 211 | ADHEr, ME2, NADH6, PFLi | 6.83907 |
| 212 | ACKr and/or PTAr, ADHEr, FRD and/or SUCD4, PGI | 6.83058 |
| 213 | ADHEr, ATPS4r, NADH6, PGI | 6.62593 |
| 214 | ADHEr, NADH6, PPCK, THD2 and/or GLUDy | 6.57106 |
| 215 | ADHEr, ATPS4r, NADH6, PFK and/or FBA and/or TPI | 6.48882 |
| 216 | ADHEr, NADH6, PGI, PPCK | 6.4075 |
| 217 | ADHEr, NADH6, PFK and/or FBA and/or TPI, PPCK | 6.35839 |
| 218 | ADHEr, MDH, PFK and/or FBA and/or TPI, PFLi | 6.3322 |
| 219 | ADHEr, ATPS4r, FUM, NADH6 | 6.33033 |
| 220 | ADHEr, ME2, NADH6, THD2 and/or GLUDy | 6.30041 |
| 221 | ADHEr, HEX1, NADH6, PFK and/or FBA and/or TPI | 6.28787 |
| 222 | ADHEr, NADH6, PGI, THD2 and/or GLUDy | 6.17721 |
| 223 | ADHEr, NADH6, PFK and/or FBA and/or TPI, THD2 and/or GLUDy | 6.08946 |
| 224 | ADHEr, ATPS4r, NADH6, PPCK | 5.95899 |
| 225 | ADHEr, GLCpts, NADH6, PPCK | 5.94641 |
| 226 | ADHEr, NADH6, PPCK, PYK | 5.88622 |
| 227 | ADHEr, GLCpts, MDH, NADH6 | 5.76626 |
| 228 | ADHEr, ATPS4r, GLCpts, PPCK | 5.74112 |
| 229 | ADHEr, FUM, ME2, NADH6 | 5.64458 |
| 230 | ADHEr, FUM, HEX1, NADH6 | 5.59255 |
| 231 | ADHEr, ATPS4r, HEX1, NADH6 | 5.58729 |
| 232 | ADHEr, HEX1, NADH6, THD2 and/or GLUDy | 5.50758 |
| 233 | ADHEr, ATPS4r, MDH, THD2 and/or GLUDy | 5.42607 |
| 234 | ADHEr, ATPS4r, FUM, PPCK | 5.41736 |
| 235 | ADHEr, ATPS4r, MDH, PPCK | 5.41736 |
| 236 | ADHEr, ATPS4r, MDH, PGL and/or G6PDHy | 5.3991 |
| 237 | ADHEr, ATPS4r, PGI, PPCK | 5.39847 |
| 238 | ADHEr, ATPS4r, PFK and/or FBA and/or TPI, PPCK | 5.2252 |
| 239 | ADHEr, ATPS4r, FUM, HEX1 | 5.09544 |
| 240 | ADHEr, ATPS4r, PGL and/or G6PDHy, PPCK | 5.02209 |
| 241 | ADHEr, PFK and/or FBA and/or TPI, PFLi, PGI | 5.01176 |
| 242 | ADHEr, ATPS4r, PFLi, PGI | 5.00885 |
| 243 | ADHEr, ATPS4r, ME2, THD2 and/or GLUDy | 4.89177 |
| 244 | ADHEr, ATPS4r, FUM, THD2 and/or GLUDy | 4.82795 |
| 245 | ADHEr, FRD and/or SUCD4, PGI, PPCK | 4.80562 |
| 246 | ADHEr, FUM, PGI, THD2 and/or GLUDy | 4.69172 |
| 247 | ADHEr, MDH, PGI, THD2 and/or GLUDy | 4.69172 |
| 248 | ADHEr, ATPS4r, FUM, ME2 | 3.93602 |
| 249 | ADHEr, ME2, PGL and/or G6PDHy, THD2 and/or GLUDy | 3.74546 |
| 250 | ACKr and/or PTAr, ADHEr, ATPS4r, SUCOAS | 3.23462 |
| 251 | ADHEr, ASNS2, ATPS4r, GLU5K | 2.42406 |

TABLE 10-continued

Growth-coupled production designs for the succinyl-CoA:MAA pathway (FIG. 2).

| Design ID | Metabolic Transformations Targeted for Removal | Predicted MAA Yield |
|---|---|---|
| 252 | ADHEr, ASNS2, ATPS4r, G5SD | 2.42406 |
| 253 | ACKr and/or PTAr, ADHEr, LDH_D, MDH, NADH6 | 11.12044 |
| 254 | ADHEr, ATPS4r, MDH, PGL and/or G6PDHy, THD2 and/or GLUDy | 10.65458 |
| 255 | ADHEr, HEX1, PFLi, PGI, THD2 and/or GLUDy | 9.97214 |
| 256 | ADHEr, ATPS4r, GLCpts, MDH, PGL and/or G6PDHy | 9.83354 |
| 257 | ADHEr, ATPS4r, GLCpts, NADH6, PFLi | 9.61783 |
| 258 | ADHEr, ME2, NADH6, PGL and/or G6PDHy, THD2 and/or GLUDy | 8.74922 |
| 259 | ADHEr, GLCpts, MDH, NADH6, THD2 and/or GLUDy | 8.51047 |
| 260 | ADHEr, FUM, ME2, NADH6, THD2 and/or GLUDy | 8.42455 |
| 261 | ADHEr, ATPS4r, MDH, NADH6, PGL and/or G6PDHy | 8.35879 |
| 262 | ADHEr, ATPS4r, MDH, PDH, PGL and/or G6PDHy | 8.19203 |
| 263 | ADHEr, ATPS4r, GLCpts, MDH, NADH6 | 8.11809 |
| 264 | ADHEr, ASPT, ATPS4r, LDH_D, MDH | 8.05129 |
| 265 | ADHEr, ASPT, ATPS4r, MDH, PYK | 7.89307 |
| 266 | ADHEr, ASPT, ATPS4r, GLCpts, MDH | 7.76592 |
| 267 | ADHEr, ATPS4r, LDH_D, NADH6, PFLi | 7.66468 |
| 268 | ADHEr, FUM, PFLi, PGI, THD2 and/or GLUDy | 7.62739 |
| 269 | ADHEr, MDH, PFLi, PGI, THD2 and/or GLUDy | 7.62739 |
| 270 | ADHEr, NADH6, PFLi, PGI, THD2 and/or GLUDy | 7.58195 |
| 271 | ADHEr, FRD and/or SUCD4, PFLi, PGI, THD2 and/or GLUDy | 7.58195 |
| 272 | ADHEr, NADH6, PFK and/or FBA and/or TPI, PFLi, THD2 and/or GLUDy | 7.55146 |
| 273 | ADHEr, ATPS4r, ME2, PGL and/or G6PDHy, THD2 and/or GLUDy | 7.45944 |
| 274 | ACKr and/or PTAr, ADHEr, ATPS4r, NADH6, PGI | 7.37787 |
| 275 | ADHEr, NADH6, PFLi, PPCK, PYK | 7.33669 |
| 276 | ADHEr, HEX1, ME2, PGL and/or G6PDHy, THD2 and/or GLUDy | 7.30328 |
| 277 | ADHEr, LDH_D, NADH6, PFLi, PPCK | 7.29288 |
| 278 | ADHEr, ME2, NADH6, PFLi, THD2 and/or GLUDy | 7.26202 |
| 279 | ADHEr, GLCpts, MDH, NADH6, PFLi | 7.1878 |
| 280 | ADHEr, ATPS4r, ME2, NADH6, PFLi | 7.18544 |
| 281 | ADHEr, ASPT, LDH_D, MDH, NADH6 | 7.1375 |
| 282 | ADHEr, ATPS4r, FUM, ME2, NADH6 | 7.09625 |
| 283 | ADHEr, ME2, NADH12, NADH6, PFLi | 7.04349 |
| 284 | ADHEr, FUM, ME2, NADH6, PFLi | 7.03739 |
| 285 | ADHEr, GLCpts, NADH6, PFLi, THD2 and/or GLUDy | 7.02149 |
| 286 | ADHEr, ATPS4r, GLCpts, NADH6, PPCK | 7.00602 |
| 287 | ADHEr, ASPT, MDH, PFLi, PGL and/or G6PDHy, PYK | 12.62367 |
| 288 | ADHEr, ATPS4r, GLCpts, MDH, NADH6, PGL and/or G6PDHy | 12.58702 |
| 289 | ACKr and/or PTAr, ADHEr, LDH_D, MDH, PFLi, THD2 and/or GLUDy | 12.17542 |
| 290 | ADHEr, ASPT, GLCpts, LDH_D, MDH, PFLi | 12.14168 |
| 291 | ADHEr, ASPT, LDH_D, MDH, PFLi, THD2 and/or GLUDy | 11.92294 |
| 292 | ADHEr, ASPT, MDH, NADH6, PGL and/or G6PDHy, PYK | 11.86695 |
| 293 | ACKr and/or PTAr, ADHEr, FRD and/or SUCD4, LDH_D, MDH, THD2 and/or GLUDy | 11.81945 |
| 294 | ADHEr, ASPT, LDH_D, MDH, PFLi, PYK | 11.70177 |
| 295 | ADHEr, ASPT, FRD and/or SUCD4, MDH, PGL and/or G6PDHy, PYK | 11.69597 |
| 296 | ACKr and/or PTAr, ADHEr, FRD and/or SUCD4, GLCpts, LDH_D, MDH | 11.67923 |
| 297 | ACKr and/or PTAr, ADHEr, LDH_D, MDH, NADH6, THD2 and/or GLUDy | 11.60977 |
| 298 | ACKr and/or PTAr, ADHEr, GLCpts, LDH_D, MDH, NADH6 | 11.4429 |
| 299 | ADHEr, ASPT, MDH, PGL and/or G6PDHy, PYK, THD2 and/or GLUDy | 11.34596 |
| 300 | ADHEr, ATPS4r, GLCpts, MDH, PGL and/or G6PDHy, THD2 and/or GLUDy | 11.31505 |
| 301 | ADHEr, ATPS4r, MDH, NADH6, PGL and/or G6PDHy, THD2 and/or GLUDy | 11.27165 |
| 302 | ACKr and/or PTAr, ADHEr, ATPS4r, GLCpts, MDH, NADH6 | 11.21212 |
| 303 | ADHEr, LDH_D, NADH6 | 5.44845 |
| 304 | ADHEr, LDH_D, PPCK | 4.25091 |
| 305 | ADHEr, FRD and/or SUCD4, LDH_D | 4.17475 |
| 306 | ADHEr, ATPS4r, LDH_D | 2.36532 |
| 307 | ADHEr, LDH_D, PGI | 1.80553 |
| 308 | ADHEr, FUM, LDH_D | 1.31393 |
| 309 | ADHEr, HEX1, LDH_D | 0.81503 |
| 310 | ADHEr, LDH_D, MDH | 0.7159 |
| 311 | ADHEr, LDH_D, PFK and/or FBA and/or TPI | 0.32284 |
| 312 | ADHEr, HEX1, LDH_D, PGI | 8.63121 |
| 313 | ADHEr, LDH_D, PFLi, PPCK | 6.93528 |
| 314 | ADHEr, FRD and/or SUCD4, LDH_D, PFLi | 6.8792 |
| 315 | ADHEr, LDH_D, NADH6, PFLi | 6.77656 |
| 316 | ADHEr, LDH_D, NADH6, PGI | 6.11877 |
| 317 | ADHEr, LDH_D, MDH, THD2 and/or GLUDy | 6.11538 |

TABLE 10-continued

Growth-coupled production designs for the succinyl-CoA:MAA pathway (FIG. 2).

| Design ID | Metabolic Transformations Targeted for Removal | Predicted MAA Yield |
|---|---|---|
| 318 | ADHEr, LDH_D, NADH6, PFK and/or FBA and/or TPI | 6.01968 |
| 319 | ADHEr, FUM, LDH_D, PFLi | 5.98191 |
| 320 | ADHEr, LDH_D, NADH6, PPCK | 5.82769 |
| 321 | ADHEr, LDH_D, MDH, NADH6 | 5.64458 |
| 322 | ADHEr, LDH_D, NADH6, THD2 and/or GLUDy | 5.57367 |
| 323 | ADHEr, FUM, LDH_D, NADH6 | 5.51162 |
| 324 | ADHEr, HEX1, LDH_D, PFLi | 5.24339 |
| 325 | ADHEr, LDH_D, MDH, PFLi | 5.21195 |
| 326 | ADHEr, LDH_D, PPCK, THD2 and/or GLUDy | 4.91251 |
| 327 | ADHEr, LDH_D, PFK and/or FBA and/or TPI, PFLi | 4.87678 |
| 328 | ADHEr, ATPS4r, LDH_D, PPCK | 4.69887 |
| 329 | ADHEr, LDH_D, PGI, PPCK | 4.67315 |
| 330 | ADHEr, FRD and/or SUCD4, LDH_D, PGI | 4.63924 |
| 331 | ADHEr, LDH_D, PFK and/or FBA and/or TPI, PPCK | 4.61324 |
| 332 | ADHEr, HEX1, LDH_D, PFK and/or FBA and/or TPI | 4.5815 |
| 333 | ADHEr, FRD and/or SUCD4, LDH_D, PFK and/or FBA and/or TPI | 4.57316 |
| 334 | ADHEr, FRD and/or SUCD4, LDH_D, MDH | 4.3526 |
| 335 | ADHEr, GLCpts, LDH_D, PPCK | 4.33751 |
| 336 | ADHEr, HEX1, LDH_D, THD2 and/or GLUDy | 4.32305 |
| 337 | ADHEr, LDH_D, MDH, PPCK | 4.3218 |
| 338 | ADHEr, FUM, LDH_D, PPCK | 4.3218 |
| 339 | ADHEr, FRD and/or SUCD4, LDH_D, ME2 | 4.27691 |
| 340 | ADHEr, FUM, LDH_D, THD2 and/or GLUDy | 4.26872 |
| 341 | ADHEr, FRD and/or SUCD4, LDH_D, THD2 and/or GLUDy | 4.26122 |
| 342 | ADHEr, FRD and/or SUCD4, GLCpts, LDH_D | 4.23155 |
| 343 | ADHEr, FUM, HEX1, LDH_D | 4.07963 |
| 344 | ADHEr, ATPS4r, LDH_D, MDH | 3.93602 |
| 345 | ADHEr, ATPS4r, LDH_D, THD2 and/or GLUDy | 3.20207 |
| 346 | ADHEr, ATPS4r, FUM, LDH_D | 2.70933 |
| 347 | ADHEr, LDH_D, PFLi, PGI | 2.48299 |
| 348 | ADHEr, LDH_D, MDH, PFK and/or FBA and/or TPI | 1.36009 |
| 349 | ADHEr, LDH_D, MDH, PGL and/or G6PDHy, THD2 and/or GLUDy | 10.50357 |
| 350 | ADHEr, HEX1, LDH_D, PFLi, PGI | 9.89317 |
| 351 | ADHEr, HEX1, LDH_D, PGI, THD2 and/or GLUDy | 8.685 |
| 352 | ADHEr, LDH_D, MDH, NADH6, THD2 and/or GLUDy | 8.42455 |
| 353 | ADHEr, LDH_D, PFLi, PGI, PPCK | 7.60434 |
| 354 | ADHEr, LDH_D, PFK and/or FBA and/or TPI, PFLi, PPCK | 7.5749 |
| 355 | ADHEr, LDH_D, NADH6, PFLi, PGI | 7.53021 |
| 356 | ADHEr, FRD and/or SUCD4, LDH_D, PFLi, PGI | 7.53021 |
| 357 | ADHEr, LDH_D, NADH6, PFK and/or FBA and/or TPI, PFLi | 7.49524 |
| 358 | ADHEr, FRD and/or SUCD4, LDH_D, PFK and/or FBA and/or TPI, PFLi | 7.49524 |
| 359 | ADHEr, HEX1, LDH_D, PFK and/or FBA and/or TPI, PFLi | 7.47549 |
| 360 | ADHEr, LDH_D, PFLi, PPCK, THD2 and/or GLUDy | 7.32448 |
| 361 | ADHEr, ATPS4r, LDH_D, MDH, NADH6 | 7.09625 |
| 362 | ADHEr, GLCpts, LDH_D, PFLi, PPCK | 7.07538 |
| 363 | ADHEr, HEX1, LDH_D, PFLi, THD2 and/or GLUDy | 7.04634 |
| 364 | ADHEr, FRD and/or SUCD4, LDH_D, ME2, PFLi | 7.04349 |
| 365 | ADHEr, LDH_D, MDH, NADH6, PFLi | 7.03739 |
| 366 | ACKr and/or PTAr, ADHEr, LDH_D, NADH6, PGI | 7.02293 |
| 367 | ACKr and/or PTAr, ADHEr, FUM, LDH_D, ME2, NADH6 | 11.12044 |
| 368 | ADHEr, FRD and/or SUCD4, LDH_D, ME2, PGL and/or G6PDHy, THD2 and/or GLUDy | 10.92104 |
| 369 | ADHEr, FUM, LDH_D, ME2, PGL and/or G6PDHy, THD2 and/or GLUDy | 10.88038 |
| 370 | ADHEr, ICL, LDH_D, MDH, PGL and/or G6PDHy, THD2 and/or GLUDy | 10.88038 |
| 371 | ADHEr, LDH_D, MALS, MDH, PGL and/or G6PDHy, THD2 and/or GLUDy | 10.88038 |
| 372 | ADHEr, GLCpts, LDH_D, MDH, PGL and/or G6PDHy, THD2 and/or GLUDy | 10.79871 |
| 373 | ADHEr, LDH_D, MDH, NADH6, PGL and/or G6PDHy, THD2 and/or GLUDy | 10.79806 |
| 374 | ADHEr, ASPT, LDH_D, MDH, PGL and/or G6PDHy, PYK | 10.7622 |
| 375 | ADHEr, ATPS4r, LDH_D, MDH, PGL and/or G6PDHy, THD2 and/or GLUDy | 10.65458 |
| 376 | ACKr and/or PTAr, ADHEr, LDH_D, MALS, MDH, THD2 and/or GLUDy | 10.65175 |
| 377 | ACKr and/or PTAr, ADHEr, FUM, LDH_D, ME2, THD2 and/or GLUDy | 10.65175 |
| 378 | ACKr and/or PTAr, ADHEr, ICL, LDH_D, MDH, THD2 and/or GLUDy | 10.65175 |
| 379 | ACKr and/or PTAr, ADHEr, FUM, LDH_D, MDH, THD2 and/or GLUDy | 10.65175 |
| 380 | ADHEr, FRD and/or SUCD4, LDH_D, MDH, PFLi, THD2 and/or GLUDy | 10.5877 |

TABLE 10-continued

Growth-coupled production designs for the succinyl-CoA:MAA pathway (FIG. 2).

| Design ID | Metabolic Transformations Targeted for Removal | Predicted MAA Yield |
|---|---|---|
| 381 | ADHEr, ASPT, ATPS4r, GLCpts, LDH_D, MDH | 10.28675 |
| 382 | ADHEr, FRD and/or SUCD4, LDH_D, MDH, PFLi, PGI | 10.27254 |
| 383 | ADHEr, FRD and/or SUCD4, FUM, LDH_D, PFLi, PGI | 10.24846 |
| 384 | ADHEr, HEX1, LDH_D, PFLi, PGI, THD2 and/or GLUDy | 9.97214 |
| 385 | ADHEr, ASPT4r, GLCpts, LDH_D, MDH, PGL and/or G6PDHy | 9.83354 |
| 386 | ADHEr, ASPT, ATPS4r, LDH_D, MDH, NADH6 | 9.76182 |
| 387 | ADHEr, ATPS4r, GLCpts, LDH_D, NADH6, PFLi | 9.61783 |
| 388 | ADHEr, ATPS4r, LDH_D, MDH, NADH6, PGL and/or G6PDHy | 9.57049 |
| 389 | ACKr and/or PTAr, ADHEr, LDH_D, MDH, PYK, THD2 and/or GLUDy | 9.52381 |
| 390 | ACKr and/or PTAr, ADHEr, CITL, LDH_D, NADH12, NADH6 | 9.3809 |
| 391 | ACKr and/or PTAr, ADHEr, FRD and/or SUCD4, LDH_D, MDH, PFLi | 9.27557 |
| 392 | ADHEr, ATPS4r, LDH_D, MDH, PDH, PGL and/or G6PDHy | 9.21865 |
| 393 | ADHEr, ASPT, LDH_D, MDH, NADH12, NADH6 | 9.04167 |
| 394 | ADHEr, FRD and/or SUCD4, LDH_D, PFLi, PPCK, THD2 and/or GLUDy | 9.01487 |
| 395 | ADHEr, ATPS4r, LDH_D, MDH, NADH6, PFLi | 8.9614 |
| 396 | ADHEr, ATPS4r, LDH_D, NADH12, NADH6, PFLi | 8.93851 |
| 397 | ADHEr, FRD and/or SUCD4, HEX1, LDH_D, MDH, THD2 and/or GLUDy | 8.89295 |
| 398 | ADHEr, LDH_D, ME2, NADH6, PGL and/or G6PDHy, THD2 and/or GLUDy | 8.74922 |
| 399 | ADHEr, GLUDy, LDH_D, MDH, PFLi, THD2 and/or GLUDy | 8.69116 |
| 400 | ACKr and/or PTAr, ADHEr, FUM, HEX1, LDH_D, NADH6 | 8.68896 |
| 401 | ADHEr, ASPT, ATPS4r, LDH_D, MDH, PGL and/or G6PDHy | 8.68776 |
| 402 | ADHEr, FUM, LDH_D, PFLi, PPCK, THD2 and/or GLUDy | 8.66 |
| 403 | ADHEr, LDH_D, MDH, PFLi, PPCK, THD2 and/or GLUDy | 8.66 |
| 404 | ADHEr, FRD and/or SUCD4, LDH_D, ME2, PFLi, THD2 and/or GLUDy | 8.6194 |
| 405 | ADHEr, LDH_D, MDH, NADH6, PFLi, THD2 and/or GLUDy | 8.58651 |
| 406 | ADHEr, ATPS4r, LDH_D, MDH, PFLi, THD2 and/or GLUDy | 8.54512 |
| 407 | ADHEr, GLCpts, LDH_D, MDH, NADH6, THD2 and/or GLUDy | 8.51047 |
| 408 | ADHEr, FUM, LDH_D, ME2, NADH6, THD2 and/or GLUDy | 8.42455 |
| 409 | ACKr and/or PTAr, ADHEr, CITL, HEX1, LDH_D, NADH6 | 8.38082 |
| 410 | ADHEr, HEX1, LDH_D, MDH, PFLi, THD2 and/or GLUDy | 8.33314 |
| 411 | ADHEr, FUM, HEX1, LDH_D, PFLi, THD2 and/or GLUDy | 8.33314 |
| 412 | ADHEr, FUM, LDH_D, ME2, PFLi, THD2 and/or GLUDy | 8.26017 |
| 413 | ACKr and/or PTAr, ADHEr, ATPS4r, FUM, LDH_D, NADH6 | 8.20955 |
| 414 | ADHEr, ASPT, ATPS4r, LDH_D, MDH, PPCK | 8.16498 |
| 415 | ADHEr, ATPS4r, GLCpts, LDH_D, MDH, NADH6 | 8.11809 |
| 416 | ADHEr, ATPS4r, LDH_D, NADH6, PFLi, PPCK | 7.80331 |
| 417 | ADHEr, ATPS4r, LDH_D, NADH6, PFLi, PPS | 7.78081 |
| 418 | ADHEr, ASPT, LDH_D, MDH, PGI, THD2 and/or GLUDy | 7.70411 |
| 419 | ADHEr, ASPT, LDH_D, MDH, PFK and/or FBA and/or TPI, THD2 and/or GLUDy | 7.69846 |
| 420 | ADHEr, FRD and/or SUCD4, LDH_D, MDH, PFK and/or FBA and/or TPI, PFLi | 7.69078 |
| 421 | ADHEr, FRD and/or SUCD4, GLCpts, LDH_D, PFLi, PPCK | 7.66606 |
| 422 | ADHEr, FRD and/or SUCD4, FUM, LDH_D, PFK and/or FBA and/or TPI, PFLi | 7.66287 |
| 423 | ADHEr, LDH_D, MDH, PFLi, PGI, THD2 and/or GLUDy | 7.62739 |
| 424 | ADHEr, FUM, LDH_D, PFLi, PGI, THD2 and/or GLUDy | 7.62739 |
| 425 | ACKr and/or PTAr, ADHEr, LDH_D, ME2, NADH12, NADH6 | 7.61395 |
| 426 | ADHEr, FUM, LDH_D, PFK and/or FBA and/or TPI, PFLi, THD2 and/or GLUDy | 7.59996 |
| 427 | ADHEr, LDH_D, MDH, PFK and/or FBA and/or TPI, PFLi, THD2 and/or GLUDy | 7.59996 |
| 428 | ADHEr, FRD and/or SUCD4, LDH_D, PFLi, PGI, THD2 and/or GLUDy | 7.58195 |
| 429 | ADHEr, LDH_D, NADH6, PFLi, PGI, THD2 and/or GLUDy | 7.58195 |
| 430 | ADHEr, ASPT, FRD and/or SUCD4, LDH_D, MDH, PPCK | 7.57014 |
| 431 | ADHEr, FRD and/or SUCD4, LDH_D, PFLi, PPCK, PYK | 7.56477 |
| 432 | ADHEr, LDH_D, NADH6, PFLi, PPCK, THD2 and/or GLUDy | 7.55966 |
| 433 | ADHEr, FRD and/or SUCD4, LDH_D, PFK and/or FBA and/or TPI, PFLi, THD2 and/or GLUDy | 7.55146 |
| 434 | ADHEr, LDH_D, NADH6, PFK and/or FBA and/or TPI, PFLi, THD2 and/or GLUDy | 7.55146 |
| 435 | ADHEr, ATPS4r, LDH_D, PFLi, PPCK, THD2 and/or GLUDy | 7.5467 |
| 436 | ADHEr, HEX1, LDH_D, PFK and/or FBA and/or TPI, PFLi, THD2 and/or GLUDy | 7.5299 |
| 437 | ADHEr, LDH_D, NADH12, NADH6, PFLi, PPCK | 7.51427 |
| 438 | ADHEr, FRD and/or SUCD4, GLUDy, LDH_D, MDH, THD2 and/or GLUDy | 7.51308 |
| 439 | ADHEr, LDH_D, MDH, NADH6, PFLi, PPCK | 7.51113 |
| 440 | ADHEr, FUM, LDH_D, NADH6, PFLi, PPCK | 7.51113 |

TABLE 10-continued

Growth-coupled production designs for the succinyl-CoA:MAA pathway (FIG. 2).

| Design ID | Metabolic Transformations Targeted for Removal | Predicted MAA Yield |
|---|---|---|
| 441 | ADHEr, ATPS4r, LDH_D, ME2, PGL and/or G6PDHy, THD2 and/or GLUDy | 7.45944 |
| 442 | ADHEr, ASPT, FRD and/or SUCD4, GLCpts, LDH_D, MDH | 7.45295 |
| 443 | ADHEr, GLCpts, LDH_D, NADH6, PFLi, PPCK | 7.44019 |
| 444 | ADHEr, ASPT, LDH_D, MDH, NADH6, PPCK | 7.43508 |
| 445 | ADHEr, GLCpts, LDH_D, PFLi, PPCK, THD2 and/or GLUDy | 7.41336 |
| 446 | ADHEr, FRD and/or SUCD4, GLCpts, LDH_D, MDH, PFLi | 7.41073 |
| 447 | ADHEr, FRD and/or SUCD4, LDH_D, PFLi, PRO1z, THD2 and/or GLUDy | 7.39974 |
| 448 | ADHEr, GLUDy, LDH_D, PFLi, PPCK, THD2 and/or GLUDy | 7.39109 |
| 449 | ADHEr, FUM, LDH_D, NADH6, PFLi, THD2 and/or GLUDy | 7.3905 |
| 450 | ADHEr, ASPT, GLCpts, LDH_D, MDH, PPCK | 7.38004 |
| 451 | ACKr and/or PTAr, ADHEr, ATPS4r, LDH_D, NADH6, PGI | 7.37787 |
| 452 | ADHEr, ASPT, FRD and/or SUCD4, LDH_D, MDH, THD2 and/or GLUDy | 7.35321 |
| 453 | ADHEr, ASPT, GLCpts, LDH_D, MDH, NADH6 | 7.31719 |
| 454 | ADHEr, GLCpts, LDH_D, MDH, PFLi, THD2 and/or GLUDy | 7.31585 |
| 455 | ADHEr, ASPT, LDH_D, MDH, PYK, THD2 and/or GLUDy | 7.30613 |
| 456 | ADHEr, HEX1, LDH_D, ME2, PGL and/or G6PDHy, THD2 and/or GLUDy | 7.30328 |
| 457 | ADHEr, ASPT, LDH_D, MDH, PPCK, THD2 and/or GLUDy | 7.2931 |
| 458 | ADHEr, FUM, GLCpts, LDH_D, PFLi, PPCK | 7.27491 |
| 459 | ADHEr, GLCpts, LDH_D, MDH, PFLi, PPCK | 7.27491 |
| 460 | ADHEr, LDH_D, ME2, NADH6, PFLi, THD2 and/or GLUDy | 7.26202 |
| 461 | ADHEr, FRD and/or SUCD4, FUM, LDH_D, ME2, PFLi | 7.25565 |
| 462 | ADHEr, LDH_D, MDH, NADH12, NADH6, PFLi | 7.25565 |
| 463 | ADHEr, FRD and/or SUCD4, HEX1, LDH_D, PFLi, THD2 and/or GLUDy | 7.23622 |
| 464 | ADHEr, ASPT, LDH_D, MDH, NADH6, THD2 and/or GLUDy | 7.23393 |
| 465 | ADHEr, HEX1, LDH_D, NADH6, PFLi, THD2 and/or GLUDy | 7.21989 |
| 466 | ADHEr, FRD and/or SUCD4, FUM, HEX1, LDH_D, PFLi | 7.2125 |
| 467 | ADHEr, FRD and/or SUCD4, FUM, LDH_D, PFLi, THD2 and/or GLUDy | 7.21135 |
| 468 | ADHEr, ATPS4r, HEX1, LDH_D, PFLi, THD2 and/or GLUDy | 7.20895 |
| 469 | ADHEr, ATPS4r, LDH_D, MDH, NADH6, THD2 and/or GLUDy | 7.19914 |
| 470 | ADHEr, FRD and/or SUCD4, GLCpts, LDH_D, ME2, PFLi | 7.19295 |
| 471 | ADHEr, ATPS4r, FUM, LDH_D, NADH6, PPCK | 7.19078 |
| 472 | ADHEr, ATPS4r, LDH_D, MDH, NADH6, PPCK | 7.19078 |
| 473 | ADHEr, ASPT, GLCpts, LDH_D, MDH, THD2 and/or GLUDy | 7.18851 |
| 474 | ADHEr, GLCpts, LDH_D, MDH, NADH6, PFLi | 7.1878 |
| 475 | ADHEr, GLUDy, HEX1, LDH_D, PFLi, THD2 and/or GLUDy | 7.13398 |
| 476 | ADHEr, ATPS4r, FUM, LDH_D, ME2, NADH6 | 7.09625 |
| 477 | ADHEr, ATPS4r, FUM, HEX1, LDH_D, NADH6 | 7.09284 |
| 478 | ADHEr, FUM, LDH_D, NADH12, NADH6, PFLi | 7.06106 |
| 479 | ADHEr, LDH_D, ME2, NADH12, NADH6, PFLi | 7.04349 |
| 480 | ADHEr, FUM, LDH_D, ME2, NADH6, PFLi | 7.03739 |
| 481 | ADHEr, GLCpts, LDH_D, NADH6, PFLi, THD2 and/or GLUDy | 7.02149 |
| 482 | ADHEr, HEX1, LDH_D, NADH12, NADH6, PFLi | 7.00666 |
| 483 | ADHEr, ATPS4r, GLCpts, LDH_D, NADH6, PPCK | 7.00602 |
| 484 | ADHEr, FUM, HEX1, LDH_D, NADH6, PFLi | 7.00047 |

TABLE 11

Growth-coupled production designs for the 4-HB-CoA:MAA pathway (FIG. 6).

| Design ID | Metabolic Transformations Targeted for Removal | Predicted MAA Yield |
|---|---|---|
| 1 | ATPS4r | 1.41919 |
| 2 | ADHEr, NADH6 | 5.51519 |
| 3 | ADHEr, PPCK | 4.28804 |
| 4 | ADHEr, FRD and/or SUCD4 | 4.21382 |
| 5 | PFLi, PGI | 2.45706 |
| 6 | ATPS4r, THD2 and/or GLUDy | 1.92124 |
| 7 | ADHEr, PGI | 1.8023 |
| 8 | ADHEr, FUM | 1.29828 |
| 9 | FRD and/or SUCD4, PFLi | 1.06442 |
| 10 | NADH6, PFLi | 1.06442 |
| 11 | PFLi, PPCK | 0.93931 |
| 12 | ADHEr, HEX1 | 0.80948 |

TABLE 11-continued

Growth-coupled production designs for the 4-HB-CoA:MAA pathway (FIG. 6).

| Design ID | Metabolic Transformations Targeted for Removal | Predicted MAA Yield |
|---|---|---|
| 13 | ADHEr, PFK and/or FBA and/or TPI | 0.32133 |
| 14 | ADHEr, HEX1, PGI | 8.71082 |
| 15 | HEX1, PFLi, PGI | 7.22213 |
| 16 | ADHEr, NADH6, PFLi | 6.8792 |
| 17 | ADHEr, NADH6, PGI | 6.18566 |
| 18 | ADHEr, NADH6, PFK and/or FBA and/or TPI | 6.09754 |
| 19 | ADHEr, MDH, THD2 and/or GLUDy | 6.05682 |
| 20 | ADHEr, NADH6, PPCK | 5.89771 |
| 21 | ADHEr, MDH, NADH6 | 5.71411 |
| 22 | ADHEr, NADH6, THD2 and/or GLUDy | 5.63485 |
| 23 | ADHEr, FUM, NADH6 | 5.58019 |
| 24 | ATPS4r, HEX1, PFLi | 5.2123 |
| 25 | ADHEr, PFLi, PPCK | 5.15556 |
| 26 | ATPS4r, PFLi, PGI | 5.00885 |
| 27 | ADHEr, PPCK, THD2 and/or GLUDy | 4.91748 |
| 28 | ATPS4r, PFK and/or FBA and/or TPI, PFLi | 4.90696 |
| 29 | ADHEr, PGI, PPCK | 4.71025 |
| 30 | ADHEr, FRD and/or SUCD4, PGI | 4.67759 |
| 31 | ADHEr, PFK and/or FBA and/or TPI, PPCK | 4.65664 |
| 32 | ADHEr, HEX1, PFK and/or FBA and/or TPI | 4.62311 |
| 33 | ADHEr, FRD and/or SUCD4, PFK and/or FBA and/or TPI | 4.61796 |
| 34 | ATPS4r, ME2, THD2 and/or GLUDy | 4.44391 |
| 35 | ADHEr, FRD and/or SUCD4, MDH | 4.39382 |
| 36 | ADHEr, GLCpts, PPCK | 4.3754 |
| 37 | ADHEr, FUM, PPCK | 4.36046 |
| 38 | ADHEr, MDH, PPCK | 4.36046 |
| 39 | ADHEr, FRD and/or SUCD4, ME2 | 4.31642 |
| 40 | ADHEr, FUM, THD2 and/or GLUDy | 4.30511 |
| 41 | ADHEr, FRD and/or SUCD4, THD2 and/or GLUDy | 4.29689 |
| 42 | ADHEr, FRD and/or SUCD4, GLCpts | 4.27312 |
| 43 | ADHEr, FUM, HEX1 | 4.11519 |
| 44 | ACKr and/or PTAr, AKGD, ATPS4r | 3.45333 |
| 45 | ME2, PGL and/or G6PDHy, THD2 and/or GLUDy | 3.397 |
| 46 | ACKr and/or PTAr, ATPS4r, SUCOAS | 3.23462 |
| 47 | ADHEr, HEX1, THD2 and/or GLUDy | 3.09661 |
| 48 | MDH, PFLi, THD2 and/or GLUDy | 3.00855 |
| 49 | ATPS4r, PPCK, PYK | 2.7407 |
| 50 | PFLi, PPCK, THD2 and/or GLUDy | 1.87744 |
| 51 | ACKr and/or PTAr, FRD and/or SUCD4, PFLi | 1.17455 |
| 52 | ACKr and/or PTAr, NADH6, PFLi | 1.17455 |
| 53 | MDH, PGL and/or G6PDHy, THD2 and/or GLUDy | 1.07056 |
| 54 | ACKr and/or PTAr, PFLi, PPCK | 1.03613 |
| 55 | FUM, PFLi, THD2 and/or GLUDy | 0.95467 |
| 56 | ADHEr, ASPT, MDH | 0.77578 |
| 57 | FUM, HEX1, PFLi | 0.70584 |
| 58 | HEX1, PFK and/or FBA and/or TPI, PFLi | 0.51097 |
| 59 | HEX1, PFLi, THD2 and/or GLUDy | 0.43064 |
| 60 | ASPT, FUM, PFLi | 0.26432 |
| 61 | ASPT, MDH, PFLi | 0.22676 |
| 62 | ADHEr, MDH, PGL and/or G6PDHy, THD2 and/or GLUDy | 9.4382 |
| 63 | ADHEr, ATPS4r, GLCpts, NADH6 | 8.91415 |
| 64 | ADHEr, ATPS4r, NADH6, PGI | 7.77864 |
| 65 | ADHEr, FRD and/or SUCD4, PFLi, PGI | 7.64241 |
| 66 | ADHEr, NADH6, PFLi, PGI | 7.64241 |
| 67 | ADHEr, FRD and/or SUCD4, PFK and/or FBA and/or TPI, PFLi | 7.61537 |
| 68 | ADHEr, NADH6, PFK and/or FBA and/or TPI, PFLi | 7.61537 |
| 69 | ACKr and/or PTAr, HEX1, PFLi, PGI | 7.28181 |
| 70 | ADHEr, ATPS4r, MDH, NADH6 | 7.05818 |
| 71 | ADHEr, ASPT, LDH_D, MDH | 7.03701 |
| 72 | ADHEr, NADH6, PFLi, THD2 and/or GLUDy | 6.99958 |
| 73 | ADHEr, FRD and/or SUCD4, LDH_D, PFLi | 6.98499 |
| 74 | ADHEr, MDH, NADH6, THD2 and/or GLUDy | 6.81498 |
| 75 | ADHEr, PFLi, PPCK, THD2 and/or GLUDy | 6.6221 |
| 76 | ADHEr, NADH6, PPCK, THD2 and/or GLUDy | 6.57996 |
| 77 | ADHEr, ATPS4r, NADH6, PPCK | 6.53047 |
| 78 | ADHEr, HEX1, NADH6, PFK and/or FBA and/or TPI | 6.36651 |
| 79 | ADHEr, ATPS4r, HEX1, NADH6 | 6.24352 |
| 80 | ADHEr, NADH6, PGI, THD2 and/or GLUDy | 6.23747 |
| 81 | ADHEr, FRD and/or SUCD4, ME2, THD2 and/or GLUDy | 6.22745 |
| 82 | ADHEr, ME2, NADH6, THD2 and/or GLUDy | 6.21872 |
| 83 | ADHEr, NADH6, PFK and/or FBA and/or TPI, THD2 and/or GLUDy | 6.15963 |
| 84 | ADHEr, ATPS4r, MDH, THD2 and/or GLUDy | 6.13586 |
| 85 | ADHEr, FUM, ME2, THD2 and/or GLUDy | 6.05682 |

TABLE 11-continued

Growth-coupled production designs for the 4-HB-CoA:MAA pathway (FIG. 6).

| Design ID | Metabolic Transformations Targeted for Removal | Predicted MAA Yield |
|---|---|---|
| 86 | ADHEr, GLCpts, NADH6, PPCK | 6.01786 |
| 87 | ADHEr, FUM, PFLi, THD2 and/or GLUDy | 5.92596 |
| 88 | ADHEr, ATPS4r, MDH, PPCK | 5.89299 |
| 89 | ADHEr, ATPS4r, FUM, PPCK | 5.89299 |
| 90 | ADHEr, ASPT, MDH, PYK | 5.87822 |
| 91 | ATPS4r, FUM, PFLi, THD2 and/or GLUDy | 5.87538 |
| 92 | ADHEr, GLCpts, MDH, NADH6 | 5.83728 |
| 93 | ADHEr, FRD and/or SUCD4, GLCpts, PFLi | 5.82636 |
| 94 | ATPS4r, ME2, PGL and/or G6PDHy, THD2 and/or GLUDy | 5.77678 |
| 95 | ADHEr, FUM, ME2, NADH6 | 5.71411 |
| 96 | ADHEr, ATPS4r, FUM, HEX1 | 5.67609 |
| 97 | ADHEr, FUM, HEX1, NADH6 | 5.6596 |
| 98 | ADHEr, HEX1, NADH6, THD2 and/or GLUDy | 5.56588 |
| 99 | ME2, PFLi, PGL and/or G6PDHy, THD2 and/or GLUDy | 5.37063 |
| 100 | ADHEr, HEX1, PFLi, PPS | 5.23221 |
| 101 | ADHEr, FUM, HEX1, PFLi | 5.20022 |
| 102 | ADHEr, HEX1, MDH, PFLi | 5.20022 |
| 103 | ATPS4r, PFLi, PPCK, PYK | 5.11897 |
| 104 | ADHEr, ATPS4r, HEX1, MDH | 4.91648 |
| 105 | ADHEr, FUM, PFK and/or FBA and/or TPI, PFLi | 4.88964 |
| 106 | ADHEr, MDH, PFK and/or FBA and/or TPI, PFLi | 4.88964 |
| 107 | ADHEr, PFK and/or FBA and/or TPI, PFLi, PPS | 4.88619 |
| 108 | ADHEr, FRD and/or SUCD4, HEX1, PFK and/or FBA and/or TPI | 4.77488 |
| 109 | ADHEr, FUM, PGI, THD2 and/or GLUDy | 4.72683 |
| 110 | ADHEr, MDH, PGI, THD2 and/or GLUDy | 4.72683 |
| 111 | ADHEr, FUM, PFK and/or FBA and/or TPI, THD2 and/or GLUDy | 4.67659 |
| 112 | ADHEr, MDH, PFK and/or FBA and/or TPI, THD2 and/or GLUDy | 4.67659 |
| 113 | ADHEr, FRD and/or SUCD4, PPCK, PYK | 4.5823 |
| 114 | ADHEr, FRD and/or SUCD4, LDH_D, PPCK | 4.50446 |
| 115 | ADHEr, FRD and/or SUCD4, GLCpts, MDH | 4.48854 |
| 116 | ADHEr, GLCpts, MDH, THD2 and/or GLUDy | 4.48038 |
| 117 | ADHEr, MDH, PYK, THD2 and/or GLUDy | 4.46392 |
| 118 | ADHEr, GLCpts, MDH, PPCK | 4.44991 |
| 119 | ADHEr, FUM, GLCpts, PPCK | 4.44991 |
| 120 | ADHEr, GLCpts, PPCK, THD2 and/or GLUDy | 4.43743 |
| 121 | ADHEr, MDH, PPCK, PYK | 4.43142 |
| 122 | ADHEr, FUM, PPCK, PYK | 4.43142 |
| 123 | ADHEr, FRD and/or SUCD4, GLCpts, ME2 | 4.40879 |
| 124 | ADHEr, FRD and/or SUCD4, FUM, ME2 | 4.39382 |
| 125 | ADHEr, FUM, GLCpts, THD2 and/or GLUDy | 4.3649 |
| 126 | ADHEr, FRD and/or SUCD4, GLCpts, THD2 and/or GLUDy | 4.3533 |
| 127 | ME2, NADH6, PGL and/or G6PDHy, THD2 and/or GLUDy | 4.08146 |
| 128 | ADHEr, HEX1, PGL and/or G6PDHy, THD2 and/or GLUDy | 4.06156 |
| 129 | ADHEr, ATPS4r, FUM, PGL and/or G6PDHy | 3.76615 |
| 130 | ADHEr, ATPS4r, HEX1, THD2 and/or GLUDy | 3.73541 |
| 131 | ACKr and/or PTAr, AKGD, ATPS4r, THD2 and/or GLUDy | 3.65142 |
| 132 | ACKr and/or PTAr, ME2, PGL and/or G6PDHy, THD2 and/or GLUDy | 3.52563 |
| 133 | ADHEr, ASPT, ATPS4r, MDH | 3.50899 |
| 134 | ACKr and/or PTAr, ATPS4r, SUCOAS, THD2 and/or GLUDy | 3.4624 |
| 135 | ACKr and/or PTAr, ATPS4r, PFK and/or FBA and/or TPI, SUCOAS | 3.3813 |
| 136 | ATPS4r, PPCK, PYK, THD2 and/or GLUDy | 3.23342 |
| 137 | ACKr and/or PTAr, MDH, PFLi, THD2 and/or GLUDy | 3.16308 |
| 138 | ATPS4r, NADH6, PDH, PFLi | 3.01078 |
| 139 | FUM, ME2, PFLi, THD2 and/or GLUDy | 3.00855 |
| 140 | AKGD, MDH, PGL and/or G6PDHy, THD2 and/or GLUDy | 2.70882 |
| 141 | MDH, PGL and/or G6PDHy, SUCOAS, THD2 and/or GLUDy | 2.58524 |
| 142 | ACKr and/or PTAr, GLU5K, PFLi, PGI | 2.51808 |
| 143 | ACKr and/or PTAr, G5SD, PFLi, PGI | 2.51808 |
| 144 | ATPS4r, MDH, PGL and/or G6PDHy, THD2 and/or GLUDy | 2.13925 |
| 145 | ME2, NADH6, PFLi, THD2 and/or GLUDy | 1.97605 |
| 146 | ACKr and/or PTAr, PFLi, PPCK, THD2 and/or GLUDy | 1.96877 |
| 147 | FUM, MDH, PGL and/or G6PDHy, THD2 and/or GLUDy | 1.58766 |
| 148 | ADHEr, ATPS4r, HEX1, PPS | 1.57755 |
| 149 | ACKr and/or PTAr, MDH, PGL and/or G6PDHy, THD2 and/or GLUDy | 1.20253 |
| 150 | ACKr and/or PTAr, FUM, PFLi, THD2 and/or GLUDy | 1.05304 |
| 151 | ACKr and/or PTAr, ADHEr, ASPT, MDH | 0.90077 |
| 152 | ACKr and/or PTAr, FUM, HEX1, PFLi | 0.88292 |
| 153 | ACKr and/or PTAr, HEX1, PFLi, THD2 and/or GLUDy | 0.61521 |
| 154 | ACKr and/or PTAr, HEX1, PFK and/or FBA and/or TPI, PFLi | 0.56359 |
| 155 | ASPT, FUM, PDH, PFLi | 0.43285 |
| 156 | ASPT, MDH, PDH, PFLi | 0.39171 |
| 157 | ADHEr, ASPT, ATPS4r, GLCpts, MDH | 13.10515 |

TABLE 11-continued

Growth-coupled production designs for the 4-HB-CoA:MAA pathway (FIG. 6).

| Design ID | Metabolic Transformations Targeted for Removal | Predicted MAA Yield |
|---|---|---|
| 158 | ACKr and/or PTAr, ADHEr, LDH_D, MDH, NADH6 | 11.66583 |
| 159 | ADHEr, ATPS4r, MDH, PGL and/or G6PDHy, THD2 and/or GLUDy | 11.54962 |
| 160 | ATPS4r, MDH, PDH, PGL and/or G6PDHy, THD2 and/or GLUDy | 11.18163 |
| 161 | ADHEr, LDH_D, MDH, PGL and/or G6PDHy, THD2 and/or GLUDy | 10.87211 |
| 162 | ADHEr, ASPT, MDH, PGL and/or G6PDHy, PYK | 10.85118 |
| 163 | ADHEr, FUM, ME2, PGL and/or G6PDHy, THD2 and/or GLUDy | 10.79537 |
| 164 | ADHEr, MALS, MDH, PGL and/or G6PDHy, THD2 and/or GLUDy | 10.79537 |
| 165 | ADHEr, ICL, MDH, PGL and/or G6PDHy, THD2 and/or GLUDy | 10.79537 |
| 166 | ADHEr, ASPT, ATPS4r, LDH_D, MDH | 10.36931 |
| 167 | ATPS4r, GLCpts, NADH6, PDH, PFLi | 10.18817 |
| 168 | ADHEr, ATPS4r, GLCpts, NADH6, PFLi | 10.10757 |
| 169 | ACKr and/or PTAr, ADHEr, MDH, PGL and/or G6PDHy, THD2 and/or GLUDy | 9.4975 |
| 170 | ADHEr, FRD and/or SUCD4, ME2, PGL and/or G6PDHy, THD2 and/or GLUDy | 9.20833 |
| 171 | ADHEr, ATPS4r, LDH_D, NADH6, PFLi | 9.04248 |
| 172 | ADHEr, GLCpts, MDH, NADH6, THD2 and/or GLUDy | 8.60394 |
| 173 | ADHEr, ME2, NADH6, PGL and/or G6PDHy, THD2 and/or GLUDy | 8.57189 |
| 174 | ADHEr, ATPS4r, LDH_D, MDH, NADH6 | 8.07655 |
| 175 | FUM, MDH, PGL and/or G6PDHy, PYK, THD2 and/or GLUDy | 8.03861 |
| 176 | MDH, ME2, PGL and/or G6PDHy, PYK, THD2 and/or GLUDy | 8.03861 |
| 177 | ADHEr, FRD and/or SUCD4, LDH_D, PFLi, PPCK | 7.63009 |
| 178 | ADHEr, ATPS4r, FUM, LDH_D, NADH6 | 7.6151 |
| 179 | ADHEr, ASPT, MDH, PYK, THD2 and/or GLUDy | 7.44202 |
| 180 | ADHEr, ASPT, FRD and/or SUCD4, LDH_D, MDH | 7.40564 |
| 181 | ADHEr, LDH_D, NADH6, PFLi, PPCK | 7.40192 |
| 182 | ADHEr, FRD and/or SUCD4, LDH_D, MDH, PFLi | 7.36994 |
| 183 | ADHEr, ASPT, ATPS4r, MDH, PGL and/or G6PDHy | 7.36609 |
| 184 | ADHEr, ASPT, LDH_D, MDH, PPCK | 7.33413 |
| 185 | ADHEr, LDH_D, MDH, PFLi, THD2 and/or GLUDy | 7.27861 |
| 186 | ADHEr, NADH6, PFLi, PPCK, PYK | 7.27816 |
| 187 | ADHEr, ASPT, LDH_D, MDH, NADH6 | 7.2681 |
| 188 | ADHEr, FUM, LDH_D, PFLi, PPCK | 7.23481 |
| 189 | ADHEr, LDH_D, MDH, PFLi, PPCK | 7.23481 |
| 190 | ADHEr, ASPT, GLCpts, LDH_D, MDH | 7.21534 |
| 191 | ADHEr, FRD and/or SUCD4, FUM, LDH_D, PFLi | 7.16964 |
| 192 | ADHEr, FRD and/or SUCD4, LDH_D, ME2, PFLi | 7.15036 |
| 193 | ADHEr, LDH_D, MDH, NADH6, PFLi | 7.14486 |
| 194 | ADHEr, ASPT, LDH_D, MDH, THD2 and/or GLUDy | 7.14394 |
| 195 | ADHEr, FUM, LDH_D, PFLi, THD2 and/or GLUDy | 7.13176 |
| 196 | ASPT, ATPS4r, MDH, PGL and/or G6PDHy, PYK | 7.127 |
| 197 | ADHEr, FRD and/or SUCD4, HEX1, LDH_D, PFLi | 7.11053 |
| 198 | ADHEr, FRD and/or SUCD4, LDH_D, PFLi, THD2 and/or GLUDy | 7.09551 |
| 199 | ADHEr, ATPS4r, FUM, ME2, NADH6 | 7.05818 |
| 200 | ATPS4r, HEX1, ME2, PFLi, THD2 and/or GLUDy | 7.02076 |
| 201 | ADHEr, ATPS4r, NADH6, PGL and/or G6PDHy, PPCK | 6.9884 |
| 202 | ADHEr, LDH_D, NADH12, NADH6, PFLi | 6.98499 |
| 203 | ADHEr, FUM, LDH_D, NADH6, PFLi | 6.98167 |
| 204 | ATPS4r, PFLi, PPCK, PYK, THD2 and/or GLUDy | 6.96842 |
| 205 | ADHEr, HEX1, PFLi, PPS, THD2 and/or GLUDy | 6.92886 |
| 206 | ADHEr, HEX1, ME2, PGL and/or G6PDHy, THD2 and/or GLUDy | 6.88098 |
| 207 | ADHEr, FUM, ME2, NADH6, THD2 and/or GLUDy | 6.81498 |
| 208 | ADHEr, ATPS4r, HEX1, NADH6, PGL and/or G6PDHy | 6.72128 |
| 209 | ATPS4r, FUM, NADH12, PFLi, THD2 and/or GLUDy | 6.67745 |
| 210 | ADHEr, ME2, PGL and/or G6PDHy, PPCK, THD2 and/or GLUDy | 6.67685 |
| 211 | ADHEr, ATPS4r, HEX1, MDH, PFLi | 6.56359 |
| 212 | ADHEr, ATPS4r, HEX1, NADH6, PFK and/or FBA and/or TPI | 6.49377 |
| 213 | ADHEr, HEX1, MDH, PFLi, THD2 and/or GLUDy | 6.48868 |
| 214 | ADHEr, GLCpts, NADH6, PGI, PPCK | 6.48565 |
| 215 | ADHEr, GLCpts, NADH6, PFK and/or FBA and/or TPI, PPCK | 6.48238 |
| 216 | ADHEr, ATPS4r | 1.41919 |
| 217 | ADHEr, PFLi, PGI | 2.45706 |
| 218 | ADHEr, ATPS4r, THD2 and/or GLUDy | 1.92124 |
| 219 | ADHEr, ATPS4r, HEX1, PFLi | 5.2123 |
| 220 | ADHEr, ATPS4r, PFLi, PGI | 5.00885 |
| 221 | ADHEr, ATPS4r, PFK and/or FBA and/or TPI, PFLi | 4.90696 |
| 222 | ADHEr, ATPS4r, ME2, THD2 and/or GLUDy | 4.44391 |
| 223 | ACKr and/or PTAr, ADHEr, AKGD, ATPS4r | 3.45333 |
| 224 | ADHEr, ME2, PGL and/or G6PDHy, THD2 and/or GLUDy | 3.397 |
| 225 | ACKr and/or PTAr, ADHEr, ATPS4r, SUCOAS | 3.23462 |
| 226 | ADHEr, ATPS4r, PPCK, PYK | 2.7407 |
| 227 | ADHEr, ATPS4r, HEX1, PFLi, PGI | 6.94738 |
| 228 | ADHEr, ATPS4r, FUM, PFLi, THD2 and/or GLUDy | 5.87538 |
| 229 | ADHEr, ATPS4r, ME2, PGL and/or G6PDHy, THD2 and/or GLUDy | 5.77678 |

TABLE 11-continued

Growth-coupled production designs for the 4-HB-CoA:MAA pathway (FIG. 6).

| Design ID | Metabolic Transformations Targeted for Removal | Predicted MAA Yield |
|---|---|---|
| 230 | ADHEr, ME2, PFLi, PGL and/or G6PDHy, THD2 and/or GLUDy | 5.37063 |
| 231 | ADHEr, ATPS4r, PFLi, PPCK, PYK | 5.11897 |
| 232 | ADHEr, ATPS4r, MDH, PDH, PGL and/or G6PDHy, THD2 and/or GLUDy | 11.18163 |
| 233 | ADHEr, ATPS4r, GLCpts, NADH6, PDH, PFLi | 10.18817 |
| 234 | ADHEr, ATPS4r, HEX1, ME2, PFLi, THD2 and/or GLUDy | 7.02076 |
| 235 | ADHEr, ATPS4r, PFLi, PPCK, PYK, THD2 and/or GLUDy | 6.96842 |
| 236 | ADHEr, ATPS4r, FUM, NADH12, PFLi, THD2 and/or GLUDy | 6.67745 |
| 237 | ADHEr, ATPS4r, MDH, PFK and/or FBA and/or TPI, PFLi, THD2 and/or GLUDy | 6.00293 |
| 238 | ADHEr, LDH_D, MDH, THD2 and/or GLUDy | 6.05682 |
| 239 | ADHEr, LDH_D, MDH, NADH6 | 5.71411 |
| 240 | ADHEr, LDH_D, MDH, PPCK | 4.36046 |
| 241 | ADHEr, LDH_D, MDH, PGI | 1.8023 |
| 242 | ADHEr, HEX1, LDH_D, MDH | 0.71076 |
| 243 | ADHEr, HEX1, LDH_D, MDH, PGI | 8.71082 |
| 244 | ADHEr, LDH_D, MDH, NADH6, THD2 and/or GLUDy | 6.81498 |
| 245 | ACKr and/or PTAr, ADHEr, LDH_D, MDH, THD2 and/or GLUDy | 6.26208 |
| 246 | ADHEr, GLUDy, LDH_D, MDH, THD2 and/or GLUDy | 6.1932 |
| 247 | ADHEr, LDH_D, MDH, PPCK, THD2 and/or GLUDy | 6.18632 |
| 248 | ADHEr, LDH_D, MDH, NADH6, PGI | 6.18566 |
| 249 | ADHEr, ATPS4r, LDH_D, MDH, THD2 and/or GLUDy | 6.13586 |
| 250 | ADHEr, ATPS4r, LDH_D, MDH, PPCK | 5.89299 |
| 251 | ADHEr, GLCpts, LDH_D, MDH, NADH6 | 5.83728 |
| 252 | ADHEr, HEX1, LDH_D, MDH, PFLi | 5.20022 |
| 253 | ADHEr, ASPT, ATPS4r, GLCpts, LDH_D, MDH | 13.10515 |
| 254 | ADHEr, ASPT, ATPS4r, LDH_D, MDH, NADH6 | 13.09985 |
| 255 | ADHEr, ASPT, LDH_D, MDH, PFLi, THD2 and/or GLUDy | 12.43893 |
| 256 | ACKr and/or PTAr, ADHEr, LDH_D, MDH, NADH6, THD2 and/or GLUDy | 12.0485 |
| 257 | ADHEr, ATPS4r, LDH_D, MDH, PGL and/or G6PDHy, THD2 and/or GLUDy | 11.54962 |
| 258 | ADHEr, ASPT, ATPS4r, LDH_D, MDH, PFLi | 10.9713 |
| 259 | ADHEr, ASPT, ATPS4r, LDH_D, MDH, PGL and/or G6PDHy | 10.87514 |
| 260 | ADHEr, ASPT, LDH_D, MDH, PGL and/or G6PDHy, PYK | 10.85118 |
| 261 | ADHEr, ASPT, LDH_D, MDH, PFLi, PYK | 10.69852 |
| 262 | ADHEr, ASPT, ATPS4r, LDH_D, MDH, PPCK | 10.54348 |
| 263 | ADHEr, ASPT, LDH_D, MDH, NADH12, NADH6 | 9.24298 |
| 264 | ADHEr, ATPS4r, GLCpts, LDH_D, MDH, NADH6 | 8.89824 |
| 265 | ADHEr, GLUDy, LDH_D, MDH, PFLi, THD2 and/or GLUDy | 8.78148 |
| 266 | ADHEr, LDH_D, MDH, PFLi, PPCK, THD2 and/or GLUDy | 8.75525 |
| 267 | ADHEr, LDH_D, MDH, NADH6, PFLi, THD2 and/or GLUDy | 8.68453 |
| 268 | ADHEr, GLCpts, LDH_D, MDH, NADH6, THD2 and/or GLUDy | 8.60394 |
| 269 | ADHEr, ATPS4r, LDH_D, MDH, PFLi, THD2 and/or GLUDy | 8.54512 |
| 270 | ADHEr, HEX1, LDH_D, MDH, PFLi, THD2 and/or GLUDy | 8.41994 |
| 271 | ADHEr, ATPS4r, LDH_D, MDH, NADH6, THD2 and/or GLUDy | 8.22075 |
| 272 | ADHEr, LDH_D, MDH, NADH12, NADH6, THD2 and/or GLUDy | 8.20953 |
| 273 | ADHEr, ASPT, LDH_D, MDH, PGI, THD2 and/or GLUDy | 7.83287 |
| 274 | ACKr and/or PTAr, ADHEr, LDH_D, MDH, PPCK, THD2 and/or GLUDy | 7.76113 |
| 275 | ADHEr, LDH_D, MDH, PFLi, PGI, THD2 and/or GLUDy | 7.73026 |
| 276 | ADHEr, LDH_D, MDH, NADH6, PFLi, PGI | 7.64241 |
| 277 | ADHEr, LDH_D, MDH, NADH6, PFLi, PPCK | 7.62766 |
| 278 | ADHEr, ASPT, LDH_D, MDH, NADH6, PPCK | 7.5687 |
| 279 | ADHEr, ASPT, GLCpts, LDH_D, MDH, PPCK | 7.50936 |
| 280 | ADHEr, ASPT, GLCpts, LDH_D, MDH, NADH6 | 7.45108 |
| 281 | ADHEr, ASPT, LDH_D, MDH, PYK, THD2 and/or GLUDy | 7.44202 |
| 282 | ADHEr, GLCpts, LDH_D, MDH, PFLi, THD2 and/or GLUDy | 7.41734 |
| 283 | ADHEr, ASPT, LDH_D, MDH, PPCK, THD2 and/or GLUDy | 7.40692 |
| 284 | ADHEr, GLCpts, LDH_D, MDH, PFLi, PPCK | 7.38196 |
| 285 | ADHEr, LDH_D, MDH, NADH12, NADH6, PFLi | 7.36994 |
| 286 | ADHEr, ASPT, LDH_D, MDH, NADH6, THD2 and/or GLUDy | 7.35125 |
| 287 | ADHEr, ATPS4r, LDH_D, MDH, PFLi, PPCK | 7.34743 |
| 288 | ADHEr, ASPT, GLCpts, LDH_D, MDH, THD2 and/or GLUDy | 7.30247 |
| 289 | ADHEr, GLCpts, LDH_D, MDH, NADH6, PFLi | 7.29756 |
| 290 | ADHEr, ASPT, GLUDy, LDH_D, MDH, THD2 and/or GLUDy | 7.20317 |
| 291 | ACKr and/or PTAr, ADHEr, GLUDy, LDH_D, MDH, THD2 and/or GLUDy | 6.86403 |
| 292 | ADHEr, ATPS4r, HEX1, LDH_D, MDH, PFLi | 6.56359 |
| 293 | ACKr and/or PTAr, ADHEr, GLCpts, LDH_D, MDH, THD2 and/or GLUDy | 6.38107 |
| 294 | ADHEr, ATPS4r, LDH_D, MDH, PGL and/or G6PDHy, PPS | 6.33965 |
| 295 | ADHEr, LDH_D, MDH, NADH6, PYK, THD2 and/or GLUDy | 6.13919 |
| 296 | ADHEr, LDH_D, MDH, NADH6, PPCK, PYK | 6.10615 |

TABLE 11-continued

Growth-coupled production designs for the 4-HB-CoA:MAA pathway (FIG. 6).

| Design ID | Metabolic Transformations Targeted for Removal | Predicted MAA Yield |
|---|---|---|
| 297 | ADHEr, LDH_D, MDH, NADH12, NADH6, PPCK | 6.03902 |
| 298 | ADHEr, ATPS4r, LDH_D, MDH, PPCK, THD2 and/or GLUDy | 5.95979 |
| 299 | ADHEr, ATPS4r, LDH_D, MDH, PFLi, PGI | 5.00885 |
| 300 | NA | 0.40409 |
| 301 | FRD and/or SUCD4 | 0.34622 |
| 302 | ADHEr, ATPS4r, NADH6 | 0.29582 |
| 303 | ADHEr, ATPS4r, PPCK | 0.24649 |
| 304 | ADHEr, NADH12, NADH6 | 0.28919 |
| 305 | ADHEr, FRD and/or SUCD4, LDH_D | 0.26599 |
| 306 | MDH, NADH6, PFLi | 0.27181 |
| 307 | FRD and/or SUCD4, ME2, PFLi | 0.27027 |
| 308 | FRD and/or SUCD4, MDH, PFLi | 0.26589 |
| 309 | FUM, PFLi, PPCK | 0.25998 |
| 310 | MDH, PFLi, PPCK | 0.25998 |
| 311 | NADH6, PFLi, PPCK | 0.25452 |
| 312 | FRD and/or SUCD4, PFLi, PPCK | 0.24933 |
| 313 | ATPS4r, PFLi, PPCK | 0.2281 |
| 314 | FRD and/or SUCD4, FUM, PFLi | 0.30093 |
| 315 | PFK and/or FBA and/or TPI, PFLi, PPCK | 0.14537 |
| 316 | PFLi, PGI, PPCK | 0.14284 |
| 317 | ADHEr, ATPS4r, PGI | 0.23063 |
| 318 | NADH12, NADH6, PFLi | 0.30419 |
| 319 | FUM, NADH6, PFLi | 0.30486 |
| 320 | ADHEr, FRD and/or SUCD4, PPCK | 0.21424 |
| 321 | ADHEr, ATPS4r, PFK and/or FBA and/or TPI | 0.23674 |
| 322 | ADHEr, ATPS4r, HEX1 | 0.37576 |
| 323 | ADHEr, MDH, PGI | 0.24821 |
| 324 | ADHEr, FUM, PGI | 0.24821 |
| 325 | FUM, HEX1, PFK and/or FBA and/or TPI | 0.18252 |
| 326 | ADHEr, ATPS4r, HEX1, PGI | 0.08649 |
| 327 | ADHEr, ATPS4r, HEX1, PFK and/or FBA and/or TPI | 0.08878 |
| 328 | ADHEr, LDH_D, NADH6, PPCK | 0.17351 |
| 329 | ADHEr, FRD and/or SUCD4, LDH_D, MDH | 0.18263 |
| 330 | ATPS4r, MDH, PDH, PGL and/or G6PDHy | 0.19729 |
| 331 | ADHEr, ATPS4r, PPCK, THD2 and/or GLUDy | 0.21063 |
| 332 | ADHEr, FRD and/or SUCD4, FUM, LDH_D | 0.23871 |
| 333 | ADHEr, FRD and/or SUCD4, HEX1, LDH_D | 0.24228 |
| 334 | ADHEr, ME2, NADH12, NADH6 | 0.27452 |
| 335 | ADHEr, ATPS4r, MDH, PGL and/or G6PDHy | 0.26541 |
| 336 | ADHEr, ATPS4r, NADH6, PFK and/or FBA and/or TPI | 0.11424 |
| 337 | ADHEr, ATPS4r, ME2, NADH6 | 0.28029 |
| 338 | ADHEr, ATPS4r, NADH12, NADH6 | 0.28705 |
| 339 | ACKr and/or PTAr, AKGD, ATPS4r, PFK and/or FBA and/or TPI | 0.10833 |
| 340 | ADHEr, ATPS4r, FUM, THD2 and/or GLUDy | 0.23122 |
| 341 | ADHEr, HEX1, NADH12, NADH6 | 0.2788 |
| 342 | ATPS4r, FDH2, NADH6, PDH | 0.16467 |
| 343 | ATPS4r, GLCpts, MDH, PGL and/or G6PDHy | 0.23908 |
| 344 | ADHEr, FUM, LDH_D, THD2 and/or GLUDy | 0.35439 |
| 345 | ADHEr, FUM, LDH_D, NADH6 | 0.26726 |
| 346 | FUM, ME2, NADH6, PFLi | 0.27181 |
| 347 | ME2, NADH12, NADH6, PFLi | 0.27027 |
| 348 | FRD and/or SUCD4, FUM, PFLi, THD2 and/or GLUDy | 0.2584 |
| 349 | FUM, NADH6, PFLi, THD2 and/or GLUDy | 0.2584 |
| 350 | FRD and/or SUCD4, PFLi, PRO1z, THD2 and/or GLUDy | 0.25563 |
| 351 | ADHEr, HEX1, LDH_D, PPS | 0.37122 |
| 352 | FUM, NADH12, NADH6, PFLi | 0.30093 |
| 353 | ADHEr, FUM, PFLi, PGI | 0.2381 |
| 354 | ADHEr, MDH, PFLi, PGI | 0.2381 |
| 355 | ASPT, ATPS4r, FUM, PDH | 0.19443 |
| 356 | ASPT, ATPS4r, MDH, PDH | 0.18797 |
| 357 | ADHEr, ASPT, MDH, THD2 and/or GLUDy | 0.20167 |
| 358 | FUM, HEX1, PFLi, THD2 and/or GLUDy | 0.32948 |
| 359 | ACKr and/or PTAr, ADHEr, FRD and/or SUCD4, MDH | 0.22488 |
| 360 | ADHEr, HEX1, LDH_D, NADH6 | 0.28496 |
| 361 | ACKr and/or PTAr, ADHEr, NADH6, PPCK | 0.21426 |
| 362 | ACKr and/or PTAr, ADHEr, FRD and/or SUCD4, PPCK | 0.2103 |
| 363 | FBP, PFLi, PGI, PPCK | 0.14228 |
| 364 | PFK and/or FBA and/or TPI, PFLi, PGI, PPCK | 0.14228 |
| 365 | ADHEr, HEX1, LDH_D, PPCK | 0.26035 |
| 366 | MDH, PDH, PFLi, PGI | 0.21218 |
| 367 | FUM, PDH, PFLi, PGI | 0.21218 |
| 368 | ADHEr, ASPT, ATPS4r, FUM | 0.22058 |
| 369 | HEX1, NADH6, PFK and/or FBA and/or TPI, PFLi | 0.1381 |
| 370 | FUM, PFK and/or FBA and/or TPI, PFLi, THD2 and/or GLUDy | 0.13758 |

TABLE 11-continued

Growth-coupled production designs for the 4-HB-CoA:MAA pathway (FIG. 6).

| Design ID | Metabolic Transformations Targeted for Removal | Predicted MAA Yield |
|---|---|---|
| 371 | FUM, PFLi, PGI, THD2 and/or GLUDy | 0.1353 |
| 372 | HEX1, NADH6, PFLi, PGI | 0.13506 |
| 373 | ADHEr, FUM, LDH_D, PPCK | 0.20562 |
| 374 | ATPS4r, GLCpts, NADH6, PFLi | 0.26825 |
| 375 | ADHEr, FRD and/or SUCD4, FUM, THD2 and/or GLUDy | 0.2204 |
| 376 | ADHEr, FUM, NADH6, THD2 and/or GLUDy | 0.2204 |
| 377 | ADHEr, FRD and/or SUCD4, PRO1z, THD2 and/or GLUDy | 0.21775 |
| 378 | ATPS4r, HEX1, PFLi, PGI | 0.08042 |
| 379 | ATPS4r, HEX1, PFK and/or FBA and/or TPI, PFLi | 0.0824 |
| 380 | ASPT, ATPS4r, GLCpts, MDH | 0.25562 |
| 381 | ATPS4r, GLCpts, MDH, PPCK | 0.24489 |
| 382 | ATPS4r, FUM, GLCpts, PPCK | 0.24489 |
| 383 | ADHEr, ASPT, FUM, ME2 | 0.22754 |
| 384 | ADHEr, ASPT, FUM, THD2 and/or GLUDy | 0.22026 |
| 385 | ADHEr, FRD and/or SUCD4, HEX1, PGI | 0.08245 |
| 386 | ADHEr, HEX1, NADH6, PGI | 0.08245 |
| 387 | ADHEr, ASPT, FUM, LDH_D | 0.2051 |
| 388 | ATPS4r, GLCpts, MDH, THD2 and/or GLUDy | 0.23421 |
| 389 | ADHEr, HEX1, PFK and/or FBA and/or TPI, PPCK | 0.08078 |
| 390 | ADHEr, MDH, ME2, NADH6 | 0.23176 |
| 391 | ADHEr, MDH, PFLi, THD2 and/or GLUDy | 2.6304 |
| 392 | ADHEr, FRD and/or SUCD4, FUM, PFLi | 0.37735 |
| 393 | ADHEr, HEX1, PGI, PPCK | 0.13376 |
| 394 | ADHEr, FRD and/or SUCD4, HEX1, PFLi | 0.03691 |
| 395 | ADHEr, ATPS4r, GLCpts, MDH, PDH, PGL and/or G6PDHy | 9.03958 |
| 396 | ADHEr, ATPS4r, LDH_D, NADH12, NADH6, PFLi | 9.0297 |
| 397 | ADHEr, ATPS4r, LDH_D, MDH, NADH6, PGL and/or G6PDHy | 8.92362 |
| 398 | ACKr and/or PTAr, ADHEr, ATPS4r, MDH, NADH6, PGL and/or G6PDHy | 8.83429 |
| 399 | ACKr and/or PTAr, ADHEr, ATPS4r, GLCpts, MDH, PGL and/or G6PDHy | 8.62906 |
| 400 | ADHEr, MDH, ME2, PGL and/or G6PDHy, PYK, THD2 and/or GLUDy | 8.50911 |
| 401 | ADHEr, FUM, MDH, PGL and/or G6PDHy, PYK, THD2 and/or GLUDy | 8.50911 |
| 402 | ACKr and/or PTAr, ADHEr, FRD and/or SUCD4, LDH_D, MDH, THD2 and/or GLUDy | 8.37268 |
| 403 | ADHEr, ATPS4r, GLCpts, MDH, PGL and/or G6PDHy, THD2 and/or GLUDy | 8.32112 |
| 404 | ADHEr, ATPS4r, GLCpts, MDH, PGL and/or G6PDHy, PPCK | 7.82056 |
| 405 | ADHEr, FRD and/or SUCD4, HEX1, LDH_D, PFLi, THD2 and/or GLUDy | 7.65378 |
| 406 | ACKr and/or PTAr, ADHEr, FRD and/or SUCD4, LDH_D, MDH, PGI | 7.4765 |
| 407 | ADHEr, ME2, NADH12, NADH6, PGL and/or G6PDHy, THD2 and/or GLUDy | 7.16841 |
| 408 | ADHEr, HEX1, LDH_D, PFLi, PPS, THD2 and/or GLUDy | 6.91902 |
| 409 | ACKr and/or PTAr, ADHEr, ATPS4r, GLCpts, NADH6, PGI | 6.85613 |
| 410 | ADHEr, ATPS4r, FUM, LDH_D, NADH6, PPCK | 6.78808 |
| 411 | ADHEr, ATPS4r, FUM, LDH_D, ME2, NADH6 | 6.71695 |
| 412 | ADHEr, ASPT, ATPS4r, GLCpts, MDH, PGL and/or G6PDHy | 6.67975 |
| 413 | ACKr and/or PTAr, ADHEr, FRD and/or SUCD4, LDH_D, PPCK, THD2 and/or GLUDy | 6.31121 |
| 414 | ADHEr, ATPS4r, ME2, PGL and/or G6PDHy, PPCK, THD2 and/or GLUDy | 6.23672 |
| 415 | ACKr and/or PTAr, ADHEr, FUM, LDH_D, ME2, NADH6 | 6.19739 |
| 416 | ADHEr, ATPS4r, FUM, LDH_D, NADH6, THD2 and/or GLUDy | 6.15859 |
| 417 | ACKr and/or PTAr, ADHEr, FUM, HEX1, LDH_D, NADH6 | 6.06031 |
| 418 | ADHEr, ATPS4r, FUM, HEX1, LDH_D, NADH6 | 5.95481 |
| 419 | ACKr and/or PTAr, ADHEr, HEX1, LDH_D, NADH6, THD2 and/or GLUDy | 5.89694 |
| 420 | ADHEr, FUM, HEX1, LDH_D, PPS, THD2 and/or GLUDy | 5.87873 |
| 421 | ADHEr, FUM, HEX1, LDH_D, NADH12, NADH6 | 5.87075 |
| 422 | ADHEr, ATPS4r, NADH12, NADH6, PRO1z, THD2 and/or GLUDy | 5.87047 |
| 423 | ADHEr, FUM, HEX1, LDH_D, ME2, THD2 and/or GLUDy | 5.85008 |
| 424 | ACKr and/or PTAr, ADHEr, LDH_D, ME2, NADH12, NADH6 | 5.77866 |
| 425 | ACKr and/or PTAr, ADHEr, FUM, HEX1, LDH_D, THD2 and/or GLUDy | 5.77062 |
| 426 | ADHEr, HEX1, LDH_D, NADH12, NADH6, THD2 and/or GLUDy | 5.74841 |
| 427 | ADHEr, FRD and/or SUCD4, HEX1, LDH_D, PPS, THD2 and/or GLUDy | 5.74605 |
| 428 | ACKr and/or PTAr, ADHEr, CITL, LDH_D, NADH12, NADH6 | 5.71072 |
| 429 | ADHEr, ATPS4r, MDH, NADH6, PGL and/or G6PDHy, THD2 and/or GLUDy | 5.70312 |
| 430 | ACKr and/or PTAr, ADHEr, ATPS4r, GLCpts, ME2, NADH6 | 5.68643 |

TABLE 11-continued

Growth-coupled production designs for the 4-HB-CoA:MAA pathway (FIG. 6).

| Design ID | Metabolic Transformations Targeted for Removal | Predicted MAA Yield |
|---|---|---|
| 431 | ADHEr, ATPS4r, FUM, LDH_D, PFLi, THD2 and/or GLUDy | 5.64027 |
| 432 | ACKr and/or PTAr, ADHEr, CITL, HEX1, LDH_D, NADH6 | 5.63442 |
| 433 | ADHEr, FUM, LDH_D, ME2, NADH6, THD2 and/or GLUDy | 5.58306 |
| 434 | ADHEr, ATPS4r, FUM, GLCpts, ME2, PGL and/or G6PDHy | 5.57201 |
| 435 | ADHEr, ATPS4r, HEX1, ME2, PGL and/or G6PDHy, THD2 and/or GLUDy | 5.55702 |
| 436 | ADHEr, FRD and/or SUCD4, GLUDy, LDH_D, PFLi, THD2 and/or GLUDy | 5.54389 |
| 437 | ADHEr, FUM, GLUDy, LDH_D, ME2, THD2 and/or GLUDy | 5.50066 |
| 438 | ADHEr, ATPS4r, HEX1, LDH_D, NADH6, THD2 and/or GLUDy | 5.47201 |
| 439 | ADHEr, FUM, GLUDy, LDH_D, PFLi, THD2 and/or GLUDy | 5.4078 |
| 440 | ACKr and/or PTAr, ADHEr, ATPS4r, GLCpts, NADH6, PPCK | 5.36087 |
| 441 | ADHEr, FRD and/or SUCD4, HEX1, LDH_D, PPCK, THD2 and/or GLUDy | 5.34992 |
| 442 | ADHEr, ATPS4r, FUM, GLCpts, NADH6, PPCK | 5.25122 |
| 443 | ACKr and/or PTAr, ADHEr, ATPS4r, CITL, GLCpts, NADH6 | 5.24209 |
| 444 | ADHEr, ATPS4r, FUM, LDH_D, PGL and/or G6PDHy, PPCK | 5.21165 |
| 445 | ADHEr, ASPT, ATPS4r, MDH, PDH, PGL and/or G6PDHy | 5.10503 |
| 446 | ADHEr, FUM, HEX1, LDH_D, PFLi, THD2 and/or GLUDy | 5.07597 |
| 447 | ADHEr, FRD and/or SUCD4, HEX1, LDH_D, PFLi, PGI | 5.0175 |
| 448 | ADHEr, ICL, LDH_D, MDH, PGL and/or G6PDHy, THD2 and/or GLUDy | 10.42846 |
| 449 | ADHEr, LDH_D, MALS, MDH, PGL and/or G6PDHy, THD2 and/or GLUDy | 10.42846 |
| 450 | ADHEr, GLCpts, LDH_D, MDH, PGL and/or G6PDHy, THD2 and/or GLUDy | 10.30271 |
| 451 | ADHEr, ATPS4r, LDH_D, MDH, NADH6, PFLi | 8.05255 |
| 452 | ACKr and/or PTAr, ADHEr, ATPS4r, LDH_D, MDH, NADH6 | 6.92399 |
| 453 | ADHEr, ATPS4r, LDH_D, MDH, NADH6, PPCK | 6.78808 |
| 454 | ACKr and/or PTAr, ADHEr, GLCpts, LDH_D, MDH, NADH6 | 6.43185 |
| 455 | ADHEr, ATPS4r, GLCpts, LDH_D, MDH, PGL and/or G6PDHy | 5.57201 |
| 456 | ADHEr, LDH_D, MDH, NADH12, NADH6, PGI | 5.02702 |

TABLE 12

Enzyme names, abbreviations, and the corresponding reaction stoichiometries of designs in Tables 10 and 11.

| Abbrev. | Enzyme Name | Equation |
|---|---|---|
| ABTA | 4-aminobutyrate transaminase | [c]: 4abut + akg --> glu-L + sucsal |
| ACKr | acetate kinase | [c]: ac + atp <==> actp + adp |
| ACS | acetyl-CoA synthetase | [c]: ac + atp + coa --> accoa + amp + ppi |
| ACt6 | acetate transport in/out via proton symport | ac[e] + h[e] <==> ac[c] + h[c] |
| ADHEr | acetaldehyde-CoA dehydrogenase | [c]: accoa + (2) h + (2) nadh <==> coa + etoh + (2) nad |
| AKGD | 2-oxoglutarate dehydrogenase | [c]: akg + coa + nad --> co2 + nadh + succoa |
| ASNN | L-asparaginase | [c]: asn-L + h2o --> asp-L + nh4 |
| ASNS1 | asparagine synthase (glutamine-hydrolysing) | [c]: asp-L + atp + gln-L + h2o --> amp + asn-L + glu-L + h + ppi |
| ASNS2 | asparagine synthetase | [c]: asp-L + atp + nh4 --> amp + asn-L + h + ppi |
| ASPT | L-aspartase | [c]: asp-L --> fum + nh4 |
| ATPS4r | ATP synthase (four protons for one ATP) | adp[c] + (4) h[e] + pi[c] <==> atp[c] + (3) h[c] + h2o[c] |
| CBMK2 | Carbamate kinase | [c]: atp + co2 + nh4 --> adp + cbp + (2) h |
| CITL | Citrate lyase | [c]: cit --> ac + oaa |
| DAAD | D-Amino acid dehydrogenase | [c]: ala-D + fad + h2o --> fadh2 + nh4 + pyr |
| EDA | 2-dehydro-3-deoxy-phosphogluconate aldolase | [c]: 2ddg6p --> g3p + pyr |
| FADH4 | FADH dehydrogenaase | [c]: fadh2 + mqn8 --> fad + mql8 |
| FBA | fructose-bisphosphate aldolase | [c]: fdp <==> dhap + g3p |
| FBP | fructose-bisphosphatase | [c]: fdp + h2o --> f6p + pi |
| FRD | fumarate reductase | [c]: fum + [electron donor] --> [electron acceptor] + succ |

TABLE 12-continued

Enzyme names, abbreviations, and the corresponding reaction stoichiometries of designs in Tables 10 and 11.

| Abbrev. | Enzyme Name | Equation |
| --- | --- | --- |
| FUM | fumarase | [c]: fum + h2o <==> mal-L |
| G5SD | glutamate-5-semialdehyde dehydrogenase | [c]: glu5p + h + nadph --> glu5sa + nadp + pi |
| G6PDHy | glucose 6-phosphate dehydrogenase | [c]: g6p + nadp <==> 6pgl + h + nadph |
| G6PDHy | glucose 6-phosphate dehydrogenase | [c]: g6p + nadp <==> 6pgl + h + nadph |
| GLCpts | D-glucose transport via PEP:Pyr PTS | glc-D[e] + pep[c] --> g6p[c] + pyr[c] |
| GLU5K | glutamate 5-kinase | [c]: atp + glu-L --> adp + glu5p |
| GLUDC | glutamate decarboxylase | [c]: glu-L + h --> 4abut + co2 |
| GLUDy | glutamate dehydrogenase (NADP) | [c]: glu-L + h2o + nadp <==> akg + h + nadph + nh4 |
| GLUDy | glutamate dehydrogenase (NADP) | [c]: glu-L + h2o + nadp <==> akg + h + nadph + nh4 |
| GLUSy | glutamate synthase (NADPH) | [c]: akg + gln-L + h + nadph --> (2) glu-L + nadp |
| GLYCL | Glycine Cleavage System | [c]: gly + nad + thf --> co2 + mlthf + nadh + nh4 |
| HEX1 | hexokinase (D-glucose:ATP) | [c]: atp + glc-D --> adp + g6p + h |
| ICL | Isocitrate lyase | [c]: icit --> glx + succ |
| LDH_D | D-lactate dehydrogenase | [c]: lac-D + nad <==> h + nadh + pyr |
| MALS | malate synthase | [c]: accoa + glx + h2o --> coa + h + mal-L |
| MDH | malate dehydrogenase | [c]: mal-L + nad <==> h + nadh + oaa |
| ME1x | malic enzyme (NAD) | [c]: mal-L + nad --> co2 + nadh + pyr |
| ME2 | malic enzyme (NADP) | [c]: mal-L + nadp --> co2 + nadph + pyr |
| NACODA | N-acetylornithine deacetylase | [c]: acg5sa + h2o --> ac + glu5sa |
| NADH12 | NADH dehydrogenase | [c]: h + nadh + ubq8 --> nad + ubq8h2 |
| NADH6 | NADH dehydrogenase | (4.5) h[c] + nadh[c] + ubq8[c] --> (3.5) h[e] + nad[c] + ubq8h2[c] |
| ORNTA | ornithine transaminase | [c]: akg + orn-L --> glu-L + glu5sa |
| P5CD | 1-pyrroline-5-carboxylate dehydrogenase | [c]: 1pyr5c + (2) h2o + nad --> glu-L + h + nadh |
| PDH | pyruvate dehydrogenase | [c]: coa + nad + pyr --> accoa + co2 + nadh |
| PFK | phosphofructokinase | [c]: atp + f6p --> adp + fdp + h |
| PFLi | pyruvate formate lyase | [c]: coa + pyr --> accoa + for |
| PGDH | phosphogluconate dehydrogenase | [c]: 6pgc + nadp --> co2 + nadph + ru5p-D |
| PGDHY | phosphogluconate dehydratase | [c]: 6pgc --> 2ddg6p + h2o |
| PGI | glucose-6-phosphate isomerase | [c]: g6p <==> f6p |
| PGL | 6-phosphogluconolactonase | [c]: 6pgl + h2o --> 6pgc + h |
| PGL | 6-phosphogluconolactonase | [c]: 6pgl + h2o --> 6pgc + h |
| PGM | phosphoglycerate mutase | [c]: 3pg <==> 2pg |
| PPCK | phosphoenolpyruvate carboxykinase | [c]: atp + oaa --> adp + co2 + pep |
| PPS | phosphoenolpyruvate synthase | [c]: atp + h2o + pyr --> amp + (2) h + pep + pi |
| PRO1z | proline oxidase | [c]: fad + pro-L --> 1pyr5c + fadh2 + h |
| PTAr | phosphotransacetylase | [c]: accoa + pi <==> actp + coa |
| PYK | pyruvate kinase | [c]: adp + h + pep --> atp + pyr |
| RPE | ribulose 5-phosphate 3-epimerase | [c]: ru5p-D <==> xu5p-D |
| SERD_L | L-serine deaminase | [c]: ser-L --> nh4 + pyr |
| SUCD4 | succinate dehyrdogenase | [c]: fadh2 + ubq8 <==> fad + ubq8h2 |
| SUCD4 | succinate dehyrdogenase | [c]: fadh2 + ubq8 <==> fad + ubq8h2 |
| SUCOAS | succinyl-CoA synthetase (ADP-forming) | [c]: atp + coa + succ <==> adp + pi + succoa |
| TAL | transaldolase | [c]: g3p + s7p <==> e4p + f6p |
| THD2 | NAD(P) transhydrogenase | (2) h[e] + nadh[c] + nadp[c] --> (2) h[c] + nad[c] + nadph[c] |
| THD2 | NAD(P) transhydrogenase | (2) h[e] + nadh[c] + nadp[c] --> (2) h[c] + nad[c] + nadph[c] |
| THD5 | NAD transhydrogenase | [c]: nad + nadph --> nadh + nadp |
| TKT1 | transketolase | [c]: r5p + xu5p-D <==> g3p + s7p |
| TKT2 | transketolase | [c]: e4p + xu5p-D <==> f6p + g3p |
| TPI | triose-phosphate isomerase | [c]: dhap <==> g3p |

TABLE 12-continued

Enzyme names, abbreviations, and the corresponding reaction stoichiometries of designs in Tables 10 and 11.

| Abbrev. | Enzyme Name | Equation |
|---|---|---|
| VALTA | valine transaminase | [c]: akg + val-L <==> 3mob + glu-L |
| VPAMT | Valine-pyruvate aminotransferase | [c]: 3mob + ala-L --> pyr + val-L |

TABLE 13

Metabolite names corresponding to the abbreviations in the reaction equations.

| Abbreviation | Name |
|---|---|
| 1pyr5c | 1-Pyrroline-5-carboxylate |
| 2ddg6p | 2-Dehydro-3-deoxy-D-gluconate 6-phosphate |
| 2pg | D-Glycerate 2-phosphate |
| 3mob | 3-Methyl-2-oxobutanoate |
| 3pg | 3-Phospho-D-glycerate |
| 4abut | 4-Aminobutanoate |
| 6pgc | 6-Phospho-D-gluconate |
| 6pgl | 6-phospho-D-glucono-1,5-lactone |
| ac | Acetate |
| accoa | Acetyl-CoA |
| acg5sa | N-Acetyl-L-glutamate 5-semialdehyde |
| adp | ADP |
| akg | 2-Oxoglutarate |
| ala-D | D-Alanine |
| ala-L | L-Alanine |
| amp | AMP |
| asn-L | L-Asparagine |
| asp-L | L-Aspartate |
| atp | ATP |
| cbp | Carbamoyl phosphate |
| cit | Citrate |
| co2 | CO2 |
| coa | Coenzyme A |
| dhap | Dihydroxyacetone phosphate |
| e4p | D-Erythrose 4-phosphate |
| etoh | Ethanol |
| f6p | D-Fructose 6-phosphate |
| fad | FAD |
| fadh2 | FADH2 |
| fdp | D-Fructose 1,6-bisphosphate |
| for | Formate |
| fum | Fumarate |
| g3p | Glyceraldehyde 3-phosphate |
| g6p | D-Glucose 6-phosphate |
| glc-D | D-Glucose |

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A non-naturally occurring microbial organism, comprising a methacrylic acid pathway, said microbial organism comprising at least one exogenous nucleic acid encoding a methacrylic acid pathway enzyme expressed in a sufficient amount to produce methacrylic acid, said methacrylic acid pathway comprising:
   3-hydroxyisobutyrate dehydratase;
   3-hydroxyisobutyrate dehydratase, methylmalonyl-CoA mutase, methylmalonyl-CoA reductase and 3-hydroxyisobutyrate dehydrogenase;
   methylmalonyl-CoA mutase, alcohol/aldehyde dehydrogenase, and 3-hydroxyisobutyrate dehydratase;
   methylmalonyl-CoA mutase, methylmalonyl-CoA reductase, 3-amino-2-methylpropionate transaminase, and 3-amino-2-methylpropionate ammonia lyase;
   4-hydroxybutyryl-CoA mutase, 3-hydroxyisobutyryl-CoA synthetase or 3-hydroxyisobutyryl-CoA hydrolase or 3-hydroxyisobutyryl-CoA transferase, and 3-hydroxyisobutyrate dehydratase;
   aspartate aminotransferase, glutamate mutase, 3-methylaspartase, and mesaconate decarboxylase;
   alpha-ketoglutarate reductase, 2-hydroxyglutamate mutase, 3-methylmalate dehydratase, and mesaconate decarboxylase;
   acetoacetyl-CoA thiolase, acetoacetyl-CoA reductase, 3-hydroxybutyryl-CoA mutase, 2-hydroxyisobutyryl-CoA dehydratase, and methacrylyl-CoA transferase or methacrylyl-CoA hydrolase or methacrylyl-CoA synthetase;
   acetoacetyl-CoA thiolase, acetoacetyl-CoA reductase, 3-hydroxybutyryl-CoA mutase, 2-hydroxyisobutyryl-CoA dehydratase, enoyl-CoA hydratase, and 3-hydroxyisobutyryl-CoA hydrolase or 3-hydroxyisobutyryl-CoA synthetase or 3-hydroxyisobutyryl-CoA transferase, and 3-hydroxyisobutyrate dehydratase;
   4-hydroxybutyryl-CoA dehydratase, vinylacetyl-CoA Δ-isomerase, crotonase, 3-hydroxybutyryl-CoA mutase, 2-hydroxyisobutyryl-CoA dehydratase, and methacrylyl-CoA hydrolase or methacrylyl-CoA synthetase or methacrylyl-CoA transferase; or
   4-hydroxybutyryl-CoA mutase, 3-hydroxyisobutyryl-CoA dehydratase, and methacrylyl-CoA synthetase or methacrylyl-CoA hydrolase or methacrylyl-CoA transferase.

2. The non-naturally occurring microbial organism of claim 1, wherein said methacrylic acid pathway further comprises methylmalonyl-CoA epimerase.

3. The non-naturally occurring microbial organism of claim 1, wherein said at least one exogenous nucleic acid is a heterologous nucleic acid.

4. The non-naturally occurring microbial organism of claim 1, wherein said non-naturally occurring microbial organism is in a substantially anaerobic culture medium.

5. The non-naturally occurring microbial organism of claim 1, wherein said non-naturally occurring microbial organism further comprises a genetic modification that increases the activity of at least one enzyme selected from citrate synthase, aconitase, isocitrate lyase, malate synthase, pyruvate dehydrogenase, pyruvate ferredoxin oxidoreductase and phosphoenolpyruvate carboxykinase, wherein the increase in activity is relative to the absence of said genetic modification.

6. The non-naturally occurring microbial organism of claim 1, wherein said methacrylic acid pathway comprises 3-hydroxyisobutyrate dehydratase.

7. The non-naturally occurring microbial organism of claim 6, wherein said non-naturally occurring microbial organism further comprises a genetic modification that increases the activity of at least one enzyme selected from citrate synthase, aconitase, isocitrate lyase, malate synthase, pyruvate dehydrogenase, pyruvate ferredoxin oxidoreductase and phosphoenolpyruvate carboxykinase, wherein the increase in activity is relative to the absence of said genetic modification.

8. The non-naturally occurring microbial organism of claim 1, wherein said methacrylic acid pathway comprises 3-hydroxyisobutyrate dehydratase, methylmalonyl-CoA mutase, methylmalonyl-CoA reductase and 3-hydroxyisobutyrate dehydrogenase.

9. The non-naturally occurring microbial organism of claim 8, wherein said non-naturally occurring microbial organism further comprises a genetic modification that increases the activity of at least one enzyme selected from citrate synthase, aconitase, isocitrate lyase, malate synthase, pyruvate dehydrogenase, pyruvate ferredoxin oxidoreductase and phosphoenolpyruvate carboxykinase, wherein the increase in activity is relative to the absence of said genetic modification.

10. The non-naturally occurring microbial organism of claim 8, wherein the microbial organism comprises exogenous nucleic acids encoding 3-hydroxyisobutyrate dehydratase, methylmalonyl-CoA mutase, methylmalonyl-CoA reductase and 3-hydroxyisobutyrate dehydrogenase.

11. The non-naturally occurring microbial organism of claim 10, wherein said non-naturally occurring microbial organism further comprises a genetic modification that increases the activity of at least one enzyme selected from citrate synthase, aconitase, isocitrate lyase, malate synthase, pyruvate dehydrogenase, pyruvate ferredoxin oxidoreductase and phosphoenolpyruvate carboxykinase, wherein the increase in activity is relative to the absence of said genetic modification.

12. The non-naturally occurring microbial organism of claim 8, wherein said methacrylic acid pathway further comprises methylmalonyl-CoA epimerase.

13. The non-naturally occurring microbial organism of claim 12, wherein said non-naturally occurring microbial organism further comprises a genetic modification that increases the activity of at least one enzyme selected from citrate synthase, aconitase, isocitrate lyase, malate synthase, pyruvate dehydrogenase, pyruvate ferredoxin oxidoreductase and phosphoenolpyruvate carboxykinase, wherein the increase in activity is relative to the absence of said genetic modification.

14. The non-naturally occurring microbial organism of claim 12, wherein the microbial organism comprises exogenous nucleic acids encoding 3-hydroxyisobutyrate dehydratase, methylmalonyl-CoA mutase, methylmalonyl-CoA reductase, 3-hydroxyisobutyrate dehydrogenase and methylmalonyl-CoA epimerase.

15. The non-naturally occurring microbial organism of claim 14, wherein said non-naturally occurring microbial organism further comprises a genetic modification that increases the activity of at least one enzyme selected from citrate synthase, aconitase, isocitrate lyase, malate synthase, pyruvate dehydrogenase, pyruvate ferredoxin oxidoreductase and phosphoenolpyruvate carboxykinase, wherein the increase in activity is relative to the absence of said genetic modification.

16. The non-naturally occurring microbial organism of claim 1, wherein said methacrylic acid pathway comprises methylmalonyl-CoA mutase, alcohol/aldehyde dehydrogenase, and 3-hydroxyisobutyrate dehydratase.

17. The non-naturally occurring microbial organism of claim 16, wherein said non-naturally occurring microbial organism further comprises a genetic modification that increases the activity of at least one enzyme selected from citrate synthase, aconitase, isocitrate lyase, malate synthase, pyruvate dehydrogenase, pyruvate ferredoxin oxidoreductase and phosphoenolpyruvate carboxykinase, wherein the increase in activity is relative to the absence of said genetic modification.

18. The non-naturally occurring microbial organism of claim 16, wherein the microbial organism comprises exogenous nucleic acids encoding methylmalonyl-CoA mutase, alcohol/aldehyde dehydrogenase, and 3-hydroxyisobutyrate dehydratase.

19. The non-naturally occurring microbial organism of claim 18, wherein said non-naturally occurring microbial organism further comprises a genetic modification that increases the activity of at least one enzyme selected from citrate synthase, aconitase, isocitrate lyase, malate synthase, pyruvate dehydrogenase, pyruvate ferredoxin oxidoreductase and phosphoenolpyruvate carboxykinase, wherein the increase in activity is relative to the absence of said genetic modification.

20. The non-naturally occurring microbial organism of claim 16, wherein said methacrylic acid pathway further comprises methylmalonyl-CoA epimerase.

21. The non-naturally occurring microbial organism of claim 20, wherein said non-naturally occurring microbial organism further comprises a genetic modification that increases the activity of at least one enzyme selected from citrate synthase, aconitase, isocitrate lyase, malate synthase, pyruvate dehydrogenase, pyruvate ferredoxin oxidoreductase and phosphoenolpyruvate carboxykinase, wherein the increase in activity is relative to the absence of said genetic modification.

22. The non-naturally occurring microbial organism of claim 20, wherein the microbial organism comprises exogenous nucleic acids encoding methylmalonyl-CoA mutase, alcohol/aldehyde dehydrogenase, 3-hydroxyisobutyrate dehydratase and methylmalonyl-CoA epimerase.

23. The non-naturally occurring microbial organism of claim 22, wherein said non-naturally occurring microbial organism further comprises a genetic modification that increases the activity of at least one enzyme selected from citrate synthase, aconitase, isocitrate lyase, malate synthase, pyruvate dehydrogenase, pyruvate ferredoxin oxidoreductase and phosphoenolpyruvate carboxykinase, wherein the increase in activity is relative to the absence of said genetic modification.

24. The non-naturally occurring microbial organism of claim 1, wherein said methacrylic acid pathway comprises methylmalonyl-CoA mutase, methylmalonyl-CoA reductase, 3-amino-2-methylpropionate transaminase, and 3-amino-2-methylpropionate ammonia lyase.

25. The non-naturally occurring microbial organism of claim 24, wherein said non-naturally occurring microbial organism further comprises a genetic modification that increases the activity of at least one enzyme selected from citrate synthase, aconitase, isocitrate lyase, malate synthase, pyruvate dehydrogenase, pyruvate ferredoxin oxidoreductase and phosphoenolpyruvate carboxykinase, wherein the increase in activity is relative to the absence of said genetic modification.

26. The non-naturally occurring microbial organism of claim 24, wherein the microbial organism comprises exogenous nucleic acids encoding methylmalonyl-CoA mutase, methylmalonyl-CoA reductase, 3-amino-2-methylpropionate transaminase, and 3-amino-2-methylpropionate ammonia lyase.

27. The non-naturally occurring microbial organism of claim 26, wherein said non-naturally occurring microbial organism further comprises a genetic modification that increases the activity of at least one enzyme selected from citrate synthase, aconitase, isocitrate lyase, malate synthase, pyruvate dehydrogenase, pyruvate ferredoxin oxidoreductase and phosphoenolpyruvate carboxykinase, wherein the increase in activity is relative to the absence of said genetic modification.

28. The non-naturally occurring microbial organism of claim 24, wherein said methacrylic acid pathway further comprises methylmalonyl-CoA epimerase.

29. The non-naturally occurring microbial organism of claim 28, wherein said non-naturally occurring microbial organism further comprises a genetic modification that increases the activity of at least one enzyme selected from citrate synthase, aconitase, isocitrate lyase, malate synthase, pyruvate dehydrogenase, pyruvate ferredoxin oxidoreductase and phosphoenolpyruvate carboxykinase, wherein the increase in activity is relative to the absence of said genetic modification.

30. The non-naturally occurring microbial organism of claim 28, wherein the microbial organism comprises exogenous nucleic acids encoding methylmalonyl-CoA mutase, methylmalonyl-CoA reductase, 3-amino-2-methylpropionate transaminase, 3-amino-2-methylpropionate ammonia lyase and methylmalonyl-CoA epimerase.

31. The non-naturally occurring microbial organism of claim 30, wherein said non-naturally occurring microbial organism further comprises a genetic modification that increases the activity of at least one enzyme selected from citrate synthase, aconitase, isocitrate lyase, malate synthase, pyruvate dehydrogenase, pyruvate ferredoxin oxidoreductase and phosphoenolpyruvate carboxykinase, wherein the increase in activity is relative to the absence of said genetic modification.

32. The non-naturally occurring microbial organism of claim 1, wherein said methacrylic acid pathway comprises 4-hydroxybutyryl-CoA mutase, 3-hydroxyisobutyryl-CoA synthetase or 3-hydroxyisobutyryl-CoA hydrolase or 3-hydroxyisobutyryl-CoA transferase, and 3-hydroxyisobutyrate dehydratase.

33. The non-naturally occurring microbial organism of claim 32, wherein said non-naturally occurring microbial organism further comprises a genetic modification that increases the activity of at least one enzyme selected from citrate synthase, aconitase, isocitrate lyase, malate synthase, pyruvate dehydrogenase, pyruvate ferredoxin oxidoreductase and phosphoenolpyruvate carboxykinase, wherein the increase in activity is relative to the absence of said genetic modification.

34. The non-naturally occurring microbial organism of claim 32, wherein the microbial organism comprises exogenous nucleic acids encoding 4-hydroxybutyryl-CoA mutase, 3-hydroxyisobutyryl-CoA synthetase or 3-hydroxyisobutyryl-CoA hydrolase or 3-hydroxyisobutyryl-CoA transferase, and 3-hydroxyisobutyrate dehydratase.

35. The non-naturally occurring microbial organism of claim 34, wherein said non-naturally occurring microbial organism further comprises a genetic modification that increases the activity of at least one enzyme selected from citrate synthase, aconitase, isocitrate lyase, malate synthase, pyruvate dehydrogenase, pyruvate ferredoxin oxidoreductase and phosphoenolpyruvate carboxykinase, wherein the increase in activity is relative to the absence of said genetic modification.

36. The non-naturally occurring microbial organism of claim 32, wherein said methacrylic acid pathway comprises 4-hydroxybutyryl-CoA mutase, 3-hydroxyisobutyryl-CoA synthetase, and 3-hydroxyisobutyrate dehydratase.

37. The non-naturally occurring microbial organism of claim 36, wherein said exogenous nucleic acids encode 4-hydroxybutyryl-CoA mutase, 3-hydroxyisobutyryl-CoA synthetase, and 3-hydroxyisobutyrate dehydratase.

38. The non-naturally occurring microbial organism of claim 32, wherein said methacrylic acid pathway comprises 4-hydroxybutyryl-CoA mutase, 3-hydroxyisobutyryl-CoA hydrolase, and 3-hydroxyisobutyrate dehydratase.

39. The non-naturally occurring microbial organism of claim 38, wherein said exogenous nucleic acids encode 4-hydroxybutyryl-CoA mutase, 3-hydroxyisobutyryl-CoA hydrolase, and 3-hydroxyisobutyrate dehydratase.

40. The non-naturally occurring microbial organism of claim 32, wherein said methacrylic acid pathway comprises 4-hydroxybutyryl-CoA mutase, 3-hydroxyisobutyryl-CoA transferase, and 3-hydroxyisobutyrate dehydratase.

41. The non-naturally occurring microbial organism of claim 40, wherein said exogenous nucleic acids encode 4-hydroxybutyryl-CoA mutase, 3-hydroxyisobutyryl-CoA transferase, and 3-hydroxyisobutyrate dehydratase.

42. The non-naturally occurring microbial organism of claim 1, wherein said methacrylic acid pathway comprises aspartate aminotransferase, glutamate mutase, 3-methylaspartase, and mesaconate decarboxylase.

43. The non-naturally occurring microbial organism of claim 42, wherein the microbial organism comprises exogenous nucleic acids encoding aspartate aminotransferase, glutamate mutase, 3-methylaspartase, and mesaconate decarboxylase.

44. The non-naturally occurring microbial organism of claim 1, wherein said methacrylic acid pathway comprises alpha-ketoglutarate reductase, 2-hydroxyglutamate mutase, 3-methylmalate dehydratase, and mesaconate decarboxylase.

45. The non-naturally occurring microbial organism of claim 44, wherein the microbial organism comprises exogenous nucleic acids encoding alpha-ketoglutarate reductase, 2-hydroxyglutamate mutase, 3-methylmalate dehydratase, and mesaconate decarboxylase.

46. The non-naturally occurring microbial organism of claim 1, wherein said methacrylic acid pathway comprises acetoacetyl-CoA thiolase, acetoacetyl-CoA reductase, 3-hydroxybutyryl-CoA mutase, 2-hydroxyisobutyryl-CoA dehydratase, and methacrylyl-CoA transferase or methacrylyl-CoA hydrolase or methacrylyl-CoA synthetase.

47. The non-naturally occurring microbial organism of claim 46, wherein the microbial organism comprises exogenous nucleic acids encoding acetoacetyl-CoA thiolase, acetoacetyl-CoA reductase, 3-hydroxybutyryl-CoA mutase, 2-hydroxyisobutyryl-CoA dehydratase, and methacrylyl-CoA transferase or methacrylyl-CoA hydrolase or methacrylyl-CoA synthetase.

48. The non-naturally occurring microbial organism of claim 46, wherein said methacrylic acid pathway comprises acetoacetyl-CoA thiolase, acetoacetyl-CoA reductase, 3-hydroxybutyryl-CoA mutase, 2-hydroxyisobutyryl-CoA dehydratase, and methacrylyl-CoA transferase.

49. The non-naturally occurring microbial organism of claim 48, wherein said exogenous nucleic acids encode acetoacetyl-CoA thiolase, acetoacetyl-CoA reductase, 3-hydroxybutyryl-CoA mutase, 2-hydroxyisobutyryl-CoA dehydratase, and methacrylyl-CoA transferase.

50. The non-naturally occurring microbial organism of claim 46, wherein said methacrylic acid pathway comprises acetoacetyl-CoA thiolase, acetoacetyl-CoA reductase, 3-hydroxybutyryl-CoA mutase, 2-hydroxyisobutyryl-CoA dehydratase, and methacrylyl-CoA hydrolase.

51. The non-naturally occurring microbial organism of claim 50, wherein said exogenous nucleic acids encode acetoacetyl-CoA thiolase, acetoacetyl-CoA reductase, 3-hydroxybutyryl-CoA mutase, 2-hydroxyisobutyryl-CoA dehydratase, and methacrylyl-CoA hydrolase.

52. The non-naturally occurring microbial organism of claim 46, wherein said methacrylic acid pathway comprises acetoacetyl-CoA thiolase, acetoacetyl-CoA reductase, 3-hydroxybutyryl-CoA mutase, 2-hydroxyisobutyryl-CoA dehydratase, and methacrylyl-CoA synthetase.

53. The non-naturally occurring microbial organism of claim 52, wherein said exogenous nucleic acids encode acetoacetyl-CoA thiolase, acetoacetyl-CoA reductase, 3-hydroxybutyryl-CoA mutase, 2-hydroxyisobutyryl-CoA dehydratase, and methacrylyl-CoA synthetase.

54. The non-naturally occurring microbial organism of claim 1, wherein said methacrylic acid pathway comprises acetoacetyl-CoA thiolase, acetoacetyl-CoA reductase, 3-hydroxybutyryl-CoA mutase, 2-hydroxyisobutyryl-CoA dehydratase, enoyl-CoA hydratase, and 3-hydroxyisobutyryl-CoA hydrolase or 3-hydroxyisobutyryl-CoA synthetase or 3-hydroxyisobutyryl-CoA transferase, and 3-hydroxyisobutyrate dehydratase.

55. The non-naturally occurring microbial organism of claim 54, wherein the microbial organism comprises exogenous nucleic acids encoding acetoacetyl-CoA thiolase, acetoacetyl-CoA reductase, 3-hydroxybutyryl-CoA mutase, 2-hydroxyisobutyryl-CoA dehydratase, enoyl-CoA hydratase, and 3-hydroxyisobutyryl-CoA hydrolase or 3-hydroxyisobutyryl-CoA synthetase or 3-hydroxyisobutyryl-CoA transferase, and 3-hydroxyisobutyrate dehydratase.

56. The non-naturally occurring microbial organism of claim 54, wherein said methacrylic acid pathway comprises acetoacetyl-CoA thiolase, acetoacetyl-CoA reductase, 3-hydroxybutyryl-CoA mutase, 2-hydroxyisobutyryl-CoA dehydratase, enoyl-CoA hydratase, 3-hydroxyisobutyryl-CoA hydrolase, and 3-hydroxyisobutyrate dehydratase.

57. The non-naturally occurring microbial organism of claim 56, wherein said exogenous nucleic acids encode acetoacetyl-CoA thiolase, acetoacetyl-CoA reductase, 3-hydroxybutyryl-CoA mutase, 2-hydroxyisobutyryl-CoA dehydratase, enoyl-CoA hydratase, 3-hydroxyisobutyryl-CoA hydrolase, and 3-hydroxyisobutyrate dehydratase.

58. The non-naturally occurring microbial organism of claim 54, wherein said methacrylic acid pathway comprises acetoacetyl-CoA thiolase, acetoacetyl-CoA reductase, 3-hydroxybutyryl-CoA mutase, 2-hydroxyisobutyryl-CoA dehydratase, enoyl-CoA hydratase, 3-hydroxyisobutyryl-CoA synthetase, and 3-hydroxyisobutyrate dehydratase.

59. The non-naturally occurring microbial organism of claim 58, wherein said exogenous nucleic acids encode acetoacetyl-CoA thiolase, acetoacetyl-CoA reductase, 3-hydroxybutyryl-CoA mutase, 2-hydroxyisobutyryl-CoA dehydratase, enoyl-CoA hydratase, 3-hydroxyisobutyryl-CoA synthetase, and 3-hydroxyisobutyrate dehydratase.

60. The non-naturally occurring microbial organism of claim 54, wherein said methacrylic acid pathway comprises acetoacetyl-CoA thiolase, acetoacetyl-CoA reductase, 3-hydroxybutyryl-CoA mutase, 2-hydroxyisobutyryl-CoA dehydratase, enoyl-CoA hydratase, 3-hydroxyisobutyryl-CoA transferase, and 3-hydroxyisobutyrate dehydratase.

61. The non-naturally occurring microbial organism of claim 60, wherein said exogenous nucleic acids encode acetoacetyl-CoA thiolase, acetoacetyl-CoA reductase, 3-hydroxybutyryl-CoA mutase, 2-hydroxyisobutyryl-CoA dehydratase, enoyl-CoA hydratase, 3-hydroxyisobutyryl-CoA transferase, and 3-hydroxyisobutyrate dehydratase.

62. The non-naturally occurring microbial organism of claim 1, wherein said methacrylic acid pathway comprises 4-hydroxybutyryl-CoA dehydratase, vinylacetyl-CoA Δ-isomerase, crotonase, 3-hydroxybutyryl-CoA mutase, 2-hydroxyisobutyryl-CoA dehydratase, and methacrylyl-CoA hydrolase or methacrylyl-CoA synthetase or methacrylyl-CoA transferase.

63. The non-naturally occurring microbial organism of claim 62, wherein said non-naturally occurring microbial organism further comprises a genetic modification that increases the activity of at least one enzyme selected from citrate synthase, aconitase, isocitrate lyase, malate synthase, pyruvate dehydrogenase, pyruvate ferredoxin oxidoreductase and phosphoenolpyruvate carboxykinase, wherein the increase in activity is relative to the absence of said genetic modification.

64. The non-naturally occurring microbial organism of claim 62, wherein the microbial organism comprises exogenous nucleic acids encoding 4-hydroxybutyryl-CoA dehydratase, vinylacetyl-CoA Δ-isomerase, crotonase, 3-hydroxybutyryl-CoA mutase, 2-hydroxyisobutyryl-CoA dehydratase, and methacrylyl-CoA hydrolase or methacrylyl-CoA synthetase or methacrylyl-CoA transferase.

65. The non-naturally occurring microbial organism of claim 64, wherein said non-naturally occurring microbial organism further comprises a genetic modification that increases the activity of at least one enzyme selected from citrate synthase, aconitase, isocitrate lyase, malate synthase, pyruvate dehydrogenase, pyruvate ferredoxin oxidoreductase and phosphoenolpyruvate carboxykinase, wherein the increase in activity is relative to the absence of said genetic modification.

66. The non-naturally occurring microbial organism of claim 62, wherein said methacrylic acid pathway comprises 4-hydroxybutyryl-CoA dehydratase, vinylacetyl-CoA Δ-isomerase, crotonase, 3-hydroxybutyryl-CoA mutase, 2-hydroxyisobutyryl-CoA dehydratase, and methacrylyl-CoA hydrolase.

67. The non-naturally occurring microbial organism of claim 66, wherein said exogenous nucleic acids encode 4-hydroxybutyryl-CoA dehydratase, vinylacetyl-CoA Δ-isomerase, crotonase, 3-hydroxybutyryl-CoA mutase, 2-hydroxyisobutyryl-CoA dehydratase, and methacrylyl-CoA hydrolase.

68. The non-naturally occurring microbial organism of claim 62, wherein said methacrylic acid pathway comprises 4-hydroxybutyryl-CoA dehydratase, vinylacetyl-CoA Δ-isomerase, crotonase, 3-hydroxybutyryl-CoA mutase, 2-hydroxyisobutyryl-CoA dehydratase, and methacrylyl-CoA synthetase.

69. The non-naturally occurring microbial organism of claim 68, wherein said exogenous nucleic acids encode 4-hydroxybutyryl-CoA dehydratase, vinylacetyl-CoA Δ-isomerase, crotonase, 3-hydroxybutyryl-CoA mutase, 2-hydroxyisobutyryl-CoA dehydratase, and methacrylyl-CoA synthetase.

70. The non-naturally occurring microbial organism of claim 62, wherein said methacrylic acid pathway comprises 4-hydroxybutyryl-CoA dehydratase, vinylacetyl-CoA Δ-isomerase, crotonase, 3-hydroxybutyryl-CoA mutase, 2-hydroxyisobutyryl-CoA dehydratase, and methacrylyl-CoA transferase.

71. The non-naturally occurring microbial organism of claim 70, wherein said exogenous nucleic acids encode 4-hydroxybutyryl-CoA dehydratase, vinylacetyl-CoA Δ-isomerase, crotonase, 3-hydroxybutyryl-CoA mutase, 2-hydroxyisobutyryl-CoA dehydratase, and methacrylyl-CoA transferase.

72. The non-naturally occurring microbial organism of claim 1, wherein said methacrylic acid pathway comprises 4-hydroxybutyryl-CoA mutase, 3-hydroxyisobutyryl-CoA dehydratase, and methacrylyl-CoA synthetase or methacrylyl-CoA hydrolase or methacrylyl-CoA transferase.

73. The non-naturally occurring microbial organism of claim 72, wherein said non-naturally occurring microbial organism further comprises a genetic modification that increases the activity of at least one enzyme selected from citrate synthase, aconitase, isocitrate lyase, malate synthase, pyruvate dehydrogenase, pyruvate ferredoxin oxidoreductase and phosphoenolpyruvate carboxykinase, wherein the increase in activity is relative to the absence of said genetic modification.

74. The non-naturally occurring microbial organism of claim 72, wherein the microbial organism comprises exogenous nucleic acids encoding 4-hydroxybutyryl-CoA mutase, 3-hydroxyisobutyryl-CoA dehydratase, and methacrylyl-CoA synthetase or methacrylyl-CoA hydrolase or methacrylyl-CoA transferase.

75. The non-naturally occurring microbial organism of claim 74, wherein said non-naturally occurring microbial organism further comprises a genetic modification that increases the activity of at least one enzyme selected from citrate synthase, aconitase, isocitrate lyase, malate synthase, pyruvate dehydrogenase, pyruvate ferredoxin oxidoreductase and phosphoenolpyruvate carboxykinase, wherein the increase in activity is relative to the absence of said genetic modification.

76. The non-naturally occurring microbial organism of claim 72, wherein said methacrylic acid pathway comprises 4-hydroxybutyryl-CoA mutase, methacrylyl-CoA synthetase, and 3-hydroxyisobutyryl-CoA dehydratase.

77. The non-naturally occurring microbial organism of claim 76, wherein said exogenous nucleic acids encode 4-hydroxybutyryl-CoA mutase, methacrylyl-CoA synthetase, and 3-hydroxyisobutyryl-CoA dehydratase.

78. The non-naturally occurring microbial organism of claim 72, wherein said methacrylic acid pathway comprises 4-hydroxybutyryl-CoA mutase, methacrylyl-CoA hydrolase, and 3-hydroxyisobutyryl-CoA dehydratase.

79. The non-naturally occurring microbial organism of claim 78, wherein said exogenous nucleic acids encode 4-hydroxybutyryl-CoA mutase, methacrylyl-CoA hydrolase, and 3-hydroxyisobutyryl-CoA dehydratase.

80. The non-naturally occurring microbial organism of claim 72, wherein said methacrylic acid pathway comprises 4-hydroxybutyryl-CoA mutase, methacrylyl-CoA transferase, and 3-hydroxyisobutyryl-CoA dehydratase.

81. The non-naturally occurring microbial organism of claim 80, wherein said exogenous nucleic acids encode 4-hydroxybutyryl-CoA mutase, methacrylyl-CoA transferase, and 3-hydroxyisobutyryl-CoA dehydratase.

82. A method for producing methacrylic acid, comprising culturing the non-naturally occurring microbial organism of claim 1 under conditions and for a sufficient period of time to produce methacrylic acid.

83. The method of claim 82, wherein said non-naturally occurring microbial organism is in a substantially anaerobic culture medium.

84. A method for producing methacrylic acid, comprising culturing the non-naturally occurring microbial organism of claim 6 under conditions and for a sufficient period of time to produce methacrylic acid.

85. The method of claim 84, wherein said non-naturally occurring microbial organism is in a substantially anaerobic culture medium.

86. A method for producing methacrylic acid, comprising culturing the non-naturally occurring microbial organism of claim 8 under conditions and for a sufficient period of time to produce methacrylic acid.

87. The method of claim 86, wherein said non-naturally occurring microbial organism is in a substantially anaerobic culture medium.

88. A method for producing methacrylic acid, comprising culturing the non-naturally occurring microbial organism of claim 16 under conditions and for a sufficient period of time to produce methacrylic acid.

89. The method of claim 88, wherein said non-naturally occurring microbial organism is in a substantially anaerobic culture medium.

90. A method for producing methacrylic acid, comprising culturing the non-naturally occurring microbial organism of claim 24 under conditions and for a sufficient period of time to produce methacrylic acid.

91. The method of claim 90, wherein said non-naturally occurring microbial organism is in a substantially anaerobic culture medium.

92. A method for producing methacrylic acid, comprising culturing the non-naturally occurring microbial organism of claim 32 under conditions and for a sufficient period of time to produce methacrylic acid.

93. The method of claim 92, wherein said non-naturally occurring microbial organism is in a substantially anaerobic culture medium.

94. A method for producing methacrylic acid, comprising culturing the non-naturally occurring microbial organism of claim 42 under conditions and for a sufficient period of time to produce methacrylic acid.

95. The method of claim 94, wherein said non-naturally occurring microbial organism is in a substantially anaerobic culture medium.

96. A method for producing methacrylic acid, comprising culturing the non-naturally occurring microbial organism of claim 44 under conditions and for a sufficient period of time to produce methacrylic acid.

97. The method of claim 96, wherein said non-naturally occurring microbial organism is in a substantially anaerobic culture medium.

98. A method for producing methacrylic acid, comprising culturing the non-naturally occurring microbial organism of claim 46 under conditions and for a sufficient period of time to produce methacrylic acid.

99. The method of claim 98, wherein said non-naturally occurring microbial organism is in a substantially anaerobic culture medium.

100. A method for producing methacrylic acid, comprising culturing the non-naturally occurring microbial organism of claim 54 under conditions and for a sufficient period of time to produce methacrylic acid.

101. The method of claim 100, wherein said non-naturally occurring microbial organism is in a substantially anaerobic culture medium.

102. A method for producing methacrylic acid, comprising culturing the non-naturally occurring microbial organism of claim 62 under conditions and for a sufficient period of time to produce methacrylic acid.

103. The method of claim 102, wherein said non-naturally occurring microbial organism is in a substantially anaerobic culture medium.

104. A method for producing methacrylic acid, comprising culturing the non-naturally occurring microbial organism of claim 72 under conditions and for a sufficient period of time to produce methacrylic acid.

105. The method of claim 104, wherein said non-naturally occurring microbial organism is in a substantially anaerobic culture medium.

* * * * *